United States Patent
Bobbitt et al.

(10) Patent No.: US 11,292,807 B2
(45) Date of Patent: Apr. 5, 2022

(54) MOLECULES FROM SEAWEEDS WITH ANTI-CANCER ACTIVITY

(71) Applicant: OCEANS LTD., St-Johns (CA)

(72) Inventors: Judith Bobbitt, St-Johns (CA); Ahmed Zein, St-Johns (CA)

(73) Assignee: OCEANS LTD., St-Johns (CA)

(*) Notice: Subject to any disclaimer, the term of this patent is extended or adjusted under 35 U.S.C. 154(b) by 0 days.

(21) Appl. No.: 16/836,658

(22) Filed: Mar. 31, 2020

(65) Prior Publication Data
US 2020/0291054 A1  Sep. 17, 2020

Related U.S. Application Data

(62) Division of application No. 15/776,783, filed as application No. PCT/CA2016/051333 on Nov. 16, 2016, now abandoned.

(Continued)

(51) Int. Cl.
C07H 3/02 (2006.01)
C07C 69/30 (2006.01)
(Continued)

(52) U.S. Cl.
CPC .............. *C07H 3/02* (2013.01); *A61K 9/0053* (2013.01); *A61K 9/48* (2013.01); *A61K 31/122* (2013.01);
(Continued)

(58) Field of Classification Search
CPC .............. A61K 2300/00; A61K 31/23; A61K 31/7032; A61K 31/122; A61K 45/06;
(Continued)

(56) References Cited

U.S. PATENT DOCUMENTS 5,620,962 A   4/1997   Winget

FOREIGN PATENT DOCUMENTS

| CA | 2954781 | 1/2016 |
|---|---|---|
| JP | S6019716 | 1/1985 |

(Continued)

OTHER PUBLICATIONS

Banskota, A. H. et al., Mono- and digalactosyldiacylglycerols: potent nitric oxide inhibitors from the marine microalga Nannochloropsis granulata. Journal of Applied Phycology, 25, p. 349-357, 2013.

(Continued)

*Primary Examiner* — Savitha M Rao
(74) *Attorney, Agent, or Firm* — Parker Highlander PLLC

(57) ABSTRACT

The present invention provides purified compounds extracted from seaweeds having the formula (I):

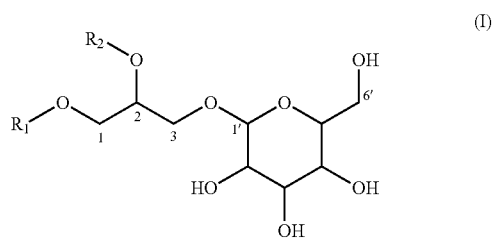

wherein $R^1$ and $R^2$ is each independently H or a fatty acid and their use for inhibiting the growth of cancer cells.

7 Claims, 107 Drawing Sheets

(*Chaetomorpha cannabina*)

(*Cladophora sericea*)

Related U.S. Application Data

(60) Provisional application No. 62/269,198, filed on Dec. 18, 2015, provisional application No. 62/256,339, filed on Nov. 17, 2015.

(51) Int. Cl.

| | |
|---|---|
| *A61K 31/7032* | (2006.01) |
| *C07H 15/06* | (2006.01) |
| *C07C 57/12* | (2006.01) |
| *A61K 31/122* | (2006.01) |
| *A61K 45/06* | (2006.01) |
| *A61K 31/23* | (2006.01) |
| *C07H 15/10* | (2006.01) |
| *C07C 59/42* | (2006.01) |
| *A61P 35/00* | (2006.01) |
| *A61K 9/00* | (2006.01) |
| *A61K 9/48* | (2006.01) |

(52) U.S. Cl.
CPC .......... *A61K 31/23* (2013.01); *A61K 31/7032* (2013.01); *A61K 45/06* (2013.01); *A61P 35/00* (2018.01); *C07C 57/12* (2013.01); *C07C 59/42* (2013.01); *C07C 69/30* (2013.01); *C07H 15/06* (2013.01); *C07H 15/10* (2013.01)

(58) Field of Classification Search
CPC ......... A61K 9/0053; A61K 9/48; A61P 35/00; C07C 57/12; C07C 59/42; C07C 69/30; C07H 15/06; C07H 15/10; C07H 3/02
See application file for complete search history.

(56) References Cited

FOREIGN PATENT DOCUMENTS

| JP | H07149786 | 6/1996 |
|---|---|---|
| JP | 2007112759 | 5/2007 |

OTHER PUBLICATIONS

Banskota, A. H. et al., Monogalactosyldiacylglycerols, potent nitric oxide inhibitors from the marine microalga Tetraselmis chui, Natural Product Research, vol. 27, No. 12, p. 1084-1090, 2013.

Banskota, A. H. et al., Polar lipids from the marine macroalga Palmaria palmata inhibit lipopolysaccharide-induced nitric oxide production in RAW264.7 macrophage cells, Phytochemistry 101, p. 101-108, 2014.

Guella, G. et al., A new solution for an old problem: the regiochemical distribution of the acyl chains in galactolipids can be established by electrospray ionization tandem mass spectrometry, Rapid Commun. Mass Spectrom., 17, p. 1982.

Jung, J. H., et al., Diacylglycerylgalactosides from Arisaema Amurense, Phytochemistry, vol. 42, No. 2, p. 447-452, 1996.

Kobayashi, M. et al., Marine Natural Products. XXIX. 1) Heterosigma-glycolipids I, II, III, and IV, Four Diacylglyceroglycolipids Possessing w3-Polyunsaturated Fatty Acid Residues, from the Raphidophycean Dirmflagellate Heterosigma, Chemical and Pharmaceutical Bulletin, vol. 40, No. 6, p. 1404-1410, 1994.

Nagatsu, A. et al., Synthesis and structure—anti-tumor-promoting activity relationship of monogalactosyl diacylglycerols, Bioorganic & Medicinal Chemistry Letters, vol. 4, No. 13, p. 1619-1622, 1994.

Nguyen, P. T., et al., In Vitro evaluation of the antioxidant and cytotoxic activities of constituents of the mangrove Lumnitzera racemosa Willd, Archives of Pharmacal Research, 38, p. 446-455, 2015.

Pettit, G. R. et al., Isolation and structure of spongilipid from the Republic of Singapore marine porifera Spongia cf. hispida, Canadian Journal of Chemistry 75, p. 920-925, 1997.

Shirahashi, H. et al., Antitumor-promoting Activities of Various Synthetic 1-0-Acyl-3-0-(6'-0-Acyl-β-D-Galactopyranosyl)-sn-Glycerols Related to Natural Product from Freshwater Cyanobacterium Anabaena flos-aquae f. flos-aquae. Chemical and Pharmaceutical Bulletin, vol. 44, No. 7, p. 1404-1406, 1996.

Tang, H.-F., et al., Using conidia of Pyricularia oryzae screening for bioactive portions from marine organisms, Academic Journal of Second Military Medical University, vol. 23, No. 3, p. 246-249, Mar. 2002. (Abstract).

Weil, M. J., et al., Tumor Cell Proliferation and Cyclooxygenase Inhibitory Constituents in Horseradish (Armoracia rusticana) and Wasabi (Wasabia japonica), Journal of Agricultural and Food Chemistry, vol. 53, No. 5, p. 1440-1444, 2005.

*Figures 1A-D*
Figure 1A. (*Chaetomorpha cannabina*) Figure 1B. (*Cladophora sericea*)
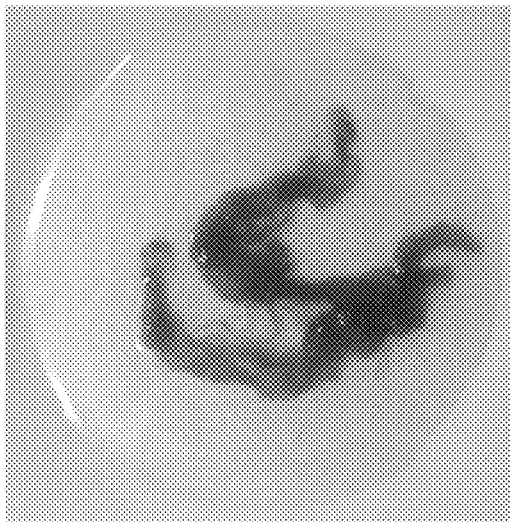 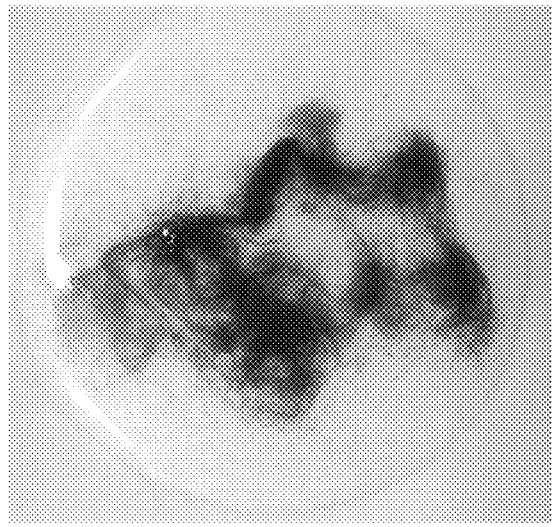
Figure 1C. (*Polysiphonia urceolata*) Figure 1D. (*Polysiphonia flexicaulis*)
 

Figure 69

MOLECULES FROM SEAWEEDS WITH ANTI-CANCER ACTIVITY

This application is a divisional of U.S. application Ser. No. 15/776,783, filed May 16, 2018, as a national phase application under 35 U.S.C. § 371 of International Application No. PCT/CA2016/051333, filed Nov. 16, 2016, which claims priority to U.S. Provisional Application No. 62/256,339, filed Nov. 17, 2015, and U.S. Provisional Application No. 62/269,198, filed Dec. 18, 2015. The entire text of each of the above referenced disclosures is specifically incorporated herein by reference.

FIELD OF THE INVENTION

The present invention relates to novel molecules extracted from seaweeds, method of preparation and use for inhibiting the growth of cancer cells.

BACKGROUND OF THE INVENTION

Cancer is a disease that seriously jeopardizes the health of human beings. Around the globe, about 6 millions people die of cancer every year, with another 10 millions seriously affected by the disease. According to the estimate of the World Health Organization, in the 21st century, cancer will become the "number one killer" of mankind.

In the past several decades, many ways of treating cancer became available, mainly including surgery, radiotherapy, chemotherapy, hormonotherapy, gene therapy, and immunotherapy, among which surgery, radiotherapy and chemotherapy have become the major means. Chemotherapy refers to treating cancer with chemical medication. It is the most rapidly expanding field in the treatment of cancer. A great number of new medicines aiming at different targets are ready for clinical application, and developments in research in mechanism of drug action and pharmacokinetics have made the clinical administration routes and means more fitting for killing tumor cells while protecting the normal tissues.

The search for natural-derived molecule for inhibiting cancer cells has led to the discovery of molecules such as Taxol or Vinblastine. Despite the utility of taxus and vinca alkaloids in the clinic, there are serious limitations to these therapies.

One major drawback when treating cancer is to achieve selectivity against this type of cancer cells. There remains a need to discover and isolate new potent compounds having selective activity against certain types of cancer cells, thereby providing highly selective anti-cancer molecules.

Against such a background, new molecules to add to the already existing armada of chemotherapeutic drugs are highly desirable.

SUMMARY OF THE INVENTION

A main aspect intended to be addressed by the present invention is to provide novel molecules extracted from seaweeds such as, for example: *Chaetomorpha cannabina* (C.C.), *Cladophora sericea* (C.S.), *Polysiphonia ureceolata* (P.U.) and *Polysiphonia flexicaulis* (P.F.).

According to a first aspect, there is provided a compound selected from:

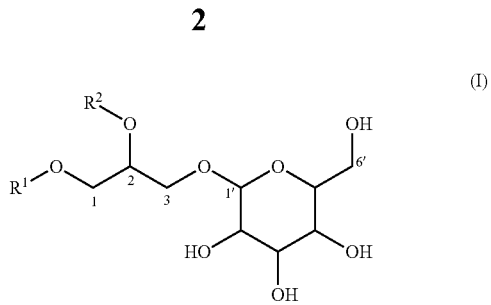

wherein $R^1$ and $R^2$ is each independently H or a fatty acid selected from the group consisting of:

| Cpd | $R^1$ | $R^2$ |
|---|---|---|
| 1 | C20:5 | C16:4; |
| 2 | C20:5 | C16:0; |
| 3 | C20:5 | C14:0; |
| 4 | C16:1 | C18:2; |
| 5 | C16:0 | H; |
| 6 | C20:5 | C16:3; |
| 7 | C20:5 | C20:5; |
| 8 | C16:0 | C16:0; |
| 9 | C16:0 | C16:1; |
| 10 | C16:0 | C18:2; |
| 11 | C16:0 | C18:1; |
| 12 | C16:0 | C18:0; |
| 13 | C20:5 | H; |
| 14 | C18:3 | C16:4; |
| 15 | C18:3 | C16:3; |
| 16 | C16:0 | C14:0; |
| 17 | C14:0 | H; and |
| 18 | C14:0 | C14:0. |

According to a second aspect, there is provided a compound having a structure selected from the group consisting of:

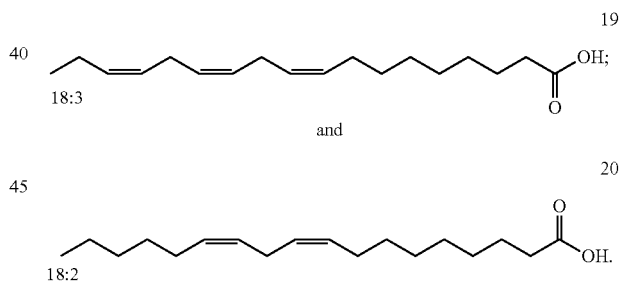

According to a further aspect, there is provided a compound having a structure selected from the group consisting of:

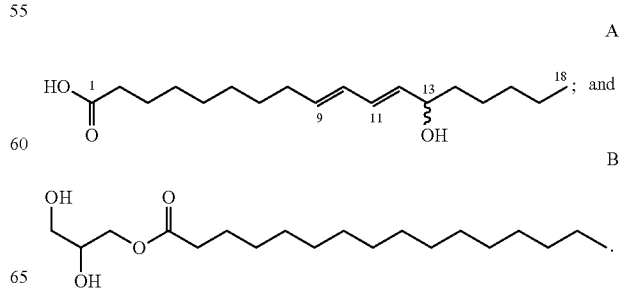

According to a further aspect of the present invention, there is provided use of any one of the compounds as defined herein for inhibiting growth of cancer cells.

According to a further aspect of the present invention, there is provided use of any one of the compounds as defined herein for the manufacture of composition for treating cancer in a mammal.

According to a further aspect, the present invention provides a composition comprising the compound as defined herein, in admixture with a physiologically acceptable excipient.

According to a further aspect, the present invention provides use of the composition as defined herein for the treatment of cancer in a mammal.

According to a further aspect, there is provided a use of compounds C or D for use in the treatment of cancer, wherein said compounds have a structure of formula:

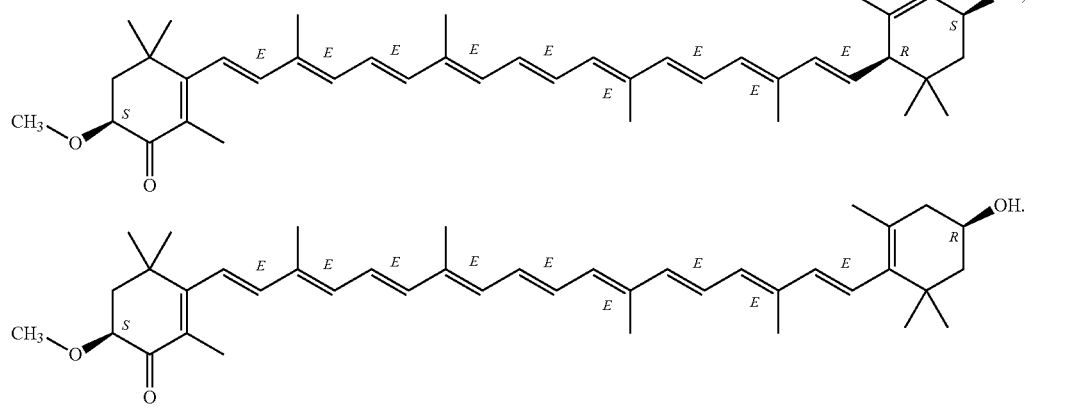

According to a further aspect, the present invention provides a method for obtaining a compound as defined herein comprising the steps of:

a) mixing material from said seaweed with a solvent to obtain a solvent mixture, wherein said seaweed is selected from the group consisting of: *Chaetomorpha Cannabina* (C.C.) or *Cladophora sericea* (C.S.), *Polysiphonia ureceolata* (P.U.) and *Polysiphonia flexicaulis* (P.F.);

b) separating a solid fraction and a liquid fraction from said mixture, said liquid fraction forming said extract from said seaweed material; and c) fractionating the extract from step b) on a C-18 column with a solvent selected from the group consisting of: from 5% aq. MeOH to 100% MeOH, and 50% MeOH: $CH_2Cl_2$ and selecting the 100% MeOH fraction and/or the 50% MeOH:$CH_2Cl_2$ fraction.

According to a further aspect, the present invention provides a method for inhibiting growth of cancer cells comprising contacting said cell with a growth-inhibiting concentration of the compound, or the composition, as defined herein.

According to a further aspect, the present invention provides a method for treating cancer in a mammal comprising administering a growth-inhibiting concentration of the composition as defined herein to the mammal.

DETAILED DESCRIPTION OF THE INVENTION

Description of the Figures

FIGS. 1A.-D. Pictures of samples from different seaweeds used for extraction.

FIG. 69. HRMS of peak RT 6.1 of NC174-13-14-1.

ABBREVIATIONS AND DEFINITIONS

Figure 2:
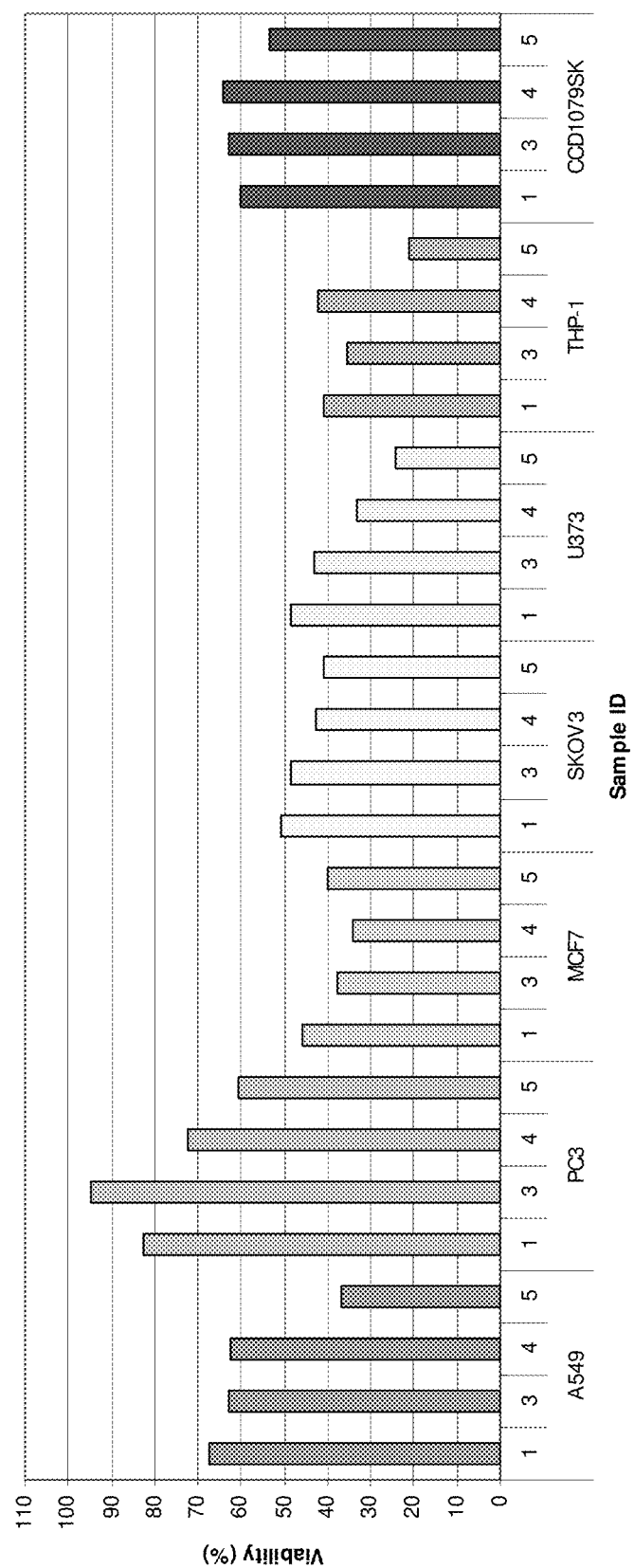
FIG. 2. In vitro activity of lead crude extracts #1 (NC77), #3 (NC130), #4 (NC133), #5 (NC169) on viability of seven cell lines.

Abbreviations bis-AAF-R110: bis-alanyl-alanyl-phenylalanyl-rhodamine 110; CIMA: colorimetric indicative of metabolic activity; GF-AFC: Gly-Phe-7-amino-4-trifluoromethylcoumarin; HILIC: hydrophilic interaction liquid chromatography. C-18 SPE: solid phase extraction on C-18 column.

Definitions

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The term "about" as used herein refers to a margin of + or −10% of the number indicated. For sake of precision, the term about when used in conjunction with, for example: 90% means 90%+/−9% i.e. from 81% to 99%. More precisely, the term about refer to + or −5% of the number indicated, where for example: 90% means 90%+/−4.5% i.e. from 86.5% to 94.5%. When used in the context of a pH, the term "about" means +/−0.5 pH unit.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" and "disorder" may be used interchangeably or may be different in that the particular anomaly or condition may not have a known causative agent (so that etiology has not yet been worked out) and it is therefore not yet recognized as a disease but only as an undesirable condition or syndrome, wherein a more or less specific set of symptoms have been identified by clinicians.

The term "subject" or "patient" as used herein refers to an animal, preferably a mammal, and most preferably a human who is the object of treatment, observation or experiment.

"Mammal" includes humans and both domestic animals such as laboratory animals and household pets, (e.g. cats, dogs, swine, cattle, sheep, goats, horses, rabbits), and non-domestic animals such as wildlife and the like.

The term "extract" as used herein means a composition prepared by contacting solvent with seaweed material, produced following the procedures of the invention, which demonstrates inhibitory activity against one or more cancer cell line in vitro. In one aspect of the invention, an extract demonstrates inhibitory activity against cancer cell growth in vivo. As used herein, the term "extract" means an extract that is: crude, fractionated, sub-fractionated, separated, isolated, enriched or purified, without being limited thereto.

The term "isolated" is used herein to indicate that the protein exists in a physical milieu distinct from that in which it occurs in nature. For example, the isolated molecule may be substantially isolated (for example enriched or purified) with respect to the complex cellular milieu in which it naturally occurs, such as in a crude extract. When the isolated molecule is enriched or purified, the absolute level of purity is not critical and those skilled in the art can readily determine appropriate levels of purity according to the use to which the material is to be put. In some circumstances, the isolated molecule forms part of a composition (for example a more or less crude extract containing many other substances) or buffer system, which may for example contain other components. In other circumstances, the isolated molecule may be purified to essential homogeneity, for example as determined spectrophotometrically, by NMR or by chromatography (for example LC-MS).

The term "crude" means compounds or molecules that have not been entirely separated from the components of the original composition in which it was present. Therefore, the terms "separating", "purifying" or "isolating" refers to methods by which one or more components of the biological sample are removed from one or more other components of the sample.

The molecule(s) described herein can be formulated as pharmaceutical compositions by formulation with additives such as pharmaceutically acceptable excipients, pharmaceutically acceptable carriers, and pharmaceutically acceptable vehicles, or as nutraceutical or nutritional formulations with additives such as nutraceutically or nutritionally acceptable excipients, nutraceutically or nutritionally acceptable carriers, and nutraceutically or nutritionally acceptable vehicles.

As used herein, the term "pharmaceutically acceptable" refers to molecular entities and compositions that are physiologically tolerable and do not typically produce an allergic or similar unwanted reaction, such as gastric upset, dizziness and the like, when administered to human. Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for injectable solutions. Suitable pharmaceutical carriers are described in "Remington's Pharmaceutical Sciences" by E. W. Martin.

The extracts, pure or mixed molecule(s) and composition(s) of the present invention can be prepared as nutritional formulations such as foods, including medical or functional foods and dietary supplements. A "medical or functional food" is defined as being consumed as part of a usual diet but which has been demonstrated to have physiological benefits and/or to reduce the risk of a disease or condition such as a chronic disease, beyond basic nutritional functions. A "dietary supplement" is defined as a product that is intended to supplement the human diet and is typically provided in the form of a pill, capsule, tablet, or like formulation. By way of example, but not limitation, a dietary supplement may include one or more of the following ingredients: vitamins, minerals, herbs, botanicals, amino acids, dietary substances intended to supplement the diet by increasing total dietary intake, and concentrates, metabolites, constituents, extracts or combinations of any of the foregoing. Dietary supplements may also be incorporated into food stuffs, such as functional foods designed to promote health or to prevent disease or disorders. If administered as a medicinal preparation, the composition can be administered, either as a prophylaxis or treatment, to a patient in any of a number of methods. The subject compositions may be administered alone or in combination with other pharmaceutical agents and can be combined with a physiologically acceptable carrier thereof. The effective amount and method of administration and aim of the particular formulation can vary based on the individual subject, the stage of the disease or condition, and other factors evident to one skilled in the art. In the case of a pharmaceutical formulation as well as a nutraceutical formulation, during the course of the treatment, the concentration of the subject compositions may be monitored (for example, blood plasma levels may be monitored) to insure that the desired level is maintained.

The term "nutraceutical" has been used to refer to any substance that is a food or a part of a food and provides medical or health benefits, including the prevention and treatment of disease or condition. Thus, a nutraceutical is a product isolated or purified from foods that is generally sold in medicinal forms not usually associated with foods. A nutraceutical is demonstrated to have a physiological benefit or provide protection against chronic disease. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease. Suitable nutraceutically acceptable excipients may include liquid solutions such as a solution comprising a vegetable- and/or animal- and/or fish-derived oil.

The terms "molecule" and "compound" are used herein interchangeably.

DETAILED DESCRIPTION OF PARTICULAR ASPECTS OF THE INVENTION

A main aspect intended to be addressed by the present invention is to provide novel molecules extracted from seaweeds such as, for example: *Chaetomorpha Cannabina* (C.C.), *Cladophora sericea* (C.S.), *Polysiphonia ureceolata* (P.U.) and *Polysiphonia flexicaulis* (P.F.).

Particularly, these compounds are active in vitro against cancer cell lines and, therefor, may be active in vivo for treating cancer, alone or in combination with other anti-cancer agents.

Solvent Extraction

With the aim of providing an alternative source of anti-cancer molecules, there is provided anti-cancer molecules extracted from seaweeds such as: *Chaetomorpha cannabina* (CC), *Cladophora sericea* (C.S.), *Polysiphonia ureceolata* (P.U.) or *Polysiphonia flexicaulis* (P.F.).

Particularly, the molecule is extracted with an organic or inorganic solvent. More particularly, the extract's solvent is water or alcohol; and even more particularly: aqueous alcohol.

Particularly, the crude extract is an aqueous ethanol extract of CC, CS, PU and/or PF. More particularly, the crude extract is a: 80%, 75%, 70%, 65%, 60%, 55%, 50%, 45%, 40%, 35%, 30%, 25% aqueous ethanol extract. Even more particularly, the crude extract is an 80% aqueous ethanol extract. Most particularly, the crude extract is a previously hexane-defatted extract.

More particularly, the extract is a C-18 fraction of the crude extract: particularly a 5%, 10%, 15%, 20%, 25%, 30%, 25%, 40%, 45%, 50%, 55%, 60%, 65%, 70%, 75%, 80%, 85%, 90%, 95% aq. MeOH, or 100% MeOH, or $CH_2Cl_2$:MeOH (1:1) fraction. Most particularly, the extract is a flash column sub-fraction of the C-18 fraction. Particularly, the sub-fraction is a 100% $CH_2Cl_2$ sub-fraction; a 60% $CH_2Cl_2$: 40% MeOH:$CH_2Cl_2$ (1:1) sub-fraction; or a 100% MeOH:$CH_2Cl_2$ (1:1) sub-fraction.

Active Molecule from Extract

According to a first aspect, there is provided a compound selected from:

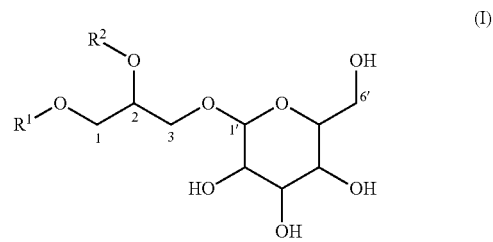

(I)

wherein $R^1$ and $R^2$ is each independently H or a fatty acid selected from the group consisting of:

| Cpd | $R^1$ | $R^2$ |
|-----|-------|-------|
| 1 | C20:5 | C16:4; |
| 2 | C20:5 | C16:0; |
| 3 | C20:5 | C14:0; |
| 4 | C16:1 | C18:2; |
| 5 | C16:0 | H; |
| 6 | C20:5 | C16:3; |
| 7 | C20:5 | C20:5; |
| 8 | C16:0 | C16:0; |
| 9 | C16:0 | C16:1; |
| 10 | C16:0 | C18:2; |
| 11 | C16:0 | C18:1; |
| 12 | C16:0 | C18:0; |
| 13 | C20:5 | H |
| 14 | C18:3 | C16:4; |
| 15 | C18:3 | C16:3; |
| 16 | C16:0 | C14:0; |
| 17 | C14:0 | H; and |
| 18 | C14:0 | C14:0. | and compounds:

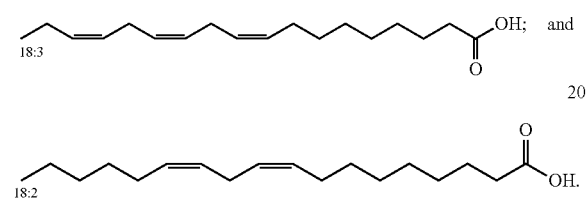

In accordance with a particular embodiment, the following compounds extracted from NC169 are selected:

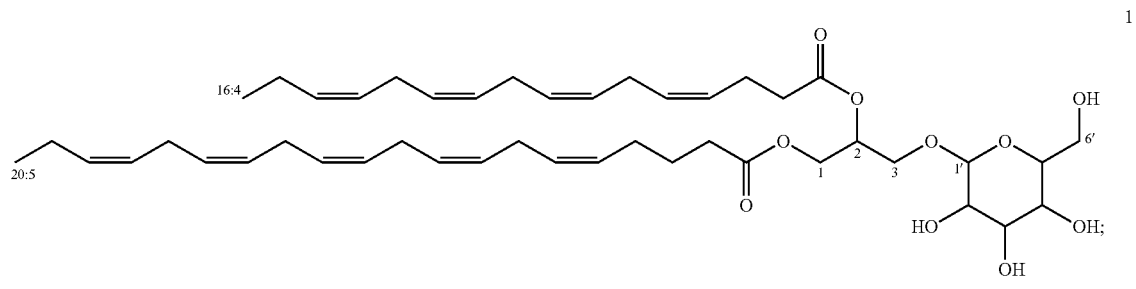
MGDG C20:5/C16:4
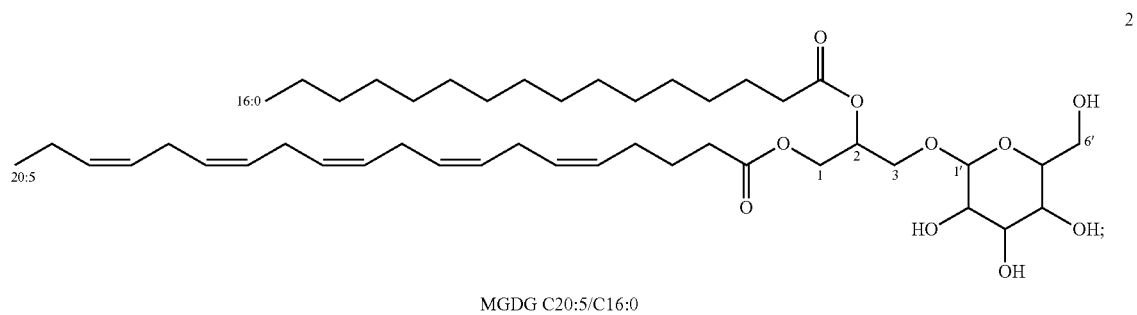
MGDG C20:5/C16:0
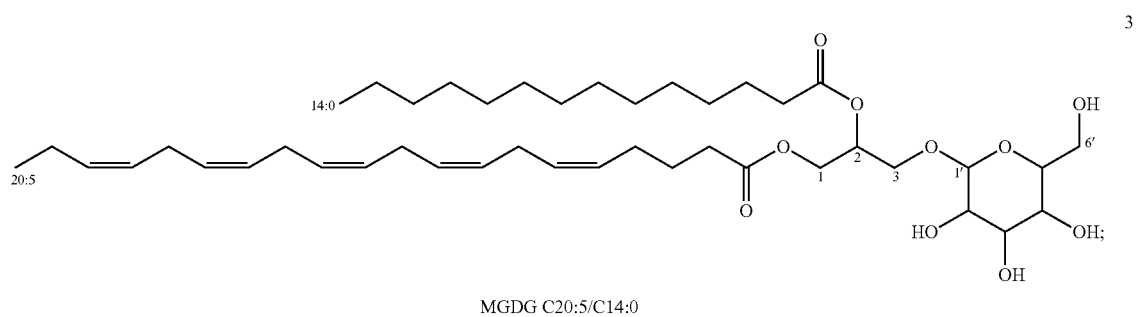
MGDG C20:5/C14:0
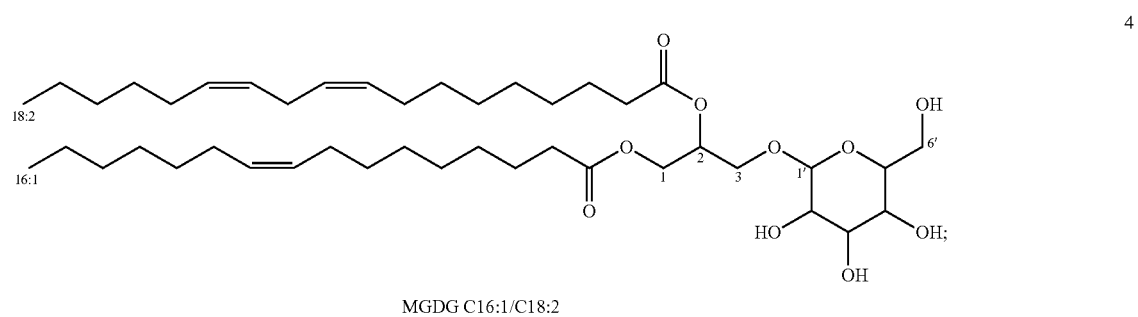
MGDG C16:1/C18:2
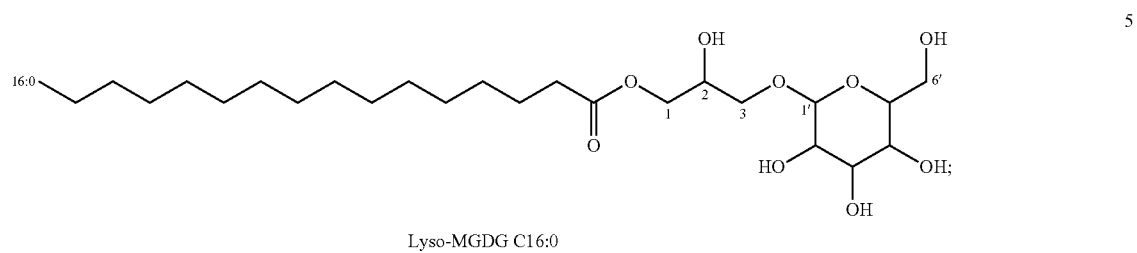
Lyso-MGDG C16:0

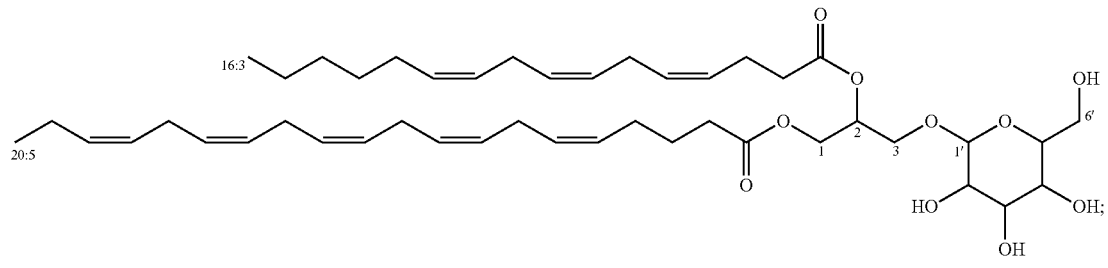
MGDG C20:5/C16:3
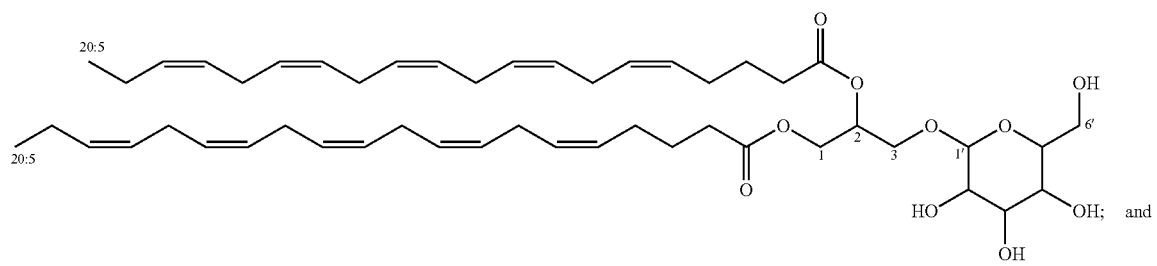
MGDG C20:5/C20:5
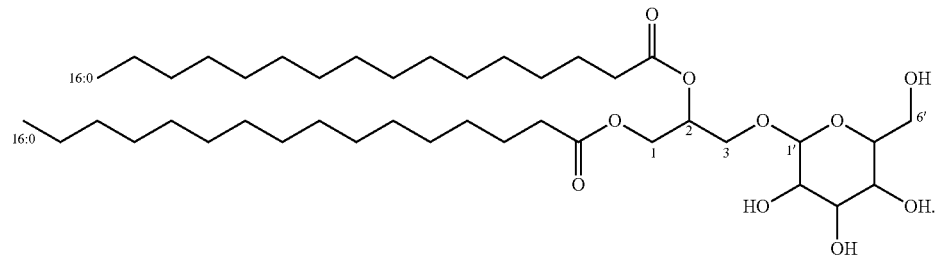
MGDG C16:0/C16:0
In accordance with a particular aspect of the present invention, the bioactive molecule is the compound having the structure no.2:
In accordance with a particular aspect of the present invention, the bioactive molecule is the compound having the structure no.5:
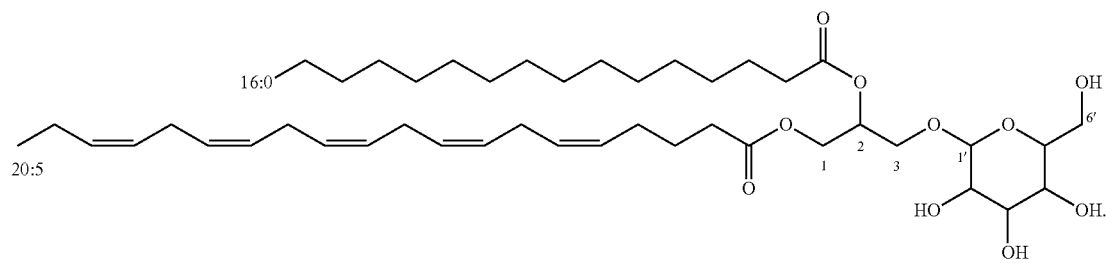

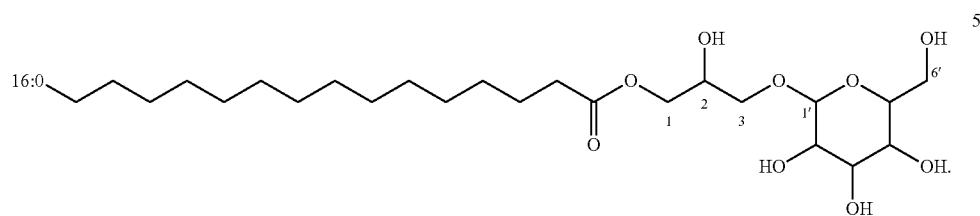
In accordance with a particular embodiment, the following compounds extracted from NC174 are selected:
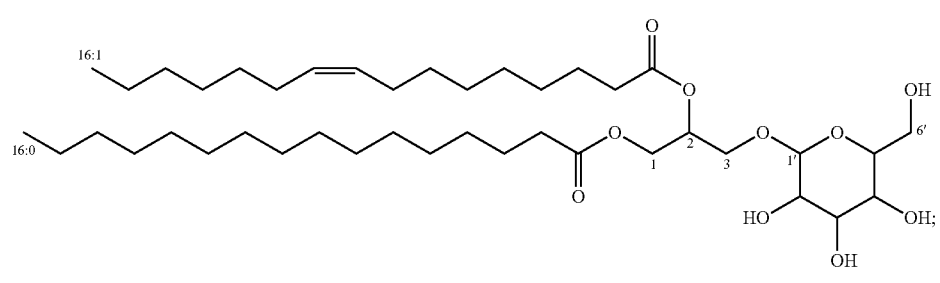
MGDG C16:0/C16:1
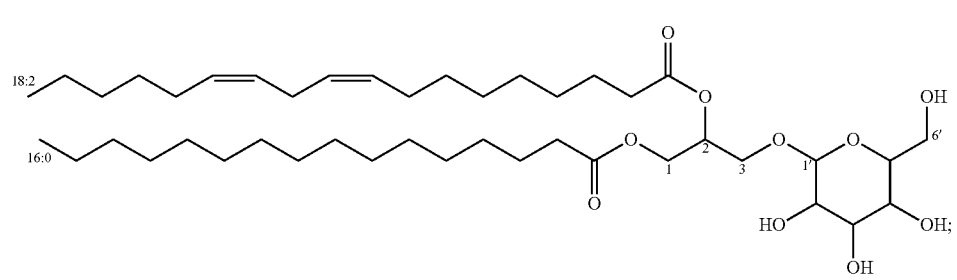
MGDG C16:0/C18:2
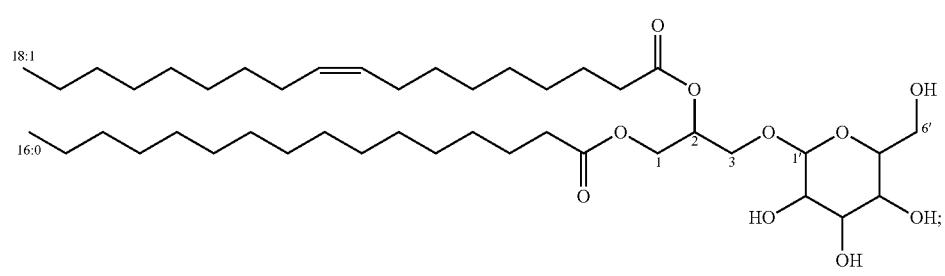
MGDG C16:0/C18:1
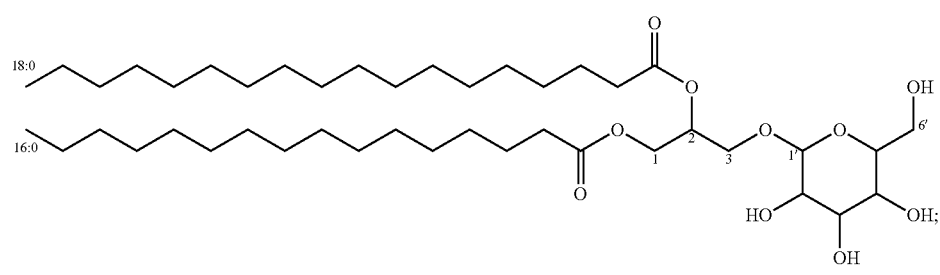
MGDG C16:0/C18:0

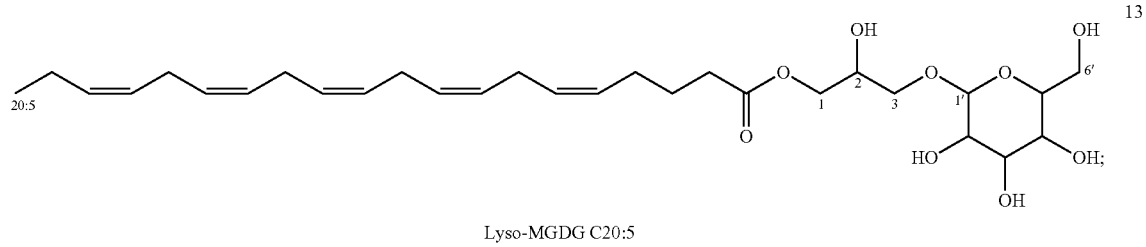
Lyso-MGDG C20:5
In accordance with a particular aspect of the present invention, the bioactive molecule is the compound having the structure no.13:
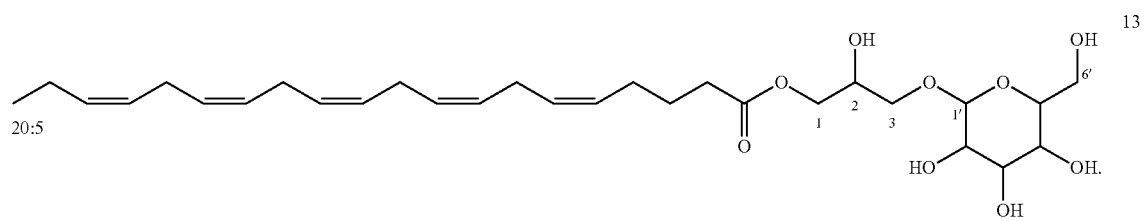 [SMILES: CC/C=C\C/C=C\C/C=C\C/C=C\C/C=C\CCCC(=O)OCC(O)COC1OC(CO)C(O)C(O)C1O]
According to a further aspect, there is provided a compound from NC175 having a structure selected from the group consisting of:
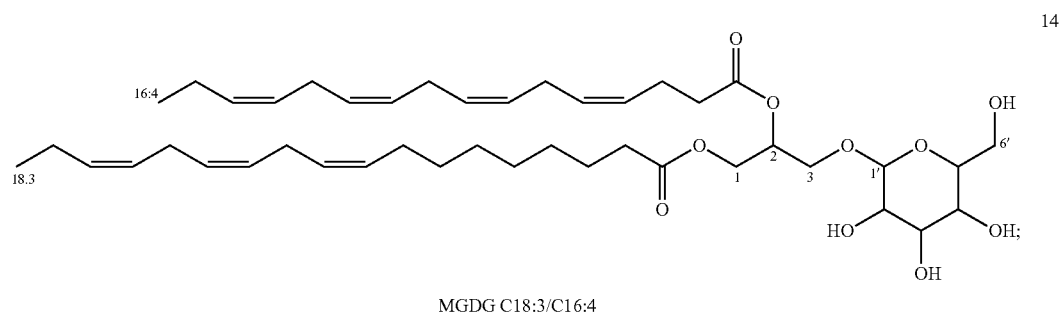
MGDG C18:3/C16:4
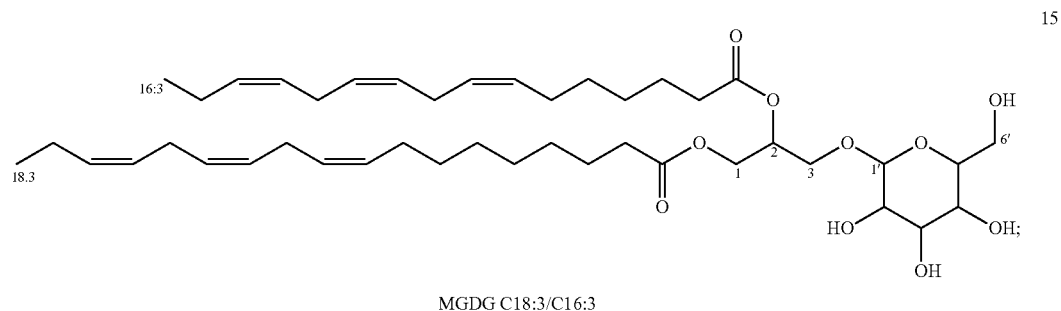
MGDG C18:3/C16:3

-continued
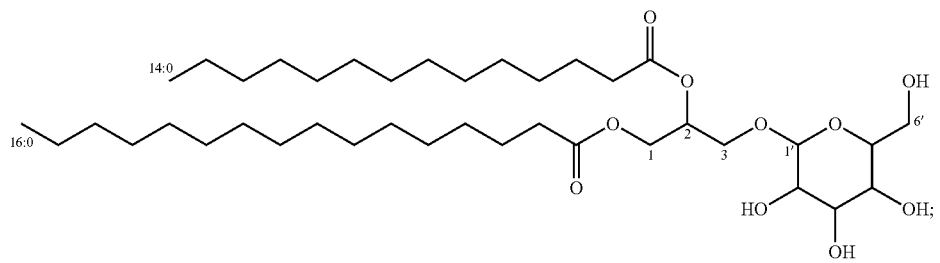
MGDG C16:0/C14:0
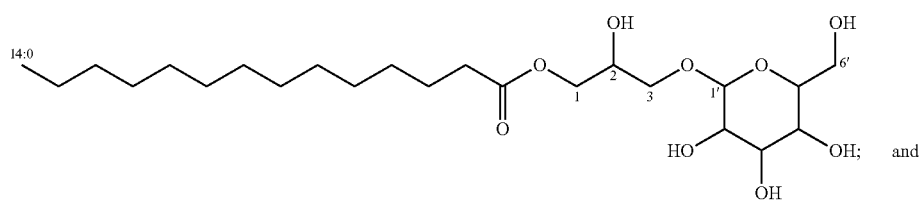
Lyso-MGDG C14:0
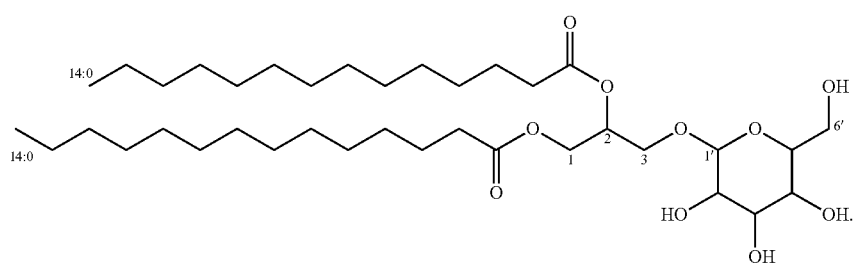
MGDG C14:0/C14:0
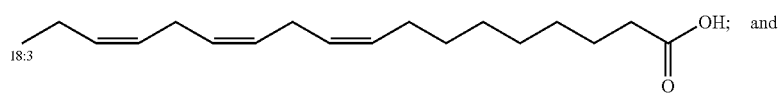
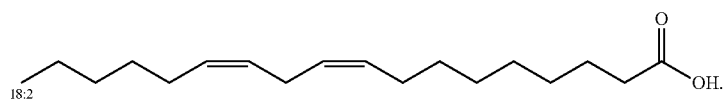
In accordance with a particular aspect of the present invention, the bioactive molecule is the compound having the structure no.14:
In accordance with a particular aspect of the present invention, the bioactive molecule is the compound having the structure no.16:
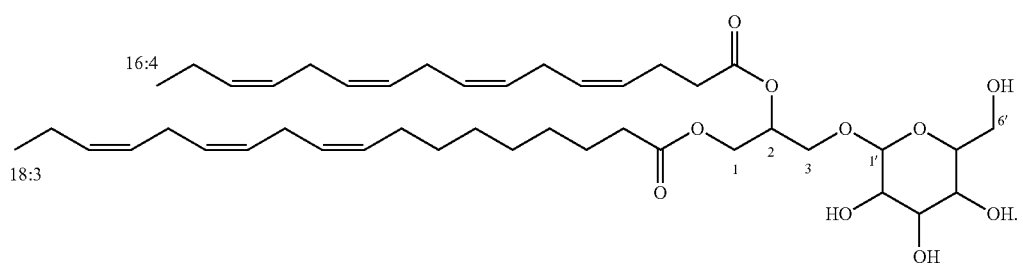

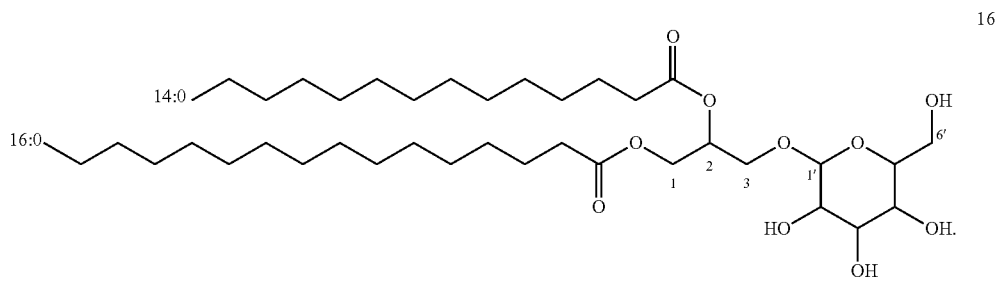 [SMILES: CCCCCCCCCCCCCCCC(=O)OCC(COC1OC(CO)C(O)C(O)C1O)OC(=O)CCCCCCCCCCCCC]
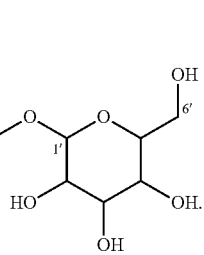

In accordance with a particular aspect of the present invention, the bioactive molecule is the compound having the structure:

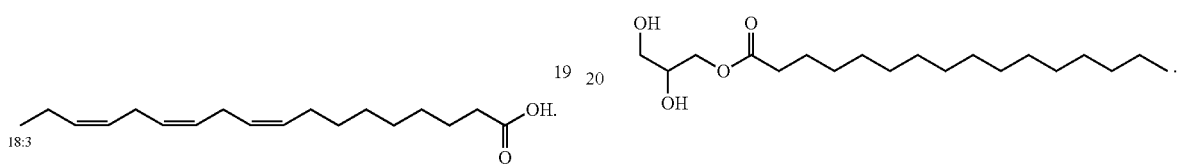

In accordance with a particular aspect of the present invention, the bioactive molecule is the compound having the structure:

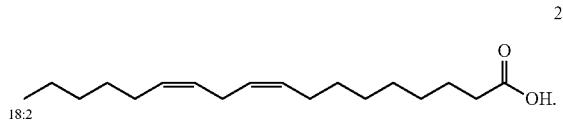

According to a further aspect, there is provided a compound from NC77 having a structure selected from the group consisting of:

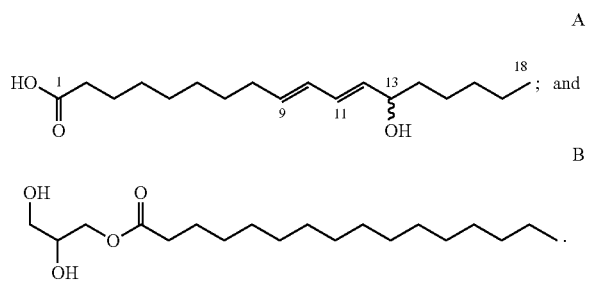

In accordance with a particular aspect of the present invention, the bioactive molecule is the compound having the structure:

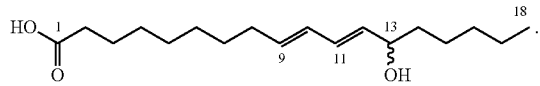

In accordance with a particular aspect of the present invention, the bioactive molecule is the compound having the structure:

B(38-41-1)

In accordance with a particular aspect of the present invention, the bioactive molecule from the above listed seaweeds is found in a 100% MeOH fraction and defined as having the following characteristics: NMR peaks at $CH_3$ signals at δ 0.8-0.9 ppm; olefinic protons (5.36 ppm); glycerol protons (3.5-4.2 ppm); major proton peaks at 1.5-3.0 ppm and 1.3 ppm; signals of anomeric proton and carbon at 4.2 and 105.8 ppm respectively.

Composition

In accordance with a particular aspect of the invention, there is provided a composition comprising at least one compound as defined herein, in admixture with a physiologically acceptable excipient.

Uses and Methods of Use

In accordance with an alternative aspect, the present invention provides the use of the compound as defined herein for inhibiting growth of cancer cells. Particularly, there is provided the use of the extract as defined herein for the manufacture of composition for treating cancer in a mammal.

In accordance with an alternative aspect of the invention, there is provided the use of the composition as defined herein for the treatment of cancer in a mammal.

In accordance with a particular aspect, the present invention provides a method of inhibiting a cancer cell growth comprising contacting said cell with a growth-inhibiting concentration of the compound as defined herein or the composition as defined herein.

More particularly, there is provided a method of treatment of cancer in a mammal comprising administering a growth-inhibiting concentration of the composition as defined herein to said mammal. Most particularly, the mammal is a pet animal or a human.

According to a further aspect, there is provided a use of compounds C or D for use in the treatment of cancer, wherein said compounds have a structure of formula:

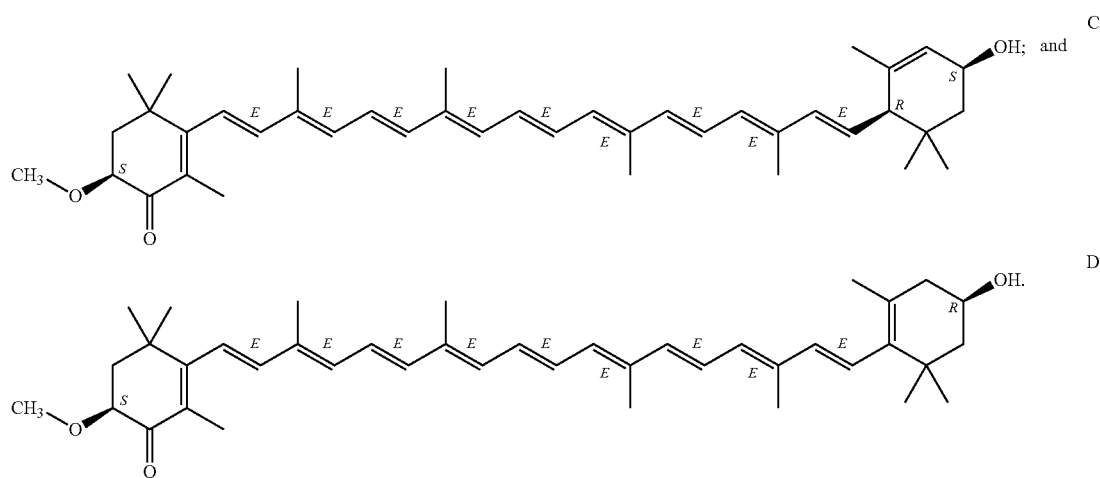

Method of Extraction and Isolation

According to a further aspect, the present invention provides a method for obtaining a compound as defined herein comprising the steps of:
- a) mixing material from said seaweed with a solvent to obtain a solvent mixture, wherein said seaweed is selected from the group consisting of: *Chaetomorpha Cannabina* (C.C.) or *Cladophora sericea* (C.S.), *Polysiphonia ureceolata* (P.U.) and *Polysiphonia flexicaulis* (P.F.);
- b) separating a solid fraction and a liquid fraction from said mixture, said liquid fraction forming an extract from said seaweed material; and
- c) fractionating the extract from step b) on a C-18 column with a solvent selected from the group consisting of: from 5% aq. MeOH to 100% MeOH, and 50% MeOH: $CH_2Cl_2$ and selecting the 100% MeOH fraction and/or the 50% MeOH:$CH_2Cl_2$ fraction.

Particularly, the solvent is organic or inorganic; more particularly: water or alcohol; and most particularly: aqueous ethanol. Still, most particularly, the solvent is 80% aqueous ethanol.

In accordance with an alternative aspect, the method of the invention further comprises a hexane-defatting step prior to step a).

In accordance with a particular aspect, the method further comprises the step of:
- d) sub-fractionating said fraction from step c) on flash HILIC column with a solvent gradient from 90% acetone to 40% acetone in water.

Alternatively, the method further comprises a step of drying the liquid fraction to obtain a dried fraction.

Particularly, the present compounds can be further purified by HPLC, NMR, or other well known methods etc. as shown in the present application.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES—Anti-Cancer Activity of Compounds Purified from Marine Seaweeds Harvested from Newfoundland and Labrador Example 1—Seaweed Collection and Identification A collection program for seaweeds was established for different geographical regions on Fortune Bay and the west coast of Newfoundland and Labrador over 2 time periods—July and September.

The general collection procedure was as follows: seaweeds were collected from the intertidal zone by hand with knives while scuba divers collected seaweed from sub tidal zones. Samples were placed in plastic sampling bags and transported to the laboratory in coolers of seawater. Upon arrival in the laboratory, each species was washed individually to remove epiphytic and extraneous matter (sand, mussels, isopods, etc.). Samples were then checked visually to ensure they were clean. If not, remaining matter was removed by hand with further washing. Seaweeds were blotted dry, weighed to the nearest g (plant wet weight) and shredded. The shredded material was transferred into Erlenmeyer flasks and frozen at −60° C. until the extracts were prepared.

A representative sample of different species were also photographed (see FIGS. 1A-D) and frozen at −20° C. for confirmation of species by Dr. Robert Hooper, a phycologist at Memorial University of Newfoundland.

Example 2. Extract Preparation 2.1 Freeze-Drying

To prepare samples for extraction the seaweed was first freeze dried. Erlenmeyer flasks containing shredded seaweeds, which had been frozen at −60° C., were placed on a freeze-dryer, and lyophilized for 72-96 h at $69\times10^{-3}$ mbar. The weight (g) of dry material was then recorded as plant dry weight (g). This step accounts for the differences in water content among seaweeds which may otherwise affect the solubility of bioactive components. Secondary plant metabolites are also more stable when stored in a dried form.

Moreover, the large-scale extraction of dried plant material may cause fewer problems than extracting fresh material. In order to preserve thermo-labile compounds, low temperature conditions are used throughout the process of extraction.

2.2 Defatting of Samples

The lipid fraction of seaweed is known to vary from 1 to 5% of the algal dry matter, which can be dominated by polyunsaturated fatty acids. Brown and red seaweeds are particularly rich in long chain polyunsaturated fatty acids such as eicosapentaenoic acid (n3, C20:5), while green seaweeds may possess a level of alpha linoleic acid (n3, C18:3). Since these polyunsaturated fatty acids are extremely susceptible to oxidation, they may result in lipid oxidation products during analysis. In order to eliminate the above oxidative processes that may have an effect on the results, samples were defatted prior to extraction of compounds.

Freeze dried seaweed samples were ground into a powder and defatted by blending the powder with hexane (1:5, w/v, 5 min) in a Waring blender at ambient temperature. Defatted samples were air-dried, vacuum packed in polyethylene pouches and kept at −20° C. until extraction.

2.3 Extraction of Crude Compounds

Different solvents or solvent systems can be used for the extraction of compounds. In general, ethanol is commonly used due to its lower toxicity compared to other solvents. Moreover, ethanol extracts have been demonstrated in many studies to have the highest antioxidant activity.

Compounds were extracted into 80% aqueous ethanol at 4° C. for 24 h. The solvent was then removed under a vacuum at 37° C. for 45 to 60 min and the resulting concentrated slurries were lyophilized for 72 to 96 h at −80° C. and $69 \times 10^{-3}$ mbar using a freeze dryer. Dry extracts were weighed (Extract dry weight in g) and stored at −60° C. until preparation for screening.

Extraction yields were calculated and expressed as g of dry extract per g of dry seaweed.

Example 3. Anti-Cancer Screening of Seaweed Crude Extract 3.1 Purification Through Bioassay-Guided Fractionation Initially, seaweed extracts were evaluated for their anti-cancer activity in in-vitro models via the CIMA assay. From these results, extracts exhibiting the greatest anti-cancer potential were selected for purification via bioassay-guided fractionation.

3.2 Compound Preparation

Stock solutions of the extracts were prepared in dimethylsulfoxide (DMSO) at 10 mg/mL and stored in 200 µl aliquots at −20° C. until analysis. This preparation ensured that the DMSO delivered to cells in culture never exceeded 1%.

3.3 CIMA Assay

Prepared extracts were assessed following chronic exposure conditions in which cells were seeded at $2 \times 10^3$ cells/well (96 well-plate) and incubated with test compounds for 72 h. Each compound was evaluated over a range of concentrations (0, 10, 25, 50 or 100 µg/ml). Cell proliferation was initially assessed using a standard colorimetric indicator of metabolic activity (CIMA) assay. In this assay, tetrazole reduction was evaluated as a measure of metabolic function that evaluates mitochondrial activity to determine the extent of cell proliferation within a culture. This assay is based on the reduction of yellow tetrazolium salt to purple formazan by mitochondrial reductases enzyme in viable cells, resulting in a color changed that confers a change in absorbance. Six human cell lines were selected for primary evaluation: U373 (glioblastoma-astrocytoma), A549 (lung carcinoma), THP-1 (acute monocytic leukemia), MCF7 (mammary gland adenocarcinoma), SKOV3 (ovarian adenocarcinoma), and CCD1079SK (fibroblast, noncancerous but proliferating) (see FIG. 2 and Table 2). From these results, lead extracts were selected for additional fractionation and evaluated in the same manner.

TABLE 1

Extraction Yields

| Species (specimen #) | Seaweed | Date Collected | Location | Extract dry weight (g) | Yield (g of dry extract/g of dry plant) |
|---|---|---|---|---|---|
| *Chaetomorpha cannabina* (extract #1 or NC77) | Green | Jul. 22$^{nd}$, 2013 | Rocky Harbour, NL | 4.88 g | 8.00% |
| *Cladophora sericea* (extract #3 or NC130) | Green | Sep. 6$^{th}$, 2014 | Pinware, NL | 1.1 g | 4.23% |
| *Cladophora sericea* (NC175) | Green | Sep. 26$^{th}$, 2015 | Pinware, NL | 2.69 g | 3.64% |
| *Polysiphonia ureceolata* (extract #4 or NC133) | Red | Sep. 9$^{th}$, 2014 | Rocky Harbour, NL | 0.9 g | 1.88% |
| *Polysiphonia ureceolata* (NC174) | Red | Sep. 27$^{th}$ & 28$^{th}$, 2015 | Rocky Harbour, NL | 8.04 g | 3.54% |
| *Polysiphonia flexicaulis* (extract #5 or NC 169) | Red | Aug. 21$^{st}$, 2014 | Mutton Bay, Quebec | 0.16 g | 1.6% |

TABLE 2

| Cell line | (ug/ml) | NC77 1 AVG | SD | NC130 3 AVG | SD | NC133 4 AVG | SD | NC169 5 AVG | SD |
|---|---|---|---|---|---|---|---|---|---|
| A549 | 100 | 67.5 | 1.6 | 62.8 | 5.4 | 62.4 | 0.8 | 36.9 | 4.3 |
|  | 50 | 77.1 | 2.4 | 89.9 | 4.5 | 79.6 | 3.6 | 72.0 | 4.9 |
|  | 25 | 78.8 | 3.1 | 95.3 | 4.3 | 95.2 | 4.9 | 93.8 | 4.4 |
|  | 10 | 81.7 | 2.7 | 96.9 | 2.8 | 100.9 | 2.9 | 96.5 | 4.2 |
|  | 1 | 94.6 | 4.6 | 101.4 | 3.1 | 100.1 | 2.9 | 101.0 | 5.6 |
|  | 0 | 100.0 | 0.0 | 100.0 | 0.0 | 100.0 | 0.0 | 100.0 | 0.0 |
|  | DMSO 1% | 92.5 | 3.1 | 92.5 | 3.1 | 92.5 | 3.1 | 92.5 | 3.1 |
|  | SDS 5% | 68.7 | 6.6 | 68.7 | 6.6 | 68.7 | 6.6 | 68.7 | 6.6 |
| PC3 | 100 | 82.5 | 2.2 | 94.8 | 7.8 | 72.1 | 7.0 | 60.7 | 1.1 |
|  | 50 | 77.2 | 4.0 | 106.6 | 8.4 | 96.8 | 7.7 | 102.4 | 20.8 |
|  | 25 | 86.4 | 3.4 | 116.0 | 13.0 | 108.8 | 8.2 | 95.9 | 10.7 |
|  | 10 | 91.7 | 2.0 | 114.6 | 8.4 | 124.0 | 38.4 | 97.5 | 11.6 |
|  | 1 | 98.2 | 1.3 | 99.8 | 9.2 | 104.4 | 13.3 | 104.0 | 8.5 |
|  | 0 | 100.0 | 0.0 | 100.0 | 0.0 | 100.0 | 0.0 | 100.0 | 0.0 |
|  | DMSO 1% | 87.0 | 4.0 | 87.0 | 4.0 | 87.0 | 4.0 | 87.0 | 4.0 |
|  | SDS 5% | 77.3 | 13.3 | 77.3 | 13.3 | 77.3 | 13.3 | 77.3 | 13.3 |
| MCF7 | 100 | 45.6 | 1.0 | 37.9 | 4.8 | 34.0 | 3.9 | 40.1 | 0.7 |
|  | 50 | 60.3 | 2.6 | 48.7 | 3.1 | 43.6 | 3.9 | 50.7 | 1.7 |
|  | 25 | 72.7 | 3.6 | 77.5 | 6.7 | 56.7 | 3.6 | 84.6 | 3.5 |
|  | 10 | 78.7 | 3.9 | 92.9 | 4.3 | 81.4 | 1.8 | 95.9 | 3.8 |
|  | 1 | 101.8 | 12.8 | 98.8 | 8.0 | 93.5 | 4.2 | 103.8 | 2.9 |
|  | 0 | 100.0 | 0.0 | 100.0 | 0.0 | 100.0 | 0.0 | 100.0 | 0.0 |
|  | DMSO 1% | 94.7 | 6.2 | 94.7 | 6.2 | 94.7 | 6.2 | 94.7 | 6.2 |
|  | SDS 5% | 44.1 | 8.0 | 44.1 | 8.0 | 44.1 | 8.0 | 44.1 | 8.0 |
| SKOV3 | 100 | 50.9 | 4.6 | 48.3 | 1.2 | 42.7 | 1.6 | 40.8 | 1.7 |
|  | 50 | 72.3 | 3.7 | 67.5 | 3.4 | 53.9 | 1.7 | 64.6 | 4.6 |
|  | 25 | 79.8 | 4.8 | 86.2 | 4.7 | 60.8 | 2.9 | 83.1 | 4.8 |
|  | 10 | 84.7 | 4.0 | 90.8 | 5.3 | 71.7 | 3.4 | 87.8 | 3.6 |
|  | 1 | 95.5 | 5.7 | 90.0 | 2.7 | 95.0 | 2.3 | 98.0 | 10.2 |
|  | 0 | 100.0 | 0.0 | 100.0 | 0.0 | 100.0 | 0.0 | 100.0 | 0.0 |
|  | DMSO 1% | 95.3 | 7.5 | 95.3 | 7.5 | 95.3 | 7.5 | 95.3 | 7.5 |
|  | SDS 5% | 78.9 | 3.9 | 78.9 | 20.0 | 78.9 | 20.0 | 78.9 | 20.0 |
| U373 | 100 | 48.4 | 2.0 | 43.1 | 1.7 | 33.4 | 2.0 | 24.4 | 0.6 |
|  | 50 | 55.7 | 3.0 | 73.0 | 2.7 | 66.7 | 4.0 | 41.4 | 1.7 |
|  | 25 | 57.0 | 2.8 | 79.0 | 3.4 | 71.9 | 2.4 | 66.8 | 2.1 |
|  | 10 | 61.8 | 4.6 | 89.2 | 4.6 | 81.1 | 2.3 | 75.5 | 2.7 |
|  | 1 | 94.6 | 2.7 | 86.6 | 3.1 | 97.6 | 1.9 | 97.8 | 4.3 |
|  | 0 | 100.0 | 0.0 | 100.0 | 0.0 | 100.0 | 0.0 | 100.0 | 0.0 |
|  | DMSO 1% | 83.4 | 7.7 | 83.4 | 7.7 | 83.4 | 7.7 | 83.4 | 7.7 |
|  | SDS 5% | 48.4 | 6.4 | 48.4 | 6.4 | 48.4 | 6.4 | 48.4 | 6.4 |
| THP-1 | 100 | 40.8 | 1.2 | 35.3 | 4.0 | 42.4 | 4.9 | 21.3 | 2.0 |
|  | 50 | 52.2 | 1.7 | 56.0 | 1.1 | 60.2 | 6.6 | 41.9 | 4.2 |
|  | 25 | 67.9 | 4.4 | 54.9 | 1.4 | 66.5 | 3.8 | 51.3 | 4.6 |
|  | 10 | 88.2 | 3.7 | 65.4 | 4.7 | 81.9 | 1.9 | 58.2 | 6.4 |
|  | 1 | 99.4 | 7.2 | 92.7 | 7.8 | 94.6 | 3.0 | 85.7 | 9.2 |
|  | 0 | 100.0 | 0.0 | 100.0 | 0.0 | 100.0 | 0.0 | 100.0 | 0.0 |
|  | DMSO 1% | 89.2 | 3.6 | 89.2 | 3.6 | 89.2 | 3.6 | 89.2 | 3.6 |
|  | SDS 5% | 20.3 | 4.0 | 20.3 | 4.0 | 20.3 | 4.0 | 20.3 | 4.0 |
| CCD1079SK | 100 | 60.3 | 4.6 | 62.7 | 3.5 | 64.1 | 1.0 | 53.4 | 5.1 |
|  | 50 | 65.5 | 4.5 | 71.2 | 2.7 | 72.2 | 1.7 | 59.7 | 4.7 |
|  | 25 | 67.3 | 3.6 | 77.1 | 6.5 | 75.9 | 0.9 | 66.1 | 4.6 |
|  | 10 | 82.8 | 7.6 | 89.3 | 6.4 | 88.3 | 3.1 | 75.5 | 4.9 |
|  | 1 | 100.3 | 10.3 | 92.2 | 5.6 | 96.9 | 4.2 | 94.0 | 0.8 |
|  | 0 | 100.0 | 0.0 | 100.0 | 0.0 | 100.0 | 0.0 | 100.0 | 0.0 |
|  | DMSO 1% | 91.3 | 7.8 | 91.3 | 7.8 | 91.3 | 7.8 | 91.3 | 7.8 |
|  | SDS 5% | 9.4 | 0.9 | 9.4 | 0.9 | 9.4 | 0.9 | 9.4 | 0.9 |

3.4 Fractionation

Lead crude extracts were fractionated into five fractions by C-18 SPE column separation using 15 ml each of 5% methanol (fraction 1), 25% methanol (fraction 2), 50% methanol (fraction 3), 100% methanol (fraction 4) and dichloromethane (1:1) (fraction 5). Extracts were fractionated and the resulting fractions were evaluated using CIMA assay. Bio-assay guided fractionation provided detailed information regarding the compound(s) responsible for specific bioactivity.

Figure 3:
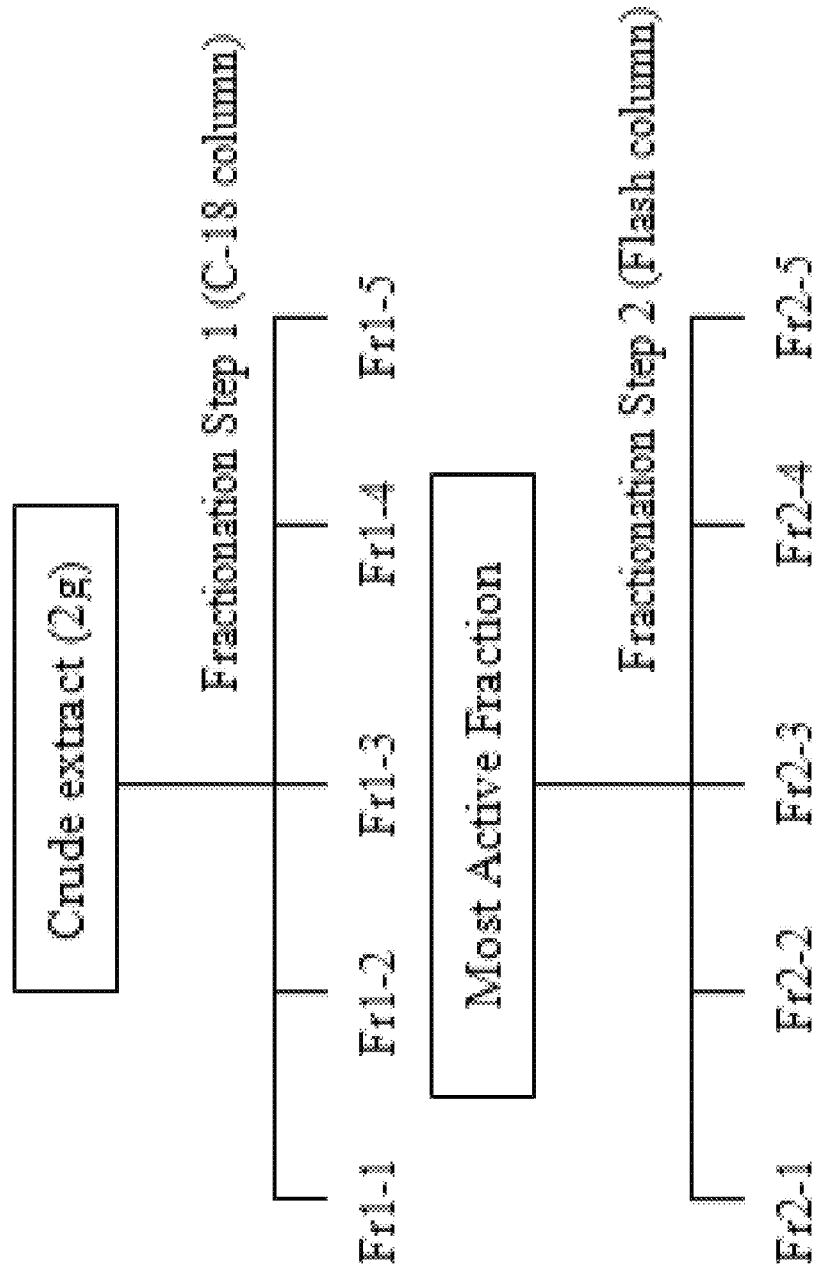
FIG. 3. Fractionation strategy for crude extracts.
Figure 4:
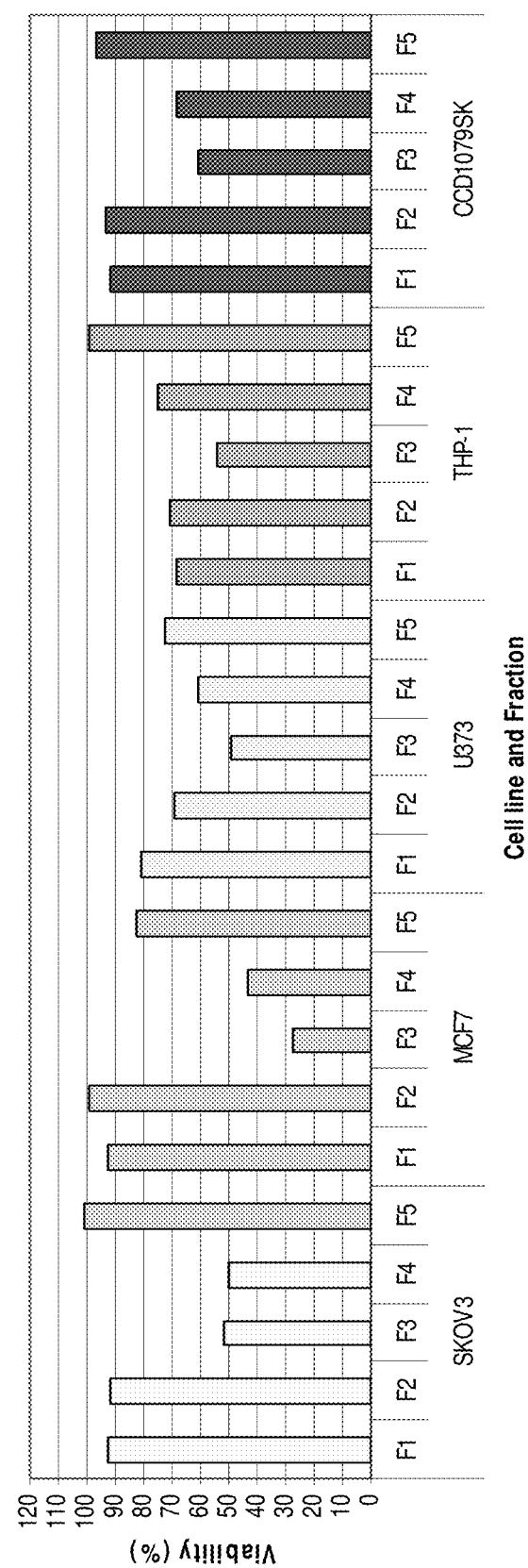
FIG. 4. In vitro activity of fractions (F1-F5) from crude extract #1 (NC77) on viability of five cancer cell lines.
Figure 5:
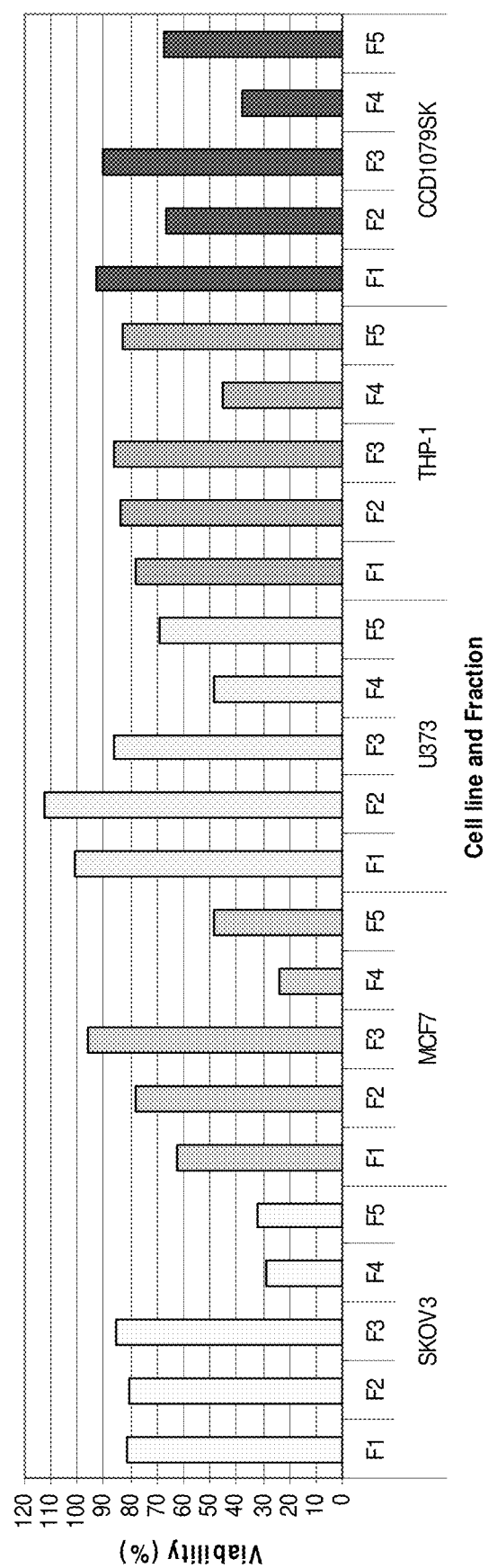
FIG. 5. In vitro activity of fractions (F1-F5) from crude extract #3 (NC130) on viability of five cancer cell lines.
Figure 6:
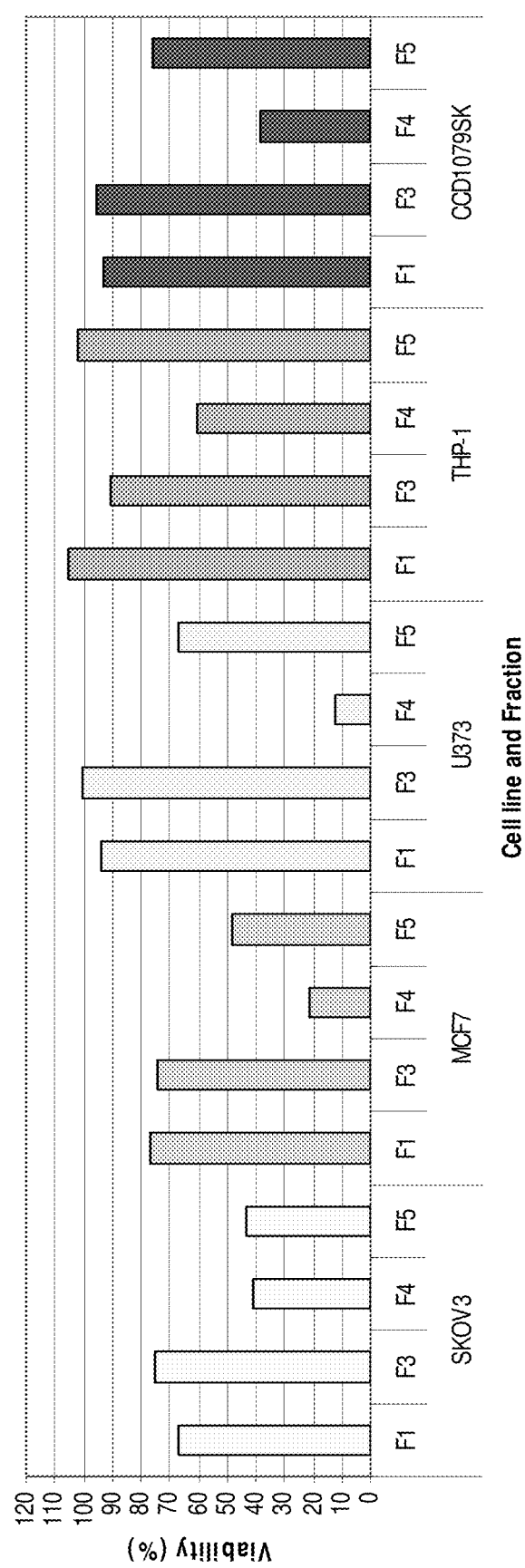
FIG. 6. In vitro activity of fractions (F1-F5) from crude extract #4 (NC133) on viability of five cancer cell lines.
Figure 7:
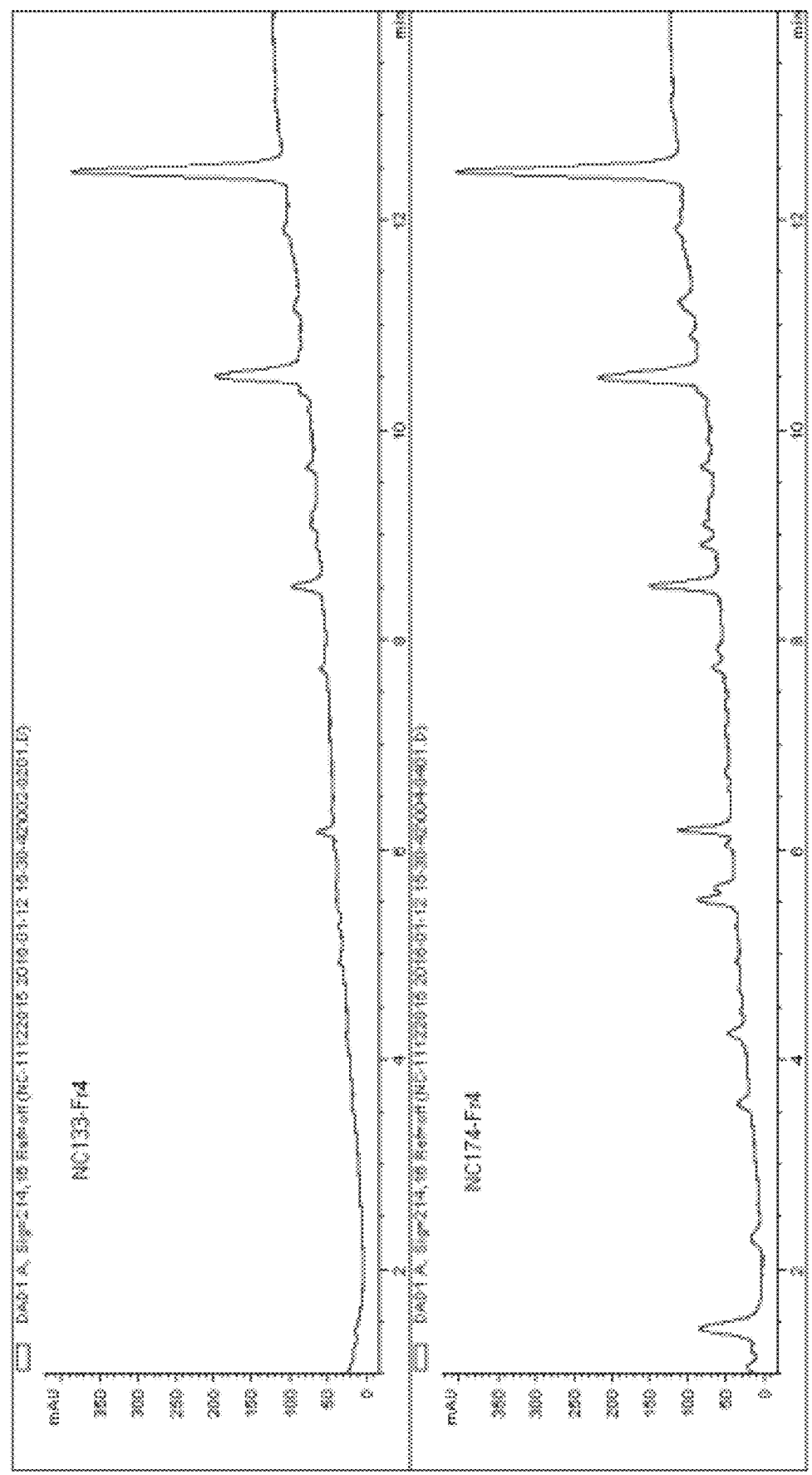
FIG. 7. HPLC comparison of two batches of NC133-Fr4 (June 2015 batch) and NC174-Fr4 (December 2015 batch).

The following amounts summarized in Table 3 were obtained from the strategy described in FIG. 3.

TABLE 3

| Sample (g) | | | | | |
|---|---|---|---|---|---|
| NC77 | | NC130 | | NC133 | |
| Extract 1 | 2.04 | Extract 3 | 0.569 | Extract 4 | 0.795 |
| F1 | 1.439 | F1 | 0.038 | F1 | 0.421 |
| F2 | 0.156 | F2 | 0.007 | F2 | — |
| F3 | 0.076 | F3 | 0.023 | F3 | 0.031 |
| F4 | 0.212 | F4 | 0.294 | F4 | 0.156 |
| F5 | 0.191 | F5 | 0.176 | F5 | 0.069 |

3.4.1 Fraction Results

As shown in FIGS. 4-8, activity was observed over most of the fractions but it was predominant in fractions 4 and 5. The fractionation results clearly indicated that anti-cancer activity was distributed in F4 and F5 of each of the lead extracts and priority selection was as follows: extract #1 (fraction 1-4), extract #3 (fraction 3-5) and extract #4 (fraction 4-4).

We have successfully isolated the fractions present in the lead extracts possibly responsible for its anti-cancer activity and tested its cytotoxic/anticancer potential. The results showed that the anti-cancer activity rests in fractions 4 and 5 in all lead extracts.

Table 4 shows results of anti-cancer screening on fractions F1-F5 from crude extract #1 (NC77), crude extract #3 (NC130), and crude extract #4 (NC133)

TABLE 4

Fractionation screening results - subfractionation identification

| | | NC77 1 | | | | | | | | | |
|---|---|---|---|---|---|---|---|---|---|---|---|
| | | F1 | | F2 | | F3 | | F4 | | F5 | |
| Cell line | (ug/ml) | AVG | SD | AVG | SD | AVG | SD | AVG | SD | AVG | SD |
| SKOV3 | 100 | 92.4 | 8.9 | 91.4 | 2.3 | 51.3 | 7.0 | 50.1* | 5.8 | 100.8 | 10.8 |
| | 50 | 104.2 | 12.5 | 92.6 | 3.5 | 77.0 | 11.0 | 53.8# | 3.4 | 96.3 | 4.3 |
| | 25 | 100.0 | 6.3 | 94.0 | 0.6 | 87.5 | 9.7 | 60.7* | 6.2 | 95.1 | 12.1 |
| | 10 | 101.0 | 11.1 | 99.5 | 3.9 | 91.4 | 10.9 | 68.3* | 4.7 | 93.9 | 12.9 |
| | 1 | 103.6 | 8.2 | 102.3 | 5.3 | 100.9 | 12.3 | 95.0 | 2.5 | 108.4 | 9.9 |
| | 0 | 100.0 | 0.0 | 100.0 | 0.0 | 100.0 | 0.0 | 100.0 | 0.0 | 100.0 | 0.0 |
| | DMSO 1% | 88.6 | 3.7 | 88.6 | 3.7 | 88.6 | 3.7 | 88.6 | 3.7 | 88.6 | 3.7 |
| | SDS 5% | 56.5 | 5.4 | 56.5 | 5.4 | 56.5 | 5.4 | 56.5 | 5.4 | 56.5 | 5.4 |
| MCF7 | 100 | 92.6 | 11.2 | 98.8 | 4.4 | 27.8 | 2.5 | 43.2# | 5.4 | 82.3 | 2.5 |
| | 50 | 98.4 | 4.9 | 99.4 | 7.3 | 52.5 | 6.2 | 50.3* | 3.0 | 91.1 | 2.9 |
| | 25 | 105.8 | 6.4 | 100.0 | 2.8 | 92.9 | 8.2 | 73.3* | 7.9 | 96.7 | 7.5 |
| | 10 | 103.4 | 2.2 | 106.8 | 5.4 | 101.1 | 4.2 | 80.4 | 15.2 | 96.0 | 3.7 |
| | 1 | 103.3 | 6.4 | 101.1 | 3.6 | 105.7 | 4.7 | 97.1 | 11.3 | 98.9 | 2.9 |
| | 0 | 100.0 | 0.0 | 100.0 | 0.0 | 100.0 | 0.0 | 100.0 | 0.0 | 100.0 | 0.0 |
| | DMSO 1% | 92.1 | 5.9 | 92.1 | 5.9 | 92.1 | 5.9 | 92.1 | 5.9 | 92.1 | 5.9 |
| | SDS 5% | 49.9 | 5.6 | 49.9 | 5.6 | 49.9 | 5.6 | 49.9 | 5.6 | 49.9 | 5.6 |
| U373 | 100 | 81.1 | 3.6 | 69.0 | 6.3 | 49.2 | 3.1 | 60.7 | 4.2 | 72.2 | 1.9 |
| | 50 | 85.3 | 8.4 | 82.3 | 5.9 | 83.0 | 5.8 | 87.2 | 5.4 | 84.4 | 3.1 |
| | 25 | 85.4 | 9.2 | 92.1 | 7.9 | 102.6 | 9.2 | 93.4 | 6.9 | 90.3 | 2.0 |
| | 10 | 103.9 | 6.3 | 103.2 | 10.1 | 102.2 | 8.1 | 93.6 | 7.0 | 106.0 | 2.6 |
| | 1 | 103.1 | 12.3 | 101.6 | 8.2 | 97.8 | 6.2 | 103.2 | 14.9 | 117.7 | 7.4 |
| | 0 | 100.0 | 0.0 | 100.0 | 0.0 | 100.0 | 0.0 | 100.0 | 0.0 | 100.0 | 0.0 |
| | DMSO 1% | 94.7 | 6.2 | 94.7 | 6.2 | 94.7 | 6.2 | 94.7 | 6.2 | 94.7 | 6.2 |
| | SDS 5% | 44.1 | 8.0 | 44.1 | 8.0 | 44.1 | 8.0 | 44.1 | 8.0 | 44.1 | 8.0 |
| THP-1 | 100 | 68.1 | 0.9 | 70.8 | 4.1 | 54.3 | 1.7 | 74.9 | 3.7 | 98.8 | 9.5 |
| | 50 | 79.5 | 3.2 | 78.2 | 8.4 | 75.5 | 4.1 | 78.8 | 4.1 | 99.1 | 10.9 |
| | 25 | 74.5 | 3.1 | 80.0 | 4.9 | 75.6 | 5.0 | 79.1 | 5.8 | 92.4 | 8.6 |
| | 10 | 75.9 | 3.7 | 78.9 | 5.1 | 75.0 | 3.1 | 81.3 | 3.2 | 93.2 | 7.5 |
| | 1 | 75.7 | 1.8 | 80.4 | 3.5 | 82.7 | 5.9 | 87.0 | 7.8 | 93.9 | 5.6 |
| | 0 | 100.0 | 0.0 | 100.0 | 0.0 | 100.0 | 0.0 | 100.0 | 0.0 | 100.0 | 0.0 |
| | DMSO 1% | 103.3 | 6.2 | 103.3 | 6.2 | 103.3 | 6.2 | 103.3 | 6.2 | 103.3 | 6.2 |
| | SDS 5% | 36.2 | 4.6 | 36.2 | 4.6 | 36.2 | 4.6 | 36.2 | 4.6 | 36.2 | 4.6 |
| CCD10795K | 100 | 91.9 | 4.5 | 93.3 | 8.8 | 60.6 | 8.4 | 68.1 | 6.7 | 96.6 | 4.1 |
| | 50 | 102.4 | 8.2 | 103.0 | 12.1 | 85.6 | 8.6 | 76.8 | 6.0 | 100.1 | 4.5 |
| | 25 | 99.3 | 1.5 | 101.8 | 11.5 | 85.8 | 13.8 | 81.2 | 3.4 | 98.8 | 6.2 |
| | 10 | 100.7 | 5.1 | 99.5 | 13.5 | 93.8 | 8.1 | 84.0 | 1.5 | 96.9 | 5.1 |
| | 1 | 102.7 | 4.4 | 98.3 | 9.8 | 97.3 | 10.9 | 89.2 | 4.7 | 98.5 | 1.9 |
| | 0 | 100.0 | 0.0 | 100.0 | 0.0 | 100.0 | 0.0 | 100.0 | 0.0 | 100.0 | 0.0 |
| | DMSO 1% | 87.2 | 9.7 | 87.2 | 9.7 | 87.2 | 9.7 | 87.2 | 9.7 | 87.2 | 9.7 |
| | SDS 5% | 11.3 | 0.6 | 11.3 | 0.6 | 11.3 | 0.6 | 11.3 | 0.6 | 11.3 | 0.6 |

| | | NC130 3 | | | | | | | | | |
|---|---|---|---|---|---|---|---|---|---|---|---|
| | | F1 | | F2 | | F3 | | F4 | | F5 | |
| Cell line | (ug/ml) | AVG | SD | AVG | SD | AVG | SD | AVG | SD | AVG | SD |
| SKOV3 | 100 | 81.6 | 3.0 | 80.6 | 8.2 | 85.3 | 15.4 | 29.1 | 3.5 | 32.3# | 3.9 |
| | 50 | 82.2 | 4.9 | 79.5 | 5.6 | 86.3 | 9.8 | 83.3 | 7.7 | 46.1# | 4.6 |
| | 25 | 92.0 | 4.4 | 84.1 | 4.4 | 90.5 | 6.7 | 79.9 | 3.0 | 56.1# | 1.3 |
| | 10 | 86.1 | 6.7 | 81.9 | 0.5 | 89.8 | 3.7 | 75.2 | 3.3 | 67.6# | 1.1 |
| | 1 | 91.2 | 6.8 | 96.3 | 4.7 | 96.5 | 0.6 | 87.7 | 1.4 | 92.5 | 4.4 |
| | 0 | 100.0 | 0.0 | 100.0 | 0.0 | 100.0 | 0.0 | 100.0 | 0.0 | 100.0 | 0.0 |
| | DMSO 1% | 88.6 | 3.7 | 88.6 | 3.7 | 88.6 | 3.7 | 88.6 | 3.7 | 88.6 | 3.7 |
| | SDS 5% | 56.5 | 5.4 | 56.5 | 5.4 | 56.5 | 5.4 | 56.5 | 5.4 | 56.5 | 5.4 |
| MCF7 | 100 | 62.5* | 8.9 | 77.8 | 8.2 | 95.8 | 13.6 | 23.8 | 1.1 | 48.3 | 4.7 |
| | 50 | 68.0* | 8.4 | 78.0 | 4.5 | 95.3 | 10.4 | 53.2 | 5.4 | 63.9 | 9.7 |
| | 25 | 70.4 | 10.2 | 80.4 | 5.5 | 103.6 | 15.1 | 89.2 | 8.3 | 81.8 | 4.5 |
| | 10 | 71.8 | 10.2 | 83.8 | 1.4 | 89.3 | 3.3 | 85.2 | 12.3 | 82.2 | 3.5 |

TABLE 4-continued

Fractionation screening results - subfractionation identification

|  |  | | | | | | | | | |
|---|---|---|---|---|---|---|---|---|---|---|
|  | 1 | 88.1 | 7.2 | 88.9 | 1.6 | 104.0 | 12.4 | 95.6 | 6.2 | 87.6 | 6.3 |
|  | 0 | 100.0 | 0.0 | 100.0 | 0.0 | 100.0 | 0.0 | 100.0 | 0.0 | 100.0 | 0.0 |
|  | DMSO 1% | 92.1 | 5.9 | 92.1 | 5.9 | 92.1 | 5.9 | 92.1 | 5.9 | 92.1 | 5.9 |
|  | SDS 5% | 49.9 | 5.6 | 49.9 | 5.6 | 49.9 | 5.6 | 49.9 | 5.6 | 49.9 | 5.6 |
| U373 | 100 | 101.5 | 5.3 | 112.4 | 16.5 | 86.6 | 2.6 | 48.2 | 4.9 | 68.7* | 3.2 |
|  | 50 | 106.0 | 12.0 | 98.3 | 12.1 | 83.9 | 6.4 | 71.2 | 3.2 | 61.7# | 4.6 |
|  | 25 | 122.7 | 3.7 | 110.9 | 13.3 | 93.6 | 3.0 | 95.3 | 3.1 | 67.6* | 3.8 |
|  | 10 | 98.1 | 6.1 | 95.3 | 5.7 | 90.6 | 6.7 | 92.4 | 10.5 | 73.5* | 3.7 |
|  | 1 | 97.2 | 9.9 | 103.8 | 10.6 | 90.7 | 7.7 | 97.2 | 5.2 | 90.4 | 1.5 |
|  | 0 | 100.0 | 0.0 | 100.0 | 0.0 | 100.0 | 0.0 | 100.0 | 0.0 | 100.0 | 0.0 |
|  | DMSO 1% | 89.9 | 6.8 | 89.9 | 6.8 | 89.9 | 6.8 | 89.9 | 6.8 | 89.9 | 6.8 |
|  | SDS 5% | 58.1 | 4.0 | 58.1 | 4.0 | 58.1 | 4.0 | 58.1 | 4.0 | 58.1 | 4.0 |
| THP-1 | 100 | 78.4 | 7.2 | 83.8 | 6.0 | 86.7 | 2.4 | 45.0 | 2.4 | 83.3 | 10.9 |
|  | 50 | 78.3 | 4.6 | 88.9 | 8.0 | 94.6 | 7.2 | 95.4 | 6.2 | 89.5 | 9.3 |
|  | 25 | 80.7 | 3.6 | 88.8 | 5.1 | 99.2 | 13.0 | 96.6 | 3.5 | 79.7 | 9.4 |
|  | 10 | 83.6 | 6.7 | 92.9 | 7.1 | 96.9 | 3.1 | 92.9 | 4.1 | 78.0 | 8.7 |
|  | 1 | 83.3 | 4.9 | 90.1 | 6.9 | 94.9 | 6.2 | 95.7 | 3.6 | 84.4 | 6.2 |
|  | 0 | 100.0 | 0.0 | 100.0 | 0.0 | 100.0 | 0.0 | 100.0 | 0.0 | 100.0 | 0.0 |
|  | DMSO 1% | 103.3 | 6.2 | 103.3 | 6.2 | 103.3 | 6.2 | 103.3 | 6.2 | 103.3 | 6.2 |
|  | SDS 5% | 36.2 | 4.6 | 36.2 | 4.6 | 36.2 | 4.6 | 36.2 | 4.6 | 36.2 | 4.6 |
| CCD10795K | 100 | 93.1 | 1.3 | 66.5 | 6.7 | 90.8 | 0.5 | 37.8 | 3.1 | 67.1* | 1.7 |
|  | 50 | 98.9 | 7.7 | 92.1 | 8.9 | 93.7 | 1.6 | 75.4 | 2.6 | 66.7* | 4.4 |
|  | 25 | 93.6 | 5.0 | 91.6 | 2.4 | 94.9 | 4.3 | 88.1 | 2.7 | 68.4* | 1.3 |
|  | 10 | 99.3 | 5.8 | 93.5 | 3.2 | 95.9 | 4.9 | 90.5 | 4.5 | 73.81 | 2.3 |
|  | 1 | 101.6 | 0.4 | 98.6 | 2.4 | 99.7 | 8.6 | 96.6 | 2.1 | 92.3 | 1.5 |
|  | 0 | 100.0 | 0.0 | 100.0 | 0.0 | 100.0 | 0.0 | 100.0 | 0.0 | 100.0 | 0.0 |
|  | DMSO 1% | 87.2 | 9.7 | 87.2 | 9.7 | 87.2 | 9.7 | 87.2 | 9.7 | 87.2 | 9.7 |
|  | SDS 5% | 11.3 | 0.6 | 11.3 | 0.6 | 11.3 | 0.6 | 11.3 | 0.6 | 11.3 | 0.6 |

| | | NC133 4 | | | | | | | |
|---|---|---|---|---|---|---|---|---|---|
| Cell line | | F1 | | F3 | | F4 | | F5 | |
| (ug/ml) | | AVG | SD | AVG | SD | AVG | SD | AVG | SD |
| SKOV3 | 100 | 67.2 | 1.7 | 75.4 | 3.0 | 40.8# | 1.1 | 43.3* | 0.8 |
|  | 50 | 73.6 | 2.2 | 78.6 | 4.2 | 60.8# | 3.6 | 58.7* | 3.5 |
|  | 25 | 84.5 | 6.5 | 95.4 | 13.0 | 72.8* | 1.8 | 72.3* | 1.1 |
|  | 10 | 84.3 | 4.9 | 93.1 | 5.0 | 76.2 | 5.6 | 88.1 | 4.2 |
|  | 1 | 84.8 | 10.0 | 97.5 | 11.0 | 95.5 | 10.4 | 108.4 | 0.8 |
|  | 0 | 100.0 | 0.0 | 100.0 | 0.0 | 100.0 | 0.0 | 100.0 | 0.0 |
|  | DMSO 1% | 88.6 | 3.7 | 88.6 | 3.7 | 88.6 | 3.7 | 88.6 | 3.7 |
|  | SDS 5% | 56.5 | 5.4 | 56.5 | 5.4 | 56.5 | 5.4 | 56.5 | 5.4 |
| MCF7 | 100 | 76.9 | 5.7 | 74.3 | 5.4 | 21.1# | 1.2 | 48.2 | 4.2 |
|  | 50 | 81.9 | 4.4 | 82.8 | 5.6 | 23.4# | 0.7 | 55.7 | 6.8 |
|  | 25 | 96.9 | 3.5 | 99.4 | 13.0 | 59.7* | 6.1 | 81.3 | 8.7 |
|  | 10 | 82.0 | 2.0 | 90.2 | 2.4 | 70.6* | 2.8 | 90.2 | 7.0 |
|  | 1 | 87.3 | 1.3 | 101.2 | 2.6 | 91.2 | 5.6 | 103.2 | 12.3 |
|  | 0 | 100.0 | 0.0 | 100.0 | 0.0 | 100.0 | 0.0 | 100.0 | 0.0 |
|  | DMSO 1% | 92.1 | 5.9 | 92.1 | 5.9 | 92.1 | 5.9 | 92.1 | 5.9 |
|  | SDS 5% | 49.9 | 5.6 | 49.9 | 5.6 | 49.9 | 5.6 | 49.9 | 5.6 |
| U373 | 100 | 93.6 | 5.2 | 100.0 | 8.6 | 12.2 | 1.0 | 66.9 | 6.5 |
|  | 50 | 98.2 | 3.7 | 100.3 | 7.2 | 32.4 | 2.1 | 76.1 | 8.8 |
|  | 25 | 99.7 | 3.8 | 109.9 | 6.7 | 104.4 | 6.5 | 94.1 | 11.9 |
|  | 10 | 96.1 | 3.6 | 101.8 | 6.7 | 101.3 | 11.5 | 98.2 | 10.9 |
|  | 1 | 91.6 | 7.2 | 103.9 | 9.5 | 96.6 | 10.5 | 92.1 | 5.3 |
|  | 0 | 100.0 | 0.0 | 100.0 | 0.0 | 100.0 | 0.0 | 100.0 | 0.0 |
|  | DMSO 1% | 89.9 | 6.8 | 89.9 | 6.8 | 89.9 | 6.8 | 89.9 | 6.8 |
|  | SDS 5% | 58.1 | 4.0 | 58.1 | 4.0 | 58.1 | 4.0 | 58.1 | 4.0 |
| THP-1 | 100 | 105.5 | 5.5 | 90.3 | 8.3 | 60.1 | 2.6 | 102.4 | 3.9 |
|  | 50 | 108.0 | 4.2 | 115.1 | 1.1 | 98.1 | 4.0 | 99.2 | 5.7 |
|  | 25 | 110.6 | 12.0 | 122.1 | 5.9 | 105.8 | 3.7 | 104.1 | 4.8 |
|  | 10 | 117.9 | 10.1 | 117.8 | 10.5 | 114.2 | 12.8 | 96.2 | 14.7 |
|  | 1 | 120.0 | 6.1 | 116.9 | 7.2 | 115.1 | 16.6 | 71.9 | 1.9 |
|  | 0 | 100.0 | 0.0 | 100.0 | 0.0 | 100.0 | 0.0 | 100.0 | 0.0 |
|  | DMSO 1% | 103.3 | 6.2 | 103.3 | 6.2 | 103.3 | 6.2 | 103.3 | 6.2 |
|  | SDS 5% | 36.2 | 4.6 | 36.2 | 4.6 | 36.2 | 4.6 | 36.2 | 4.6 |
| CCD10795K | 100 | 93.4 | 8.2 | 95.6 | 5.8 | 38.1 | 3.1 | 75.8 | 2.6 |
|  | 50 | 94.0 | 8.7 | 99.0 | 6.7 | 64.4 | 3.9 | 83.3 | 4.4 |
|  | 25 | 99.1 | 2.7 | 103.1 | 5.6 | 88.7 | 12.4 | 103.1 | 8.1 |
|  | 10 | 97.7 | 2.0 | 103.3 | 7.5 | 101.1 | 11.7 | 97.6 | 10.0 |
|  | 1 | 96.8 | 1.4 | 104.0 | 7.5 | 107.8 | 15.2 | 101.1 | 10.8 |
|  | 0 | 100.0 | 0.0 | 100.0 | 0.0 | 100.0 | 0.0 | 100.0 | 0.0 |
|  | DMSO 1% | 87.2 | 9.7 | 87.2 | 9.7 | 87.2 | 9.7 | 87.7 | 9.7 |
|  | SDS 5% | 11.3 | 0.6 | 11.3 | 0.6 | 11.3 | 0.6 | 11.3 | 0.6 |

Student's test post hoc analysis: #p < 0.0001, *p < 0.01 and ‡p < 0.05

Comparison of Fr.4 from Different Batches

The separation was conducted on an Agilent Zorbax SB-C18 (2.1×30 mm 3.5 μm) column using Agilent HPLC 1100. Solvent A was 10 mM ammonium formate (pH 3.2) and solvent B was 90% acetonitrile with 10% 100 mM ammonium formate (pH 3.2). Gradient was 30% B to 100% B in 12 min and wash with acetonitrile with 0.1% formic acid for 2 min. Column temperature was 55° C. Flow rate was 0.5 mL/min.

Figure 8:
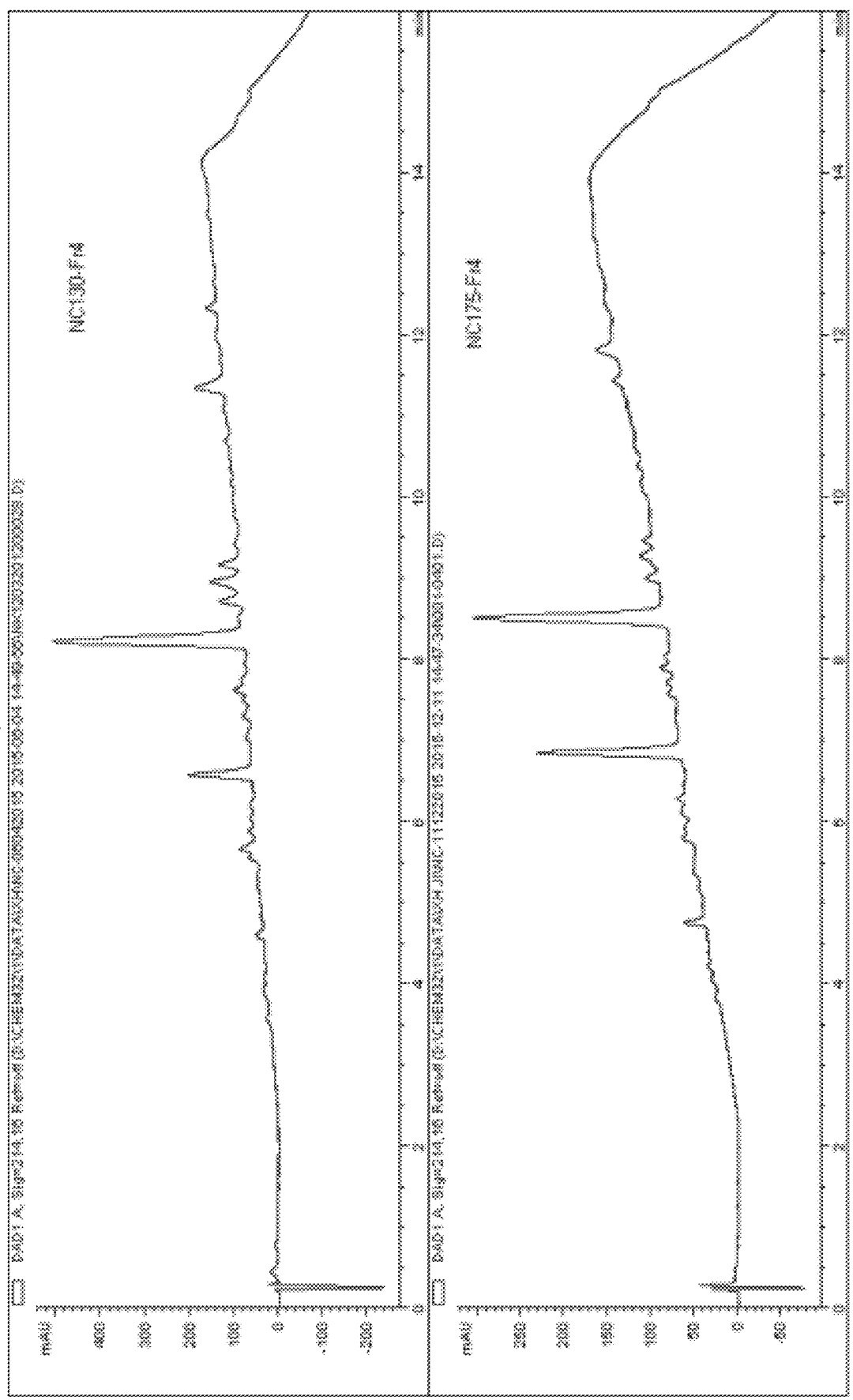
FIG. 8. HPLC comparison of two batches of NC130-Fr4 (June 2015 batch) and NC175-Fr4 (December 2015 batch).

The results confirmed that NC174 F4 (prepared in December, 2015) was the same as of NC133 F4 (prepared in June 2015) (FIG. 7), and NC175 F4 (prepared in December, 2015) was the same as of NC130 F4 (prepared in June 2015) (FIG. 8).

Example 4. Analytical Profiling

Four fractions were selected for further purification based on the bioassay results. Additional fractionation was conducted using a normal phase column. Fraction 4 from each seaweed species was dissolved in MeOH—$CH_2Cl_2$, loaded on Celite and dried via rotatory evaporation. Dried Celite was put on a 24 g Teledyne ISCO high performance GOLD silica column and sample separation was done on a CombiFlash liquid chromatography system (Teledyne ISCO). Fractionation was conducted as a gradient of Solvent A ($CH_2Cl_2$) and Solvent B (1:1 methanol:$CH_2Cl_2$) as follows:

0% B for 2 CV (column volumes)
40% B for 17 CV
100% B for 4 CV
total elution volume: 23 CV.

Fractions were combined based on thin layer chromatography (TLC) analysis and dried under rotatory evaporation and GeneVac, to yield 5 to 6 fractions for testing as shown in Table 5.

Figure 9:
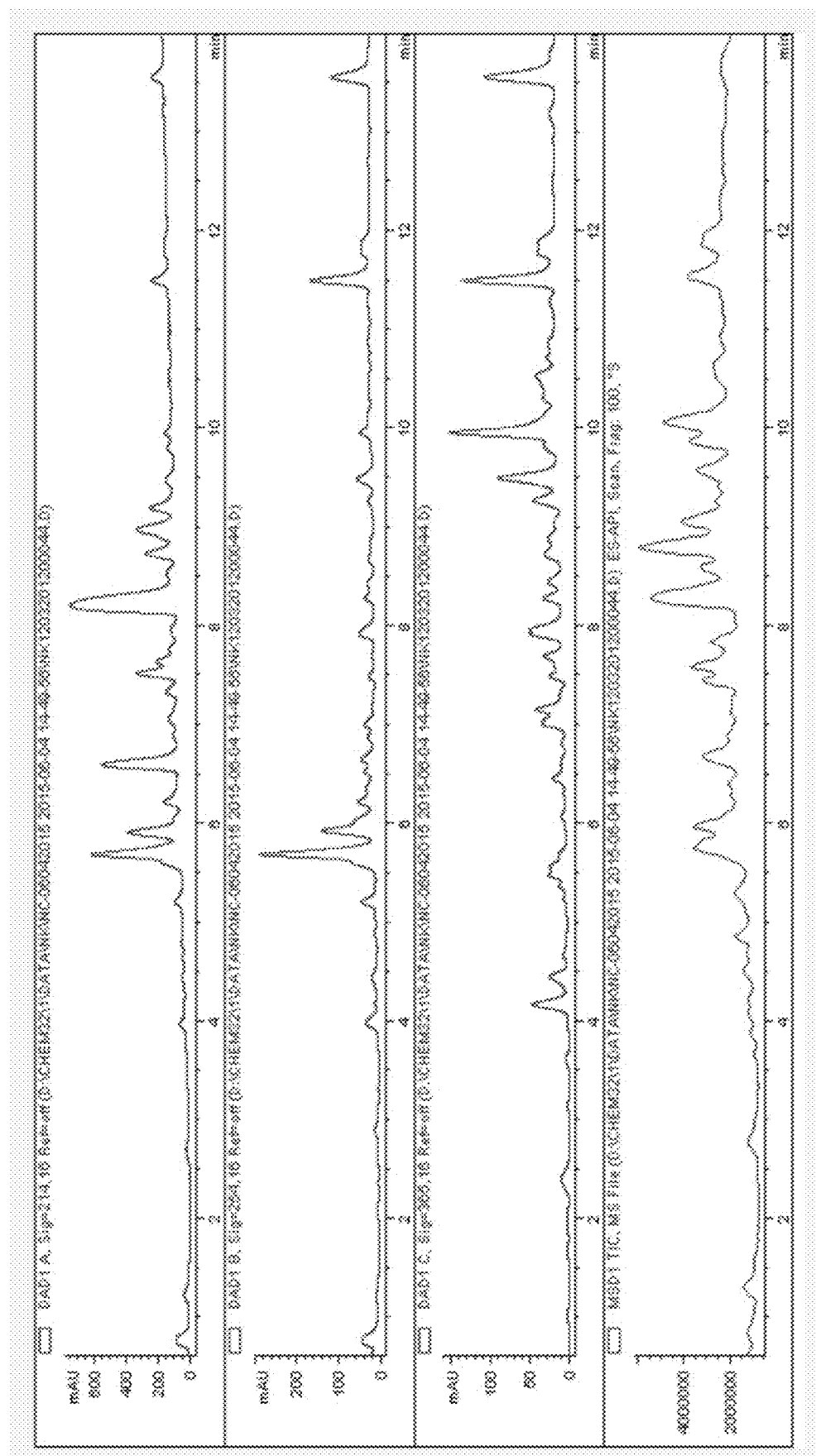
FIG. 9. HPLC-DAD/MS profile of NC133-F4-F2 fraction, with MS monitored in positive mode.
Figure 10:
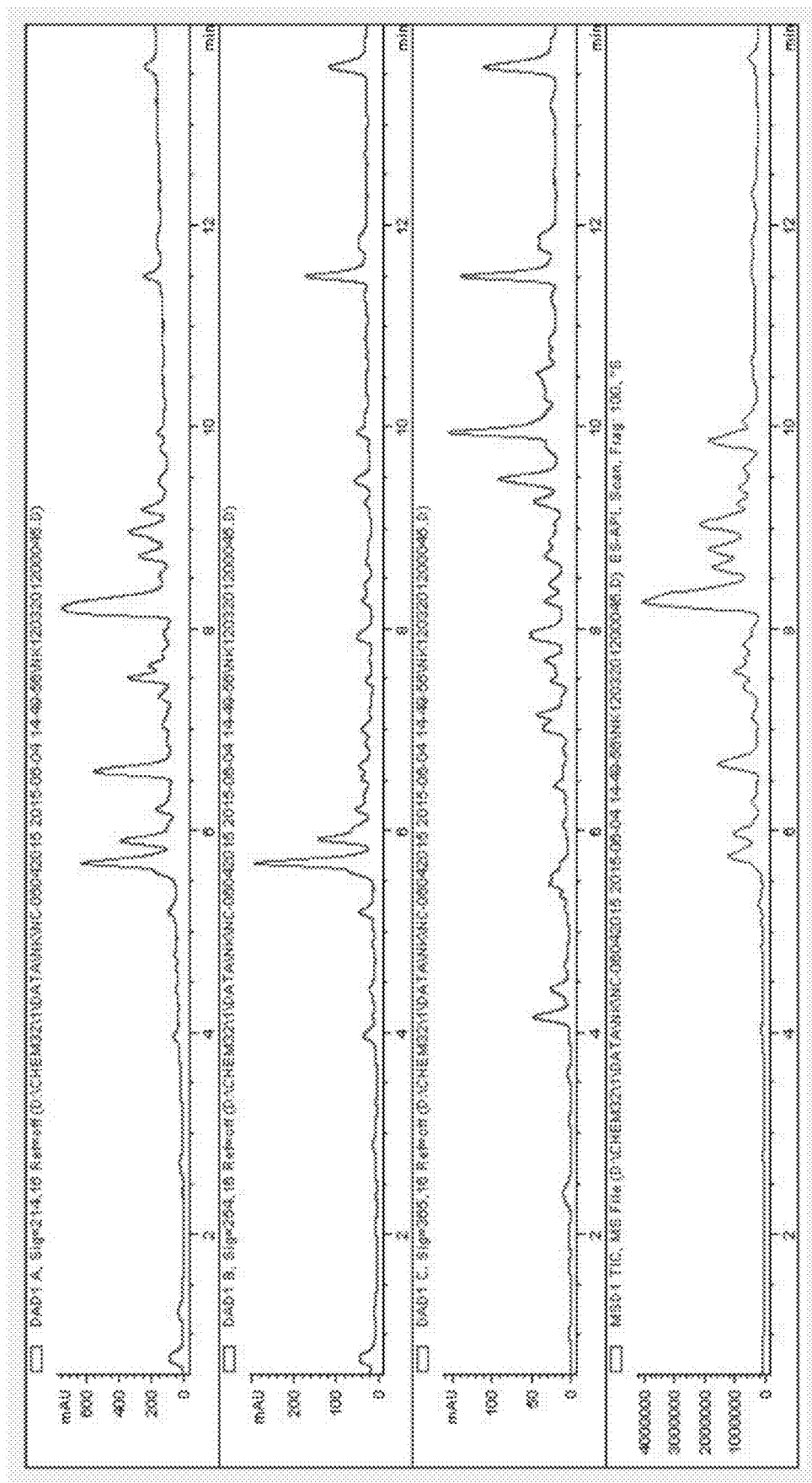
FIG. 10. HPLC-DAD/MS profile of NC133-F4-F2 fraction, with MS monitored in negative mode.

4.1 Preliminary Identification of Major Components in Bioactive Fraction:

All the fraction 4 samples from crude extraction (stage1) and 21 sub-fractions from second stage fractionation were analyzed by HPLC-DAD/MS on an Agilent HPLC system using a SB-C18 Zorbax column (3.5 μm, 2.1×30 mm) with mobile phase containing acetonitrile (with 0.1% formic acid), ammonium formate (10 mM, pH 3.2), and 90% acetonitrile (with 2% 500 mM ammonium formate) eluted gradiently. FIGS. 9, 10 show the chromatograms of the bioactive sub-fraction NC133-F4-F2 that indicate that the fraction is sufficiently diverse to prevent characterization at the single compound level without additional study.

Figure 11:
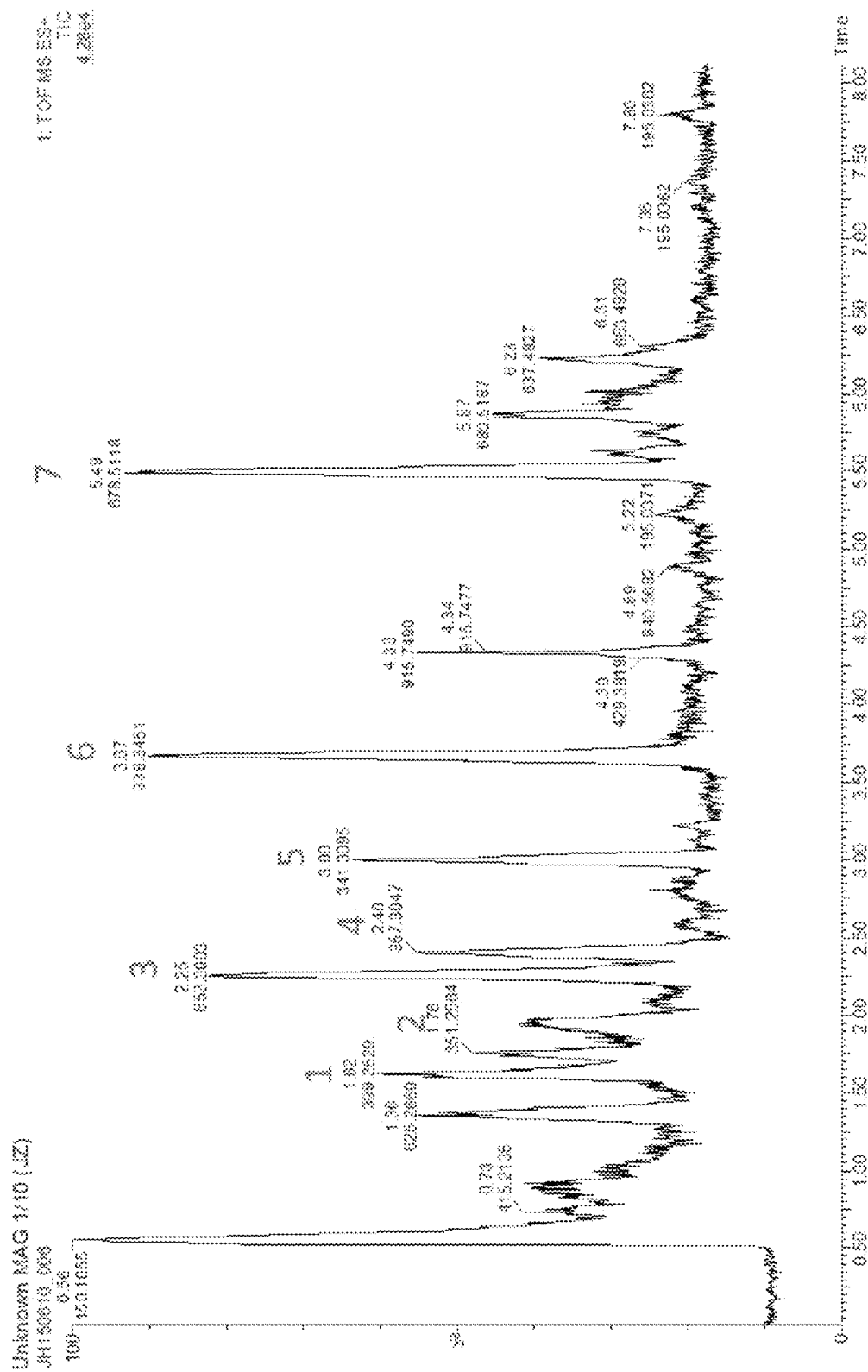
FIG. 11. LC-HRMS analysis of NC133-F4-F2 fraction.

High resolution and tandem MS (HRMS and MS/MS) analysis of bioactive fraction NC133-F4-F2 was subsequently conducted using a Waters Q-TOF Premier HRMS and an Acuity BEH-C18 column. FIG. 11 shows the LC-MS profile of NC133-F4-F2, with mass information for major components.

Figure 12A:
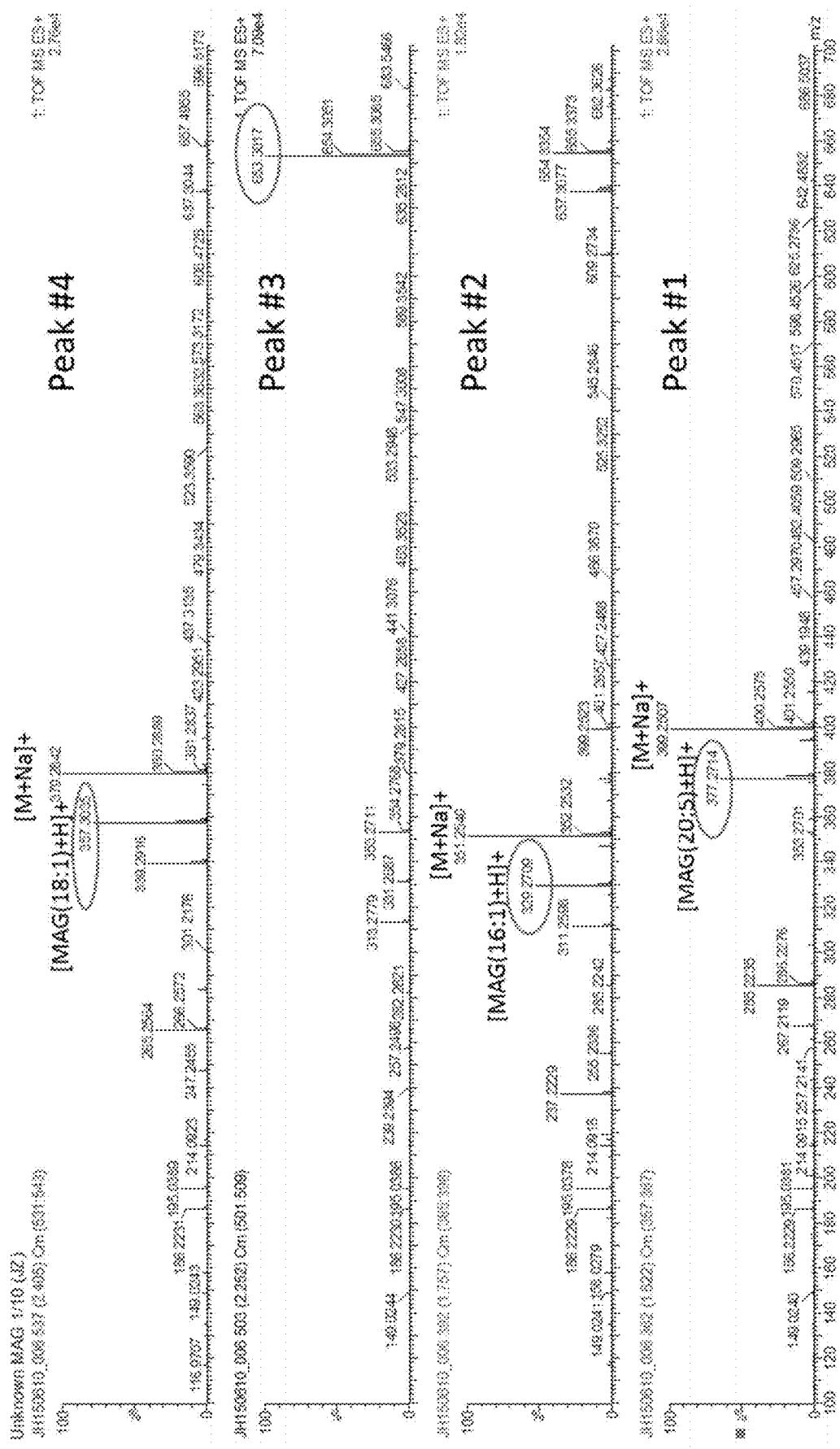
FIGS. 12A-B. HRMS (A) and MS/MS (B) data for peaks 1-4 from NC133-F4-F2 fraction.
Figure 12B:
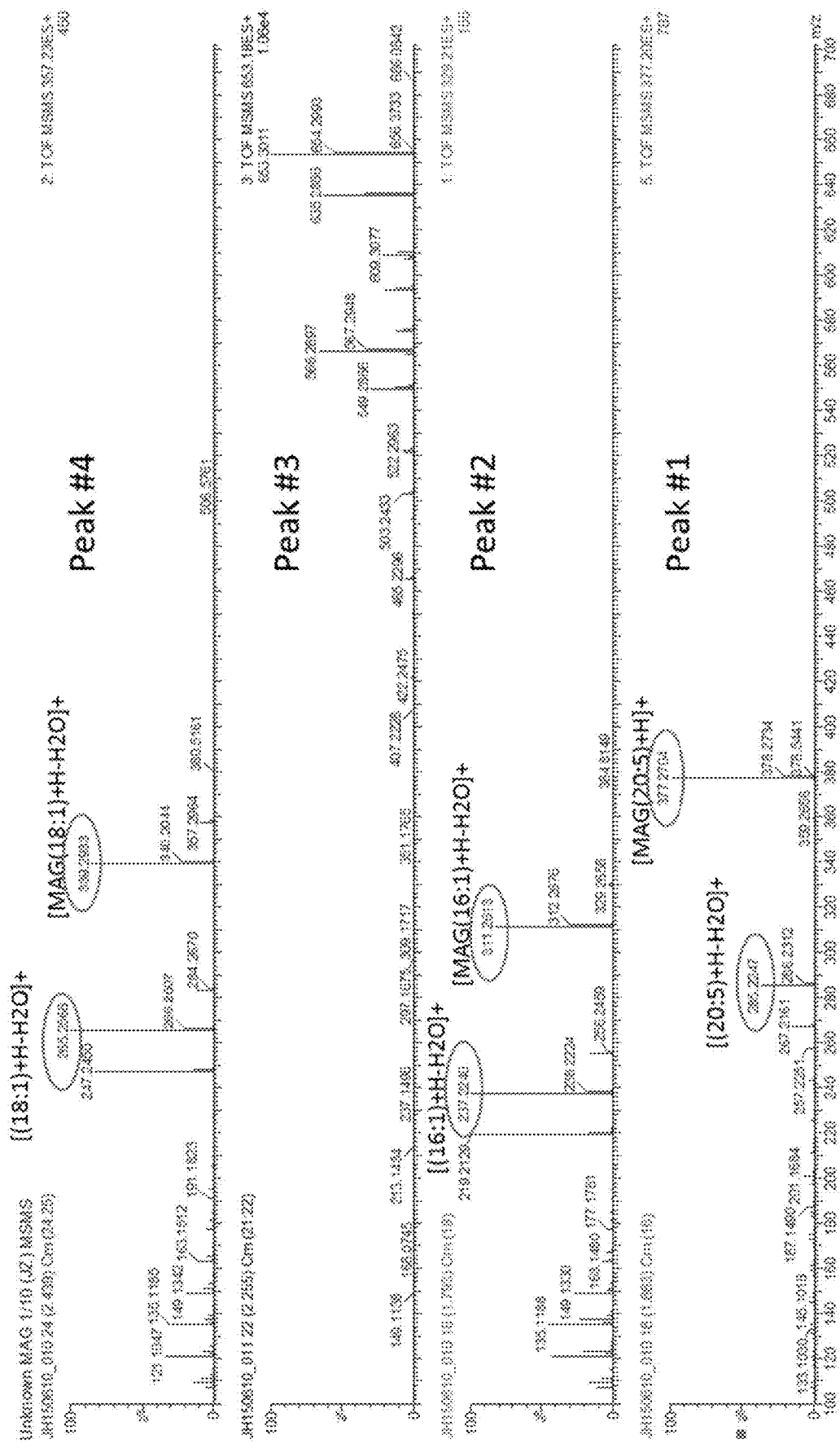
Figure 13A:
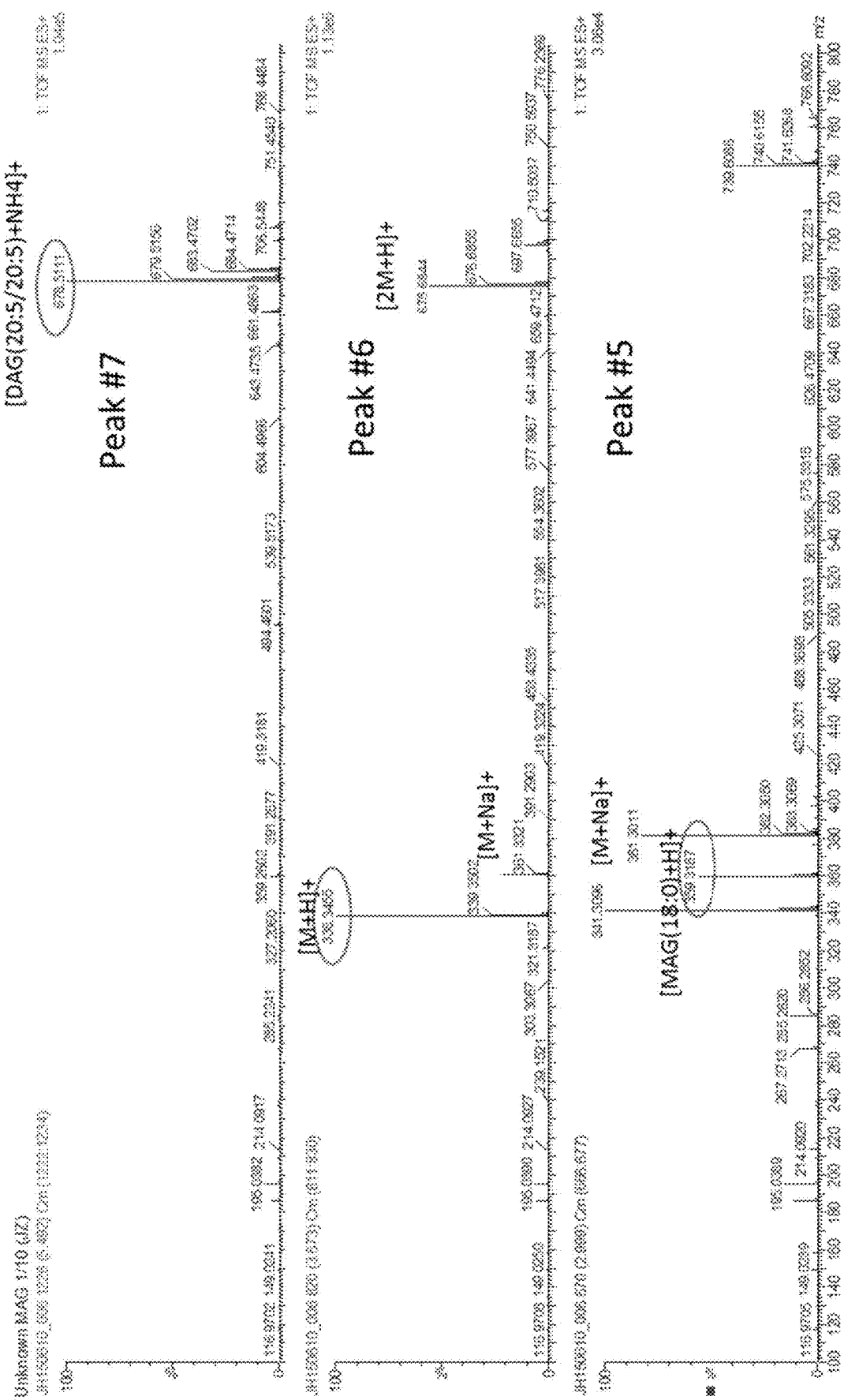
FIG. 13A-B. HRMS (A) and MS/MS (B) data for peaks 5-7 from NC133-F4-F2 fraction.
Figure 13B:
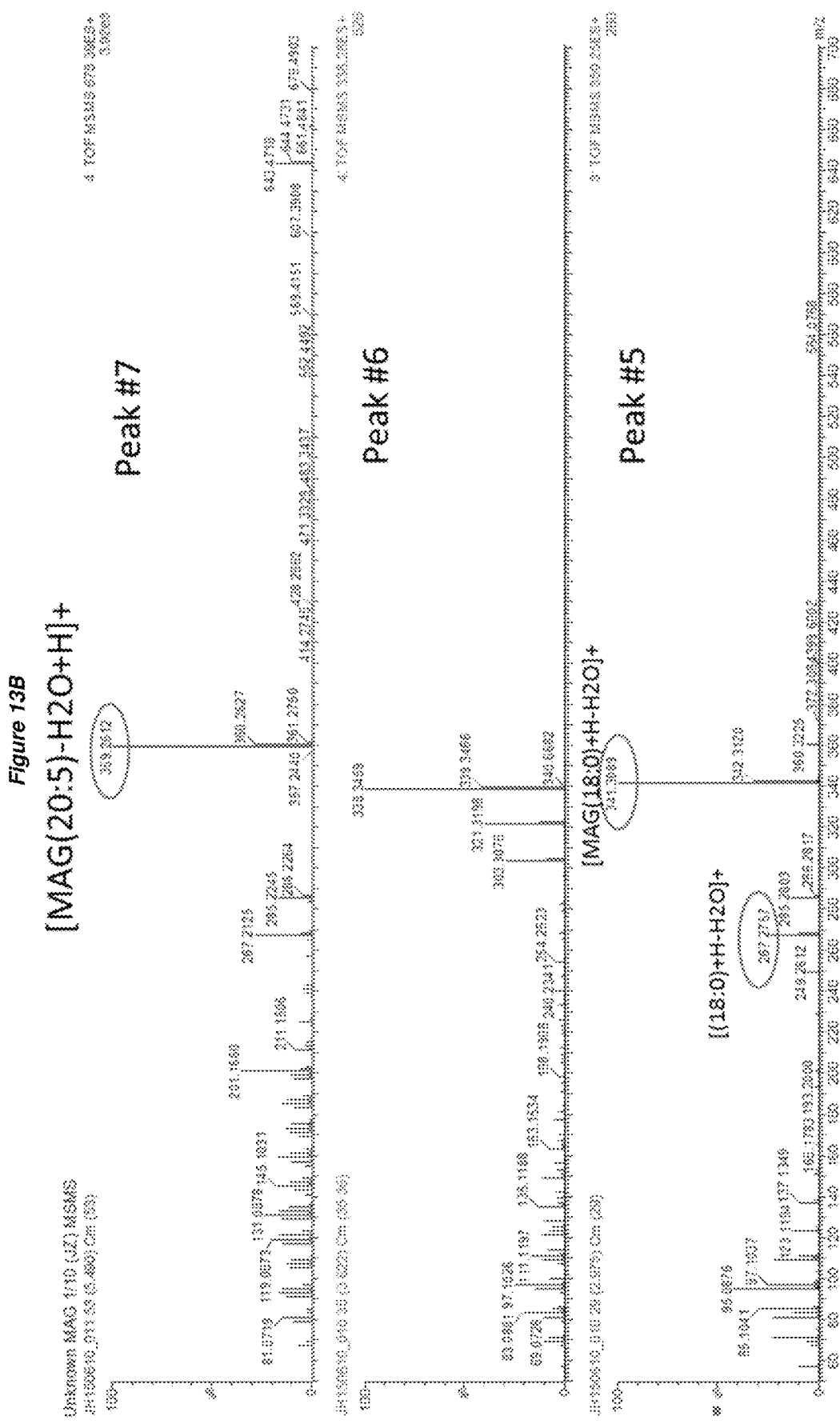

Details of HRMS and MS/MS information are shown in FIGS. 12A, B (for peaks 1-4) and FIGS. 13A, B (for peaks 5-7). The HRMS and MS/MS data revealed the presence of several monoacylglycerols (MAG) in this fraction, including MAG (20:5), MAG (16:1), MAG (18:1), MAG (18:0). One diacylglycerol compound was identified as DAG (20:5/20:5).

4.2 NMR Spectral Analysis

Figure 14:
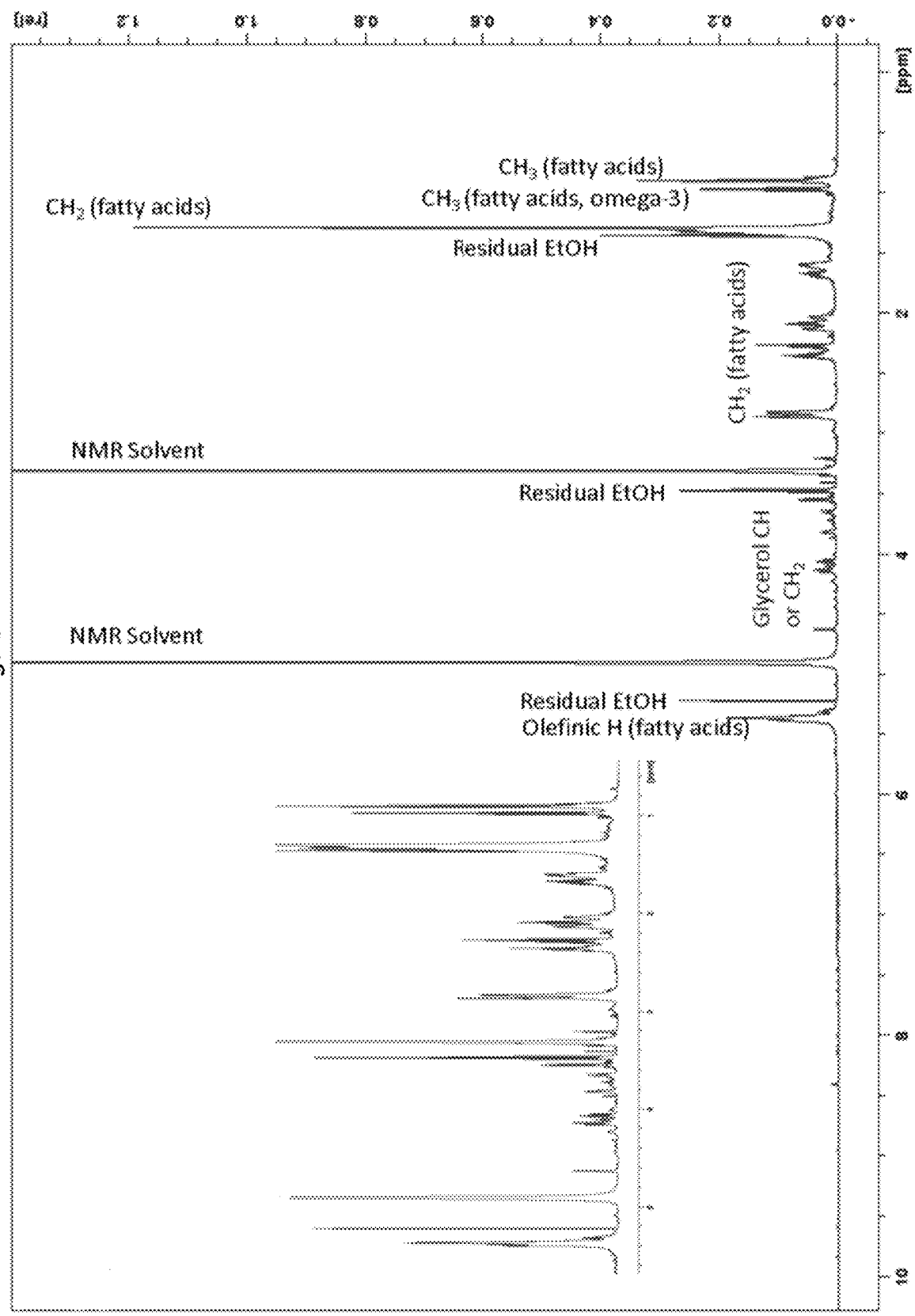
FIG. 14. $^1$H-NMR spectra of NC133-F4-F2 fraction.

NC133-F4-F2 was also analyzed on a Bruker 700 MHz NMR instrument using a cryoprobe. Several 1 D and 2D experiments including $^1$H NMR (FIG. 14), COSY, TOCSY, HSQC, and HMBC were conducted (not shown).

Examining the NMR spectra confirmed the presence of lipids as the main components. Characteristic peaks of more than two types of fatty acids (omega-3 and other saturated or unsaturated) are present ($CH_3$ signals at δ 0.8-0.9 ppm). Unsaturated fatty acids can be clearly seen by the presence of olefinic protons (5.36 ppm). The glycerol protons (3.5-4.2 ppm) demonstrated patterns of coupling of MAG and DAG molecules. Other major proton peaks shown (1.5-3.0 ppm and 1.3 ppm) are also from fatty acid chains ($CH_2$). In addition, glycolipids (signals of anomeric proton and carbon at 4.2 and 105.8 ppm respectively) might be present as minor component. The above analyses were based on examination of both 1 D and various 2D spectra. It showed that lipids in the forms of monoacyl glycerol (MAG) and diacyl glycerol (DAG) appear to be the major components of this bioactive fraction.

Example 5. Fractionation of Main Components from NC77 (*Chetomorpha cannabina*)

3.14 g of NC77 was dissolved in methanol, mixed on Celite and dried using Rotavap. The sample was then loaded on pre-conditioned and equilibrated Thermo Scientific SPE column (HYPERSEP C18 20G). Four fractions were obtained by eluting the SPE column with 5% methanol (Fr. 1), 25% methanol (Fr. 2), 50% methanol (Fr. 3) and metha-nol (Fr. 4). Fr. 4 (0.34 g) was subjected to further fractionation based on previous bioassay result.

In the second stage fractionation, Fr. 4 was dissolved in dichloromethane/methanol and mixed with Celite and dried. The sample was loaded on 24 g Teledyne ISCO High Performance GOLD silica gel column and eluted with dichloromethane/methanol on CombiFlash® Rf, Teledyne ISCO. The eluting solvent gradient (A and B) was as the following: 0% B for 2 CV (column volume) then to 40% B for 15 CV and kept at 40% B for 2 CV, to 100% B for 2 CV and kept at 100% B for 2 CV. Total elution volume was 23 CV. A is dichloromethane and B is methanol/dichloromethane (1:1). Fractions were monitored by TLC and some combined and dried using Rotavap and Genevac.

Based on TLC analysis, sub fraction 13 of Fr. 4 (Fr. 4-13, 0.11 g) was chosen for subsequent purification as it showed to contain major components. In this step, 12 g silica gel column by CombiFlash® Rf was used. The solvent (A and B) gradient was: 0% B for 2 CV then to 100% B for 25 CV and kept at 100% B for 2 CV. The total elution was 29 CV. A is dichloromethane and B is 5% methanol in dichloromethane. Again, fractions were selectively combined according to TLC.

TABLE 5

| Sample | Sample weight (g) | Fr.1 (g) | Fr.2 (g) | Fr.3 (g) | Fr.4 (g) | Fr.5 (g) | Fr.6 (g) |
| --- | --- | --- | --- | --- | --- | --- | --- |
| NC77-FR.4 | 0.21 | 0.011 | 0.044 | 0.006 | 0.036 | 0.064 | — |
| NC130-Fr.4 | 0.28 | 0.087 | 0.026 | 0.023 | 0.05 | 0.072 | — |
| NC133-Fr.4 | 0.15 | 0.019 | 0.007 | 0.044 | 0.071 | 0.008 | — |

Three sub-fractions were further purified using semi preparative HPLC (Agilent). The column used was ZORBAX SB-C18 (9.4×50 mm, 5 µm) and the mobile phase was water/acetonitrile. Eluting gradient varied for different samples so to optimize separation. The column temperature was at 55° C. and flow rate 5 mL/min.

Figure 15:
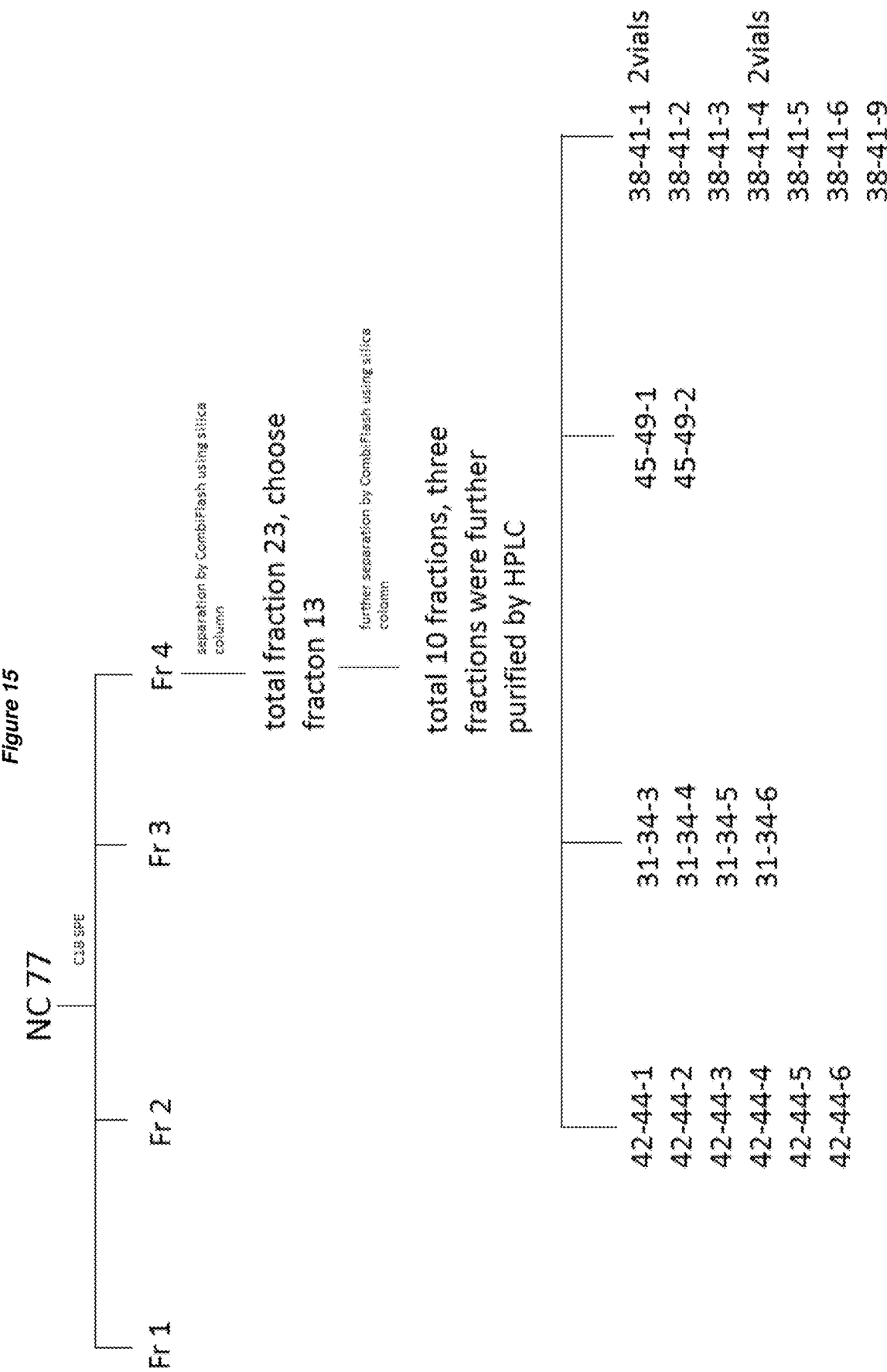
FIG. 15. Flowchart of fractionation and purification of main components from NC77.

As shown in FIG. 15, the fractionation and purification yielded 19 samples for structural analysis. Among them, samples 31-34-6 (0.6 mg), 38-41-1 (0.5 mg), and 38-41-3 (1.0 mg) were pure compounds.

Example 6. Characterization of Main Components from NC77 Bioactive Fraction 4

6.1. Sample Preparation and Analysis:
FAME Preparation and GC-MS Analysis

NC77 and NC77-Fr. 4 were analyzed by GC-MS. Samples were added 1 mL sodium methoxide solution and 1 mL hexane, with cap closed. The reaction vials were put in a heating block (80° C.) for 15 min shaking vials with hand at 5 min intervals. Added 1 mL saturated NaCl solution after cooling to room temperature and shaken by hand several times. The reaction vials were then centrifuged for 20 min at 2,000 rpm. The upper solutions were transfer to GC vials. For GC-MS analysis, Agilent 6890 with 5973 Mass Selective Detector were used. The column was Agilent DB-23 (59 m×0.25 mm, 0.15 µm), injection volume 1 µL. Oven program: 50° C. for 1 min, 25° C./min to 170° C., 2.75° C./min to 215° C. (hold 12 min), 40° C./min to 230° C. (hold 3.11 min). Total runtime was 37.65 min. FID temperature was 280° C., hydrogen flow 40 mL/min, air flow 400 mL/min, makeup flow N2 20 mL/min. Split ratio was 2:1. Carrier gas was helium and kept at constant pressure (30 psi). MSD ionization mode was EI. interface temperature 250° C., MS source 230° C., MS Quad 150° C. Mass range was 50-600 m/z.

HPLC-DAD Analysis to Compare Different Batches

The separation was conducted on an Agilent Zorbax SB-C18 (2.1×30 mm 3.5 µm) column using Agilent HPLC 1100. Solvent A was 10 mM ammonium formate (pH 3.2) and solvent B was 90% acetonitrile with 10% 100 mM ammonium formate (pH3.2). Gradient was 30% B to 100% B in 12 min and wash with acetonitrile with 0.1% formic acid for 2 min. Column temperature was 55° C. Flow rate was 0.5 mL/min.

HPLC-DAD/MS Analysis of Carotenoids

Analysis was done on Agilent 1200 system using YMC carotenoid column, 0.5 µm (250×2 mm) at 32° C. Mobile phase: solvent A 50 mM AmAc/MeOH, Solvent B MTBE, with gradient of 5-65% B in 40 min. Flow rate was 0.2 mL/min, and DAD detector monitored at 450 nm. Identification of peaks in the chromatogram was made on the basis of RT comparison to known standards: fucoxanthin, astaxanthin, lutein, zeaxanthin, canthaxanthin, α- & β-Carotene. All standards were purchased from Chromadex.

UPLC-DAD/ELSD/HRMS and MS/MS

The following instruments were used for LC-UV-ELSD-HRMS data acquisition: Accela 1250 pump (Thermo Fisher Scientific); Exactive benchtop Orbitrap mass spectrometer (Thermo Fisher) equipped with heated electrospray ionization probe; Utimate 3000 DAD (Thermo Scientific Dionex) and ELSD 3300 (Alltech). Separation was carried out on a Hypersil C18 column (50×2.1 mm, Thermo) using mobile phase consisted of (A) 0.1% formic acid and (B) 0.1% formic acid in acetonitrile, with a linear gradient from 5% B to 100% B in 4.2 min, held for 3.2 min, flow-rate was at 400 µL/min.

HRMS was acquired in positive or negative polarity at 25,000 resolution, each with a HCD scan with collision energy at 50 eV for all-ion-fragmentations with 10,000 resolution. The following optimal ion source conditions were used: sheath flow is 15, auxiliary gas flow rate of 3; spray voltage of 3 kV (−2.5 kV for negative); capillary and heater temperature of 350° C. and 250° C., respectively.

NMR

The samples were reconstituted in 100 µL of $CDCl_3$ and 60 µL of each sample was transferred to 1.7 mm NMR tubes. All spectra were run on a Bruker Avance III 700 MHz spectrometer equipped with a 1.7 mm cryogenically cooled probe operating at 16K.

6.2. Analysis of NC77 and NC77-Fr. 4

The preliminary profiling work done previously indicated that lipids were the main components in NC77-Fr. 4. As such, GC-MS analysis was performed to understand the fatty acids composition in this extract and its bioactive fraction.

Figure 16:
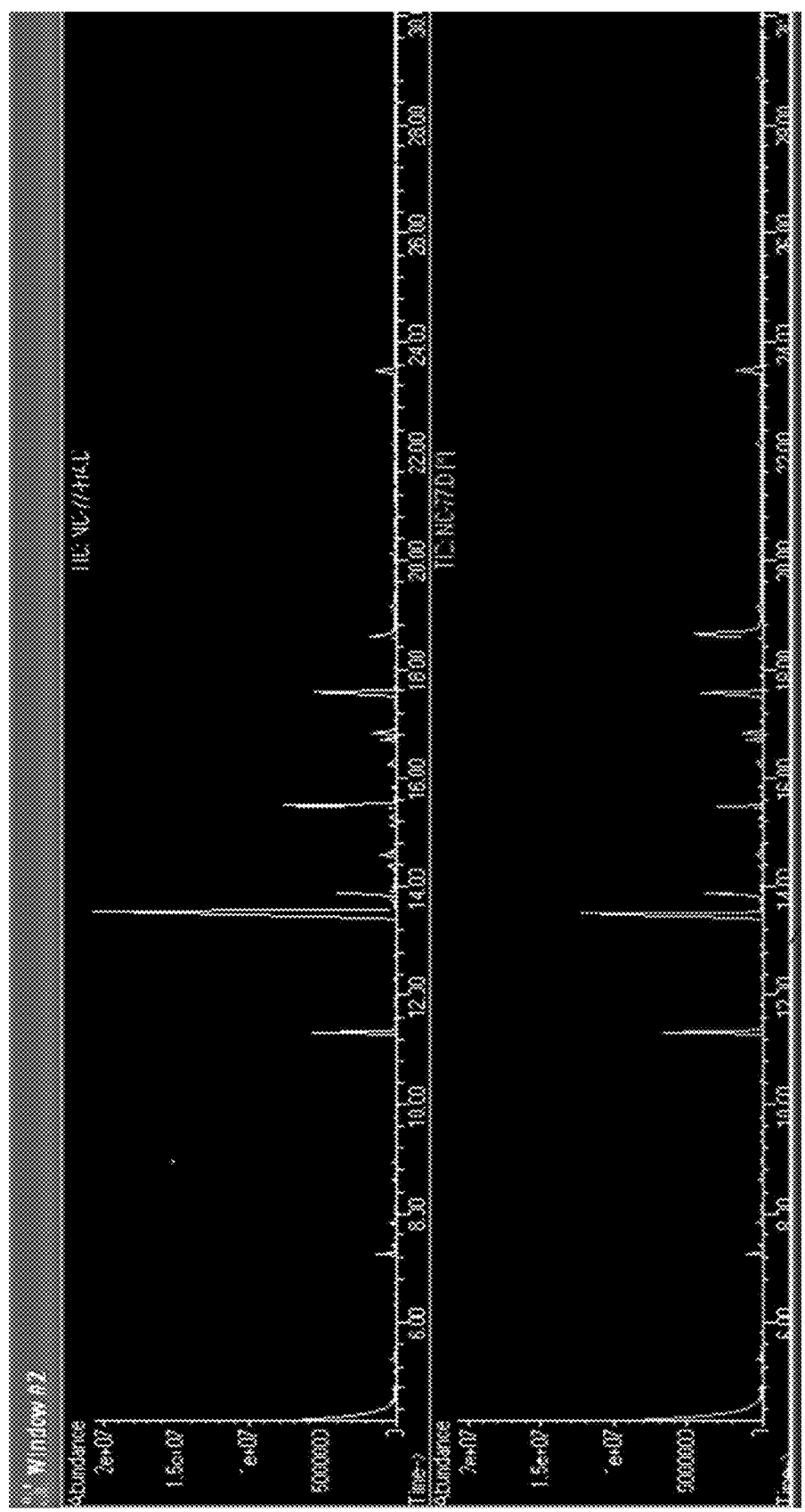
FIG. 16. GC chromatogram of FAME prepared from NC77 and NC77-Fr4 fraction.

FIG. 16 is the GC chromatogram of FAME prepared from NC77 and NC77-Fr. 4. The retention time and tentative identification based on NIST database matching are in Table 6. The major fatty acid was shown to be palmitic acid.

TABLE 6

Identification of fatty acids using GC-MS analysis of NC77 and NC77-Fr. 4

| RT (min) | compounds |
| --- | --- |
| 11.32 | Methyl tetradecanoate |
| 13.51 | Hexadecanoic acid, methyl ester |
| 13.87 | 9-Hexadecenoic acid, methyl ester, (Z)- |
| 15.49 | unknown |
| 16.71 | 8-Octadecenoic acid, methyl ester |
| 16.83 | 8-Octadecenoic acid, methyl ester |
| 17.56 | 9,12-Octadecadienoic acid (Z,Z)-, methyl ester |
| 18.66 | 1,2-15,16-Diepoxyhexadecane |
| 23.47 | Methyl eicosa-5,8,11,14,17-pentaenoate (EPA) |

We also compared the NMR and HPLC profiles of two different batches of NC77 and NC77-Fr. 4 prepared and tested earlier in 2015 and the new samples obtained this time.

Figure 17:
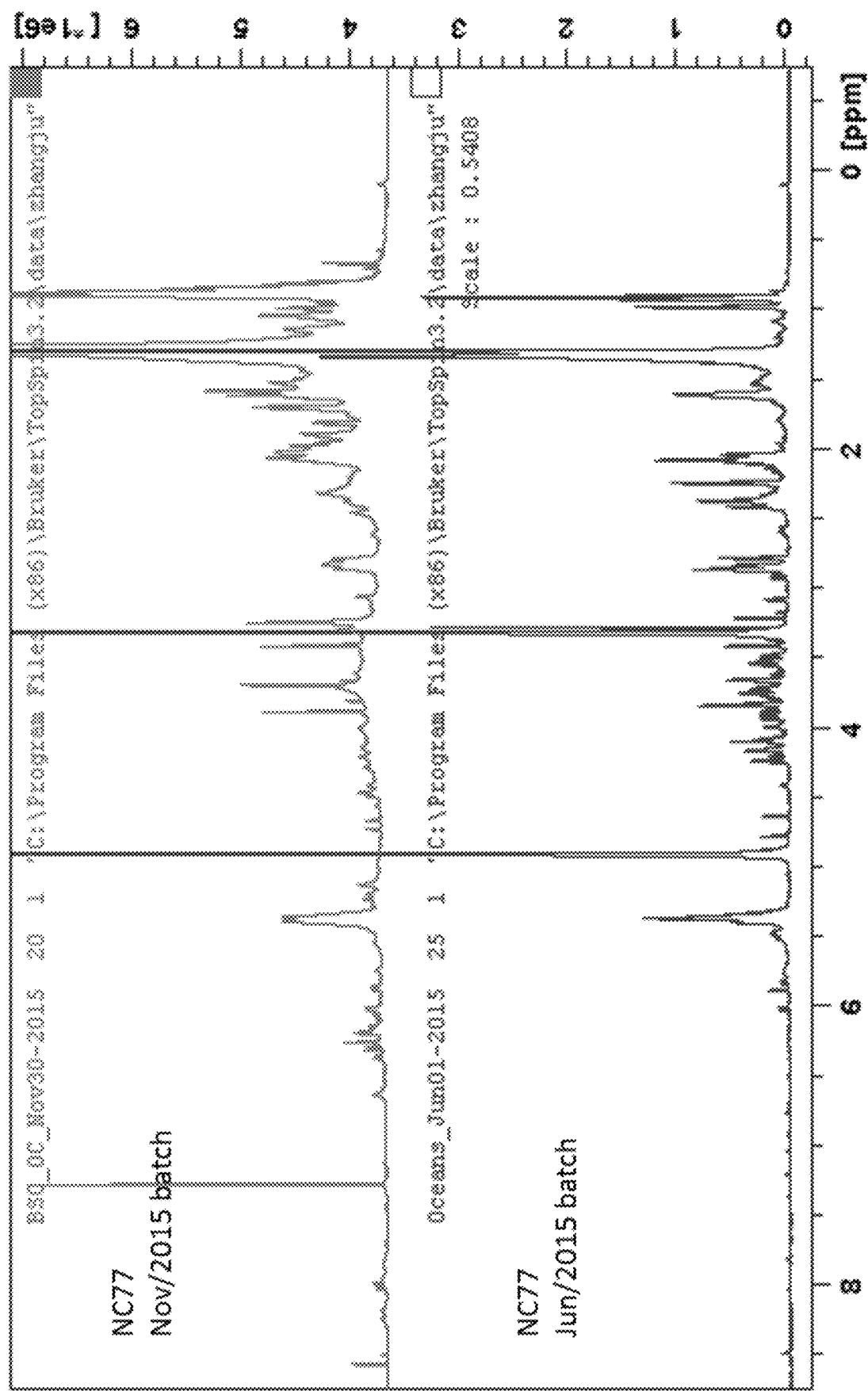
FIG. 17. $^1$H-NMR profile for two batches of NC77 extract.
Figure 18:
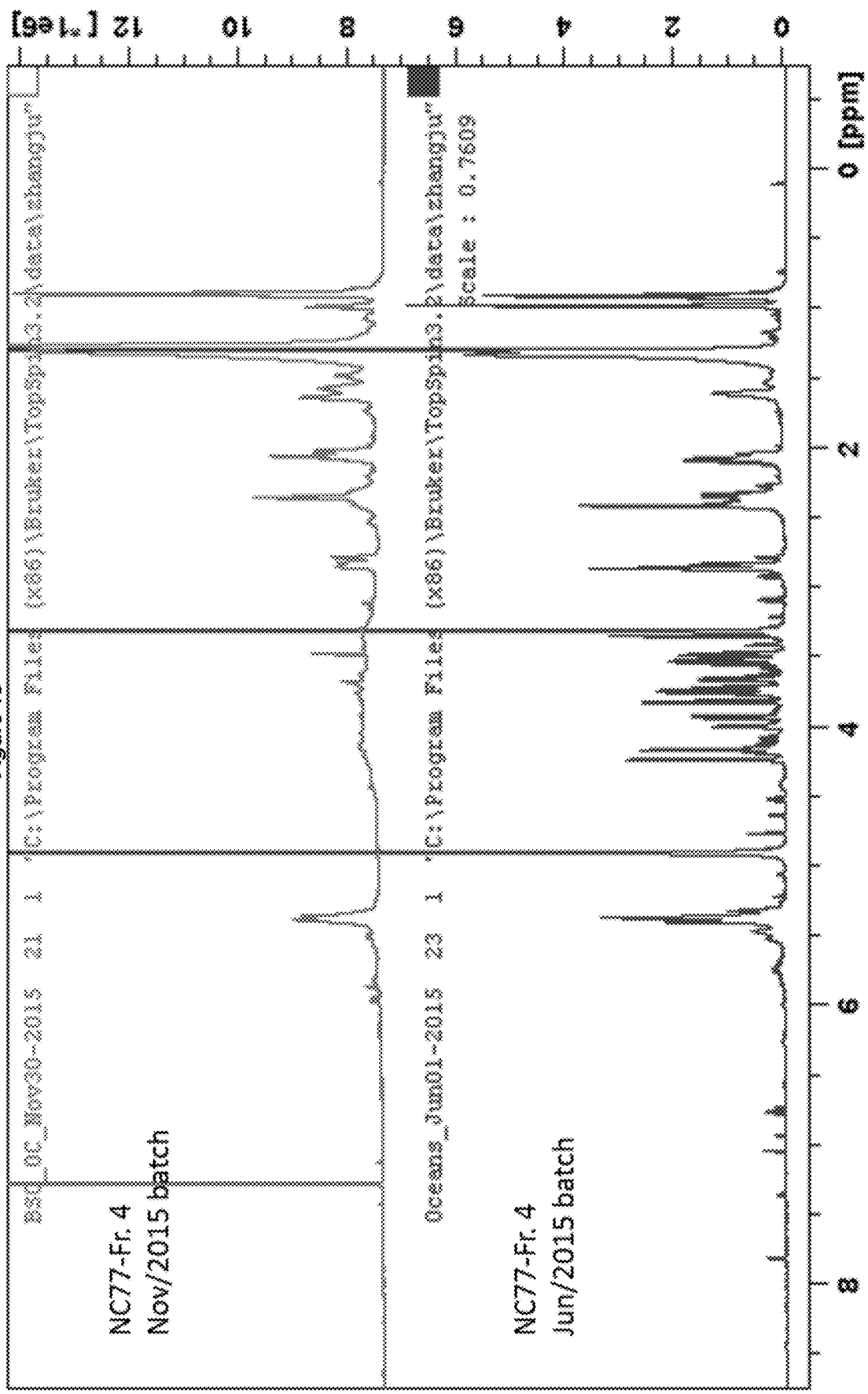
FIG. 18. $^1$H-NMR profiles for two batches of NC77-Fr4 fraction.
Figure 19:
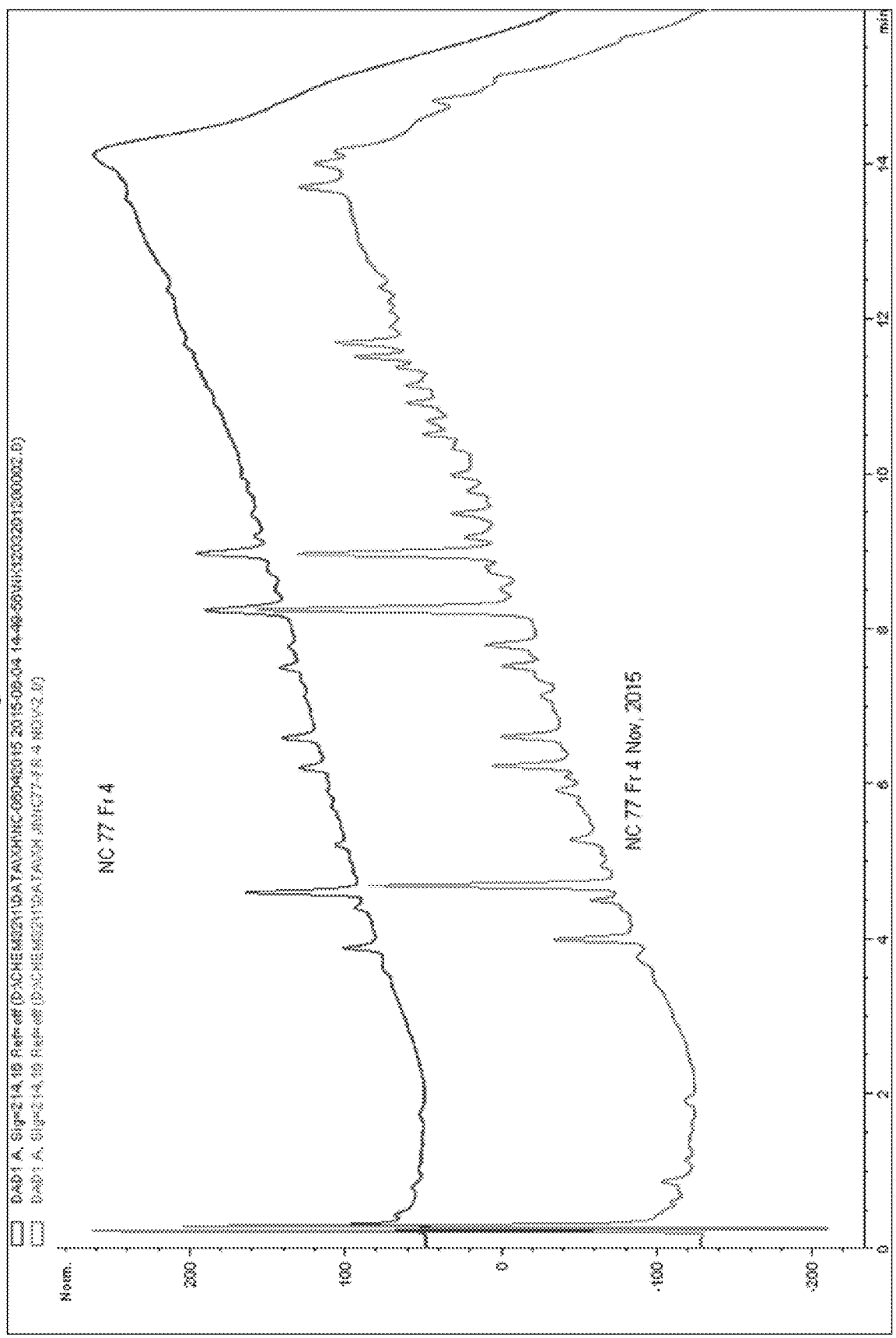
FIG. 19. HPLC comparison between two samples of NC77-Fr4 from two different harvesting dates.

As shown in FIGS. 17 and 18, NC77 and NC77-Fr. 4 prepared this time are with similar $^1$H-NMR profiles as observed from an earlier batch. Lipids (fatty acid) appeared to be the major components. HPLC comparison is shown in FIG. 19. The two appeared to have similar profiles of main components.

Example 7. Isolation and Structure Elucidation of Compounds from NC77 (*Chetomorpha cannabina*)

7.1 Compound 31-34-6

Figure 20:
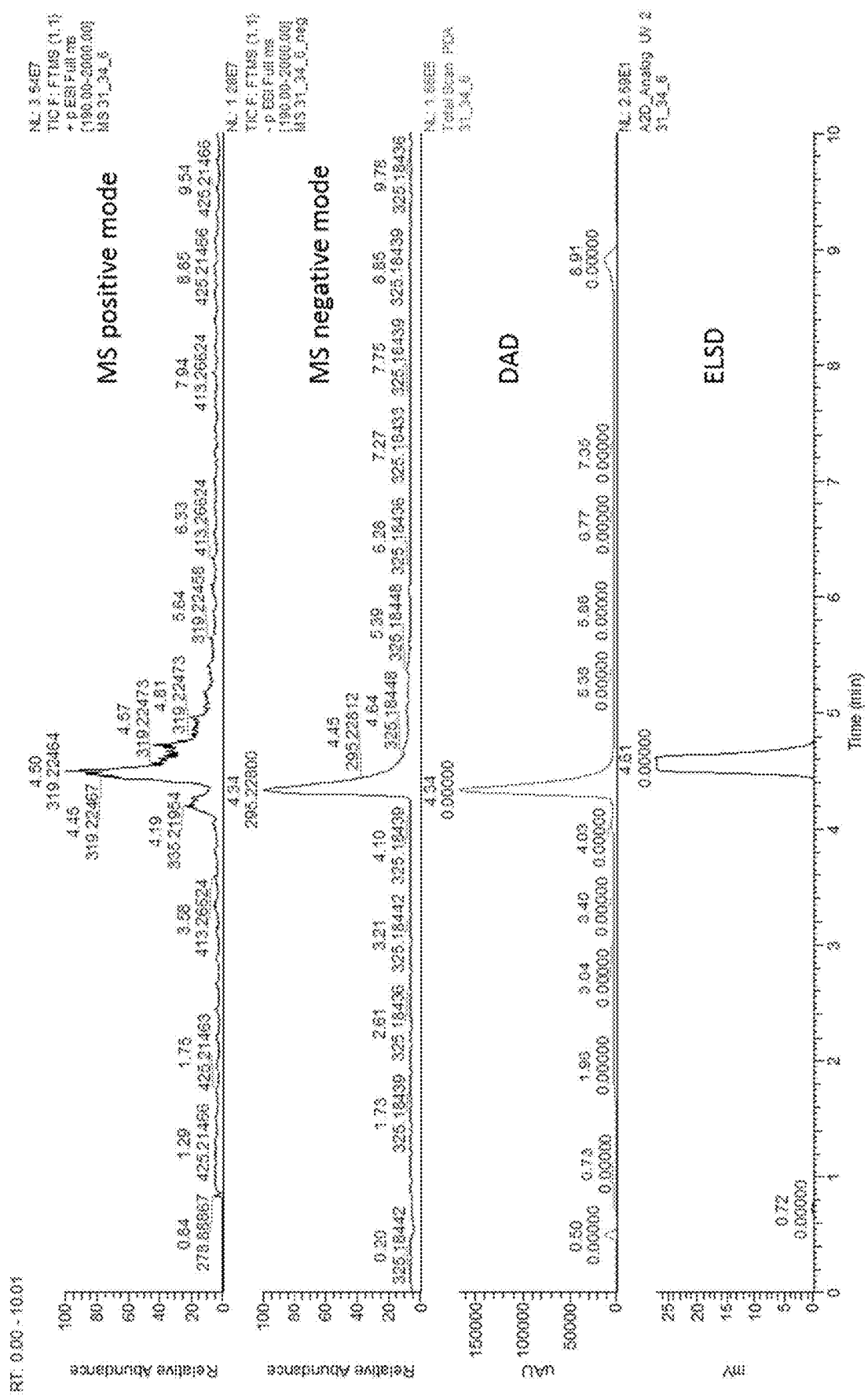
FIG. 20. UPLC-DAD/ELSD/MS chromatograms of compound NC77-31-34-6.
Figure 21:
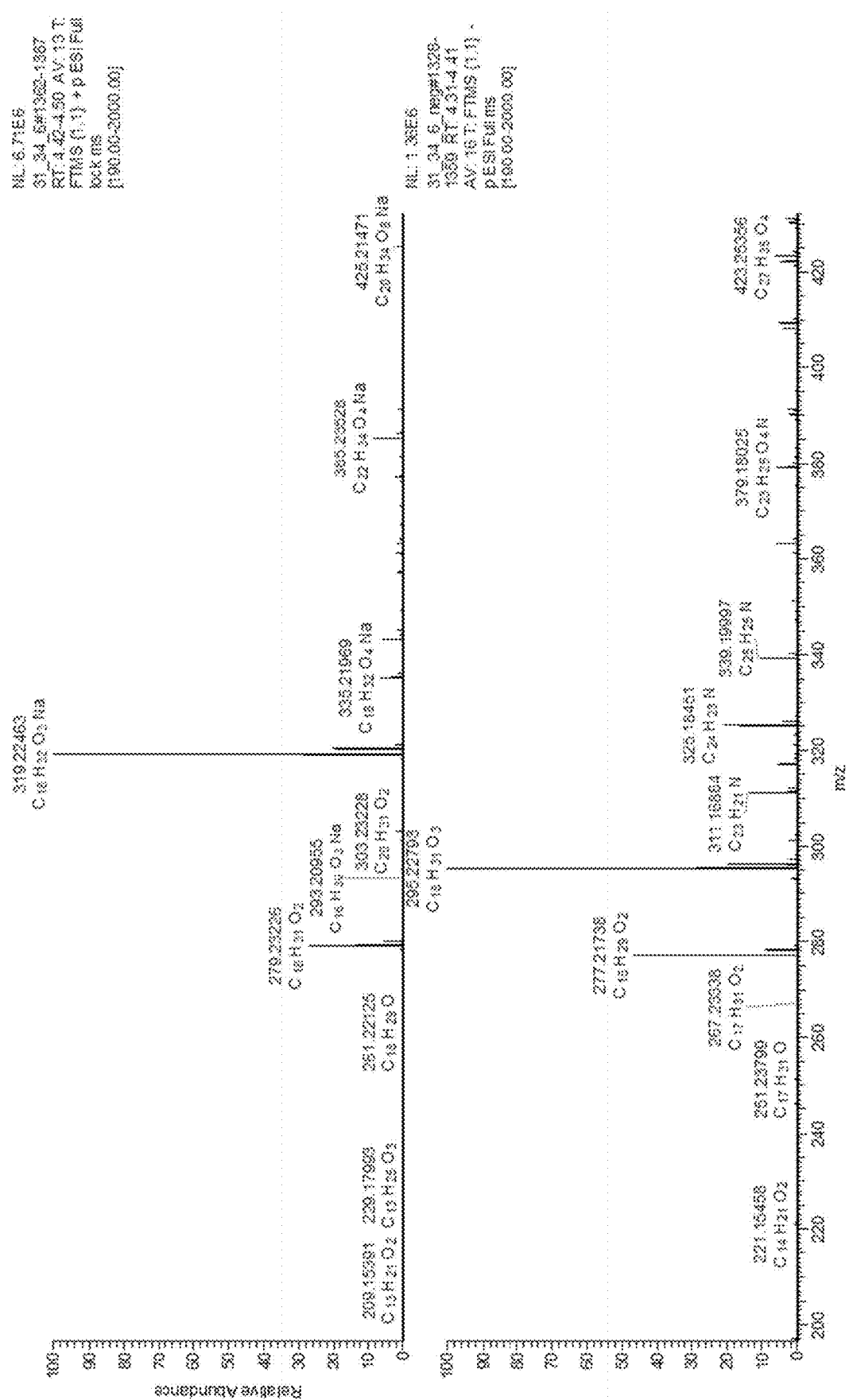
FIG. 21. HRMS spectra of compound NC77-31-34-6.

UPLC-DAD/ELSD/MS analysis clearly showed this to be a pure compound (FIG. 20). HRMS (FIG. 21) revealed molecular ions of MNa$^+$($C_{18}H_{32}O_3$Na$^+$, m/z 319.22463, calculated 319.22492) in positive mode and M$^-$($C_{18}H_{31}O_3^-$, m/z 295.22793, calculated 295.22732) in negative mode, suggesting molecular formula to be $C_{18}H_{32}O_3$.

Figure 22:
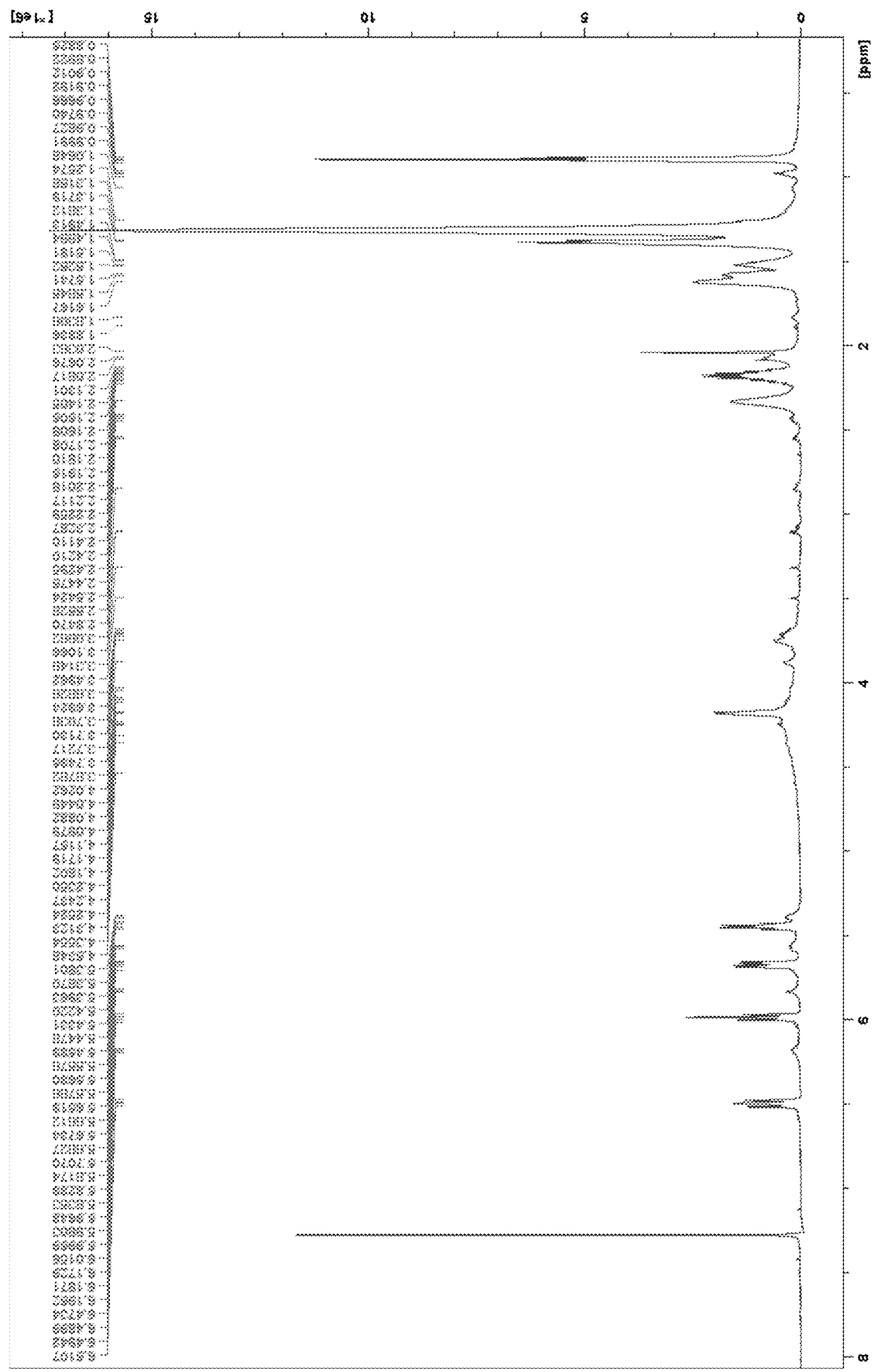
FIG. 22. NMR spectra of compound NC77-31-34-6.

$^1$H-NMR (FIG. 22) and 2D spectra (COSY, TOCSY, HSQC and HMBC, not shown) demonstrated typical unsaturated fatty acid profile, with one oxygenated methine ($\delta_C$ 74.1 and $\delta_H$ 4.18 ppm). The two double bonds are all in trans-form, and also conjugated which are revealed by coupling J value and COSY correlations. The 2D correlations also showed the oxygenated methine is adjacent to one double bond.

Figure 23:
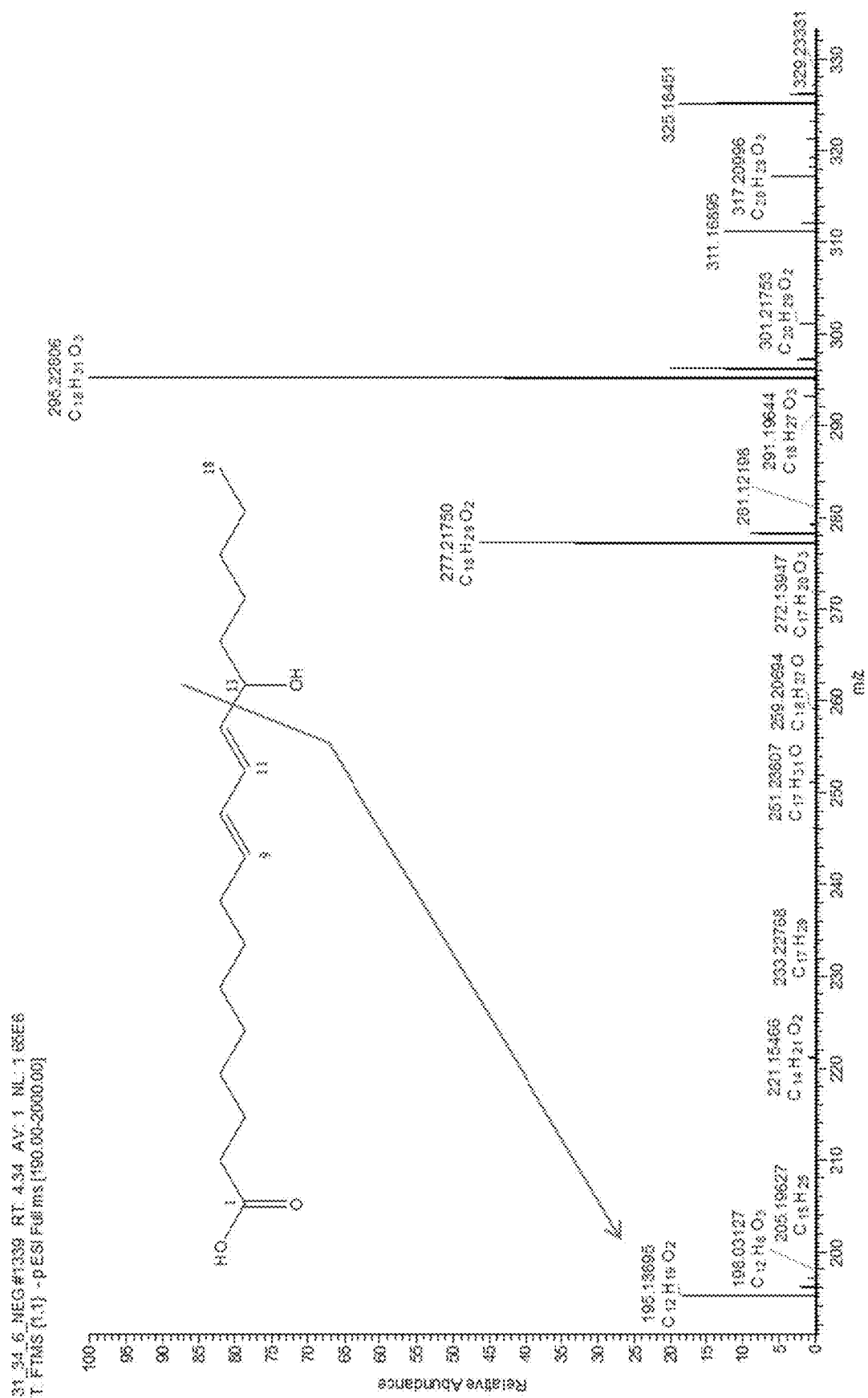
FIG. 23. HRMS of compound NC77-31-34-6.

The important piece of evidence to confirm the location of the functional moiety comprising two conjugated double bonds and oxygenated methine was from HRMS (FIG. 23) fragment ion observed at m/z 195.13895 (calculated mass for $C_{12}H_{19}O_2^+$ 195.13851). Thus, the structure of compound 31-34-6 was determined to be 13-hydroxyoctadeca-9E,11E-dienoic acid as shown below.

Structure of Compound 31-34-6

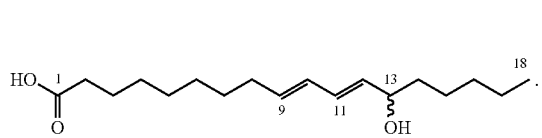

7.2 Compound 38-41-1

Figure 24:
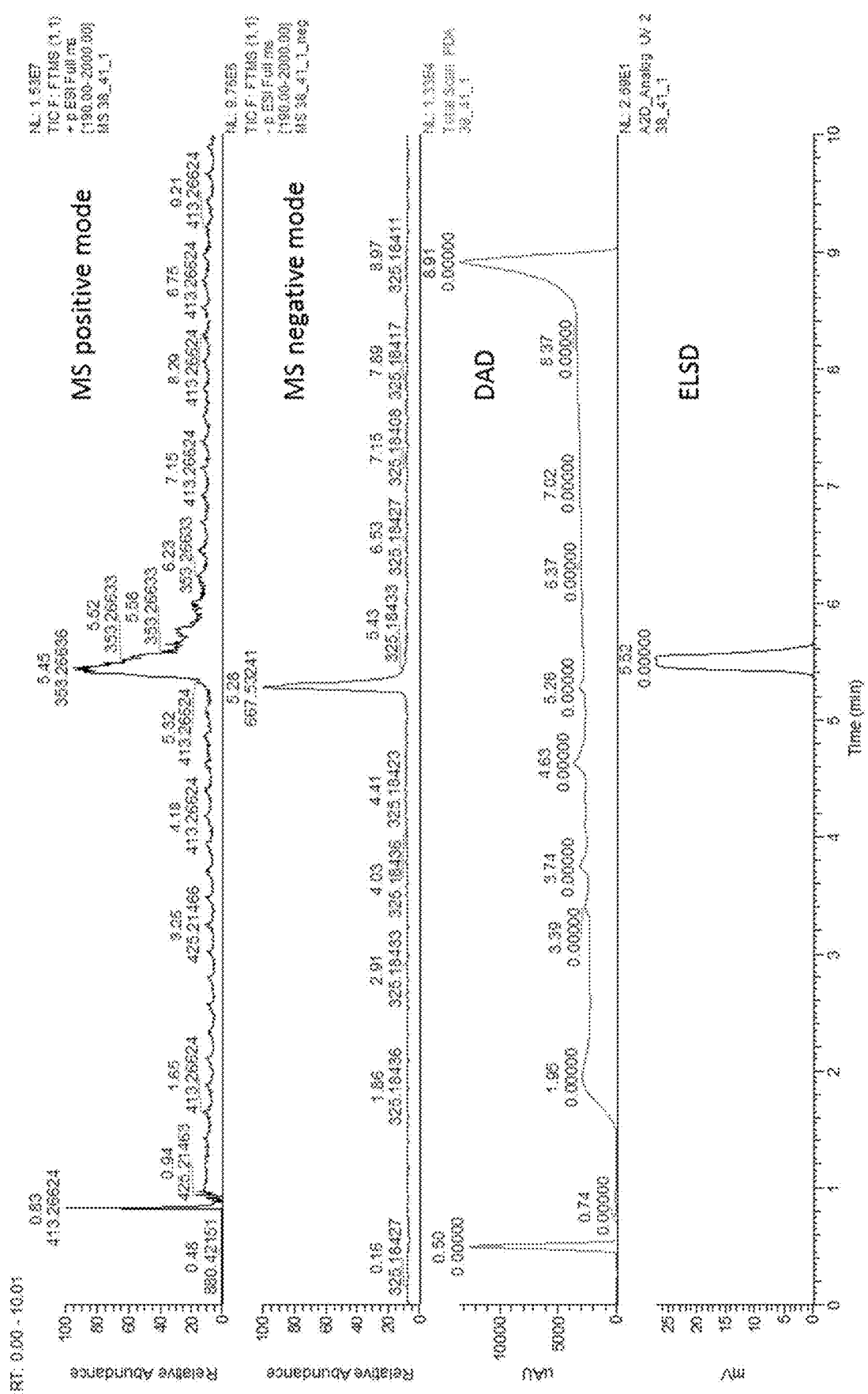
FIG. 24. UPLC-DAD/ELSD/MS chromatograms of compound NC77-38-41-1.
Figure 25:
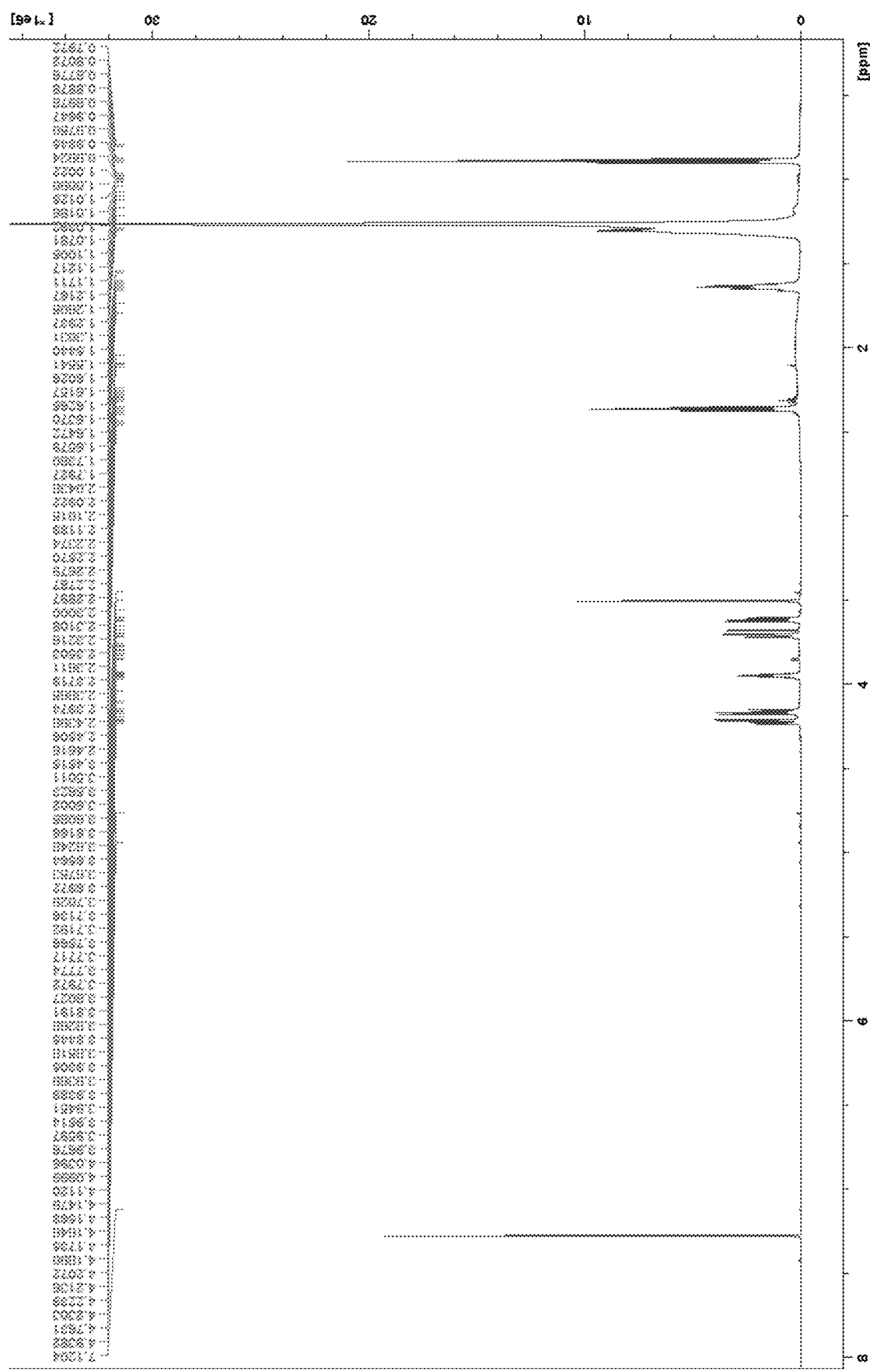
FIG. 25. 1H-NMR spectrum of compound NC77-38-41-1.

This is another fatty acid derivative, with no strong UV absorption implying a saturated FA, but ELSD and MS detectors all showed a pure compound present (FIG. 24). In proton NMR (FIG. 25), monoacylglycerol (MAG) features were clearly shown. The saturated fatty acid is on sn-1/3 position of glycerol, as revealed by the oxygenated methylene and methine peaks and their coupling pattern ($\delta_H$ 4.22 ppm, dd and 4.16 ppm, dd, J=11.7; 6.1 Hz; $\delta_H$ 3.95 ppm, m; $\delta_H$ 3.71 ppm, dd and 3.61 ppm, dd, J=11.5; 6.1 Hz).

Figure 26:
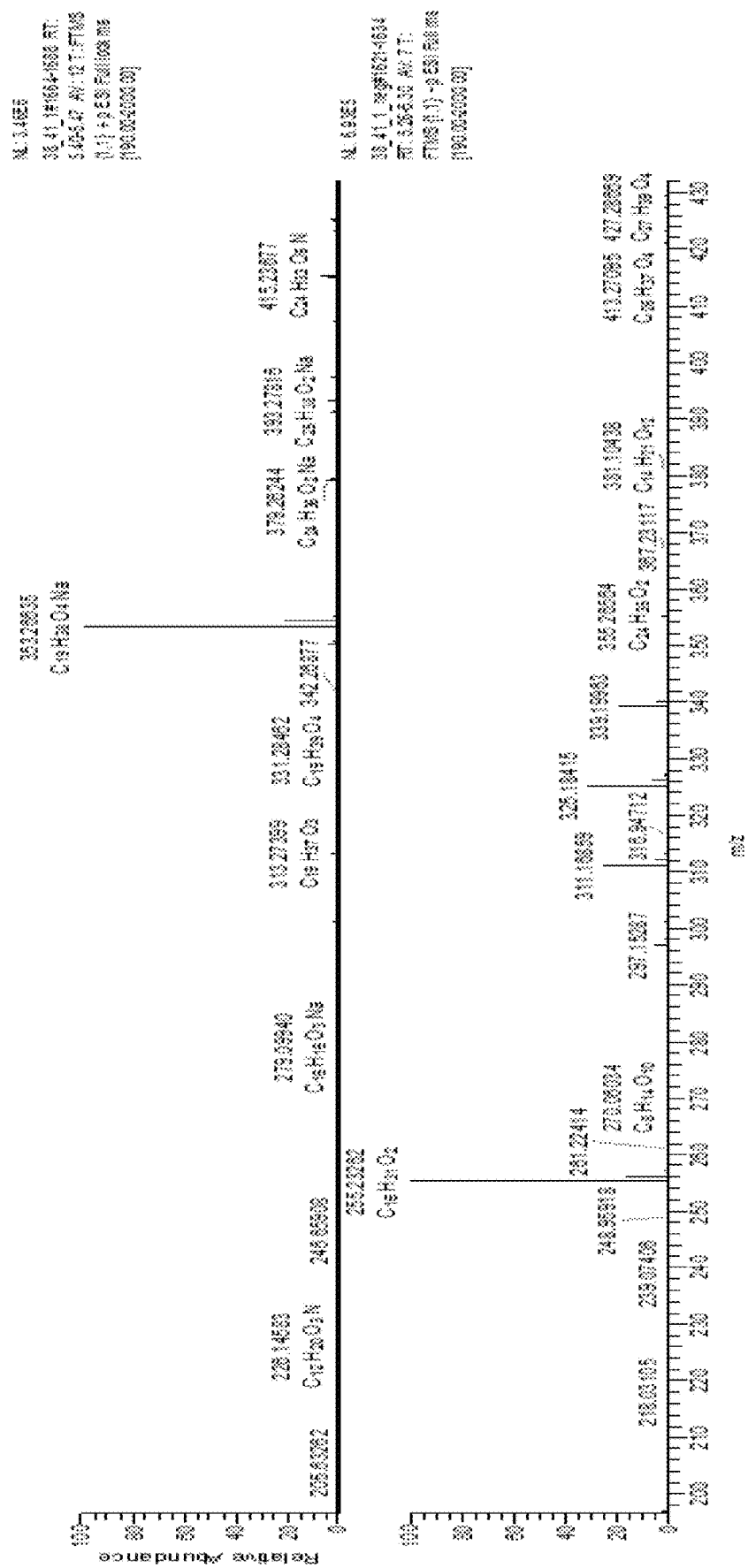
FIG. 26. HRMS of compound NC77-38-41-1.

HRMS (FIG. 26) analysis yielded molecular ion peak m/z 353.26635 (for $C_{19}H_{38}O_4$Na, calculated 353.26678), indicating the molecular formula being $C_{19}H_{38}O_4$. Also in HRMS run in negative mode, a key fragment ion peak of m/z 255.23262 (for $C_{16}H_{31}O_2$, calculated 255.23241) is identified as hexadecanoic acid or palmitic acid (C16:0). As such, compound 38-41-1 is identified as the monoglyceride of palmitic acid, MAG (C16:0), with structure shown below. This was also in agreement with GC-MS analysis of NC77 and NC77-Fr. 4 showing that MAG (C16:0) is the predominant fatty acid species in the samples.

Structure of Compound 38-41-1

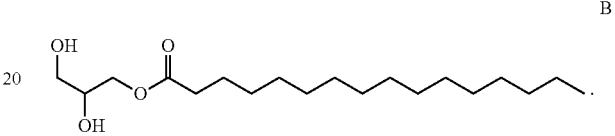

7.3 Compound 38-41-3

Figure 27:
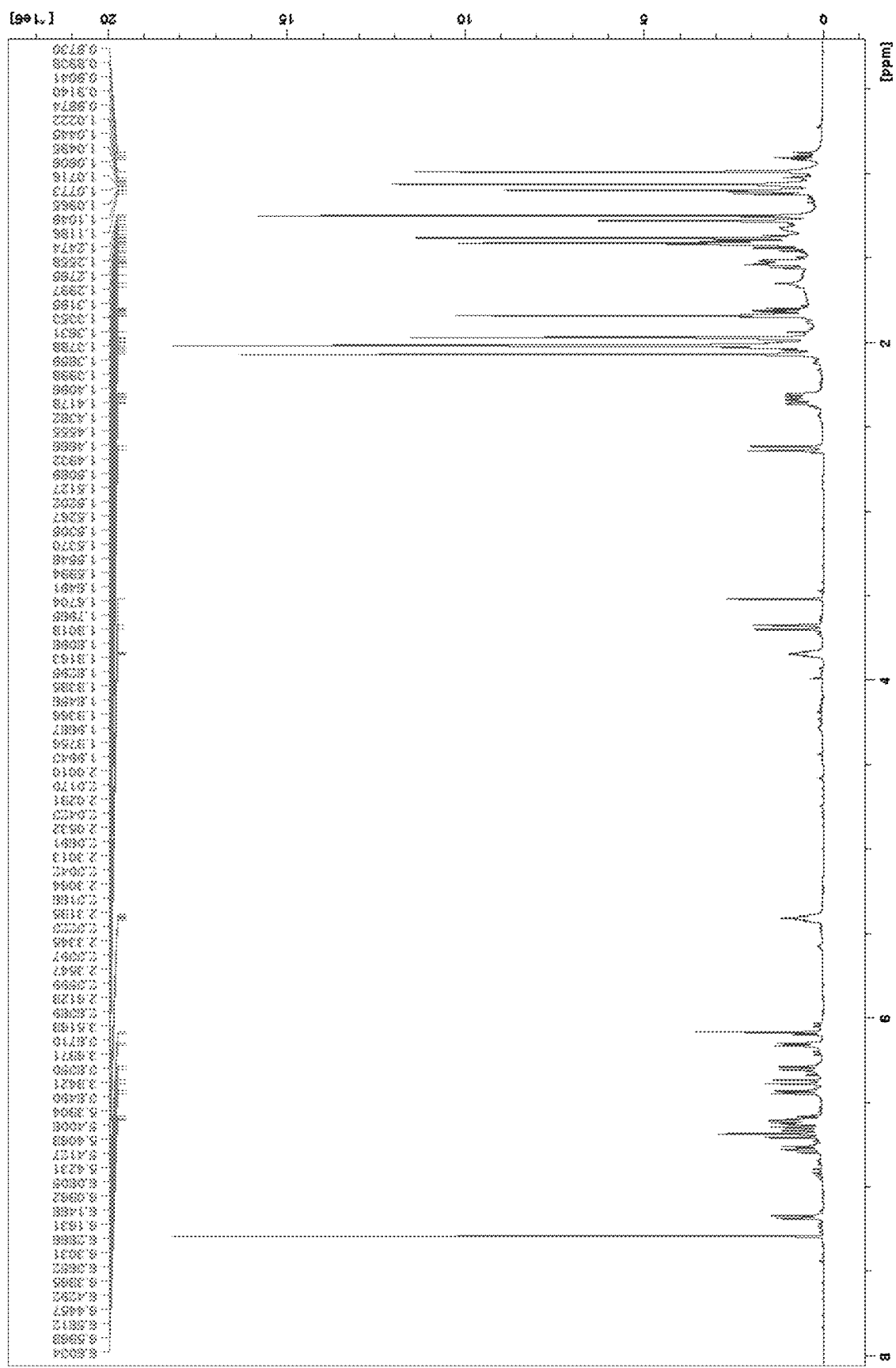
FIG. 27. 1H-NMR spectrum of compound NC77-38-41-3.
Figure 28:
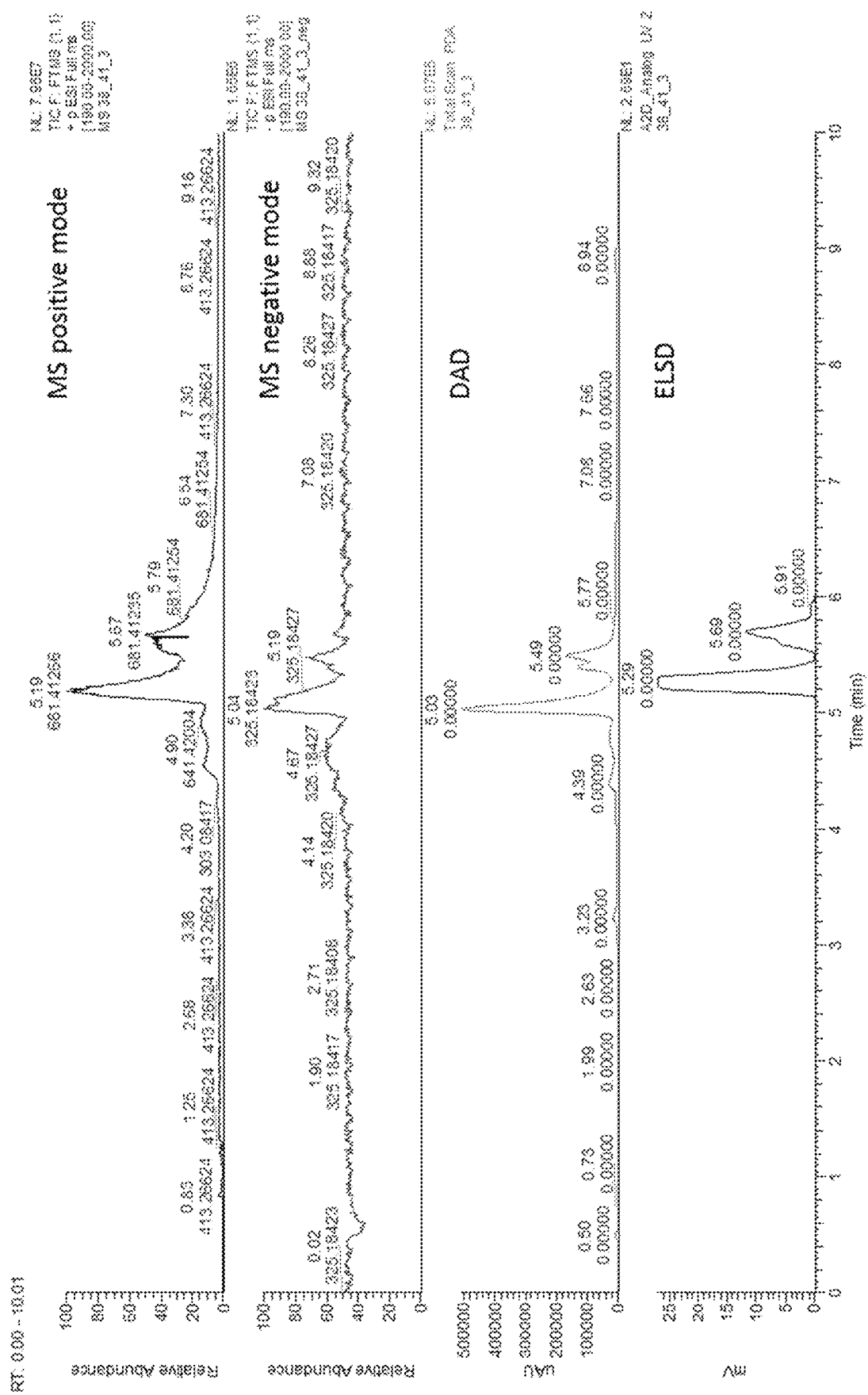
FIG. 28. UPLC-DAD/ELSD/HRMS chromatograms of compound NC77-38-41-3.
Figure 29:
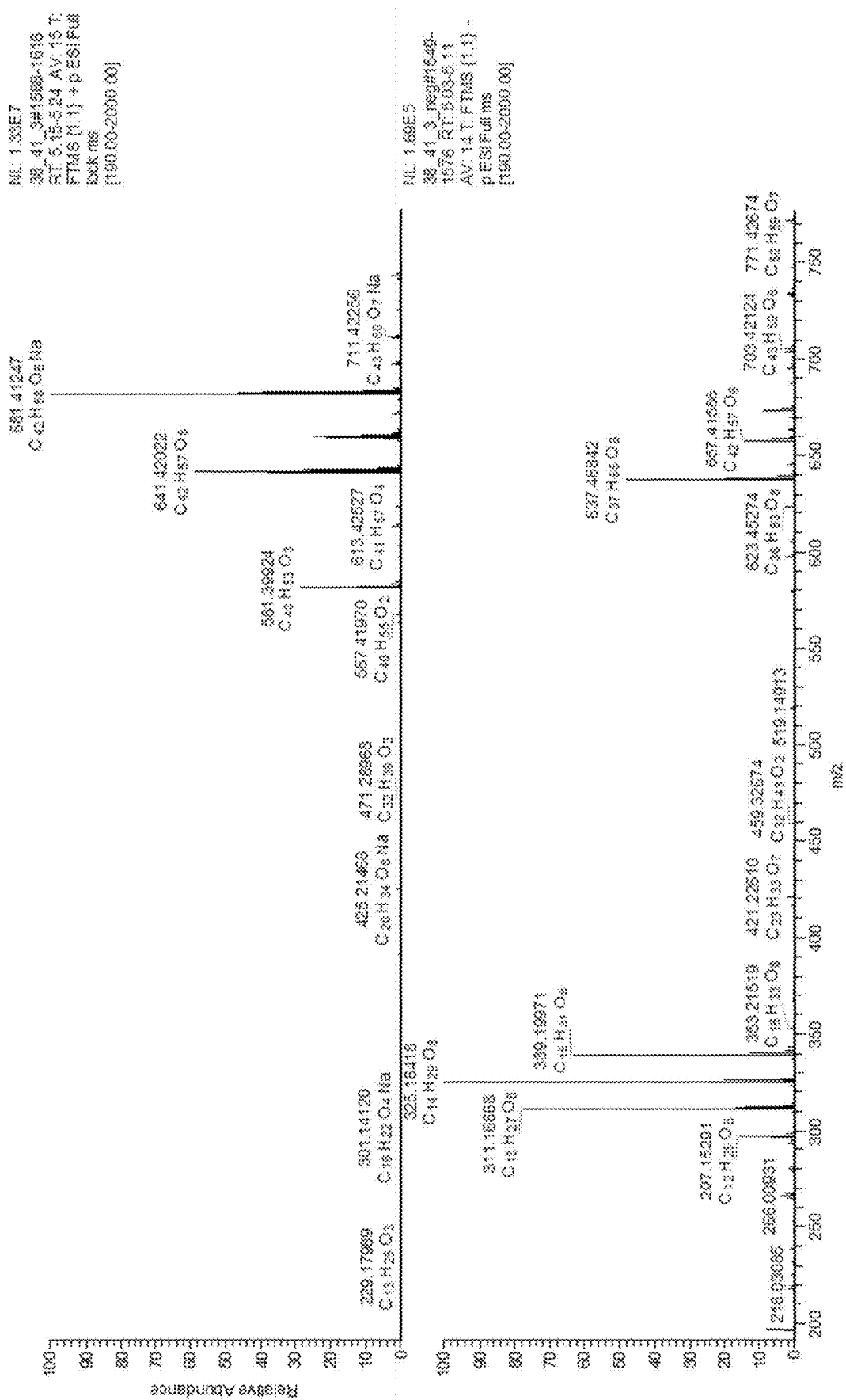
FIG. 29. HRMS of compound NC77-38-41-3.

This compound has characteristic features in $^1$H-NMR spectrum of carotenoids (FIG. 27). The UPLC profile (FIG. 28) shows it contains small amount of impurity. It has a strong DAD absorption so agrees with NMR data on possibility of being a carotenoid. HRMS (FIG. 29) revealed molecular ions of m/z 681.41249 (for $C_{42}H_{58}O_6$Na, calculated 681.41311) in positive mode and m/z 657.41587 (for C42H57O6, calculated 657.41552) in negative mode, indicating C42H58O6 as the molecular formula.

Figure 30:
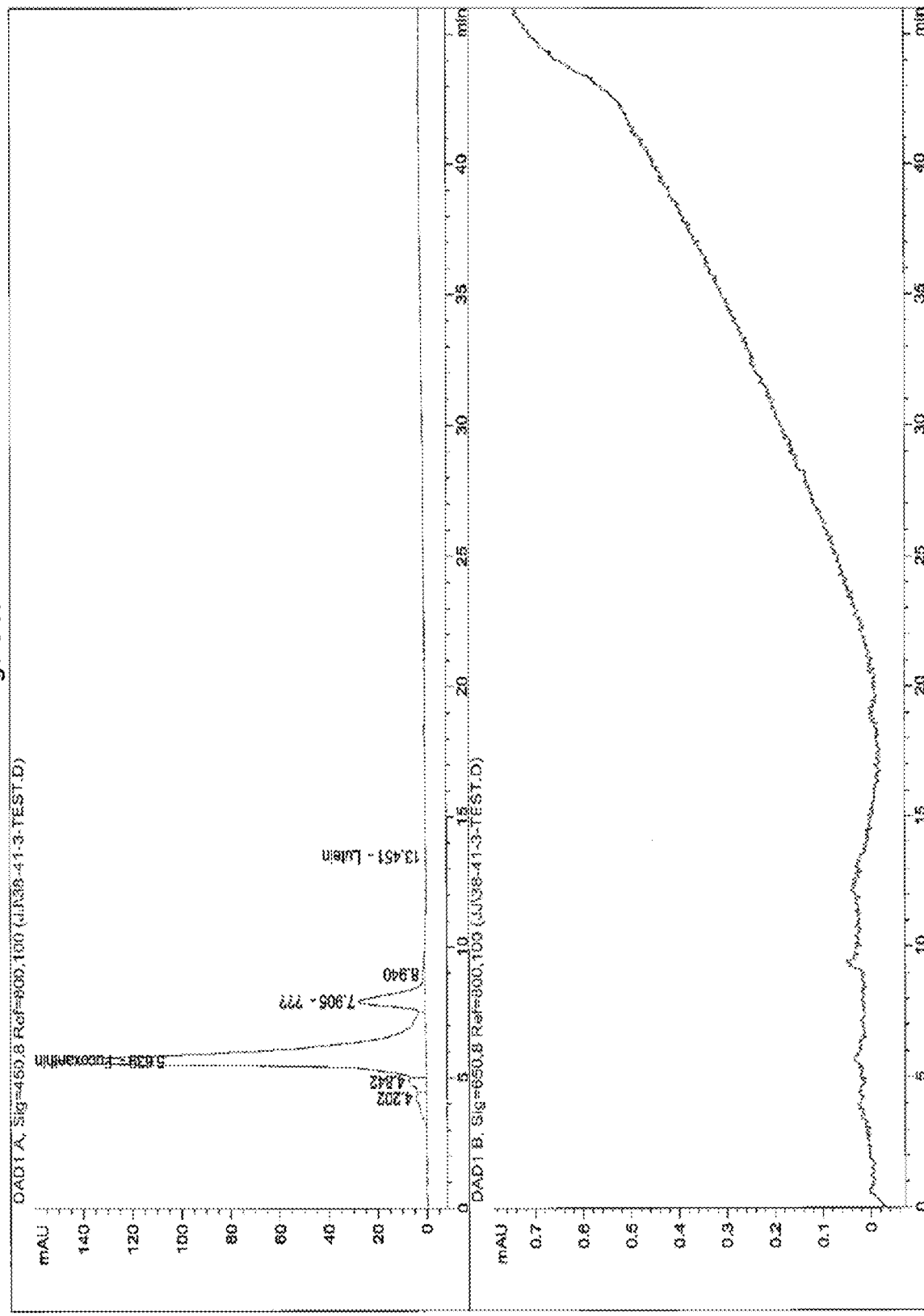
FIG. 30. HPLC profile of compound NC77-38-41-3 showing same retention time as fucoxanthin standard.

In searching literature on this molecular formula, fucoxanthin a carotenoid from marine source was a match. So HPLC/DAD analysis was done to compare this compound to several carotenoid standards, including fucoxanthin, astaxanthin, lutein, zeaxanthin, canthaxanthin, α- & β-carotene. As shown in FIG. 30, compound 38-41-3 is identical to standard fucoxanthin. As such, this compound is identified as fucoxanthin, with the structure shown below:

Structure of Compound 38-41-3

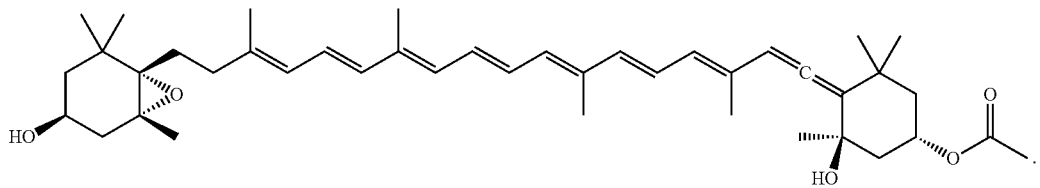

fucoxanthin 7.4 Compound 42-44-1

Figure 31:
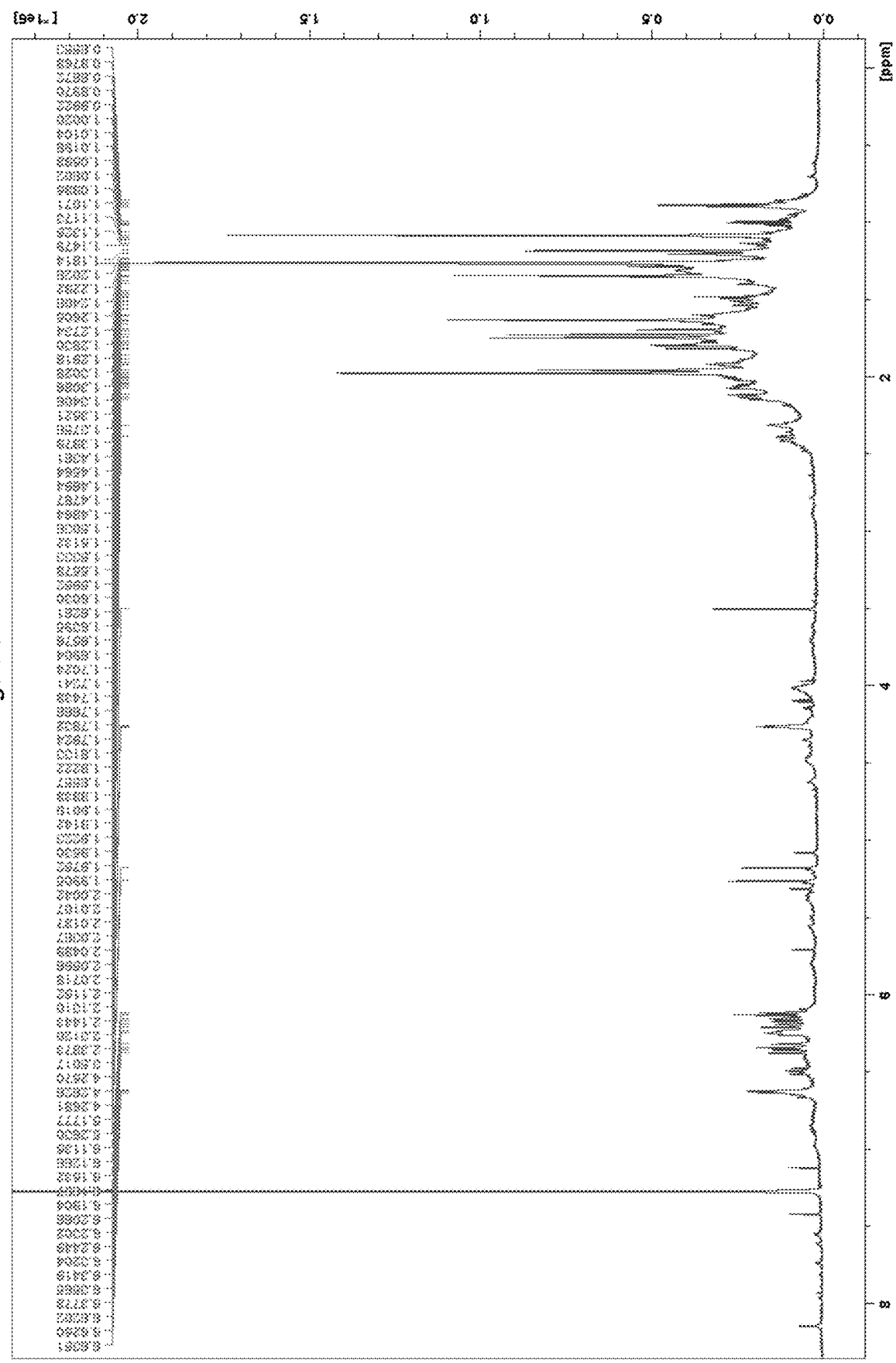
FIG. 31. 1H-NMR spectrum of compound NC77-42-44-1.
Figure 32:
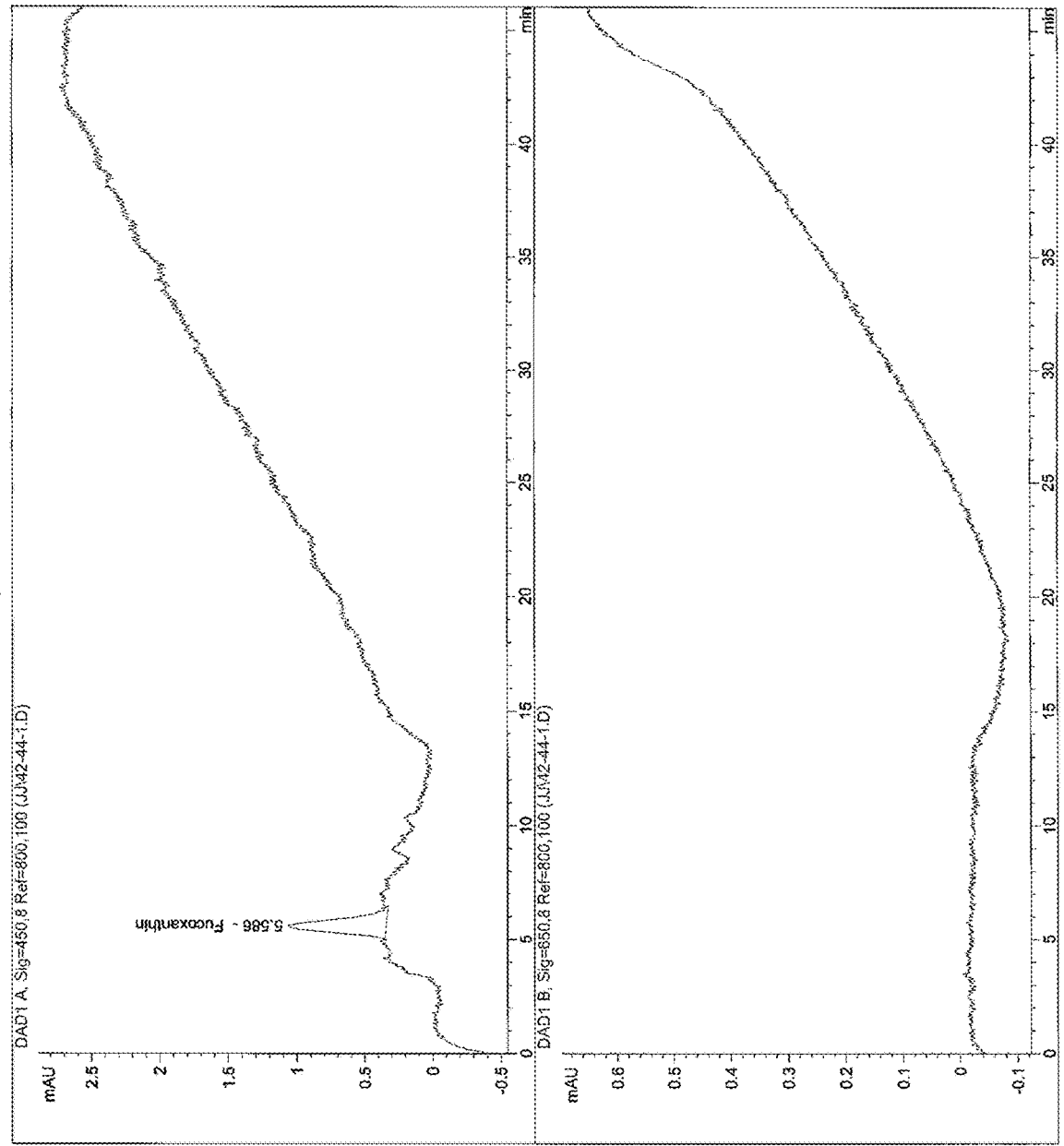
FIG. 32. HPLC-DAD chromatogram of sample NC77-42-44-1.
Figure 33:
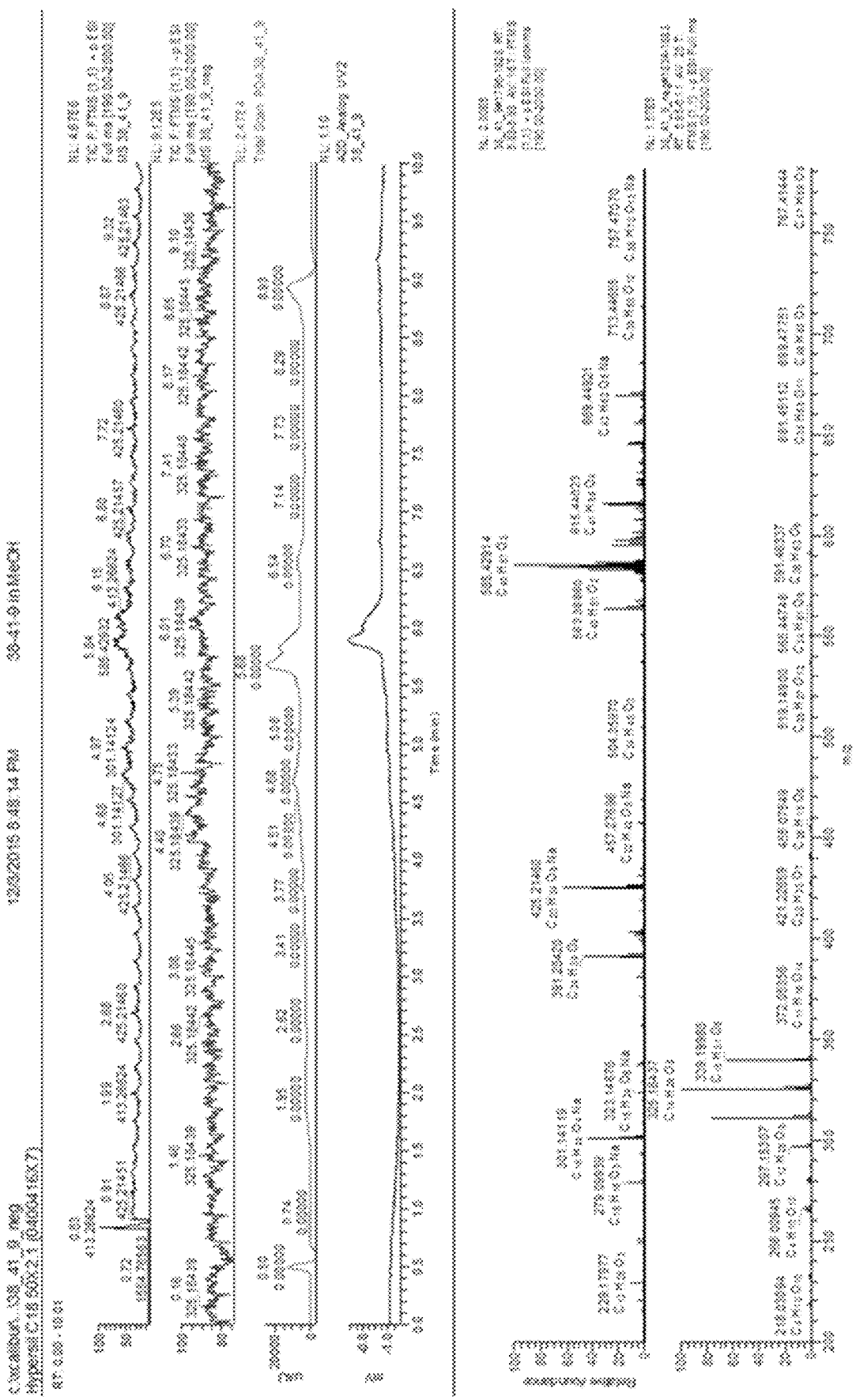
FIG. 33. UPLC-DAD/ELSD/MS chromatograms of compound NC77-42-44-1
FIG. 34. Summary flowchart of fractionation, purification and in vitro testing of compounds from NC77.

Similarly, the 1H-NMR spectrum (FIG. 31) indicated possible carotenoid structure. Also, HPLC-DAD analysis (FIG. 32) has shown similarity of this compound to fucoxanthin based on retention time. UPLC-DAD/ELSD/HRMS (FIG. 33) showed two main peaks but also with other minor components. In HRMS spectrum, one ion m/z 597.43026 (for C41H57O3, calculated 597.43077) may provide indication that a carotenoid with molecular formula C41H56O3 is present.

The search of this molecular formula for carotenoids in SciFinder generated the following possibilities of structure for a component in sample 42-44-1:

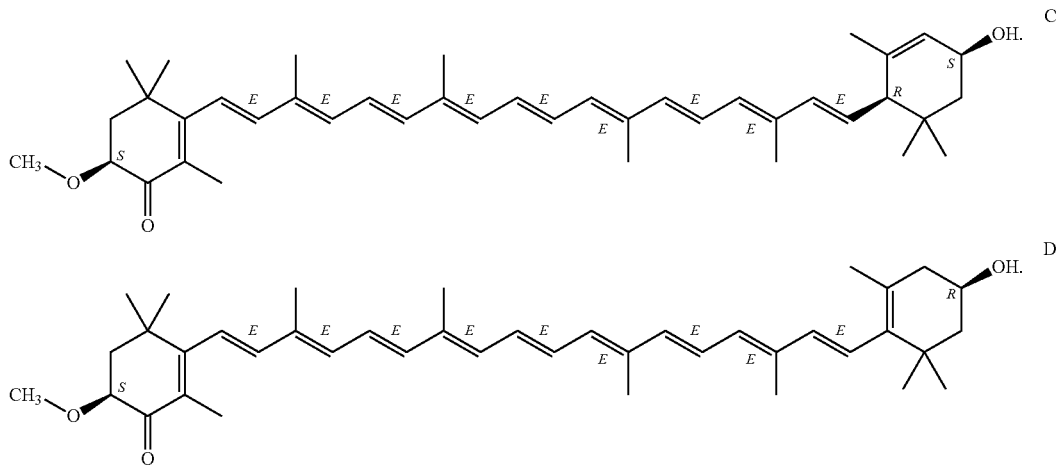

SUMMARY

Figure 34:
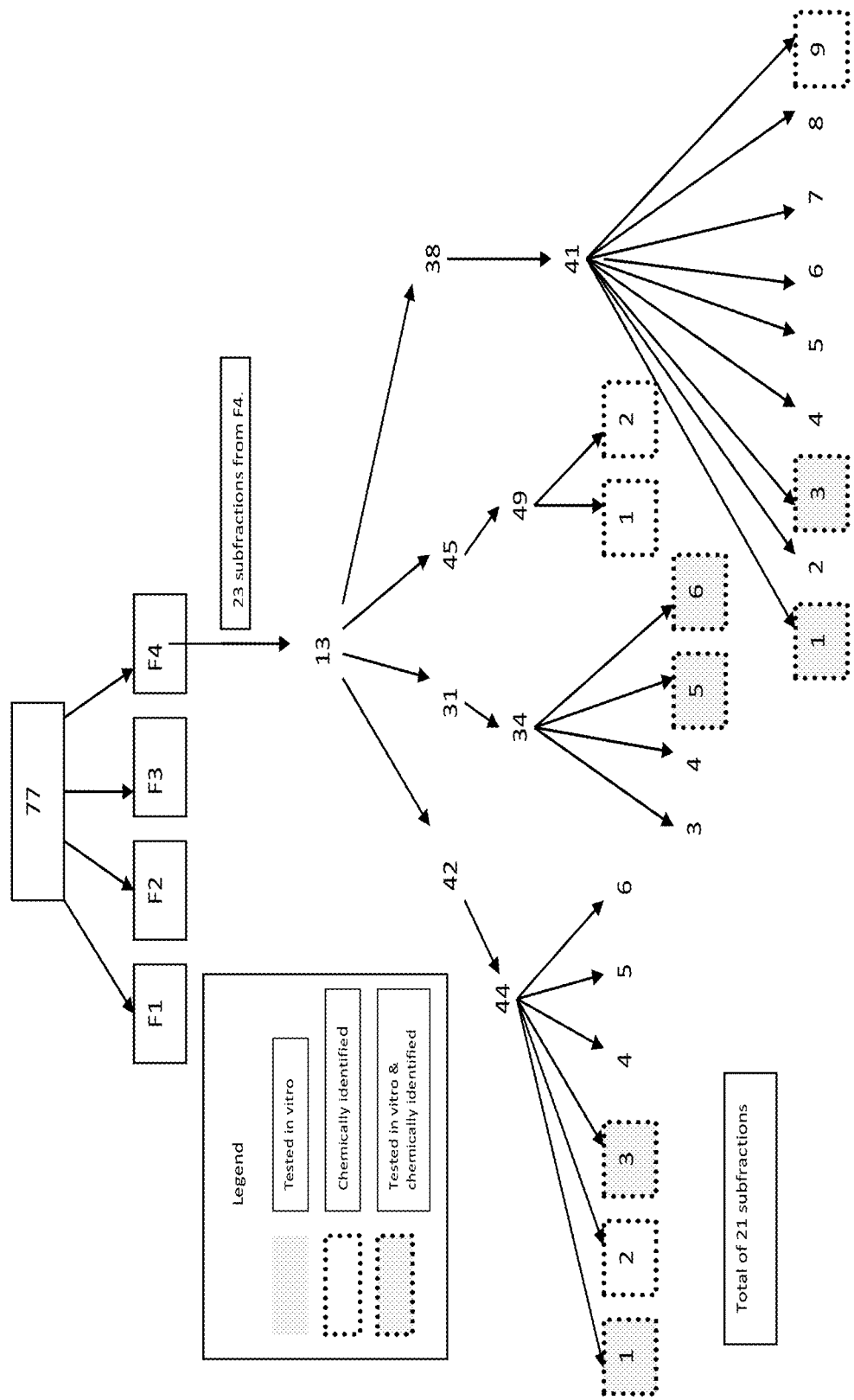

In summary, the fractionation steps from NC77 are shown in FIG. 34. In short, 21 subfractions were isolated from fraction F4. From subfraction 13, 4 further subfractions were obtained, which were further subfractionated finally in 21 subfractions that were identified. Six (6) of these 21 subfractions were tested in vitro, whereas 10 of 21 subfractions were chemically identified. Three (3) subfractions contained pure compounds. Finally, subfractions 77-42-44-1 and 77-42-44-2 require further purification to isolate its 2 compounds. The structure of these compounds and their in vitro anti-cancer activity are listed in Table 7.

TABLE 7

| Sub-fraction | Structure | | | | | | | | Mixed/Pure |
|---|---|---|---|---|---|---|---|---|---|
| 77-31-34-6 A | 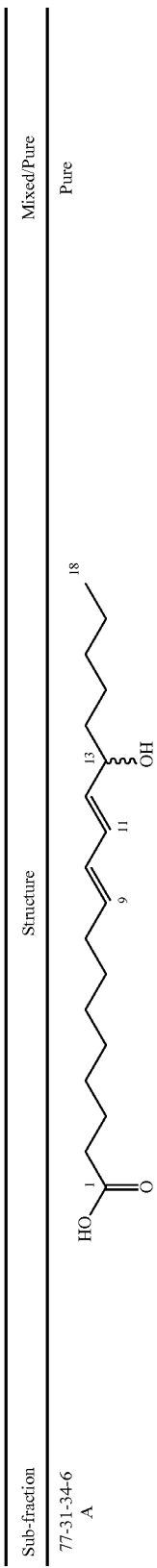 A | | | | | | | | Pure |
| | Average cell viability: | | | | | | | | |
| | Vehicle cont-DMSO | 1% | 96 | 86 | 98 | 93 | 92 | 91 | 88 |
| | Positive cont-SDS | 250 ug/ml | 8 | 11 | 4 | 9 | 14 | 5 | 16 |
| | | ug/mL | PC3 | A549 | U373 | SKOV | MDA-MB | CCD | THP-1 |
| | Positive cont-SDS | 250 ug/mL | 5 | 7 | 4 | 53 | 12 | 13 | 6 |
| | | | 0.08 | 0.13 | 0.05 | 0.10 | 0.16 | 0.06 | 0.18 |
| | | | AVG | AVG | AVG | AVG | AVG | AVG | AVG |
| | | | 0.00 | 0.01 | 0.03 | 0.00 | 0.00 | 0.00 | 0.01 |
| | | | ERROR | ERROR | ERROR | ERROR | ERROR | ERROR | ERROR |
| | | | PC3 | A549 | U373 | SKOV | MDA-MB | CCD | THP-1 |
| | Fold change in viability: | | | | | | | | |
| | | 1.00 | 0.05 | 0.04 | 0.00 | 0.57 | 0.13 | 0.14 | 0.07 |
| 77-38-41-1 B | 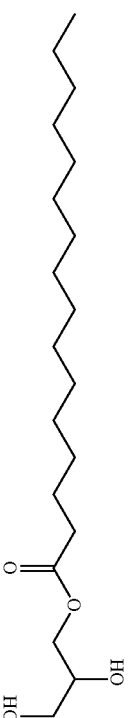 B | | | | | | | | Pure |
| | Average cell viability: | | | | | | | | |
| | Vehicle cont-DMSO | 1% | 96 | 86 | 98 | 93 | 92 | 91 | 88 |
| | Positive cont-SDS | 250 ug/ml | 8 | 11 | 4 | 9 | 14 | 5 | 16 |
| | | ug/mL | PC3 | A549 | U373 | SKOV | MDA-MB | CCD | THP-1 |
| | | 100 | 15 | 26 | 7 | 22 | 28 | 72 | 105 |
| | | 50 | 52 | 69 | 13 | 52 | 64 | 78 | 96 |

TABLE 7-continued

| Sub-fraction | Structure | | | | | | | | | | | | | Mixed/Pure | |
|---|---|---|---|---|---|---|---|---|---|---|---|---|---|---|---|
| | | | | | | Fold change in viability: | | | | | | | | | |
| Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| | | PC3 | | A549 | | U373 | | SKOV | | MDA-MB | | CCD | | THP-1 | |
| | ug/mL | AVG | ERROR | AVG | ERROR | AVG | ERROR | AVG | ERROR | AVG | ERROR | AVG | ERROR | AVG | ERROR |
| | 100 | 0.16 | 0.02 | 0.30 | 0.02 | 0.07 | 0.00 | 0.24 | 0.01 | 0.30 | 0.03 | 0.79 | 0.02 | 1.19 | 0.05 |
| | 50 | 0.54 | 0.08 | 0.81 | 0.03 | 0.13 | 0.01 | 0.56 | 0.07 | 0.70 | 0.02 | 0.85 | 0.03 | 1.10 | 0.04 |
| 77-42-44-1 C, D | 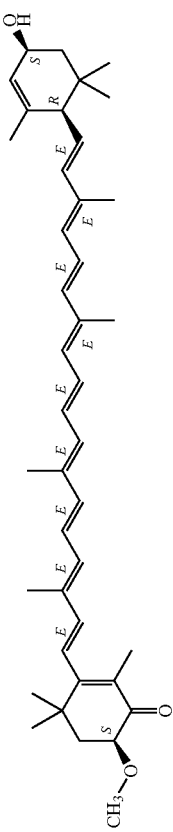 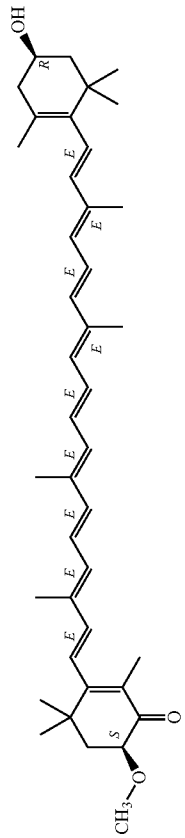 C D | | | | | | | | | | | | | Mixed | |

| | | | | | | Average cell viability: | | | | | | | | | |
|---|---|---|---|---|---|---|---|---|---|---|---|---|---|---|---|
| Vehicle cont-DMSO | 1% | | | | | | | | | | | | | | |
| Positive cont-SDS | 250 ug/ml | | | | | | | | | | | | | | |
| | ug/mL | 100 | | 96 8 | | 86 11 | | 93 9 | | 92 14 | | 91 5 | | 88 16 | |
| | | PC3 | | A549 | | U373 | | SKOV | | MDA-MB | | CCD | | THP-1 | |
| | 100 | 17 | | 65 | | 7 | | 66 | | 27 | | 25 | | 44 | |
| | | | | | | Fold change in viability: | | | | | | | | | |
| Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| | | PC3 | | A549 | | U373 | | SKOV | | MDA-MB | | CCD | | THP-1 | |
| | ug/mL | AVG | ERROR | AVG | ERROR | AVG | ERROR | AVG | ERROR | AVG | ERROR | AVG | ERROR | AVG | ERROR |
| | 100 | 0.17 | 0.02 | 0.76 | 0.03 | 0.07 | 0.01 | 0.71 | 0.05 | 0.29 | 0.02 | 0.27 | 0.01 | 0.50 | 0.01 |

Although the structures of compounds C & D are known in the art, to our knowledge, this is the first instance where these compounds have been shown to have anti-cancer activity.

Example 8. Isolation and Structure Elucidation of Compounds from NC169 (*Polysiphonia flexicaulis*)

Figure 35:
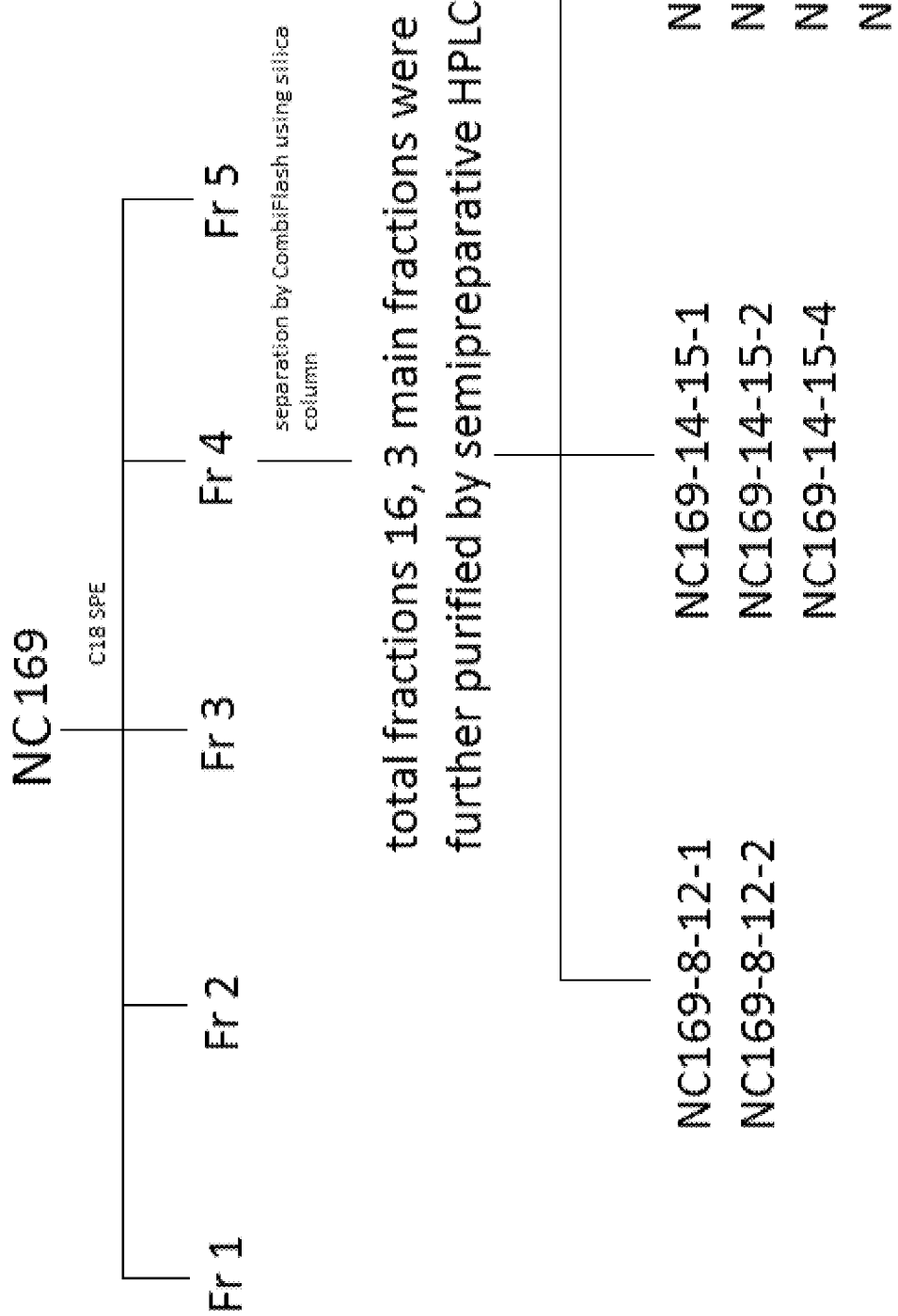
FIG. 35. Flowchart of fractionation and purification of main components from NC169.

The fractionation steps from NC169 are shown in FIG. 35. In short, 16 subfractions were collected from F4, of which 3 were purified, subfractions 8, 14 and 20. From subfractions 14, subsubfraction 15 was isolated, of which 3 pure compounds were obtained: compounds #1, 2 and 4. Subsubfraction 22 was isolated from subfraction 20, from which 3 compound were purified: compounds 3, 4 and 5.

8.1. Fractionation and Purification of Main Components from NC169

3.06 g of NC169 were dissolved in methanol, mixed with celite and dried using rotavap. The sample was then loaded on pre-conditioned and equilibrated Thermo Scientific SPE column (HYPERSEP C18 20G). Five fractions were obtained by eluting the SPE column with 5% methanol (Fr. 1), 25% methanol (Fr. 2), 50% methanol (Fr. 3), methanol (Fr. 4) and methanol/dichloromethane (1:1) (Fr. 5). Fr. 4 (0.56 g) was subjected to further fractionation based on previous bioassay result.

In the second stage fractionation, Fr. 4 was dissolved in dichloromethane/methanol and mixed with celite and dried. The sample was loaded on 24 g Teledyne ISCO High Performance GOLD silica gel column and eluted with dichloromethane/methanol on CombiFlash® Rf, Teledyne ISCO. The eluting solvent gradient (A and B) was as the following: 0% B for 2 CV (column volume) then to 40% B for 15 CV and kept at 40% B for 2 CV, to 100% B for 2 CV and kept at 100% B for 2 CV. Total elution volume was 23 CV. A is dichloromethane and B is methanol/dichloromethane (1:1). Fractions were monitored by TLC and selectively combined and dried using rotavap and Genevac.

Based on HPLC chromatograms, three sub-fractions were further purified using semi preparative HPLC (Agilent). The column used was ZORBAX SB-C18 (9.4×50 mm, 5 μm) and the mobile phase was water/acetonitrile. Eluting gradient varied for different samples so to optimize separation. The column temperature was at 55° C. and flow rate 5 mL/min.

8.2 Structure Characterization of Main Components from Bioactive Fraction (Fr. 4)
8.2.1. Sample Preparation and Analysis:
FAME Preparation and GC-MS Analysis:

Crude extract and fraction 4 of NC169 (approx. 2 mg) were used for GC-MS analysis. Samples were added 1 mL sodium methoxide solution and 1 mL hexane, with cap closed. The reaction vials were put in a heating block (80° C.) for 15 min shaking vials with hand at 5 min intervals. Added 1 mL saturated NaCl solution after cooling to room temperature and shook by hand several times. The reaction vials were then centrifuged for 20 min at 2,000 rpm. The upper solutions were transfer to GC vials. For GC-MS analysis, Agilent 6890 with 5973 Mass Selective Detector were used. The column was Agilent DB-23 (59 m×0.25 mm, 0.15 μm), injection volume 1 μL. Oven program: 50° C. for 1 min, 25° C./min to 170° C., 2.75° C./min to 215° C. (hold 12 min), 40° C./min to 230° C. (hold 3.11 min). Total runtime was 37.65 min. FID temperature was 280° C., hydrogen flow 40 mL/min, air flow 400 mL/min, makeup flow N2 20 mL/min. Split ratio was 2:1. Carrier gas was helium and kept at constant pressure (30 psi). MSD ionization mode was EI, interface temperature 250° C., MS source 230° C., MS Quad 150° C. Mass range was 50-600 m/z.

UPLC-DAD/HRMS and MS/MS:

The following instruments were used for LC-UV-HRMS data acquisition: Accela 1250 pump (Thermo Fisher Scientific); Exactive benchtop Orbitrap mass spectrometer (Thermo Fisher) equipped with heated electrospray ionization probe; Ultimate 3000 DAD (Thermo Scientific Dionex). Separation was carried out on a Hypersil C8 column (100× 2.1 mm, 1.9 μm, Thermo) using mobile phase consisted of (A) 10 mM ammonium acetate pH 5, (B) acetonitrile and (C) isopropanol/acetonitrile (80/20 v/v) with gradient as below. Flow-rate was at 500 μL/min, column temperature at 40° C.

| Time | A | B | C |
| --- | --- | --- | --- |
| 0 | 30 | 70 | 0 |
| 5 | 0 | 100 | 0 |
| 6 | 0 | 95 | 5 |
| 12 | 0 | 0 | 100 |
| 14.5 | 0 | 0 | 100 |
| 15.5 | 0 | 100 | 0 |
| 16.0 | 0 | 100 | 0 |
| 17.0 | 30 | 70 | 0 |
| 20.0 | 30 | 70 | 0 |

NMR

The sample were reconstituted in 600 L of $CDCl_3$ with 20 μL $CD_3OD$ and were trasnferred to 5 mm NMR tubes. All spectra were run on a Bruker 500 MHz spectrometer whereas 2D NMR data were obtained from Bruker Avance III 700 MHz spectrometer equipped with cooled probe operating at 16K.

8.3. Characterization of Main Components from NC169 F4

Preliminary profiling work done previously indicated that lipids were the main components in NC169 Fr. 4. As such, GC-MS analysis was done to understand the fatty acids composition in this extract and its bioactive fraction.

NC169 and NC169-Fr. 4 have similar fatty acid profile in GC/FID chromatograms (not shown). The retention time and tentative identification based on NIST GC-MS database matching are shown in Table 8. The major fatty acid is shown to be palmitic acid (C16:0) and eicosapentaenoic acid (EPA, C20:5).

TABLE 8

Tentative identification of fatty acids using GC-MS analysis of NC169 and NC169-Fr. 4

| RT (min) | Compounds |
| --- | --- |
| 11.31 | Methyl tetradecanoate (Myristic acid, C14:0) |
| 13.46 | Hexadecanoic acid, methyl ester (Palmitic acid, C16:0) |
| 13.85 | 9-Hexadecenoic acid, methyl ester, (Z)- (Palmitoleic acid, C16:1) |
| 16.28 | Octadecanoic acid, methyl ester (Stearic acid, C18:0) |
| 16.70 | 9 (or 11)-Octadecenoic acid, methyl ester (C18:1) |
| 16.82 | 11 (or 9)-Octadecenoic acid, methyl ester (C18:1) |
| 17.52 | 9,12-Octadecadienoic acid (Z,Z)-, methyl ester (Linoleic acid, C18:2) |
| 22.16 | 5,8,11,14-Eicosatetraenoic acid, methyl ester, (all-Z)- (Arachidonic acid, C20:4) |
| 23.52 | Methyl eicosa-5,8,11,14,17-pentaenoate (EPA, C20:5) |

Figure 36:
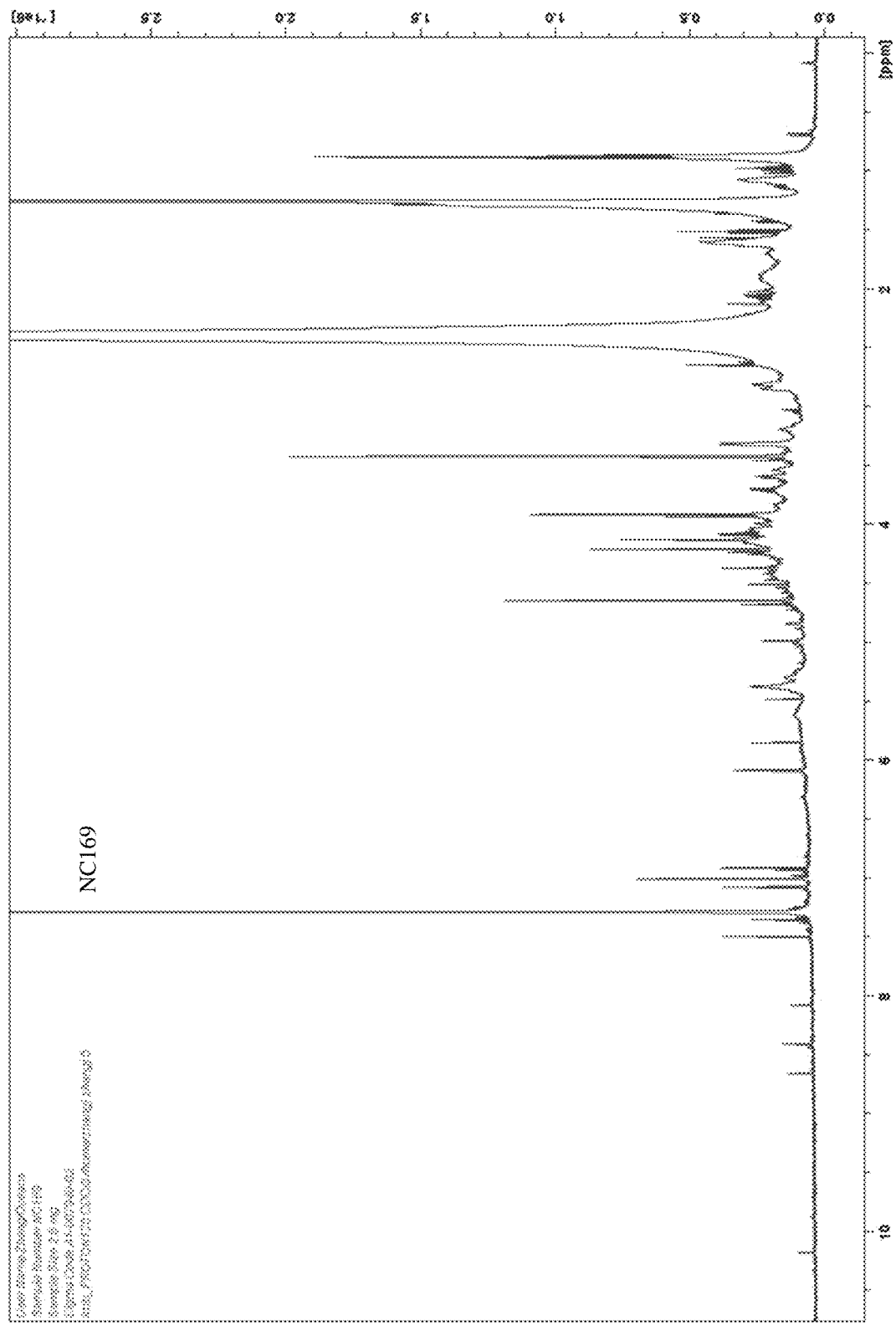
FIG. 36. Proton NMR spectrum of NC169.
Figure 37:
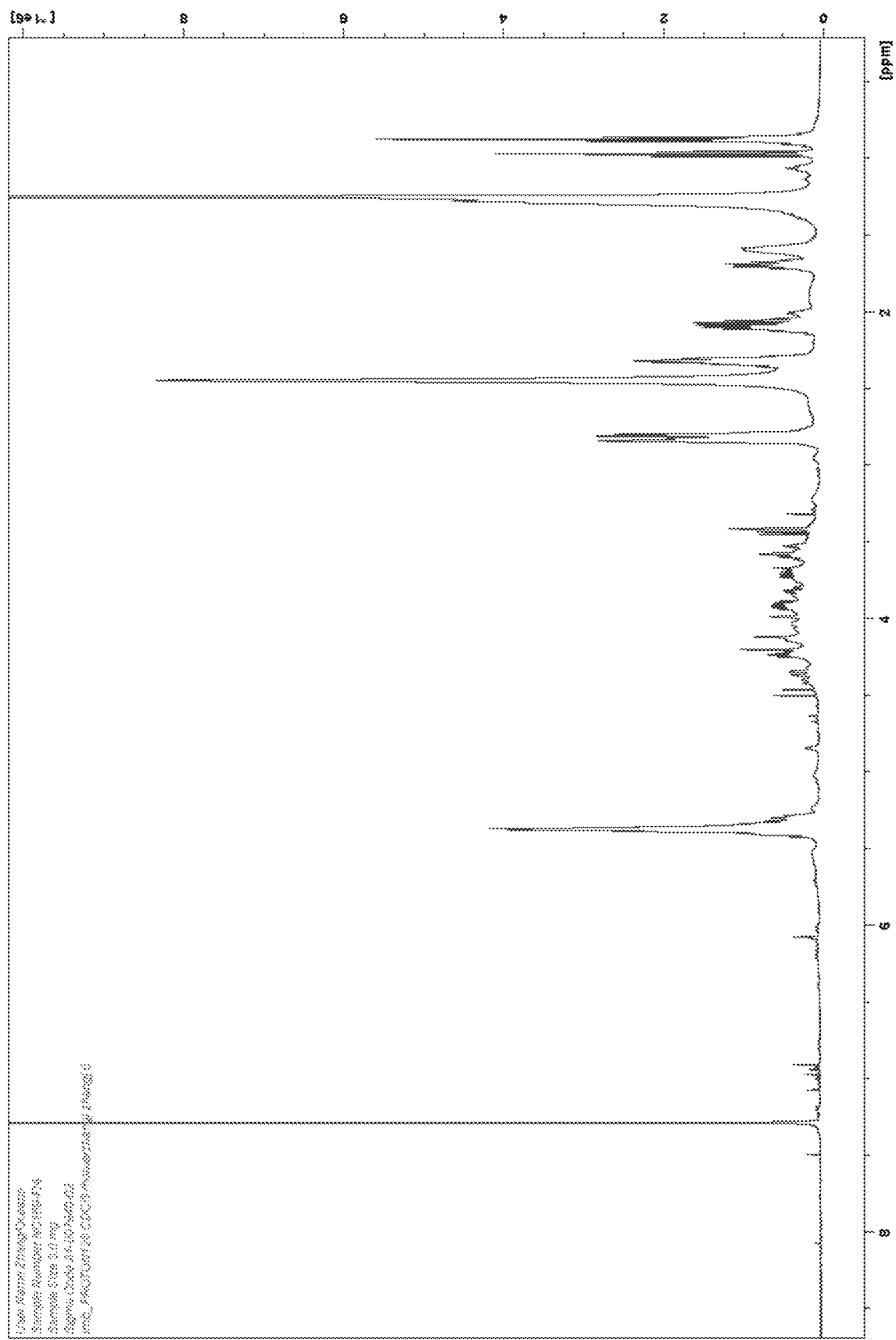
FIG. 37. Proton NMR spectrum of NC169-F4.

Proton NMR spectra of NC169 and NC169-F4 reveal the presence of lipids as major components (FIGS. 36 & 37). In NC169-F4, glycolipids features are evidently present. As such, structure determination efforts were mainly on glycolipids.

NC169-14-15-1

Figure 38:
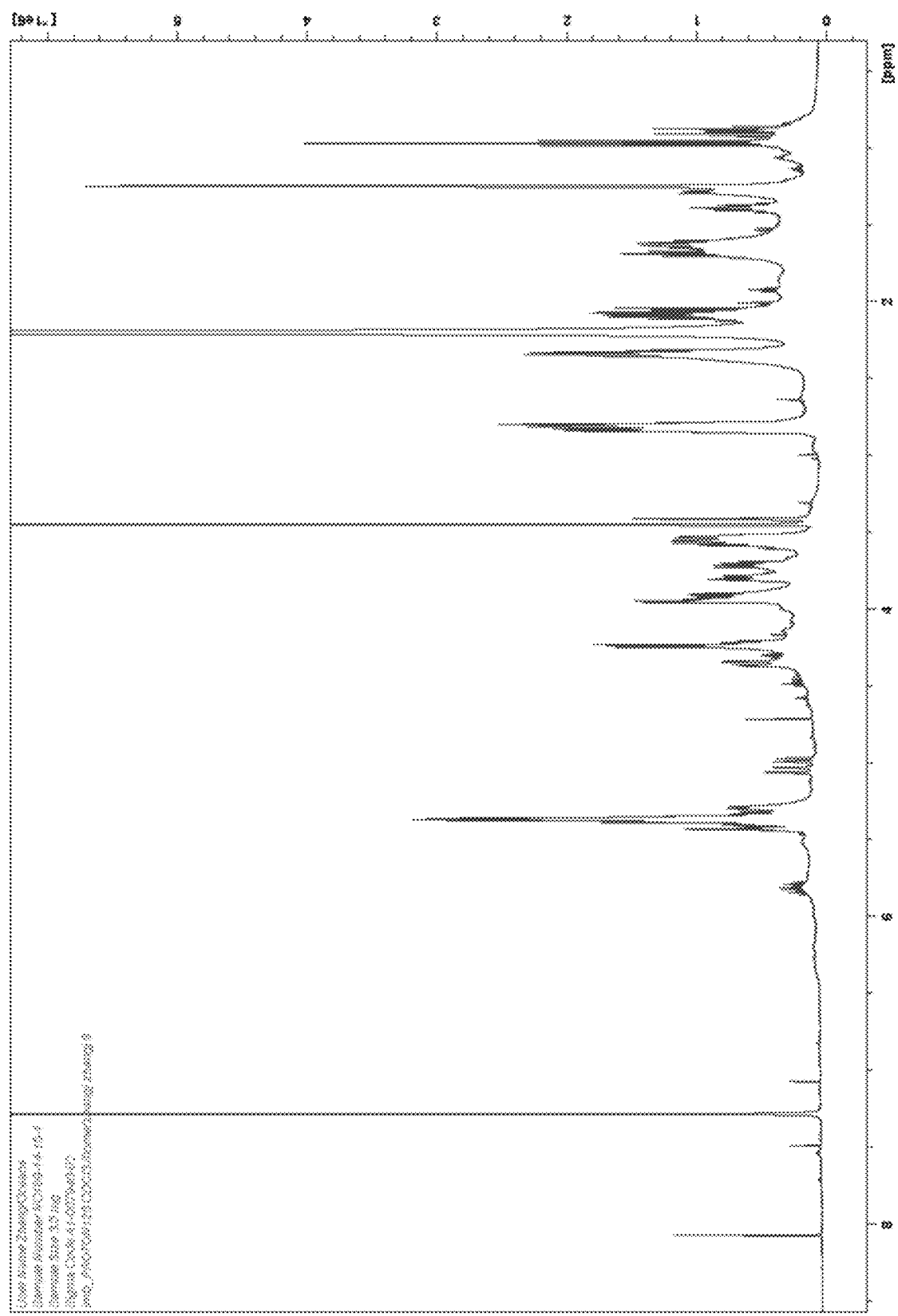
FIG. 38. Proton NMR spectrum of NC169-14-15-1.
Figure 39:
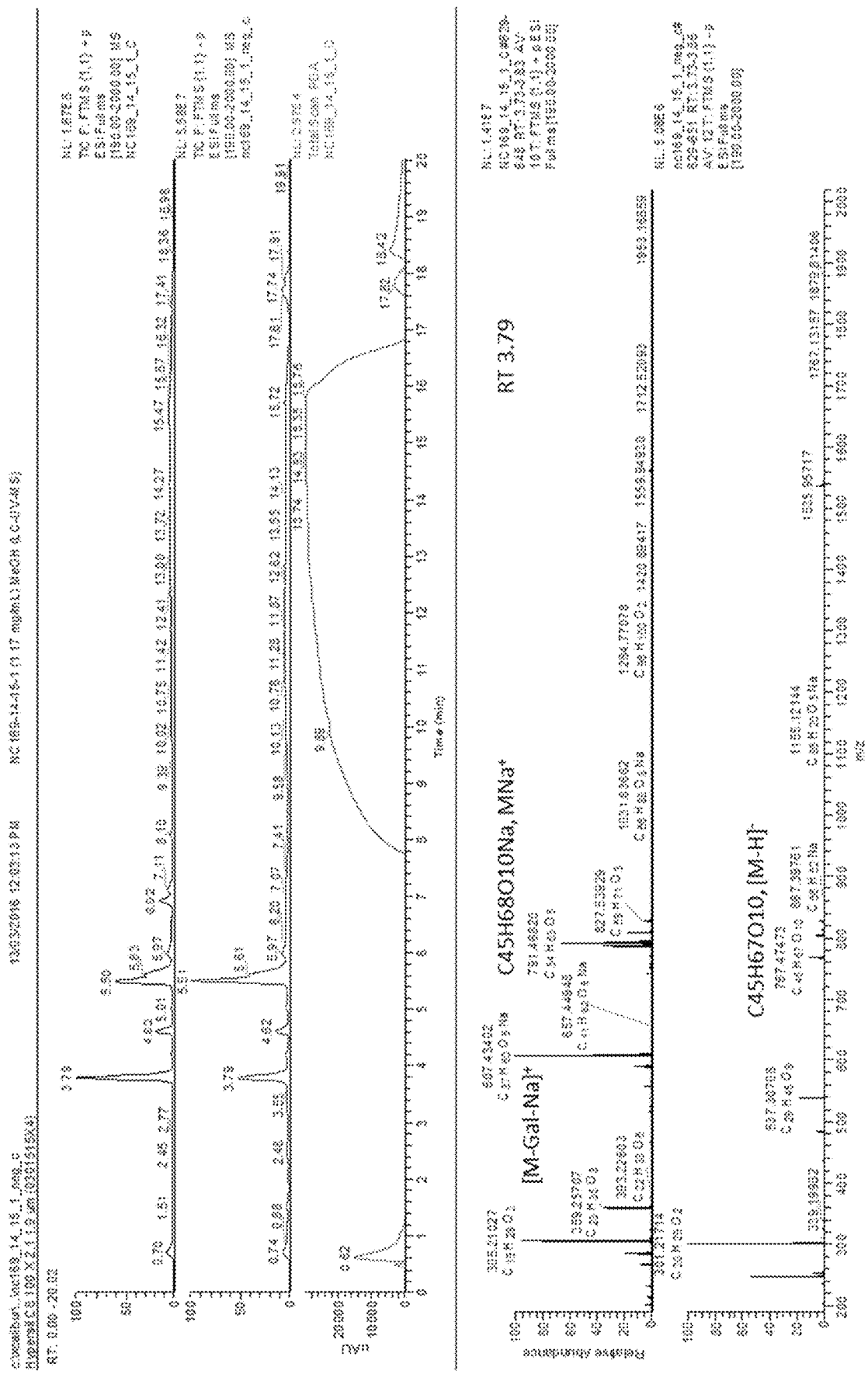
FIG. 39. UPLC-DAD/MS chromatogram of NC169-14-15-1 and HRMS spectra of peak RT 3.79.

$_1$H-NMR (FIG. 38) and HSQC spectra (not shown) of this sample show characteristic glycolipid signals, i.e., the unsaturated fatty acids, glycerol, and galactose. In UPLC-DAD/MS chromatogram (FIG. 39), several peaks were present. The HRMS of peak RT 3.79 showed in positive mode an ion m/z 791.46820 (calculated for $C_{45}H_{68}O_{10}Na_+$ 791.47047) and in negative mode an ion m/z 767.47473 (calculated for $C_{45}H_{67}O_{10-}$ 767.47397), affirming a glycolipid with molecular formula of $C_{45}H_{68}O_{10}$.

Figure 40:
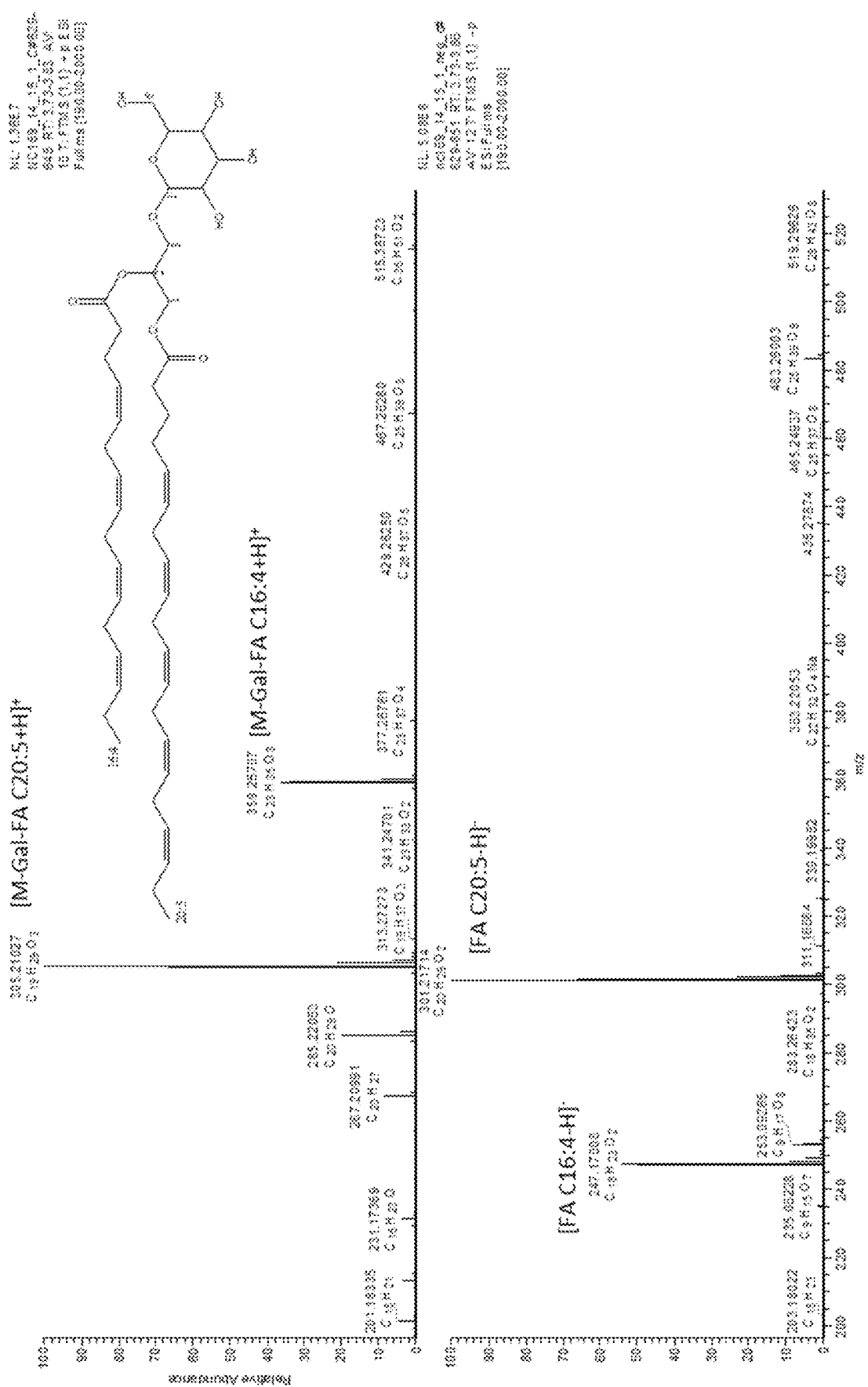
FIG. 40. Expanded HRMS of peak RT 3.79 of NC169-14-15-1.

Zooming in HRMS spectra (FIG. 40), two characteristic fatty acid anions are present, m/z 247.17008 ($C_{16}H_{23}O_{2-}$) and 301.21714 ($C_{20}H_{29}O_{2-}$) in negative mode. The relative intensity of these two fatty acid peaks also indicates the regiochemical distribution of fatty acid chains on glycerol backbone, as it was shown in literature (Guella, et al. Rapid Comm. Mass Spec. 2003; 17, 1982-1994) that fatty acid peak on sn-1 has higher intensity than that on sn-2 as it is easier to lose. The relative intensity of positive mode fragments of m/z 305.21027 for [M-Gal-FA20:5+H]$_+$ and m/z 359.25707 for [M-Gal-FA16:4+H]$_+$ also confirmed the fatty acids location. The fatty acids were determined to be n-3 based on 2D NMR COSY spectrum (not shown). As such, peak RT 3.79 is characterized to be monogalatosyldiaxylglycerol (MGDG) C20:5/C16:4 (1).

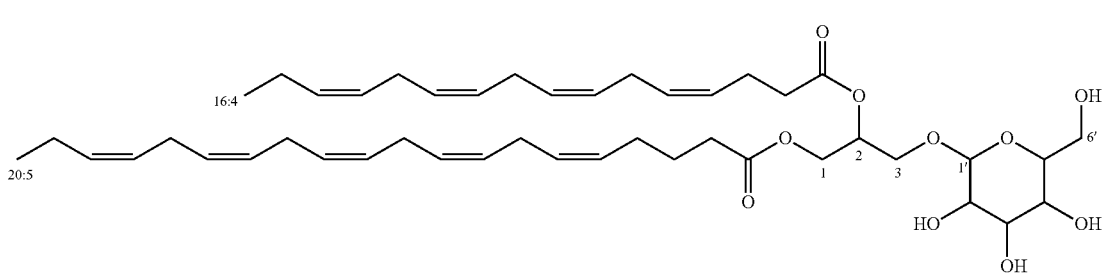

1

Figure 41:
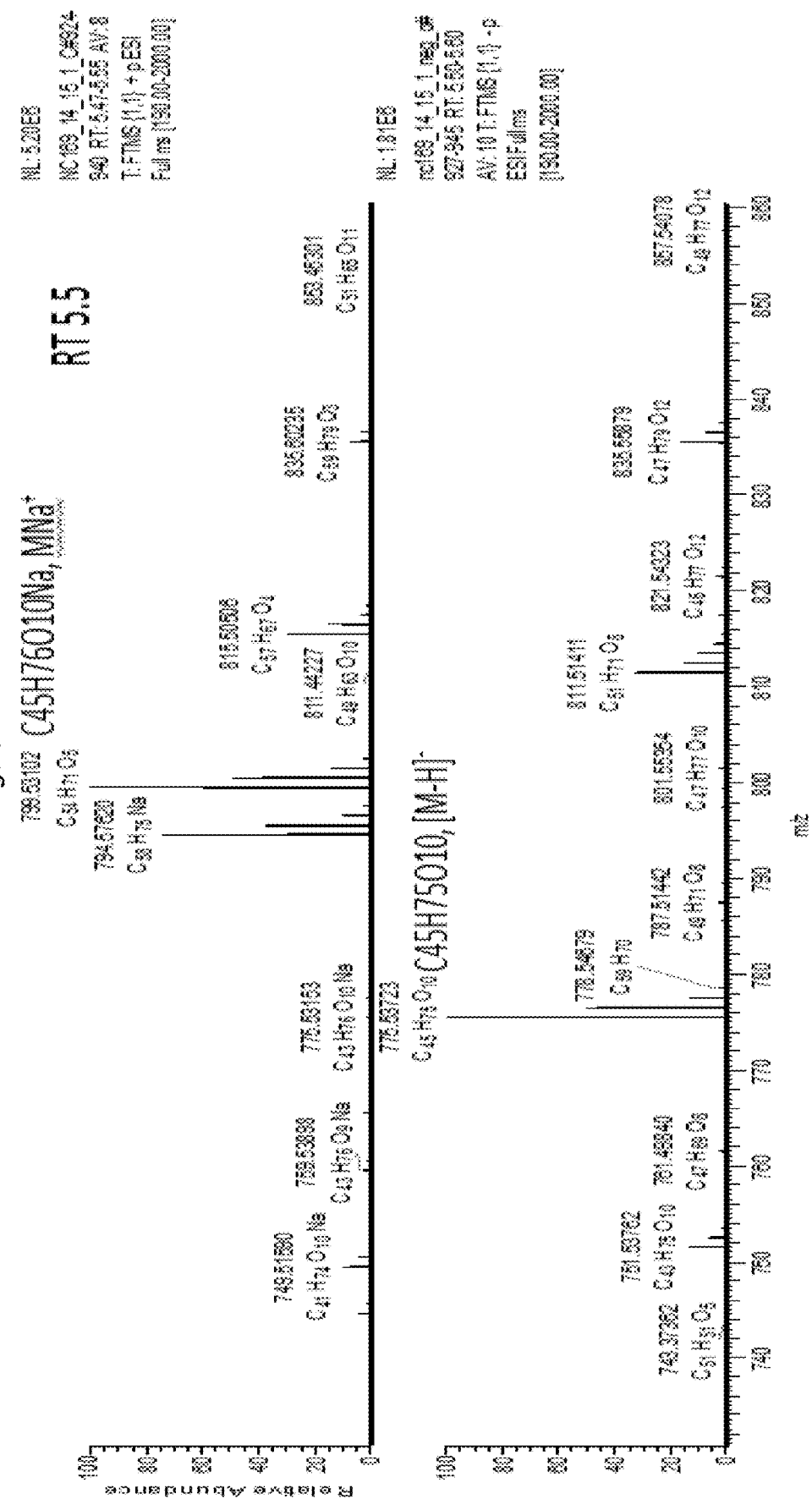
FIG. 41. HRMS spectra of peak RT 5.5 of NC169-14-15-1.
Figure 42:
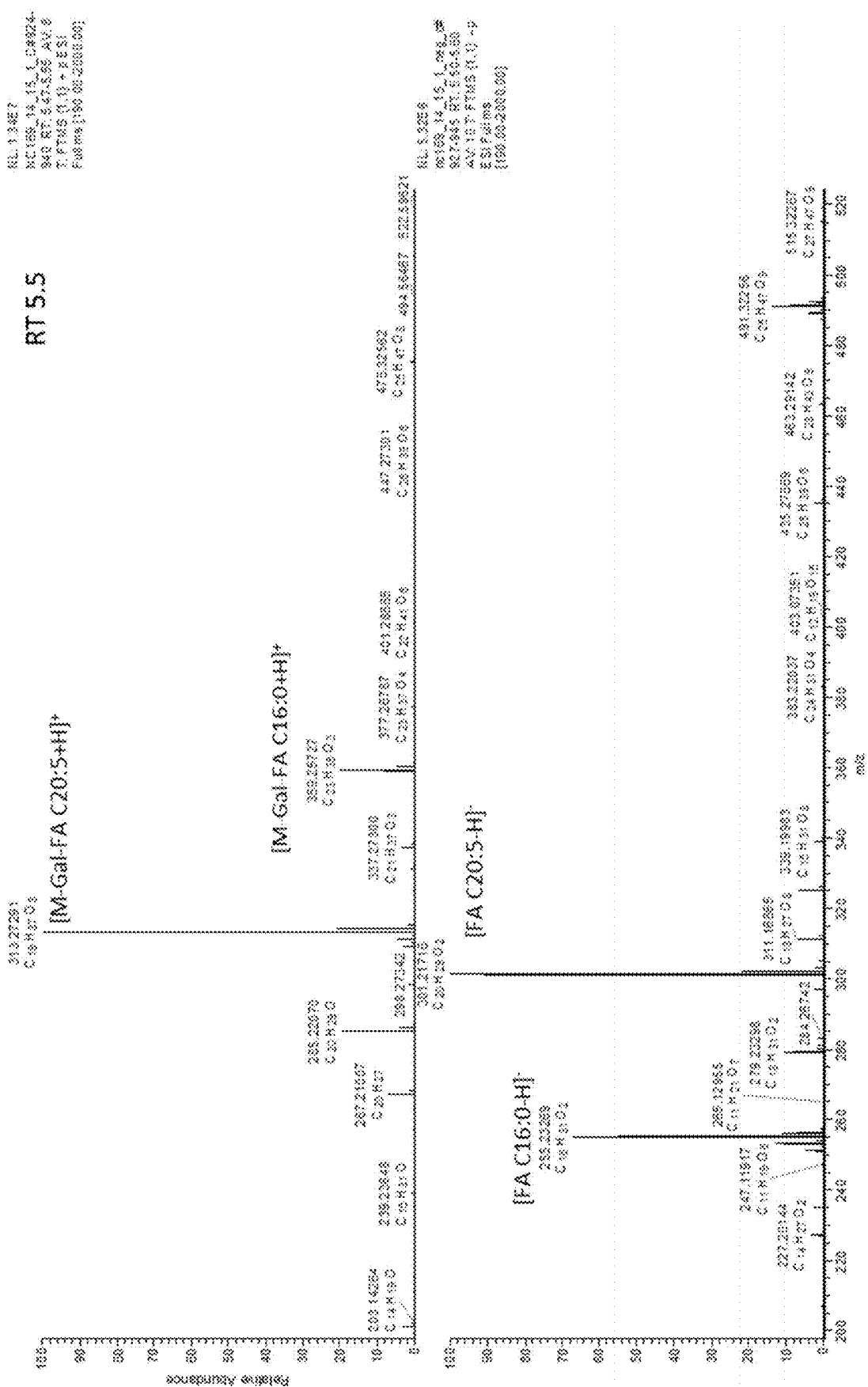
FIG. 42. HRMS of peak RT 5.5 of NC169-14-15-1 showing fatty acids fragments.

Peak RT 5.5 shows m/z 799.53102 ($C_{45}H_{76}O_{10}Na_+$, calculated 799.53307) and 775.53723 ($C_{45}H_{75}O_{10-}$, calculated 775.53657) in positive and negative mode HRMS (FIG. 41), implying a glycolipid MGDG with a molecular formula of $C_{45}H_{76}O_{10}$. FIG. 42 shows the fatty acid related fragments in HRMS. By using the similar strategy described above, peak RT 5.5 is determined to be glycolipid MGDG C20:5/C16:0 (2).

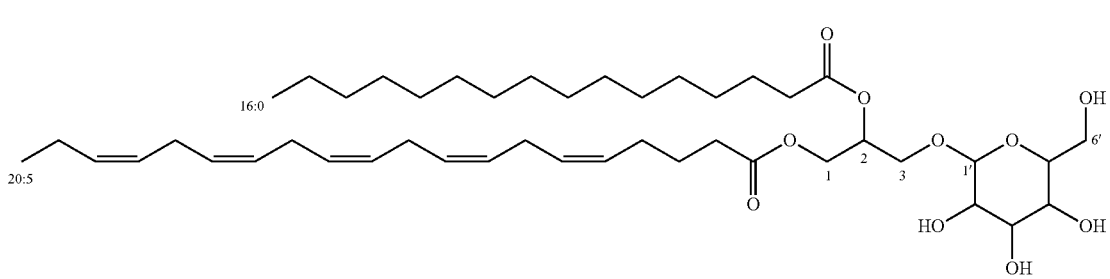

2

Figure 43:
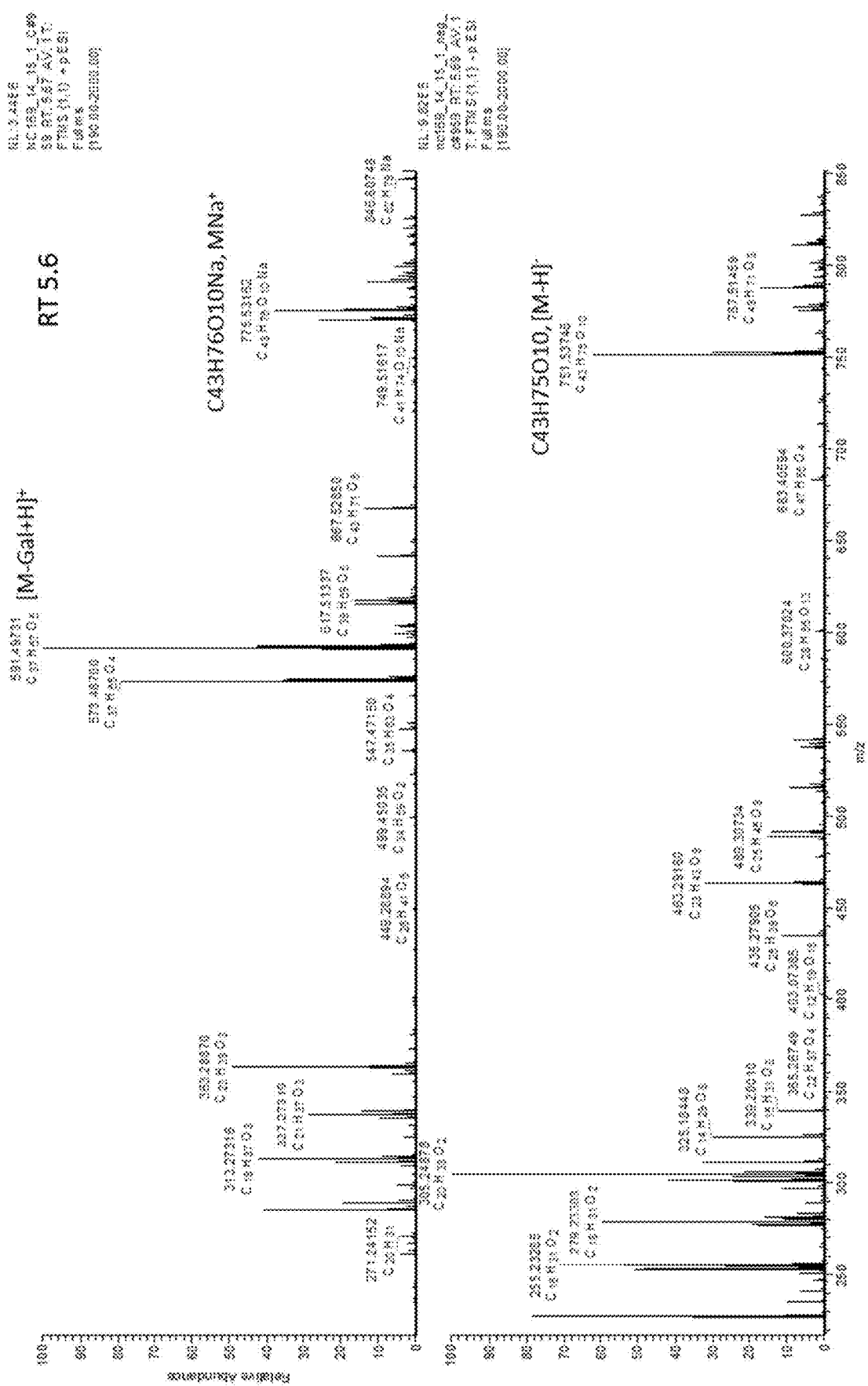
FIG. 43. HRMS of peak RT 5.6 of NC169-14-15-1.
Figure 44:
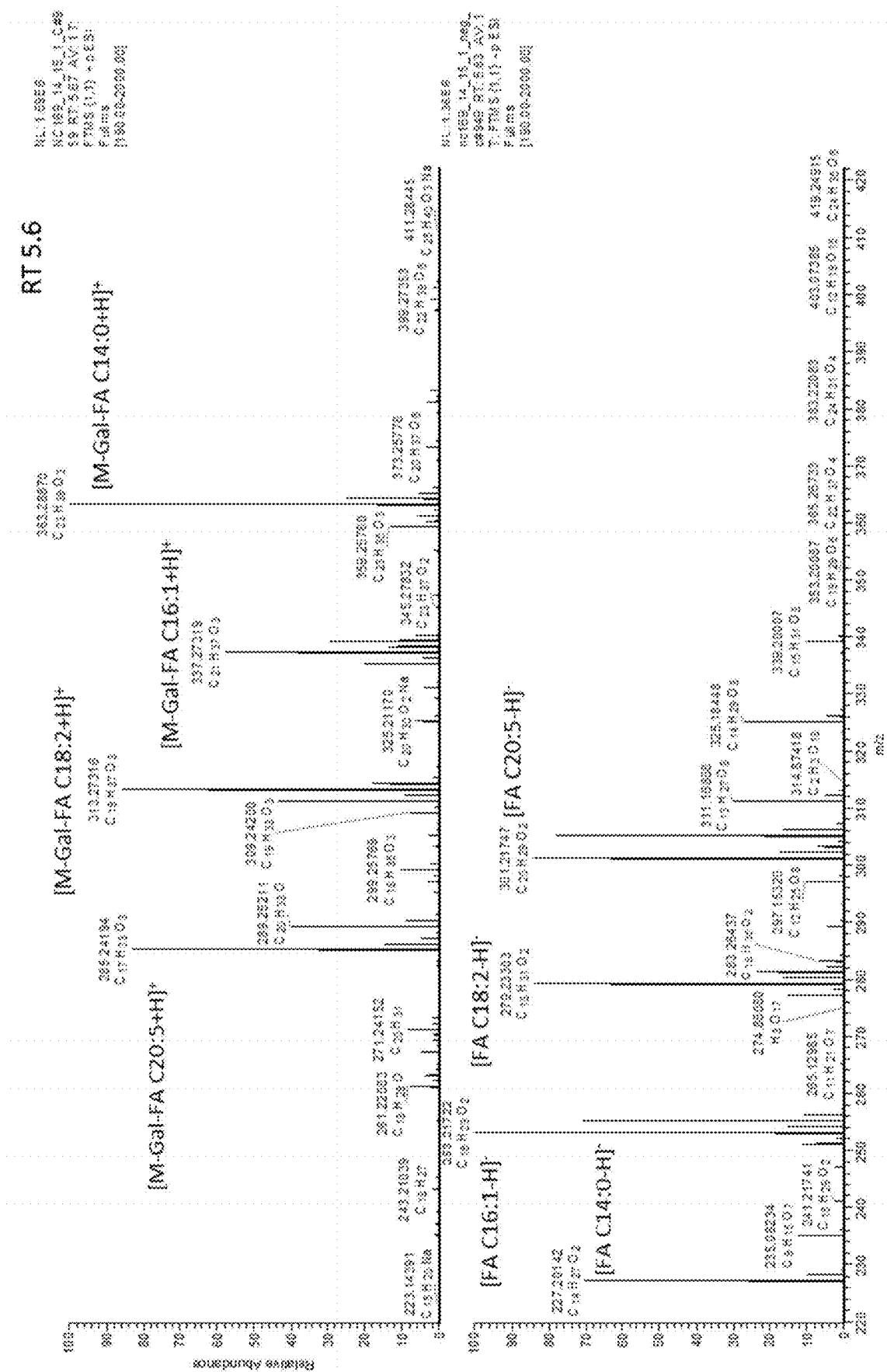
FIG. 44. HRMS of peak RT 5.6 of NC169-14-15-1 showing fatty acid related fragments.

Peak RT 5.6 shows m/z 775.53162 ($C_{43}H_{76}O_{10}Na_+$, calculated 775.53307) and 751.53748 ($C_{43}H_{75}O_{10-}$, calculated 751.53657) in positive and negative mode HRMS (FIG. 43), indicating a glycolipid MGDG with a molecular formula of $C_{43}H_{76}O_{10}$. As for fatty acid identity, however, FIG. 44 shows four fatty acids related fragments in HRMS. It is likely that peak 5.6 has two glycolipid analogs, one would be MGDG C20:5/C14:0 (3) and the other being MGDG C16:1/C18:2 (4).

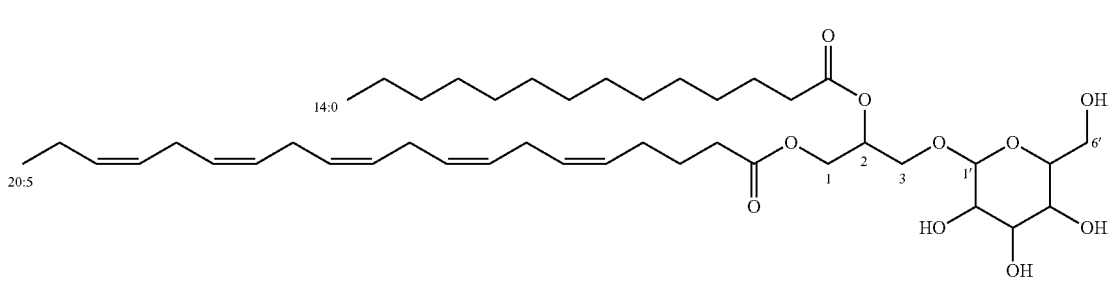

3

-continued

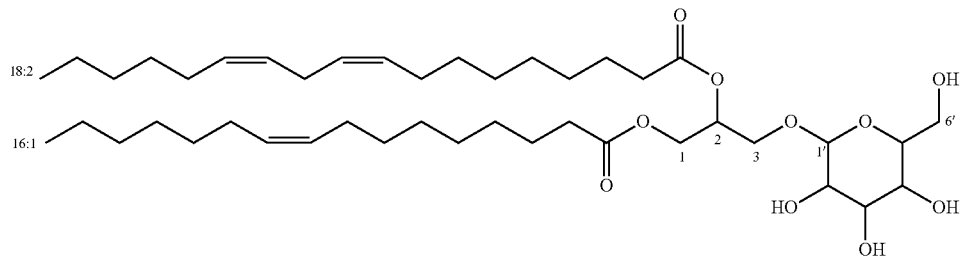

4

NC169-14-15-2

Figure 45:
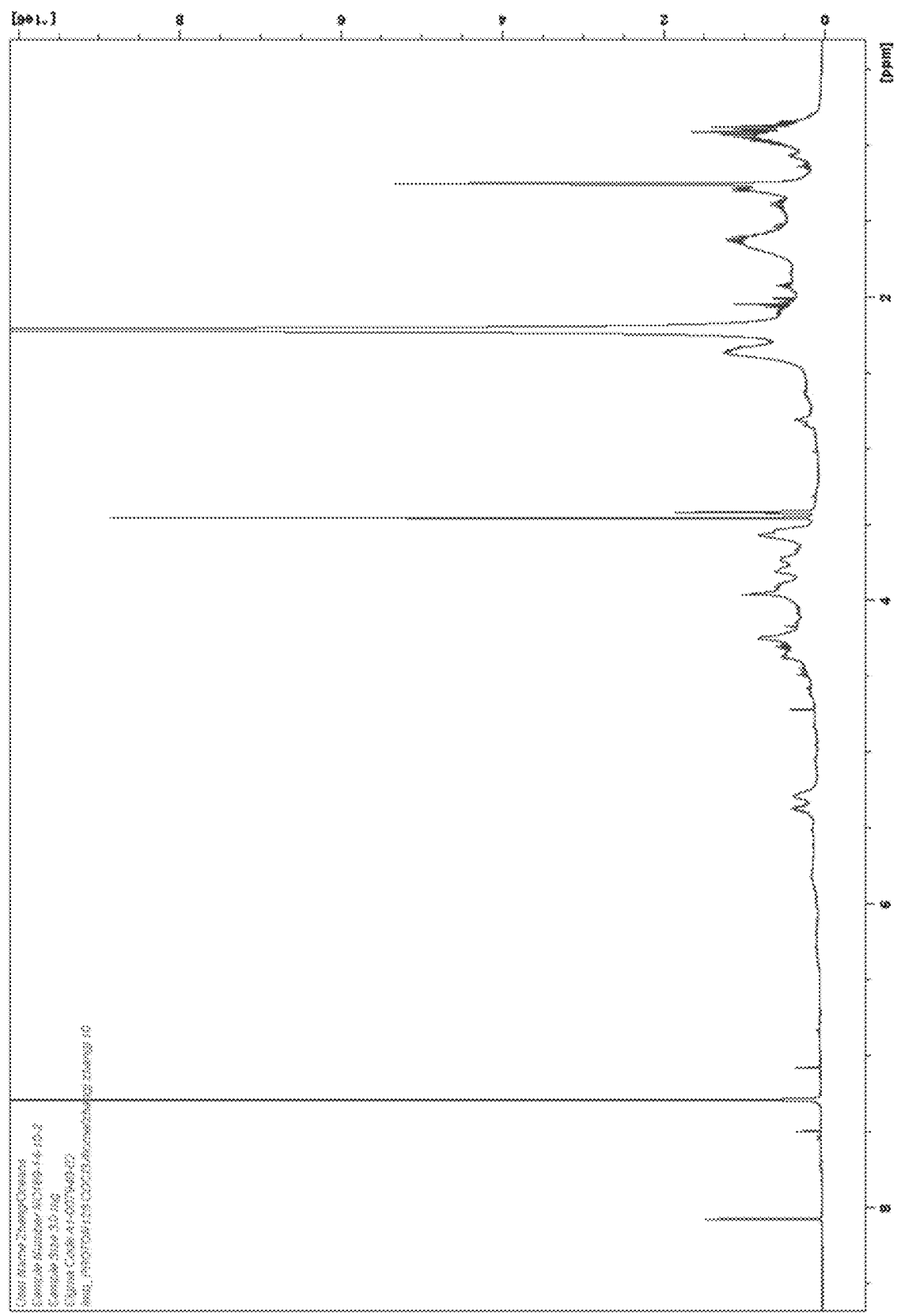
FIG. 45. 1H-NMR spectrum of NC169-14-15-2.
Figure 46:
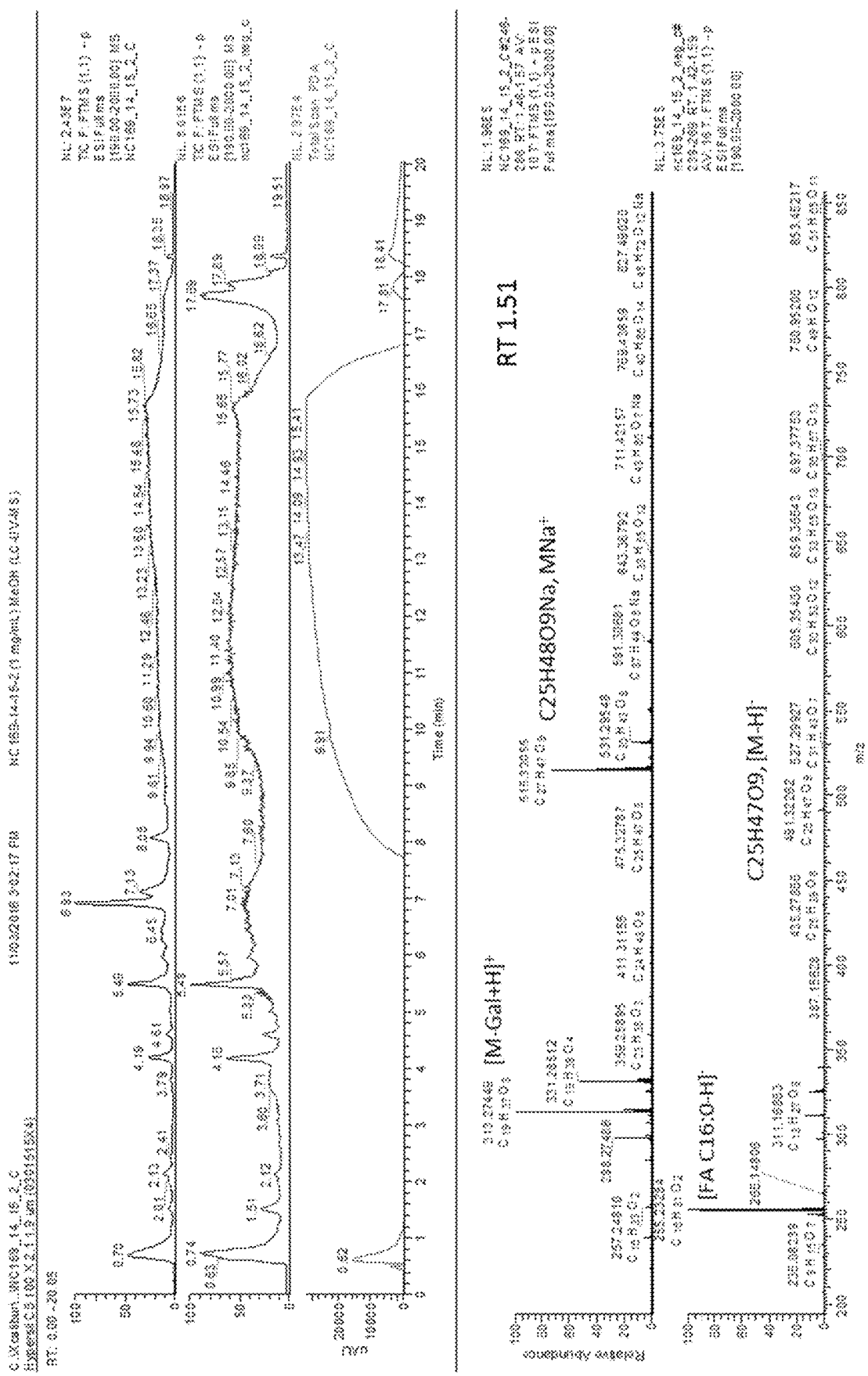
FIG. 46. UPLC-DAD/HRMS chromatogram of NC169-14-15-2 and URMS spectra of peak RT 1.51.

Similar to the previous sample, the $_1$H-NMR spectrum of NC169-14-15-2 (FIG. 45) showed glycolipid features. In UPLC-DAD/HRMS chromatogram, peak RT 1.51 was found to have a molecular formula of $C_{25}H_{48}O_9$, based on molecular ions of m/z 515.32055 ($C_{25}H_{48}O_9Na_+$, calculated 515.31960) and 491.32262 ($C_{25}H_{47}O_{9-}$, calculated 491.32256) in positive and negative mode HRMS (FIG. 46). Only one fatty acid fragment m/z 255.23284 (C16:0) was found in negative mode, indicating a lyso MGDG glycolipid. As such, the structure of peak RT 1.51 was determined to be lyso-MGDG C16:0 (5).

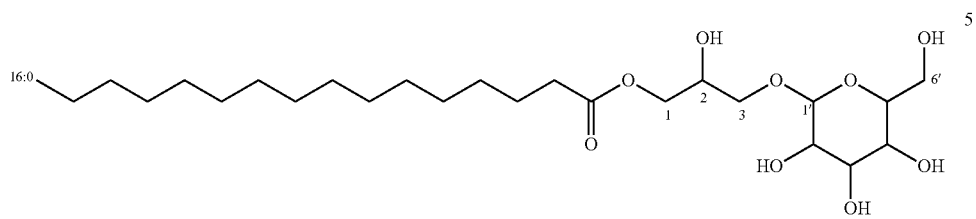 [SMILES: CCCCCCCCCCCCCCCC(=O)OCC(O)COC1OC(CO)C(O)C(O)C1O]

Figure 47:
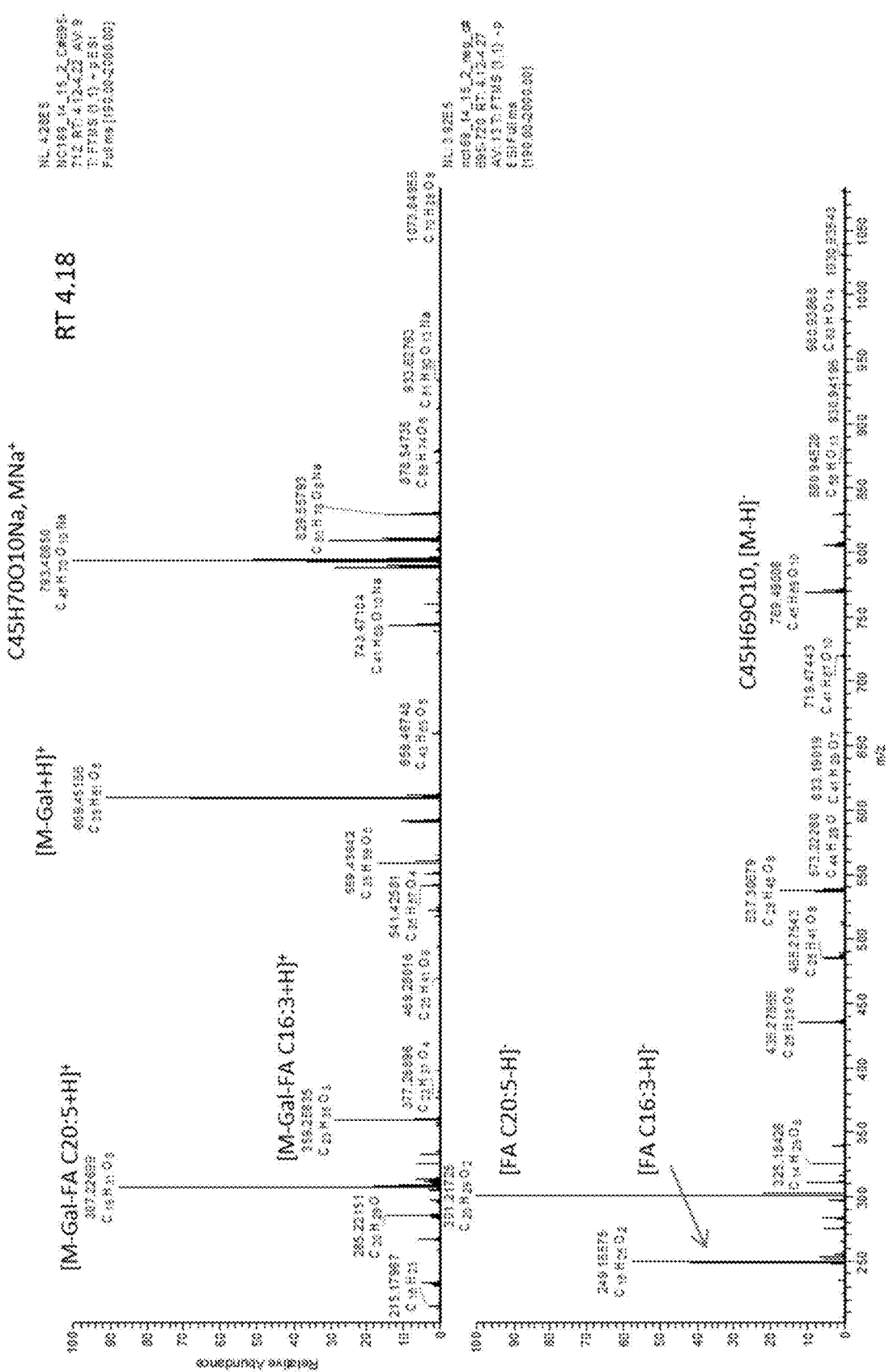
FIG. 47. HRMS spectra of peak 4.18 of NC169-14-15-2.

Peak RT 4.18 showed to have a molecular formula of $C_{45}H_{70}O_{10}$, based on molecular ions of m/z 793.48650 ($C_{45}H_{70}O_{10}Na_+$, calculated 793.48612) and 769.49008 ($C_{45}H_{69}O_{10-}$, calculated 769.48962) in positive and negative mode HRMS (FIG. 47). Combining the fatty acids fragment profile in HRMS, peak at RT 4.18 was determined to be MGDG C20:5/C16:3 (6). The unsaturation pattern on the fatty acids has to be further determined.

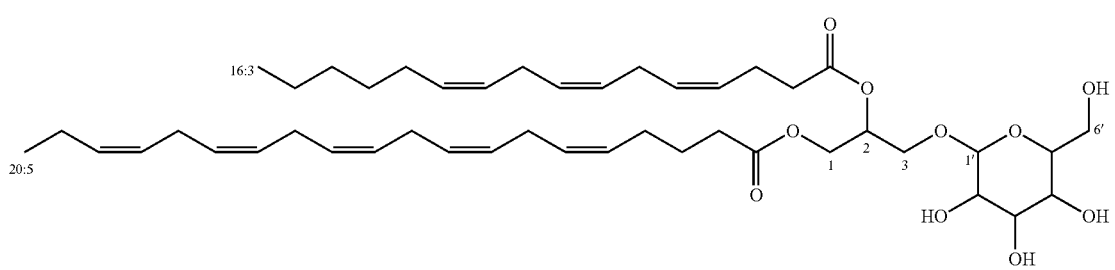

Figure 48:
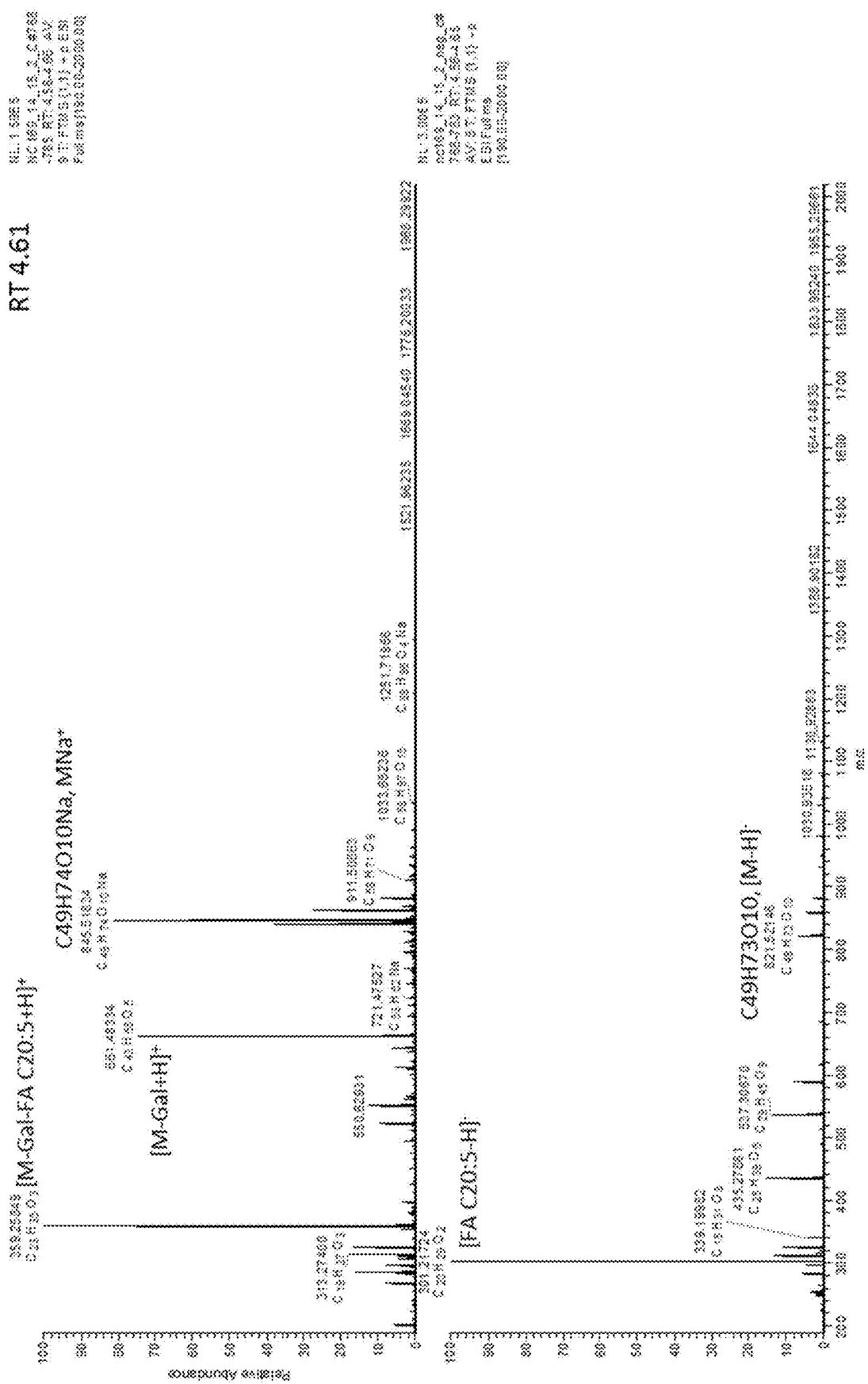
FIG. 48. HRMS spectra of peak RT 4.61 of NC169-14-15-2.

Peak at RT 4.61 has a molecular formula of C49H74O10, elucidated based on molecular ions of m/z 845.51843 (C49H74O10Na+, calculated 845.51742) and 821.52146 (C49H73O10−, calculated 821.52092) in positive and negative mode HRMS, respectively (FIG. 48). As there was only one fatty acid fragment in HRMS, peak at RT 4.18 was determined to be MGDG C20:5/C20:5 (7).

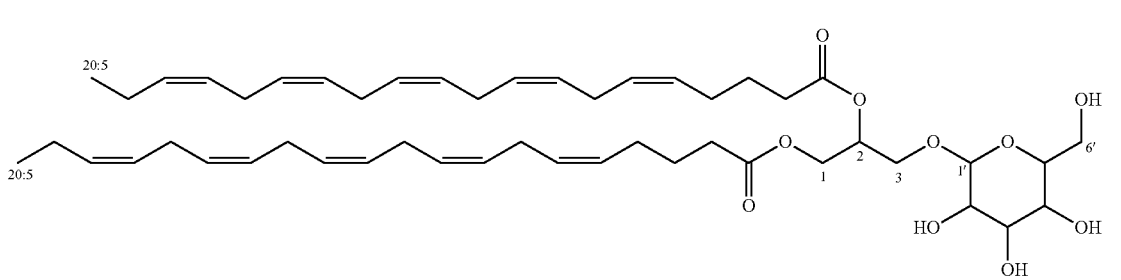

7

Figure 49:
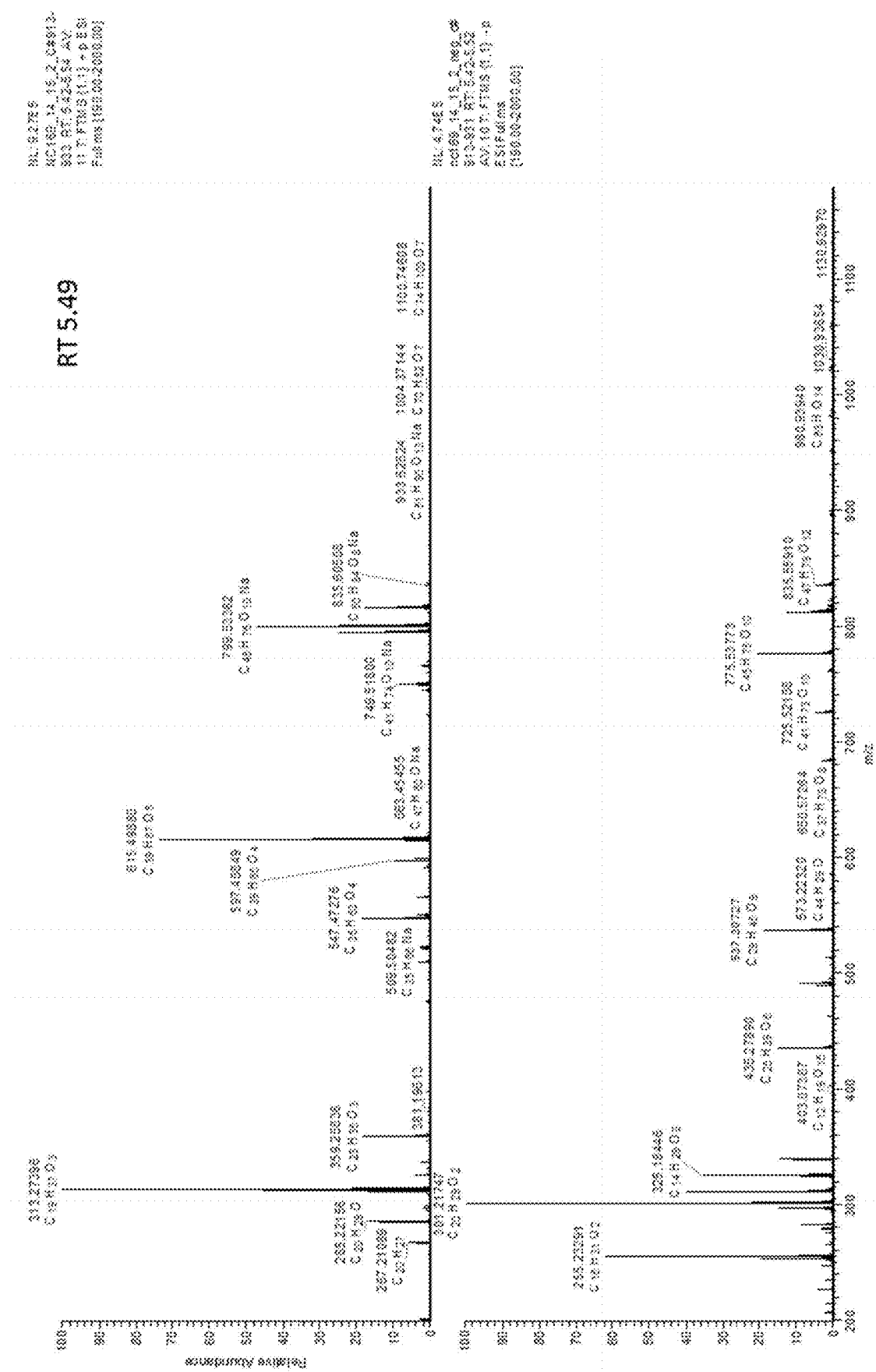
FIG. 49. HRMS spectra of peak RT 5.49 of NC169-14-15-2.

Peak RT 5.49 had the same HRMS spectra (FIG. 49) as that of glycolipid compound 2, indicating the two are the same.

NC169-14-15-4

Figure 50:
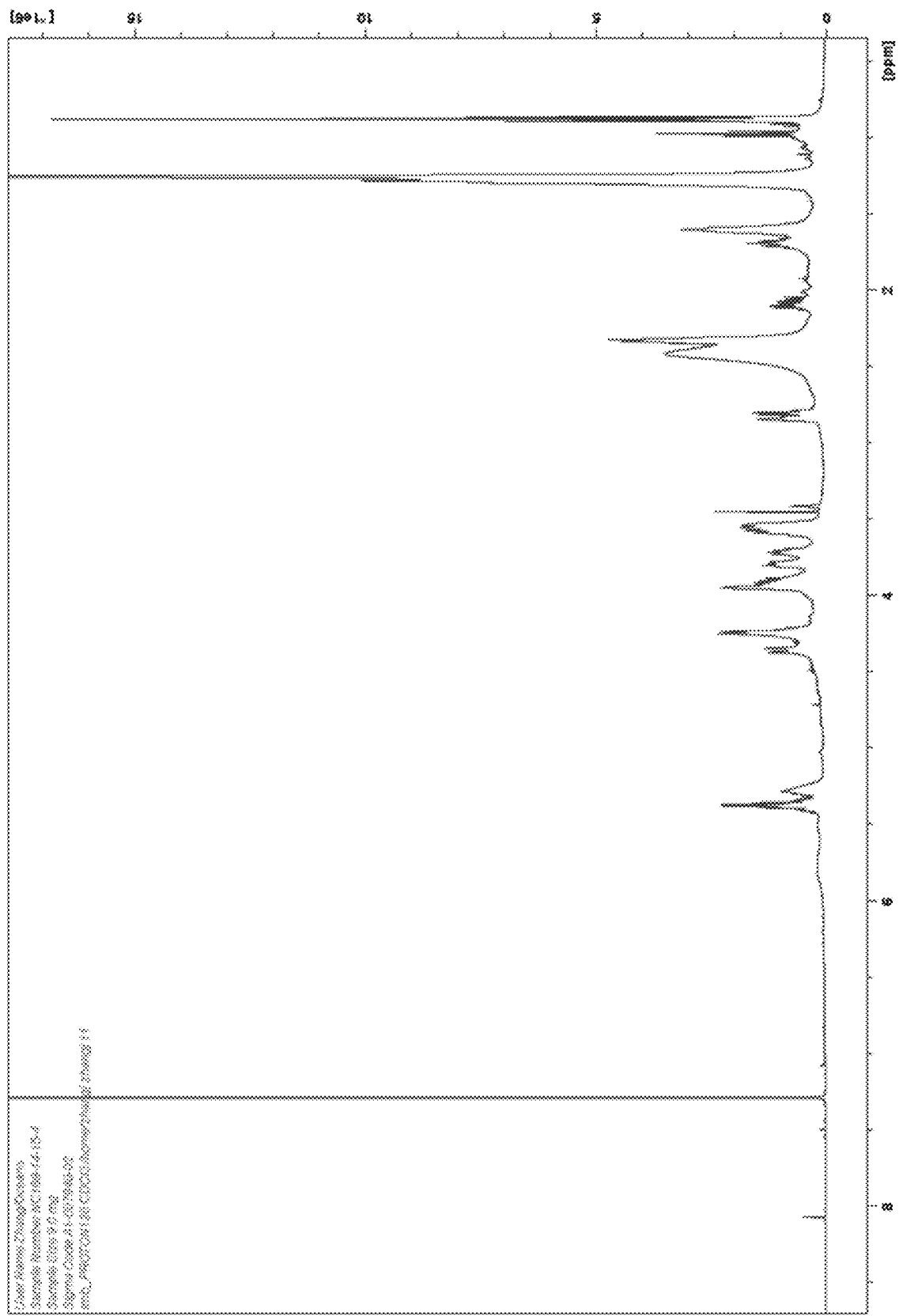
FIG. 50. 1H-NMR spectrum of NC169-14-15-4.
Figure 51:
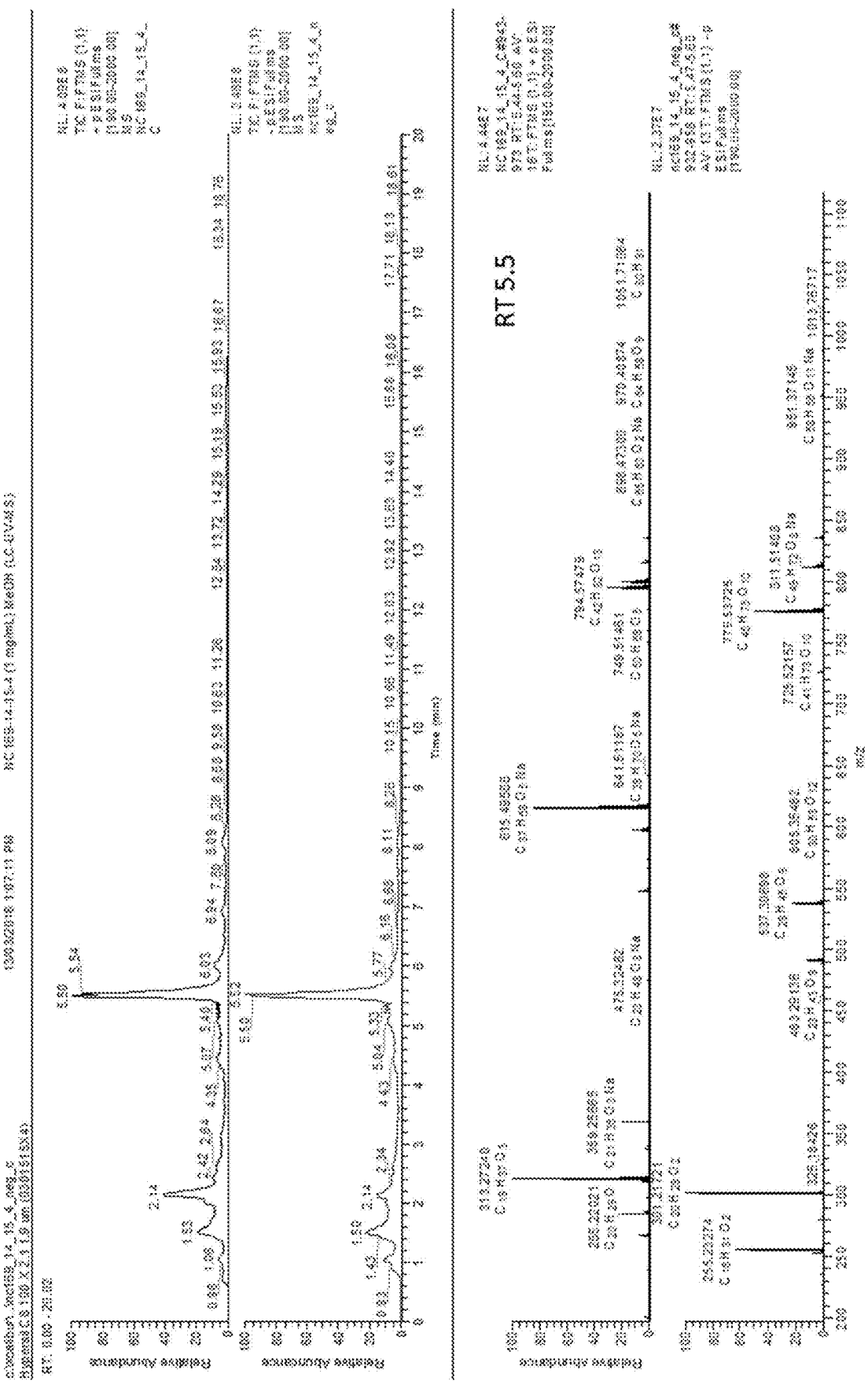
FIG. 51. UPLC-HRMS chromatogram of NC169-14-15-4 and HRMS spectra of peak RT 5.5.

$_1$H-NMR spectrum of NC169-14-15-4 (FIG. 50) shows typical glycolipid features. In UPLC-HRMS chromatogram, the main peak RT 5.5 was found to have the same HRMS spectra (FIG. 51) as glycolipid 2, thus the same structure was assigned.

NC169-20-22-3

Figure 52:
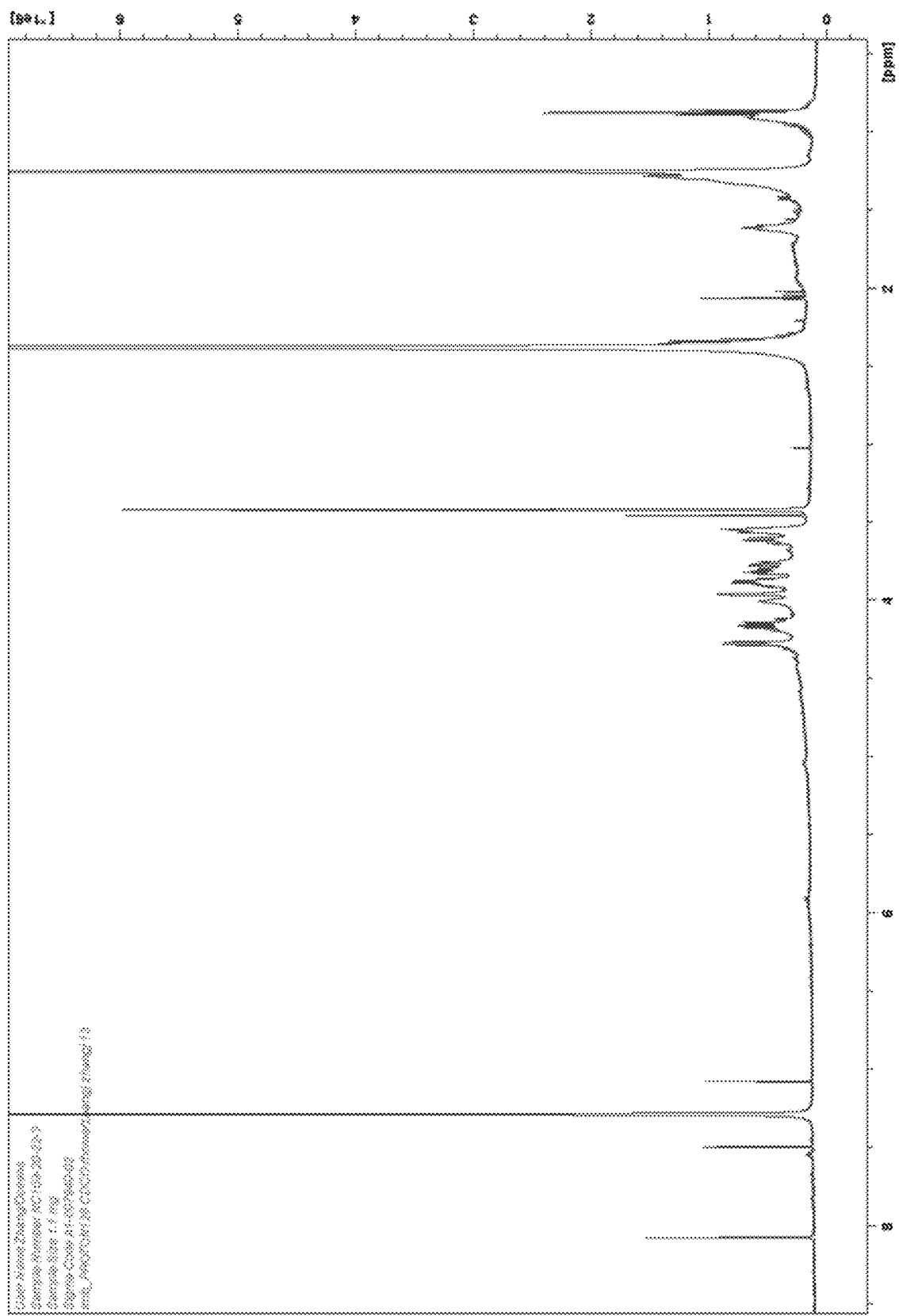
FIG. 52. 1H-NMR spectrum of NC169-20-22-3.
Figure 53:
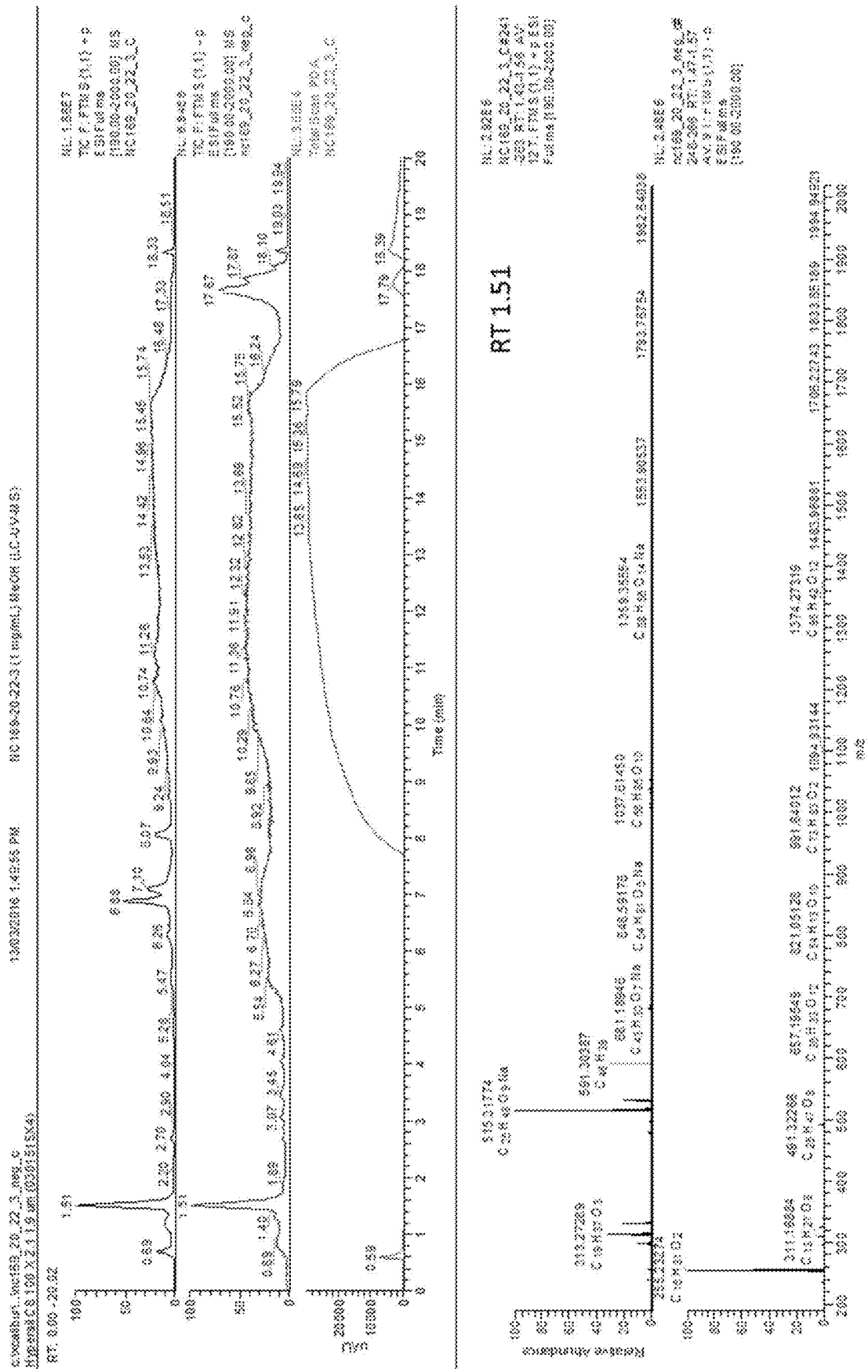
FIG. 53. UPLC-DAD/HRMS chromatograms of NC169-20-22-3 and HRMS spectra of peak RT 1.51.

Glycolipid signals are present in $_1$H-NMR spectrum of NC169-20-22-3 (FIG. 52). In UPLC-DAD/HRMS chromatogram, the main peak RT 1.51 was found to have the same HRMS spectra (FIG. 53) as glycolipid 5, thus the same structure was assigned.

NC169-20-22-4

Figure 54:
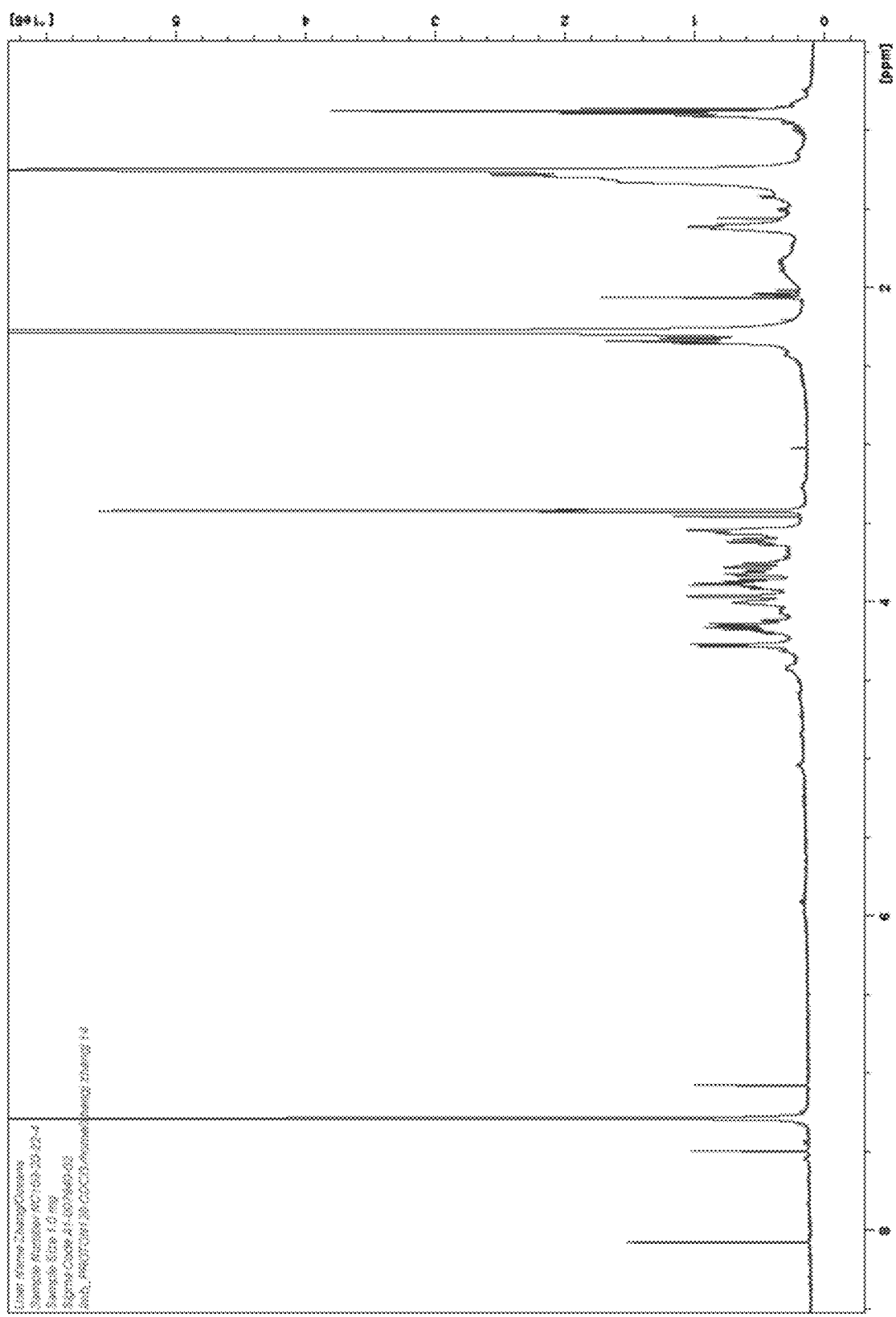
FIG. 54. 1H-NMR spectrum of NC169-20-22-4.
Figure 55:
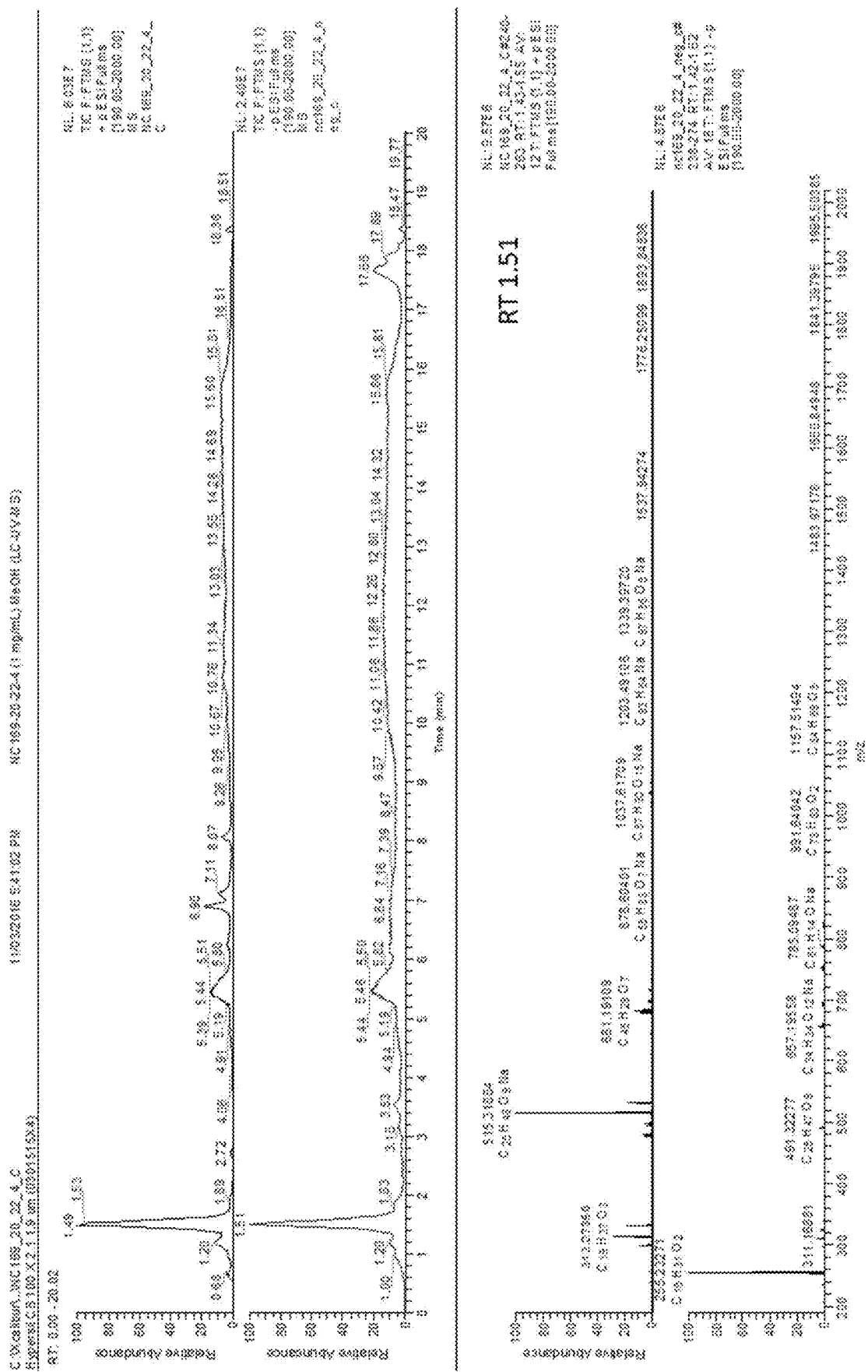
FIG. 55. UPLC-HRMS chromatograms of NC169-20-22-4 and HRMS spectra of peak RT 1.51.

This sample is similar to NC169-20-22-3 described above based on 1H-NMR spectrum (FIG. 54) and UPLC-HRMS (FIG. 55), and the main peak RT 1.51 has same HRMS spectra as glycolipid 5, thus the same structure was assigned.

NC169-20-22-5

Figure 56:
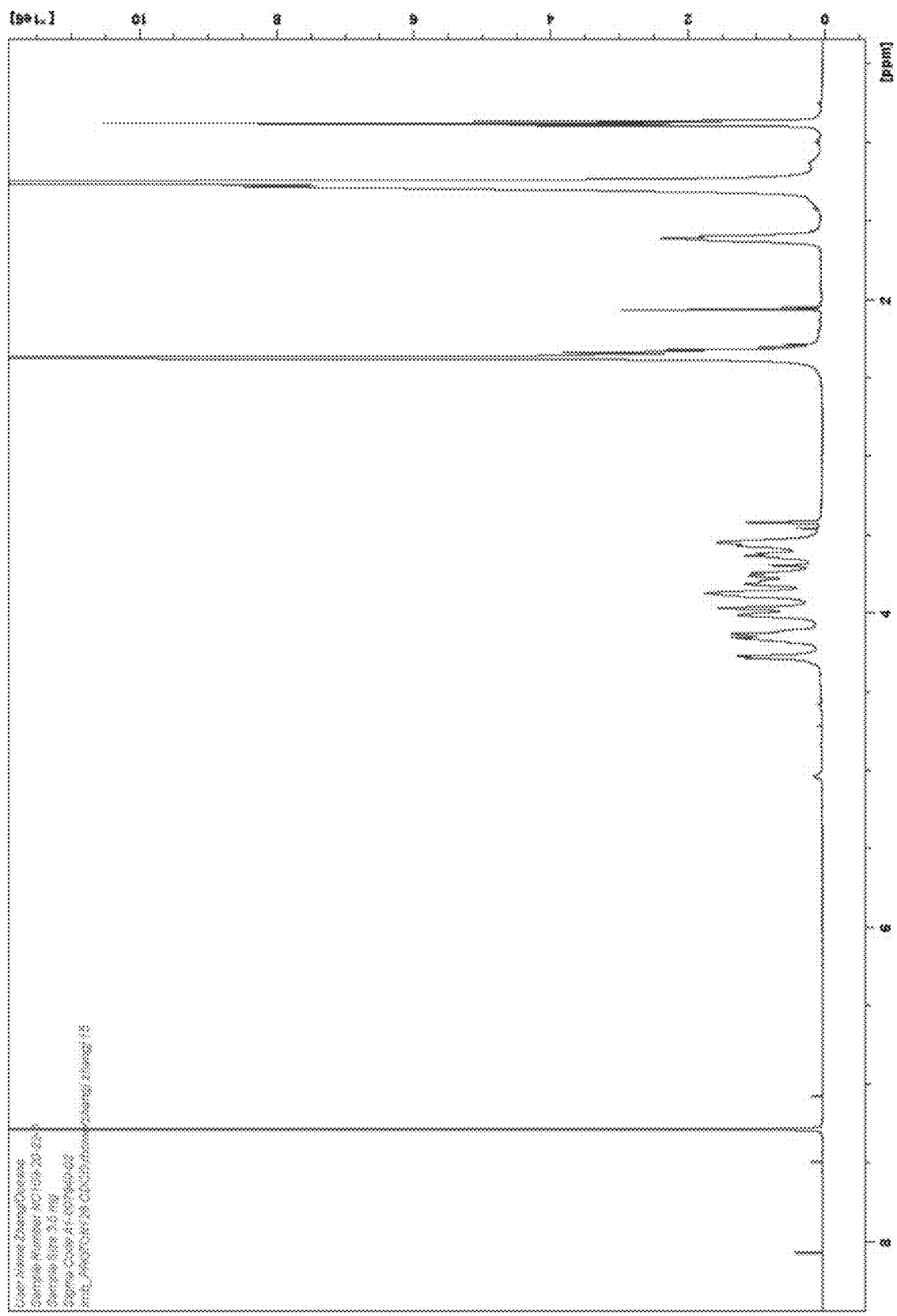
FIG. 56. 1H-NMR spectrum of NC169-20-22-5.
Figure 57:
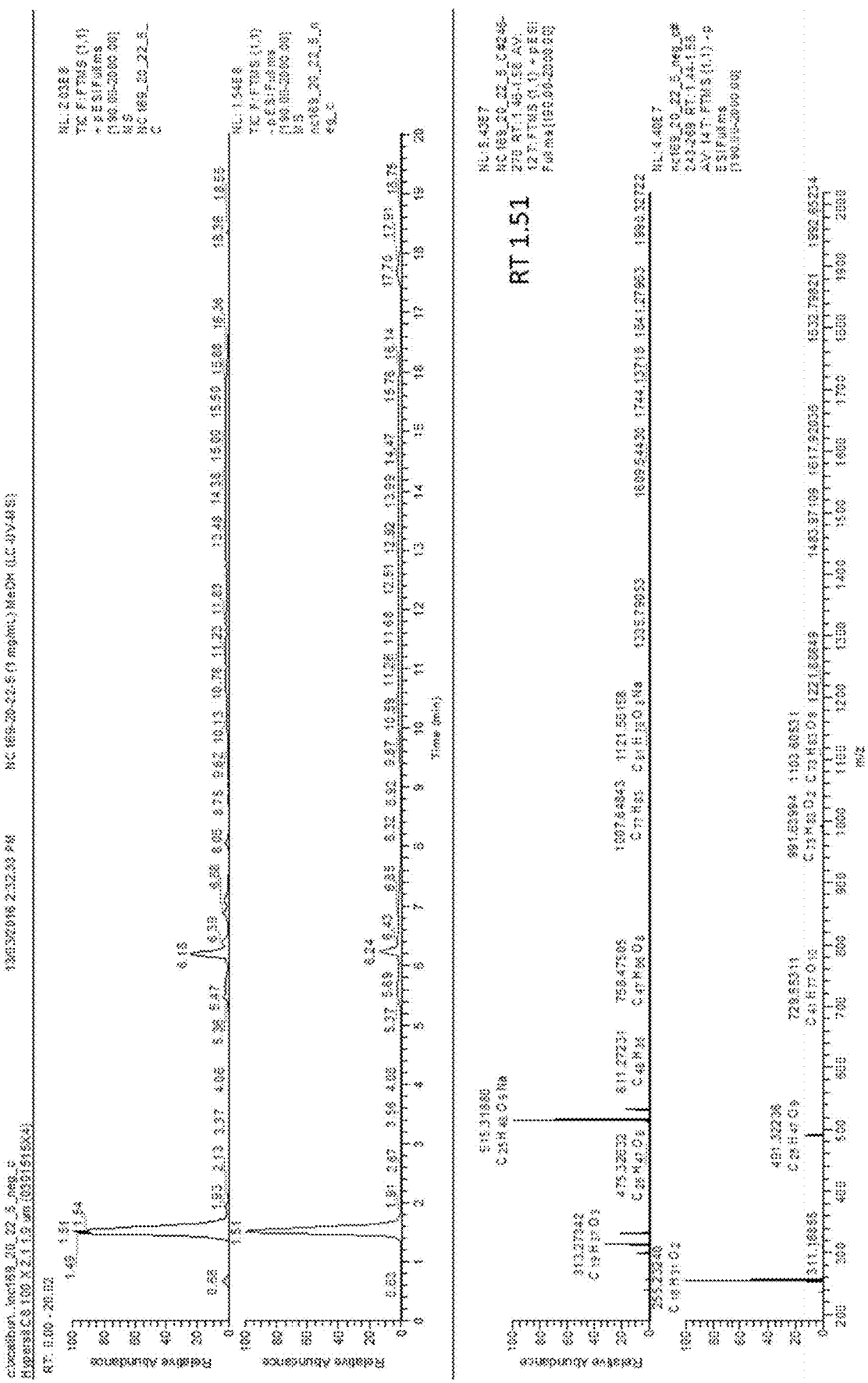
FIG. 57. UPLC-HRMS chromatograms of NC169-20-22-5 and HRMS spectra of peak 1.51.
Figure 58:
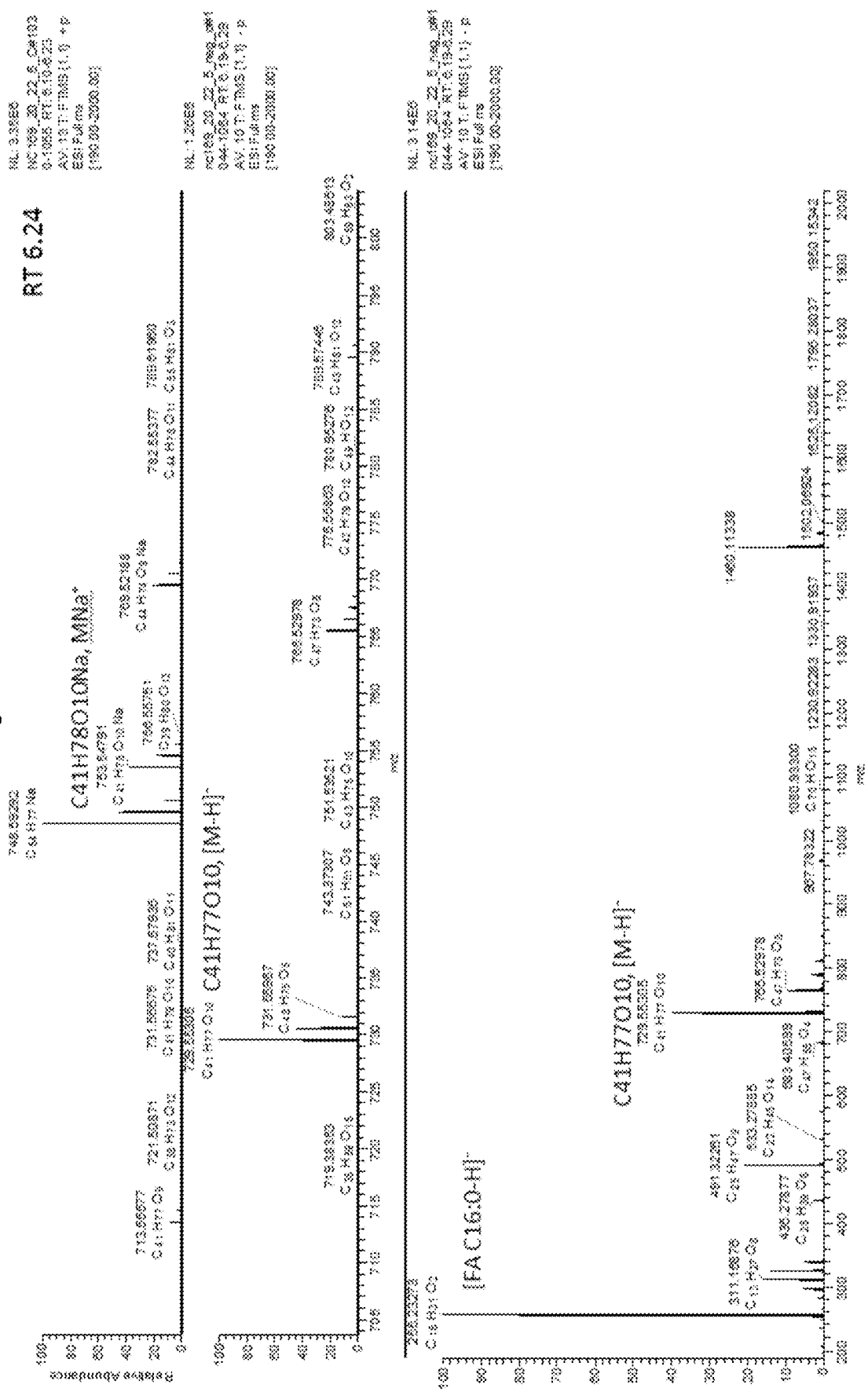
FIG. 58. HRMS spectra of peak RT 6.24 of NC169-20-22-5.

$_1$H-NMR spectrum of NC169-20-22-5 (FIG. 56) shows typical glycolipid features. The main peak, RT 1.51 was shown to be the same lyso-MGDG C16:0 (5) based on UPLC retention time and HRMS data (FIG. 57). The minor peak RT 6.24 was found to have a molecular formula of $C_{41}H_{78}O_{10}$, based on molecular ions of m/z 753.54791 ($C_{41}H_{78}O_{10}Na_+$, calculated 753.54872) and 729.55305 ($C_{41}H_{77}O_{10-}$, calculated 729.55222) in positive and negative mode HRMS (FIG. 58). Only one fatty acid fragment m/z 255.23273 (C16:0) was found in negative mode, indicating the fatty acids on both sn-1 and sn-2 positions. The structure of peak RT 6.24 was determined to be MGDG C16:0/C16:0 (8).

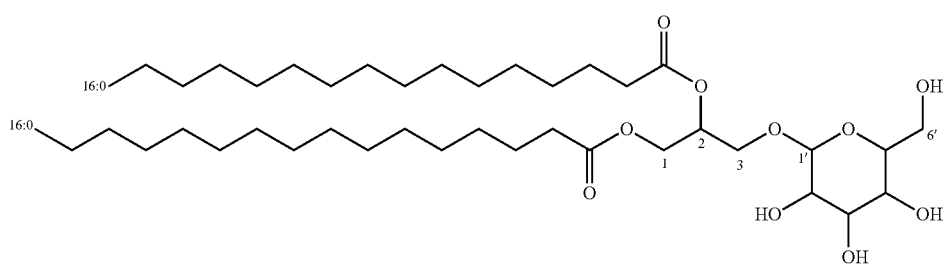

8

SUMMARY

Figure 59:
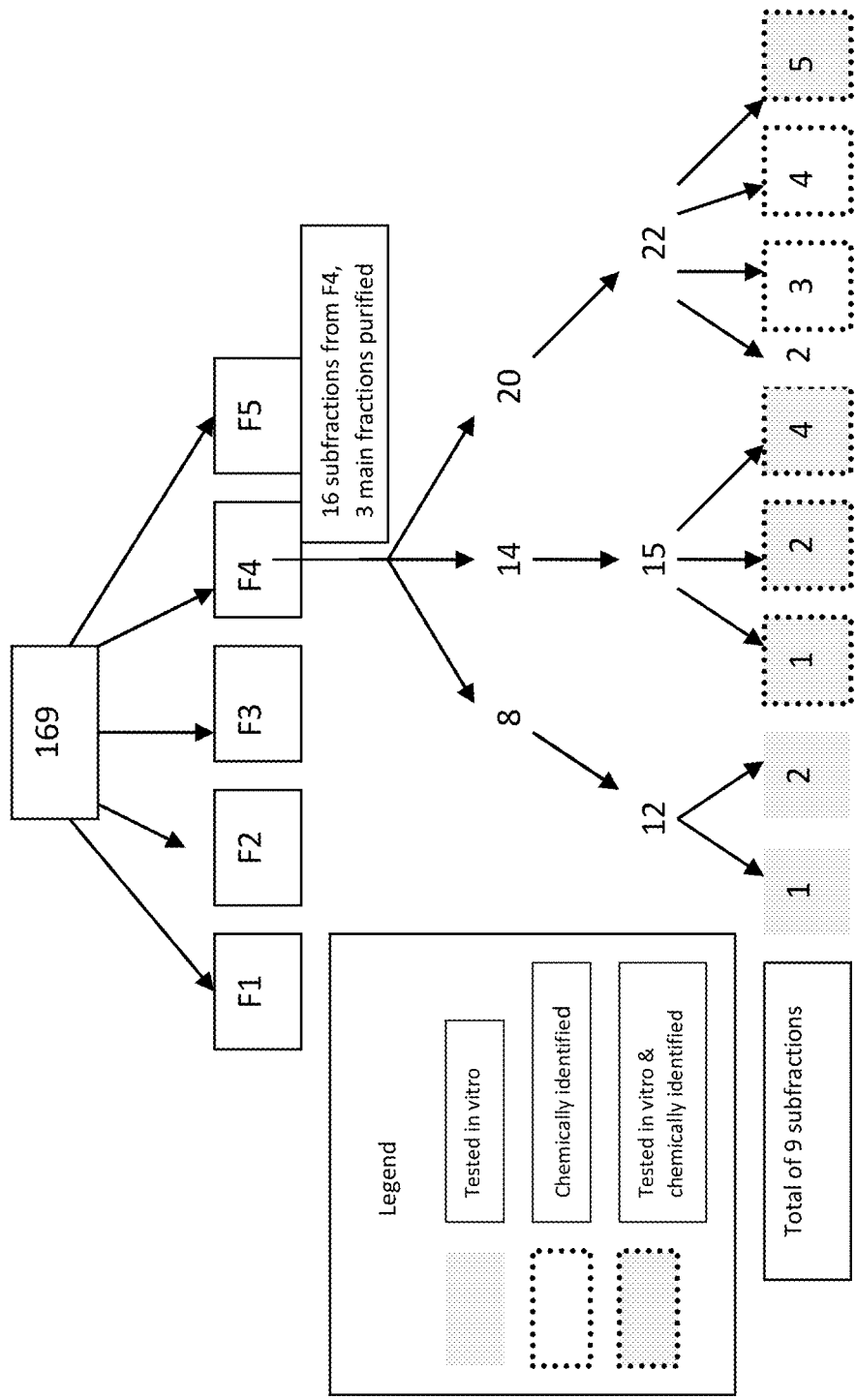
FIG. 59. Summary flowchart of fractionation, purification and in vitro testing of compounds from NC169.

A total of 9 subfractions were identified, 6 of which were tested in vitro (FIG. 59). The same 6 subfractions were chemically identified, three (3) of which contained pure compounds #2 (169-14-15-4), #5 (169-20-22-3) and again #5 (169-22-20-4), whereas subfraction 169-14-15-1 required further purification to isolate compounds 1, 3, and 4; subfraction 169-14-15-2 required further purification to isolate compounds 5, 6 and 7; and subfraction 169-20-22-5 required further purification to isolate compound 5 and 8. The structure and in vitro anti-cancer activity of these compounds is shown in Table 9.

TABLE 9

| Sub-fraction | Compound # | | | Mixed/Pure Average cell viability: | | | | | | | | | | Notes | |
|---|---|---|---|---|---|---|---|---|---|---|---|---|---|---|---|
| | | | | | | | | | | | | | | | |
| 169-14-15-1 | 1, 2, 3, 4 | | | Mixed | | | | | | | | | | | |
| | | | | AVG | ERROR | AVG | ERROR | AVG | ERROR | AVG | ERROR | AVG | ERROR | AVG | ERROR |
| | Vehicle cont-DMSO | 1% | | 96 | 8 | 86 | 11 | 98 | 4 | 93 | 9 | 92 | 14 | 91 | 5 | 88 | 16 |
| | Positive cont-SDS | 250 ug/ml | | PC3 | | A549 | | U373 | | SKOV | | MDA-MB | | CCD | | THP-1 |
| | | ug/mL | | | | | | | | | | | | | | |
| | | 100 | | 14 | | 78 | | 6 | | 59 | | 24 | | 19 | | 53 |
| | | 50 | | 25 | | 103 | | 23 | | 89 | | 45 | | 23 | | 55 |
| | | 10 | | 101 | | 102 | | 105 | | 110 | | 106 | | 103 | | 104 |
| | | 1 | | 114 | | 111 | | 109 | | 120 | | 106 | | 104 | | 104 |
| | | | | Fold change in viability: | | | | | | | | | | | | |
| Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| | | PC3 | | A549 | | U373 | | SKOV | | MDA-MB | | CCD | | THP-1 | |
| | ug/mL | AVG | ERROR | AVG | ERROR | AVG | ERROR | AVG | ERROR | AVG | ERROR | AVG | ERROR | AVG | ERROR |
| | 100 | 0.14 | 0.01 | 0.91 | 0.01 | 0.06 | 0.00 | 0.64 | 0.02 | 0.26 | 0.00 | 0.21 | 0.00 | 0.60 | 0.05 |
| | 50 | 0.26 | 0.03 | 1.20 | 0.11 | 0.23 | 0.01 | 0.96 | 0.05 | 0.49 | 0.01 | 0.25 | 0.01 | 0.62 | 0.03 |
| | 10 | 1.04 | 0.10 | 1.19 | 0.11 | 1.06 | 0.06 | 1.19 | 0.05 | 1.16 | 0.01 | 1.13 | 0.06 | 1.18 | 0.03 |
| | 1 | 1.18 | 0.10 | 1.29 | 0.06 | 1.10 | 0.11 | 1.29 | 0.06 | 1.15 | 0.01 | 1.15 | 0.08 | 1.19 | 0.02 |
| | 2, 5, 6, 7 | | | | | | | | | | | | | Structures of compounds, 6 & 7 (see Table 11) | |
| 169-14-15-2 | Vehicle cont-DMSO | 1% | | 96 | 8 | 86 | 11 | 98 | 4 | 93 | 9 | 92 | 14 | 91 | 5 | 88 | 16 |
| | Positive cont-SDS | 250 ug/mL | | PC3 | | A549 | | U373 | | SKOV | | MDA-MB | | CCD | | THP-1 |
| | | ug/mL | | | | Average cell viability: | | | | | | | | | | |
| | | 100 | | 17 | | 68 | | 16 | | 57 | | 22 | | 19 | | 53 |
| | | 50 | | 37 | | 96 | | 19 | | 93 | | 45 | | 24 | | 53 |
| | | 10 | | 93 | | 97 | | 89 | | 91 | | 99 | | 97 | | 95 |
| | | 1 | | 91 | | 95 | | 83 | | 89 | | 102 | | 92 | | 93 |

TABLE 9-continued
| Sub-fraction | Compound # | | | | | | | | | | | | | | Notes |
|---|---|---|---|---|---|---|---|---|---|---|---|---|---|---|---|
| | | | | | | Mixed/Pure | | | | | | | | | |
| | | | | | | Fold change in viability: | | | | | | | | | |
| | Positive cont-SDS | 0.08 | 0.00 | 0.13 | 0.01 | 0.05 | 0.00 | 0.10 | 0.00 | 0.16 | 0.00 | 0.06 | 0.00 | 0.18 | 0.01 THP-1 |
| | 250 ug/mL | PC3 | | A549 | | U373 | | SKOV | | MDA-MB | | CCD | | | |
| | ug/mL | AVG | ERROR | AVG | ERROR | AVG | ERROR | AVG | ERROR | AVG | ERROR | AVG | ERROR | AVG | ERROR |
| | 100 | 0.17 | 0.01 | 0.80 | 0.02 | 0.16 | 0.01 | 0.62 | 0.04 | 0.24 | 0.01 | 0.21 | 0.02 | 0.60 | 0.02 |
| | 50 | 0.38 | 0.02 | 1.12 | 0.02 | 0.19 | 0.01 | 1.01 | 0.02 | 0.49 | 0.06 | 0.27 | 0.01 | 0.60 | 0.06 |
| | 10 | 0.97 | 0.04 | 1.13 | 0.03 | 0.90 | 0.01 | 0.98 | 0.01 | 1.08 | 0.05 | 1.06 | 0.04 | 1.08 | 0.05 |
| | 1 | 0.95 | 0.05 | 1.11 | 0.04 | 0.85 | 0.02 | 0.96 | 0.02 | 1.11 | 0.02 | 1.01 | 0.03 | 1.06 | 0.01 |
| 169-14-15-4 | 2 | | | | | | | Pure | | | | | | | |
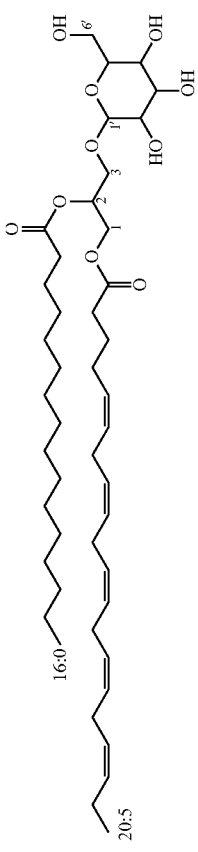
2
Average cell viability:
| | | PC3 | A549 | U373 | SKOV | MDA-MB | CCD | THP-1 |
|---|---|---|---|---|---|---|---|---|
| Vehicle cont-DMSO | 1% | 96 | 86 | 98 | 93 | 92 | 91 | 88 |
| Positive cont-SDS | 250 ug/ml | 8 | 11 | 4 | 9 | 14 | 5 | 16 |
| | ug/mL | PC3 | A549 | U373 | SKOV | MDA-MB | CCD | THP-1 |
| | 100 | 14 | 64 | 8 | 45 | 22 | 13 | 17 |
| | 50 | 49 | 84 | 30 | 67 | 45 | 32 | 27 |
| | 10 | 90 | 98 | 94 | 94 | 101 | 99 | 101 |
| | 1 | 107 | 102 | 106 | 108 | 100 | 107 | 102 |

TABLE 9-continued

| Sub-fraction | Compound # | | | | | | | Mixed/Pure Fold change in viability: | | | | | | | | Notes |
|---|---|---|---|---|---|---|---|---|---|---|---|---|---|---|---|---|
| | Positive cont-SDS | 0.08 PC3 AVG | 0.00 ERROR | 0.13 A549 AVG | 0.01 ERROR | 0.05 U373 AVG | 0.00 ERROR | 0.10 SKOV AVG | 0.00 ERROR | 0.16 MDA-MB AVG | 0.00 ERROR | 0.06 CCD AVG | 0.00 ERROR | 0.18 THP-1 AVG | 0.01 ERROR | |
| | 250 ug/mL ug/mL | | | | | | | | | | | | | | | |
| | 100 | 0.15 | 0.01 | 0.74 | 0.04 | 0.08 | 0.01 | 0.48 | 0.04 | 0.24 | 0.01 | 0.14 | 0.01 | 0.19 | 0.00 | |
| | 50 | 0.51 | 0.02 | 0.98 | 0.04 | 0.30 | 0.05 | 0.72 | 0.02 | 0.49 | 0.03 | 0.36 | 0.03 | 0.31 | 0.01 | |
| | 10 | 0.93 | 0.01 | 1.14 | 0.04 | 0.95 | 0.04 | 1.02 | 0.03 | 1.09 | 0.02 | 1.08 | 0.02 | 1.14 | 0.02 | |
| | 1 | 1.11 | 0.02 | 1.19 | 0.04 | 1.08 | 0.06 | 1.16 | 0.08 | 1.09 | 0.03 | 1.18 | 0.03 | 1.16 | 0.02 | |
| 169-20-22-3 | 5 | | | | | | Pure | | | | | | | | | |

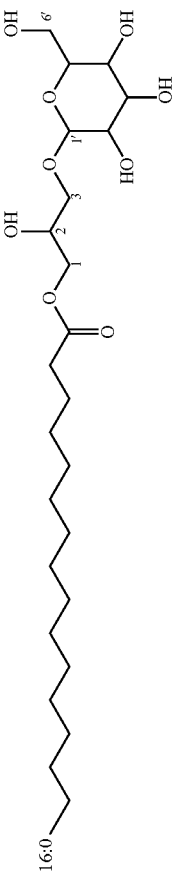

5

| | | | | | | | Pure Mixed Average cell viability | | | | | | | Structure of cpd 8 (see Table 11) | | |
|---|---|---|---|---|---|---|---|---|---|---|---|---|---|---|---|---|
| 169-20-22-4 169-20-22-5 | 5, 8 | | | PC3 | | A549 | | U373 | | SKOV | | MDA-MB | | CCD | | THP-1 |
| | Vehicle cont-DMSO | 1% | | 96 | 8 | 86 | 11 | 98 | 4 | 92 | 16 | 91 | 5 | 88 | 16 | |
| | Positive cont-SDS | 250 ug/ml | | | | | | | | | | | | | | |
| | ug/mL | | | | | | | | | | | | | | | |
| | 100 | | | 15 | 15 | 31 | 90 | 69 | 10 | 16 | 23 | 10 | 92 | 16 | 28 | |
| | 50 | | | 15 | 15 | 90 | 95 | 78 | 25 | 23 | 94 | 92 | 91 | 91 | 93 | |
| | 10 | | | 93 | 00 | 95 | 95 | 85 | 89 | 94 | 108 | 96 | 96 | 93 | |
| | 1 | | | 88 | 01 | | | 87 | 88 | | | | | | | |
| | | | | | | | | Fold change in viability: | | | | | | | | |
| | Positive cont-SDS | 0.08 PC3 AVG | 0.00 ERROR | 0.13 A549 AVG | 0.01 ERROR | 0.05 U373 AVG | 0.00 ERROR | 0.10 SKOV AVG | 0.00 ERROR | 0.16 MDA-MB AVG | 0.00 ERROR | 0.06 CCD AVG | 0.00 ERROR | 0.18 THP-1 AVG | 0.01 ERROR | |
| | 250 ug/mL ug/mL | | | | | | | | | | | | | | | |
| | 100 | 0.15 | 0.08 | 0.40 | 0.04 | 0.70 | 0.10 | 0.11 | 0.01 | 0.18 | 0.00 | 0.11 | 0.01 | 0.18 | 0.01 | |
| | 50 | 0.15 | 0.02 | 1.05 | 0.13 | 0.79 | 0.05 | 0.27 | 0.05 | 0.25 | 0.02 | 1.01 | 0.02 | 0.32 | 0.04 | |
| | 10 | 0.96 | 0.01 | 1.10 | 0.00 | 0.87 | 0.04 | 0.95 | 0.02 | 1.02 | 0.06 | 1.00 | 0.05 | 1.03 | 0.04 | |
| | 1 | 0.91 | 0.02 | 1.11 | 0.01 | 0.89 | 0.03 | 0.95 | 0.03 | 1.17 | 0.05 | 1.05 | 0.02 | 1.05 | 0.05 | |

Example 9. Isolation and Structure Elucidation of Compounds from NC174 (*Polysiphonia ureceolata*)

9.1. Fractionation and Purification of Main Components from NC174

Figure 60:
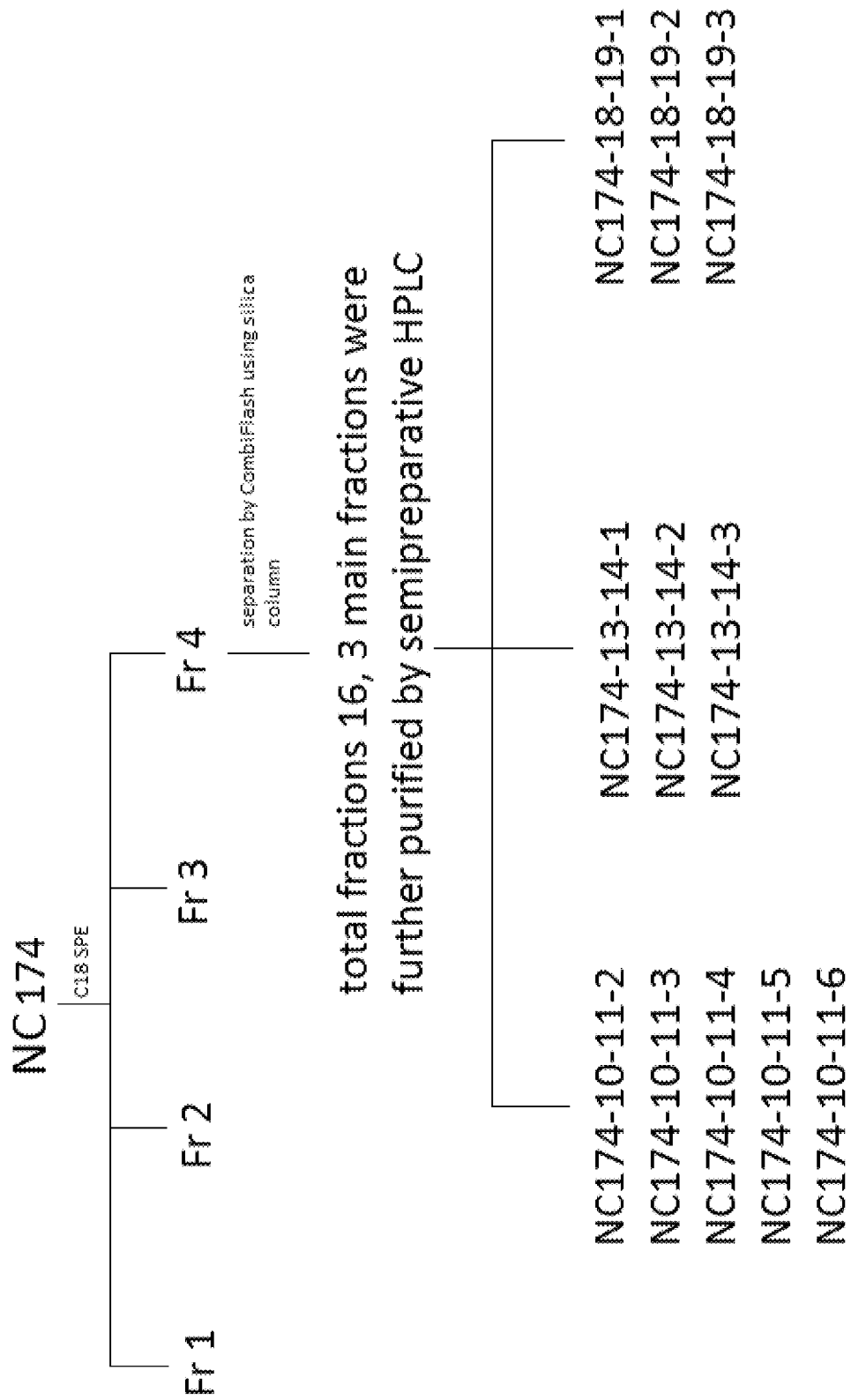
FIG. 60. Flowchart of fractionation and purification of main components from NC174.

The fractionation steps from NC174 are shown in FIG. 60. In short, 3.06 g NC174 were dissolved in methanol and fractionated using the same approach as described above to yield 4 fractions, 5% methanol (Fr. 1), 25% methanol (Fr. 2), 50% methanol (Fr. 3) and methanol (Fr. 4). Fr. 4 (0.5 g) was subjected to further fractionation based on previous bioassay result.

For further fractionation, Fr. 4 was dissolved in dichloromethane/methanol and mixed with celite and dried. The sample was loaded on 24 g Teledyne ISCO High Performance GOLD silica gel column and eluted with dichloromethane/methanol on CombiFlash® Rf, Teledyne ISCO. The eluting solvent gradient (A and B) was as the following: 0% B for 2 CV (column volume) then to 40% B for 15 CV and kept at 40% B for 2 CV, to 100% B for 2 CV and kept at 100% B for 2 CV. Total elution volume was 23 CV. A is dichloromethane and B is methanol/dichloromethane (1:1). Fractions were monitored by TLC and some combined and dried using Rotavap and Genevac.

Based on HPLC chromatograms, three sub-fractions were further purified using semi preparative HPLC (Agilent). The column used was ZORBAX SB-C18 (9.4×50 mm, 5 μm) and the mobile phase was water/acetonitrile. Eluting gradient varied for different samples so to optimize separation. The column temperature was at 55° C. and flow rate 5 mL/min.

9.2 Structure Characterization of Main Components from Bioactive Fraction (Fr. 4)

Samples' preparation and analysis were carried as in section 8.2 above.

9.3. Characterization of Main Components from NC174-F4

GC-MS analysis was done to profile the fatty acids composition in this extract and its bioactive fraction. GC/FID chromatograms show that the of NC174 and NC174-Fr. 4, profiles are similar (not shown). The retention time and tentative identification based on NIST GC-MS database matching are shown in Table 10. The major fatty acid were shown to be palmitic acid (C16:0) and eicosapentaenoic acid (EPA, C20:5).

TABLE 10

Tentative identification of fatty acids using GC-MS analysis of NC174 and NC174-F4

| RT (min) | Compounds |
|---|---|
| 11.31 | Methyl tetradecanoate (Myristic acid, C14:0) |
| 13.47 | Hexadecanoic acid, methyl ester (Palmitic acid, C16:0) |
| 13.86 | 9-Hexadecenoic acid, methyl ester, (Z)- (Palmitoleic acid, C16:1) |
| 16.71 | 9 (or 11)-Octadecenoic acid, methyl ester (C18:1) |
| 16.83 | 11 (or 9)-Octadecenoic acid, methyl ester (C18:1) |
| 17.53 | 9,12-Octadecadienoic acid (Z,Z)-, methyl ester (Linoleic acid, C18:2) |
| 22.16 | 5,8,11,14-Eicosatetraenoic acid, methyl ester, (all-Z)- (Arachidonic acid, C20:4) |
| 23.54 | Methyl eicosa-5,8,11,14,17-pentaenoate (EPA, C20:5) |

Figure 61:
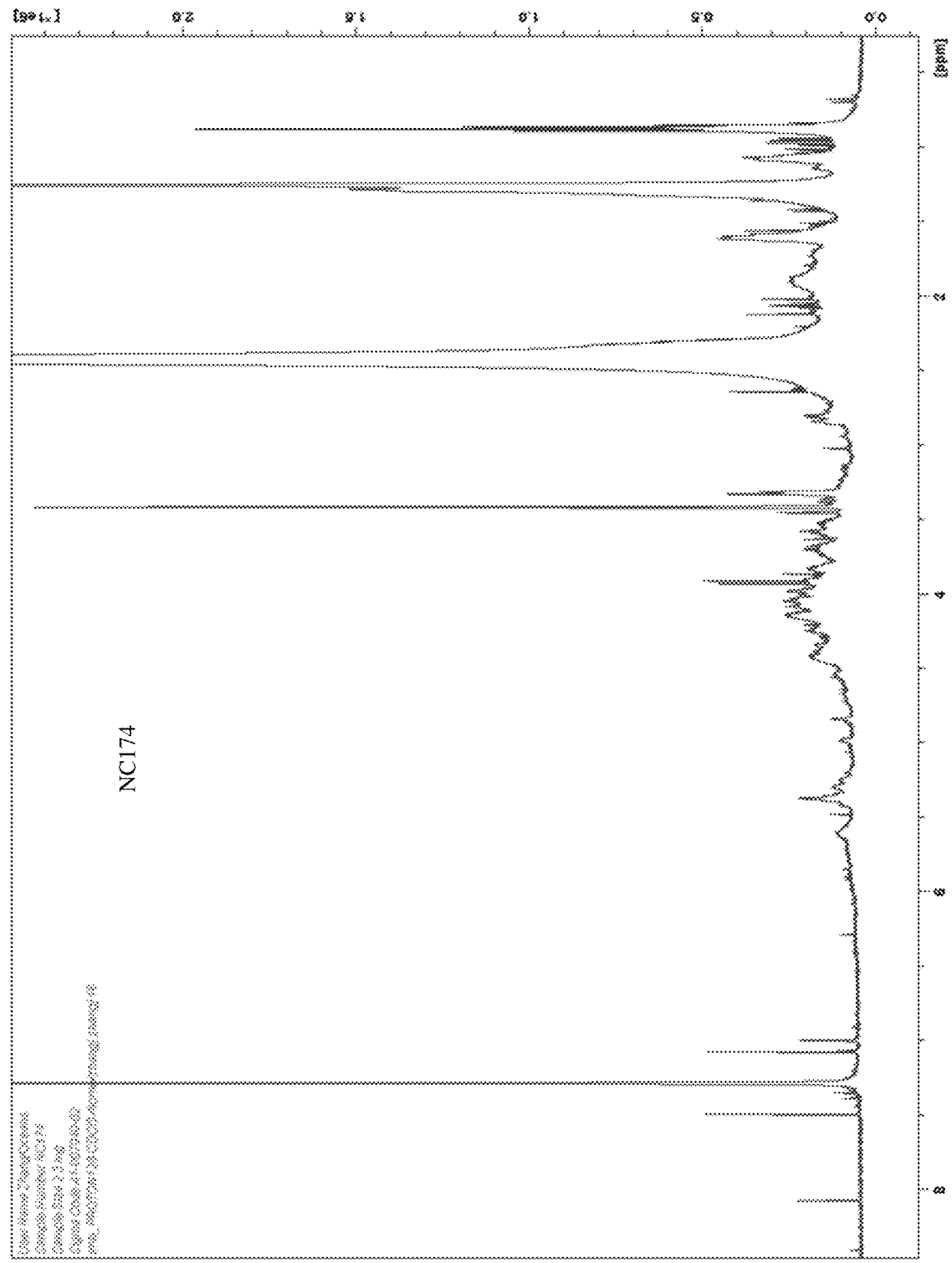
FIG. 61. 1H-NMR spectrum of NC174.
Figure 62:
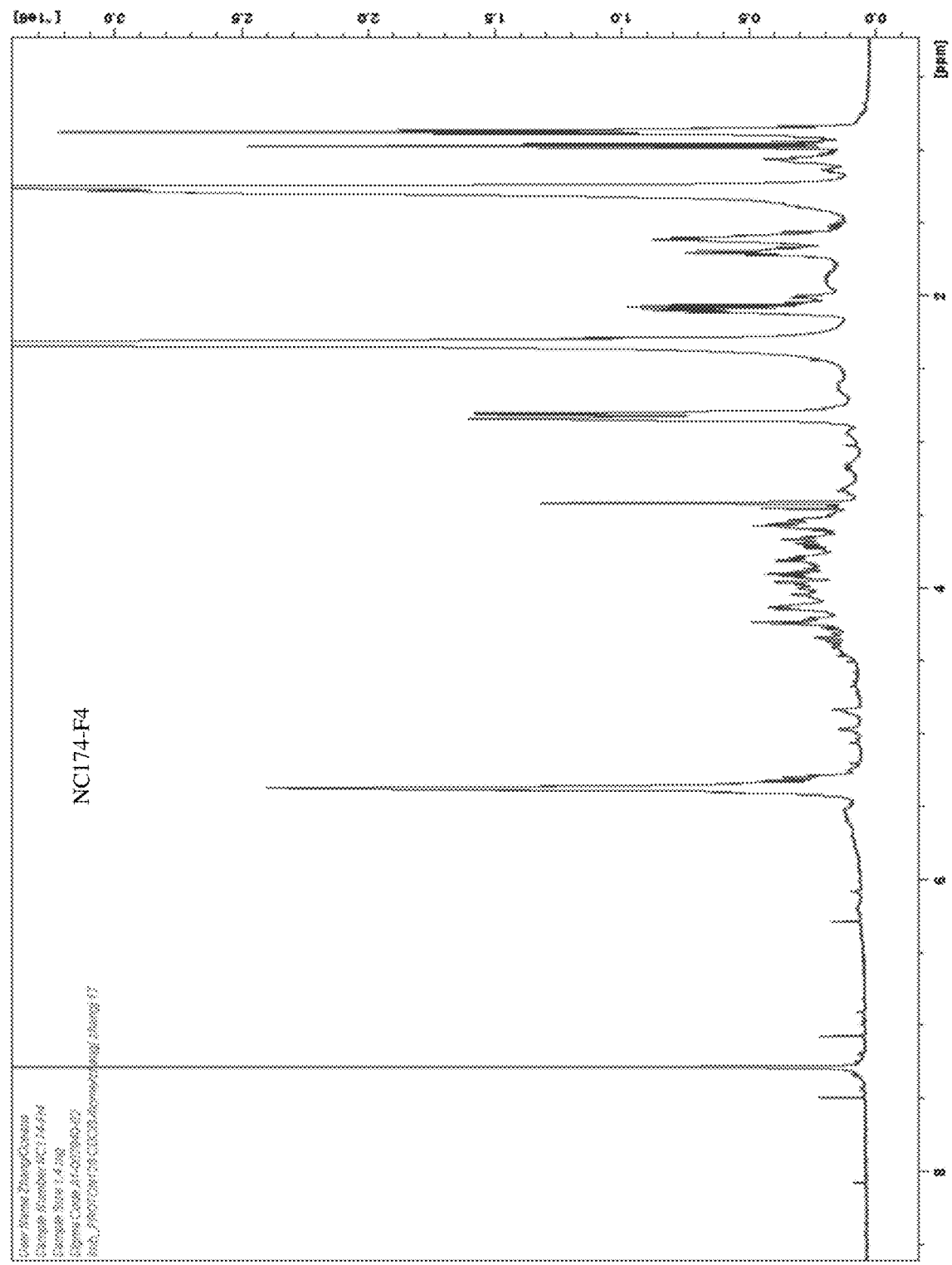
FIG. 62. 1H-NMR spectrum of NC174-F4.

$_1$H-NMR spectra of NC174 and NC174-F4 (FIGS. 61 and 62) are similar, and glycolipids appear to be the major components. In UPLC-DAD/HRMS (FIG. 34), peak RT 3.77 was found to have a molecular formula of $C_{45}H_6O_{10}$, same as to glycolipid 1 described above. The fatty acid fragments from HRMS also confirmed that peak RT 3.77 is the same as compound 1.

NC174-13-14-1

Figure 63:
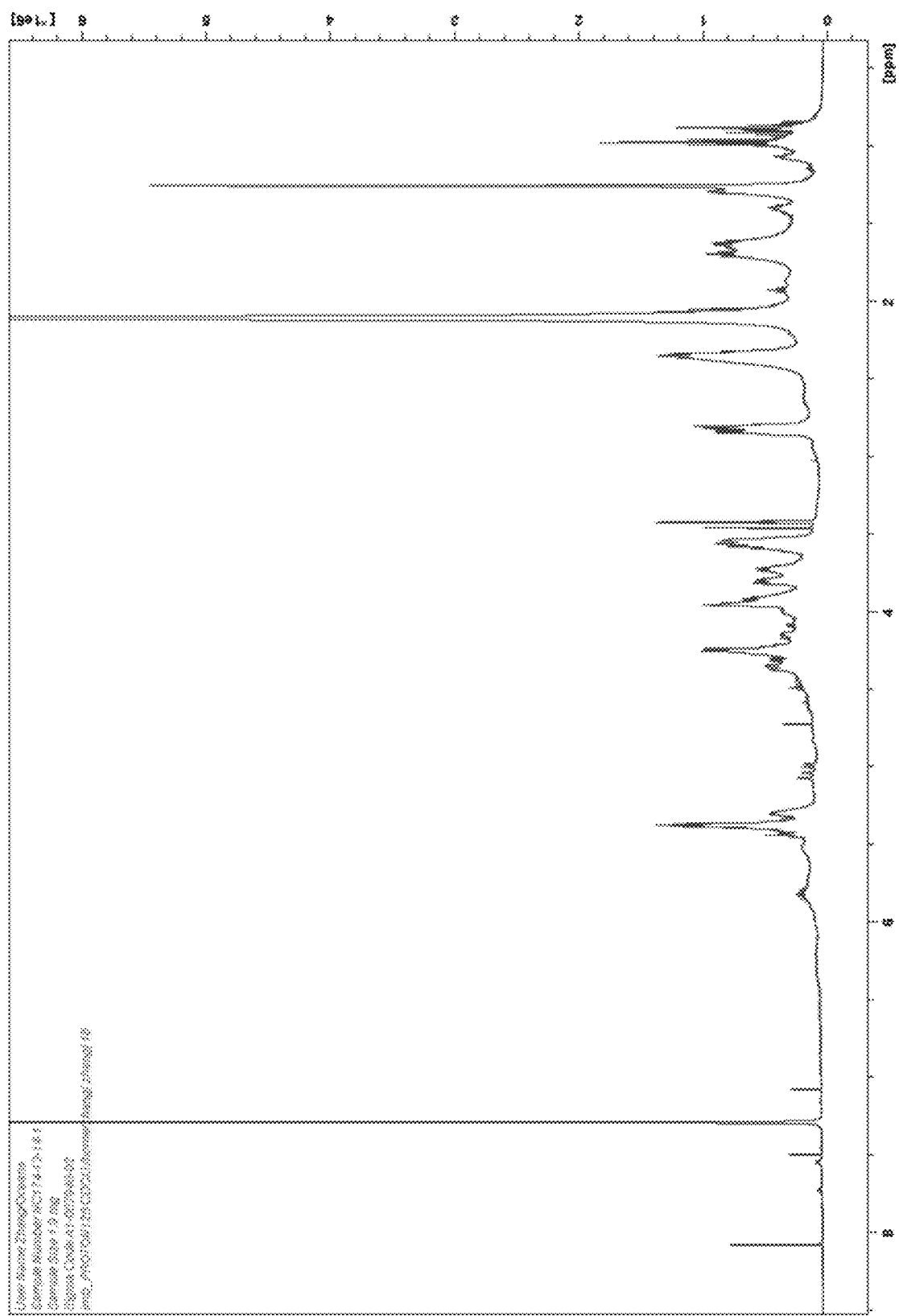
FIG. 63. 1H-NMR spectrum of NC-174-13-14-1.
Figure 64:
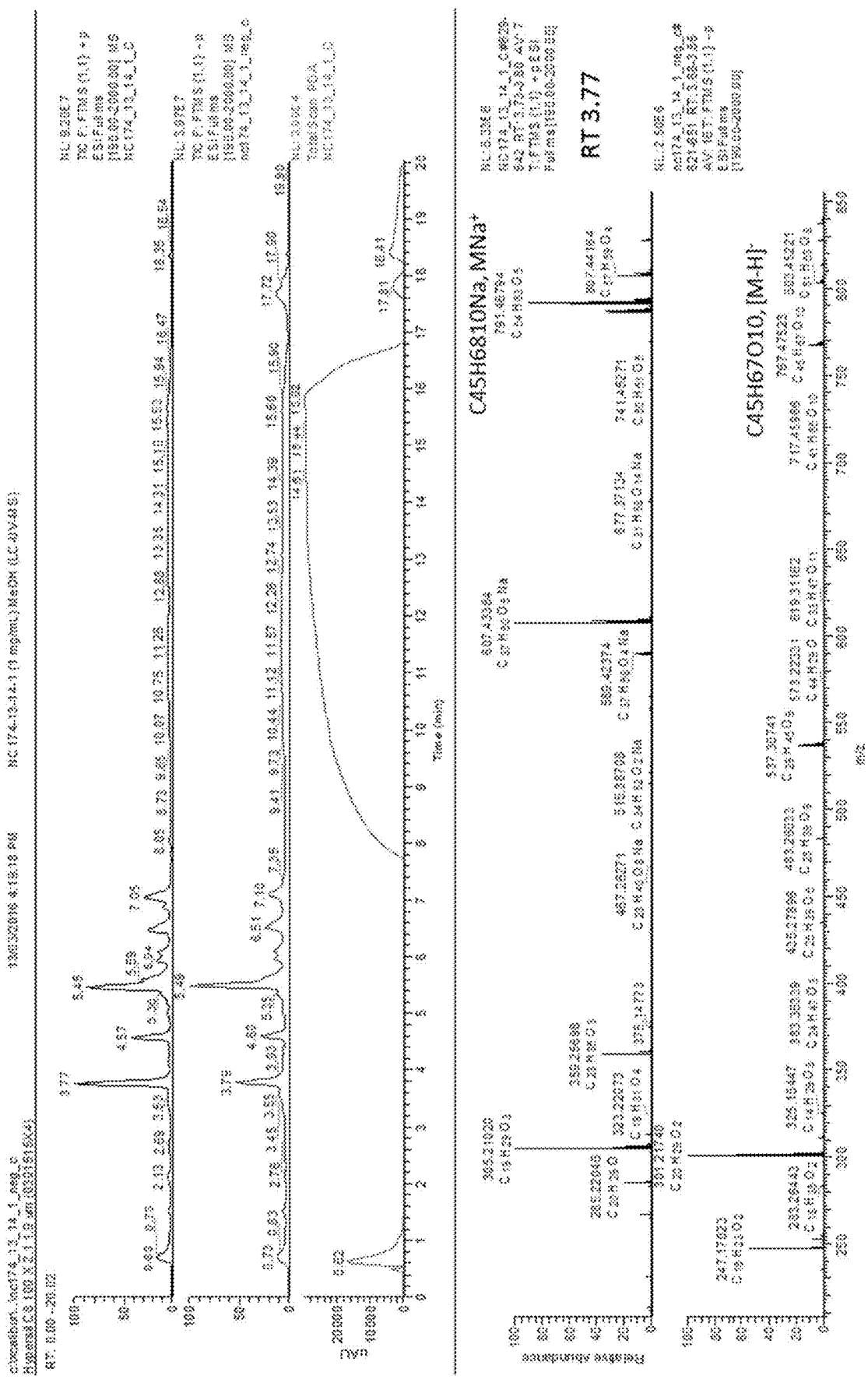
FIG. 64. UPLC-DAD/HRMS chromatograms of NC-174-13-14-1 and HRMS of peak 3.77 of NC174-13-14-1.

Glycolipid structure features are clearly shown in 1H-NMR spectrum of NC174-13-14-1 (FIG. 63). In UPLC-DAD/HRMS (FIG. 64), peak RT3.77 was found to have a molecular formula of C45H68O10 same as glyciolipid 1 described above. The fatty acid fragments from HRMS also confirmer that peak RT3.77 was the same as compound 1.

Figure 65:
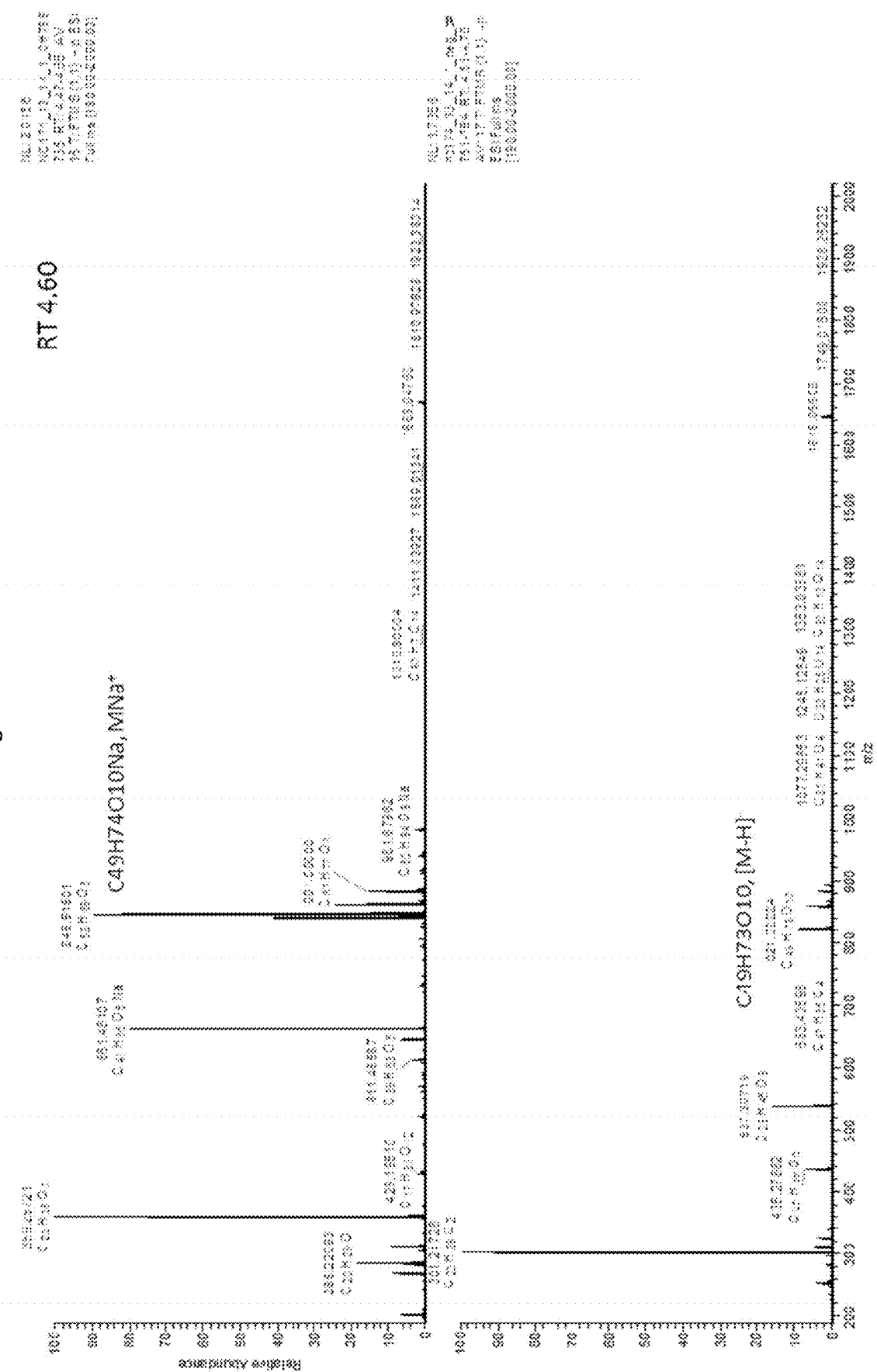
FIG. 65. HRMS spectra of peak RT 4.60 of NC174-13-14-1.
Figure 66:
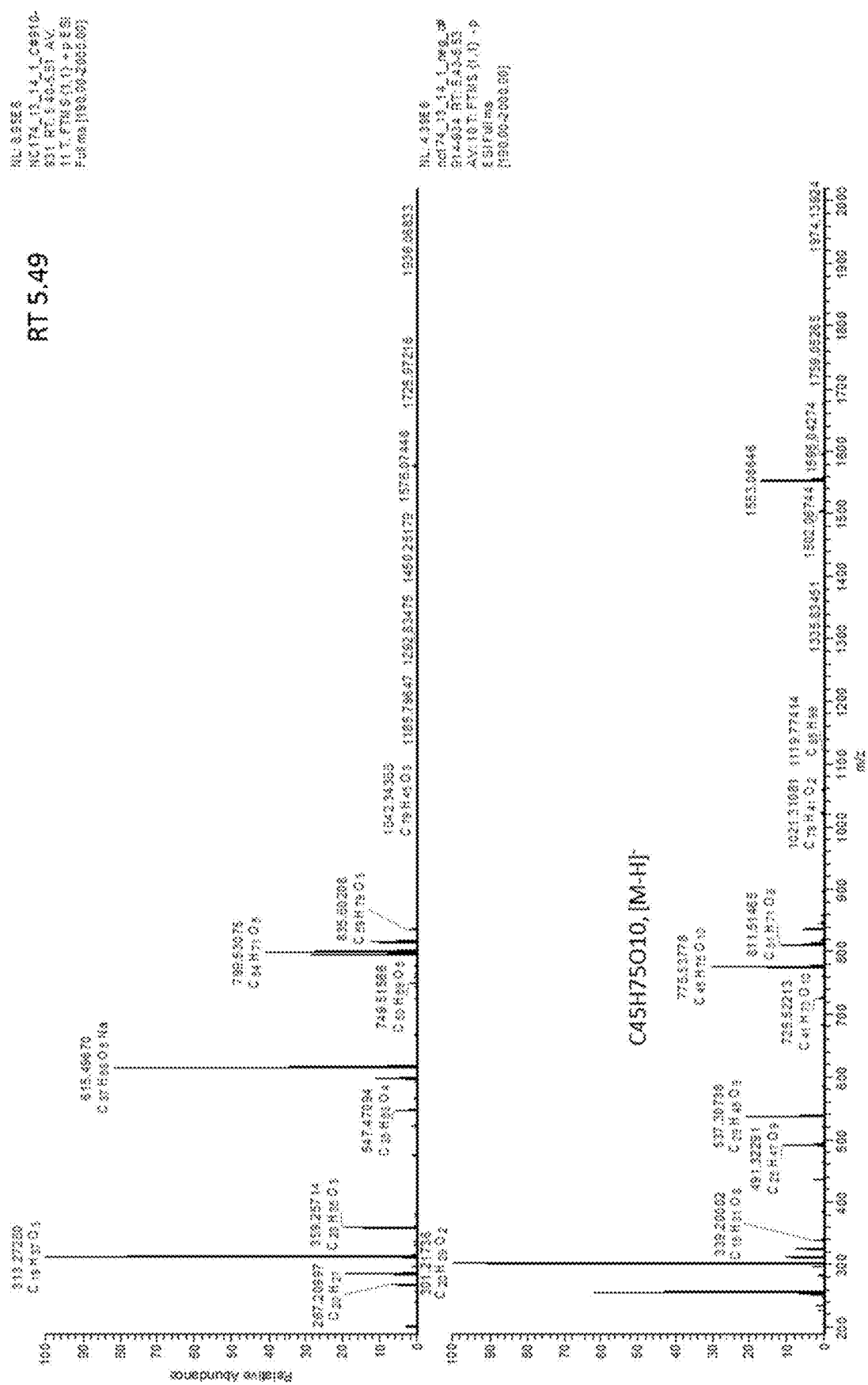
FIG. 66. HRMS spectra of peak RT 5.49 of NC174-13-14-1.
Figure 67:
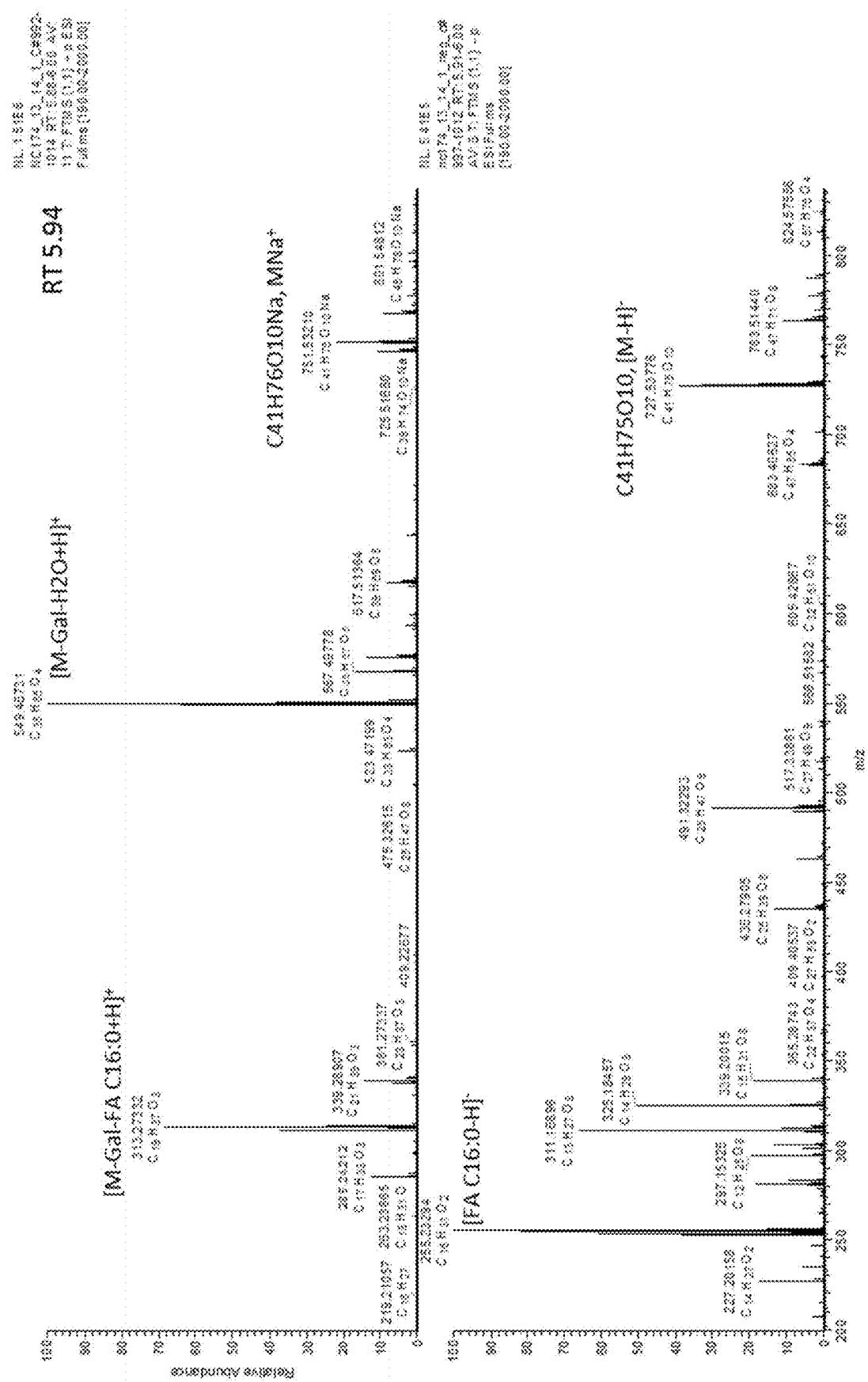
FIG. 67. HRMS of peak RT 5.94 of NC174-13-14-1.
Figure 68:
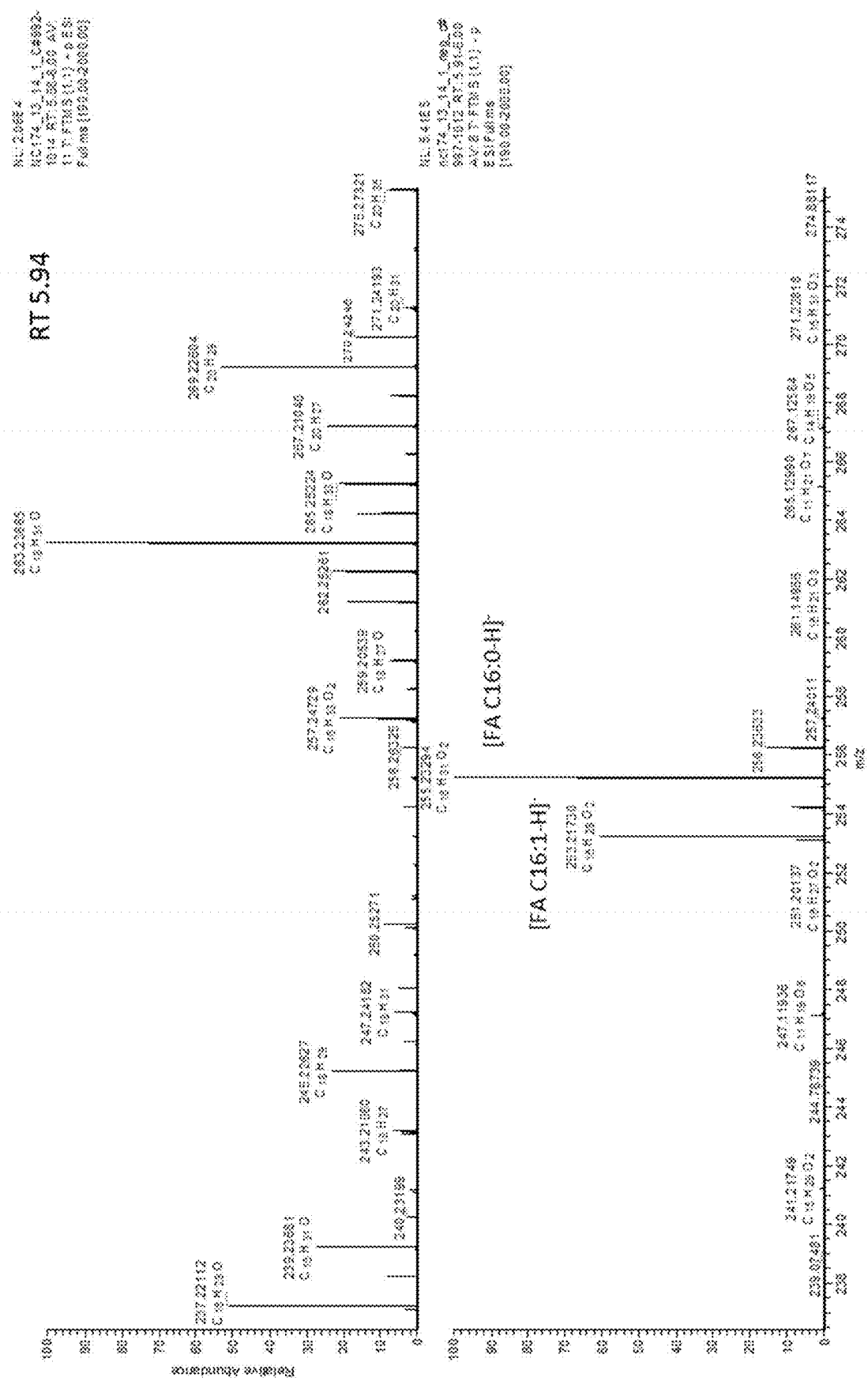
FIG. 68. HRMS of peak RT 5.94 of NC174-13-14-1 showing fatty acid fragments.

Similarly, peak RT 4.60 was identified as glycolipid 7, MGDG C20:5/C20:5 described above based on its HRMS data (FIG. 65). As well, peak RT 5.49 was identified to be the same as glycolipid 2 described earlier based on its HRMS spectra (FIG. 66). HRMS spectra of peak RT 5.94 showed molecular ions of m/z 751.53210 ($C_{41}H_{76}O_{10}Na_+$, calculated 751.53307) and 727.53776 ($C_{41}H_{75}O_{10-}$, calculated 727.53657) in positive and negative mode HRMS (FIG. 67), indicating a glycolipid MGDG with a molecular formula of $C_{41}H_{76}O_{10}$. Two fatty acids, C16:0 and C16:1, were shown in HRMS negative mode spectrum (FIG. 68). As such, the structure of peak RT 5.94 was determined to be glycolipid MGDG C16:0/16:1 (9).

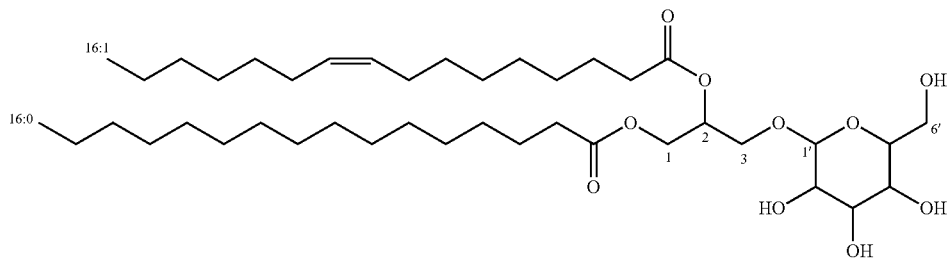

9

Figure 69:
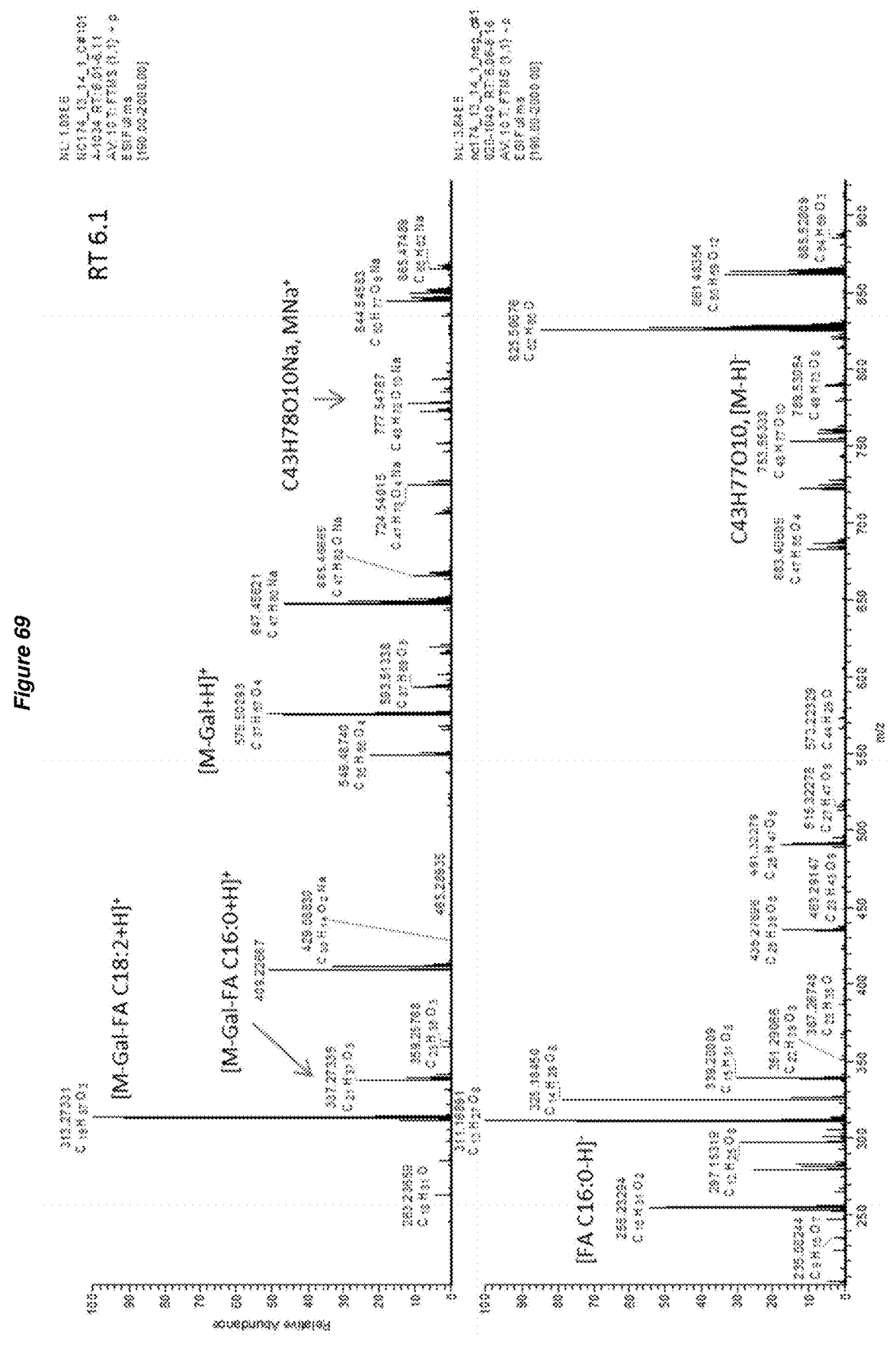
Figure 70:
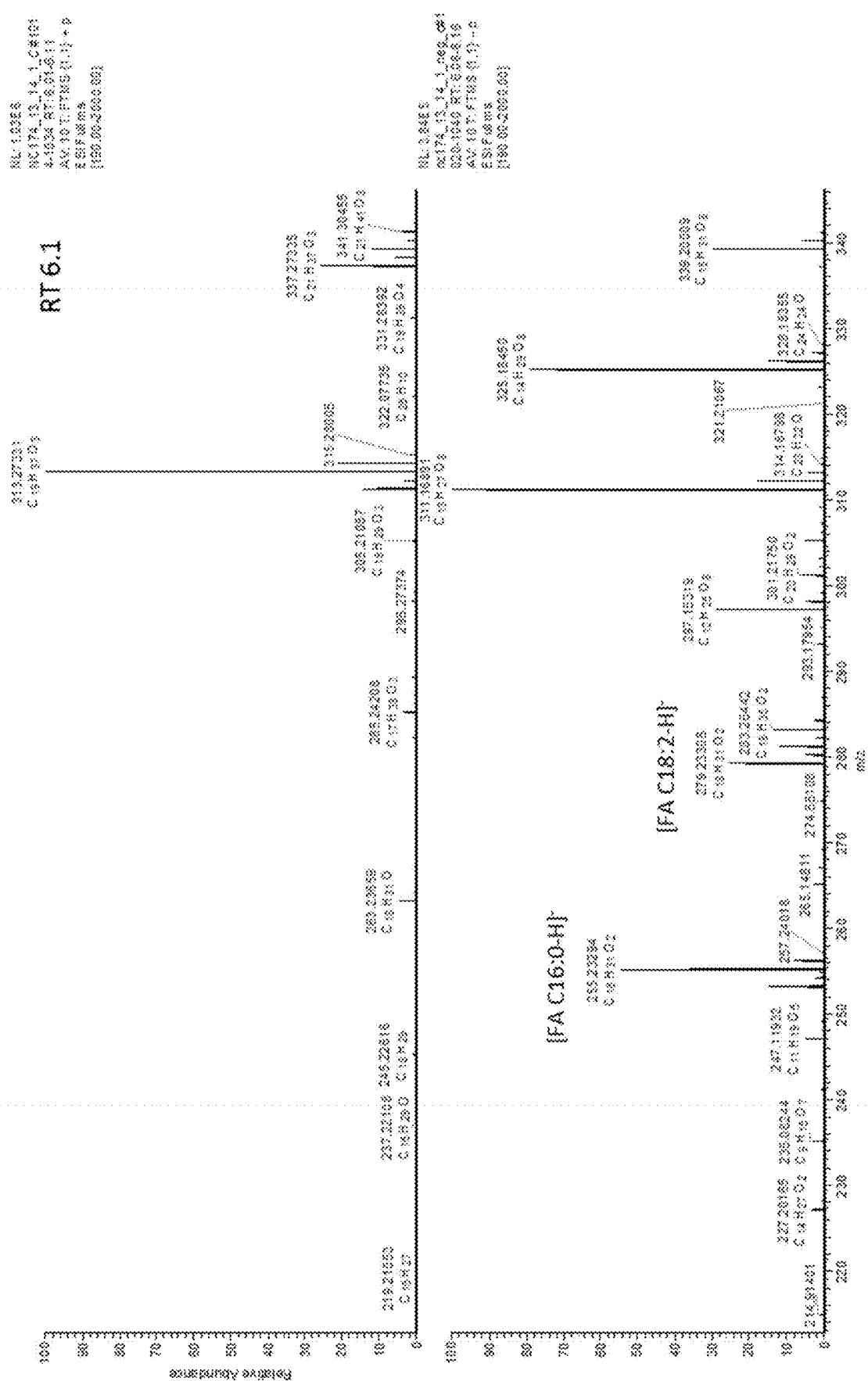
FIG. 70. HRMS of peak RT 6.1 of NC174-13-14-1 showing fatty acid fragments.

Peak RT 6.1 is determined to have a molecular formula of $C_{43}H_{78}O_{10}$ based on HRMS molecular ions of m/z 777.54787 ($C_{43}H_{78}O_{10}Na_+$, calculated 777.54872) and 753.55333 ($C_{43}H_{77}O_{10-}$, calculated 753.55222) in positive and negative mode HRMS (FIG. 69). Two fatty acids, C16:0 and C18:2, are shown in HRMS negative mode spectrum (FIG. 70). The structure of peak RT 6.1 was thus determined to be glycolipid MGDG C16:0/18:2 (10).

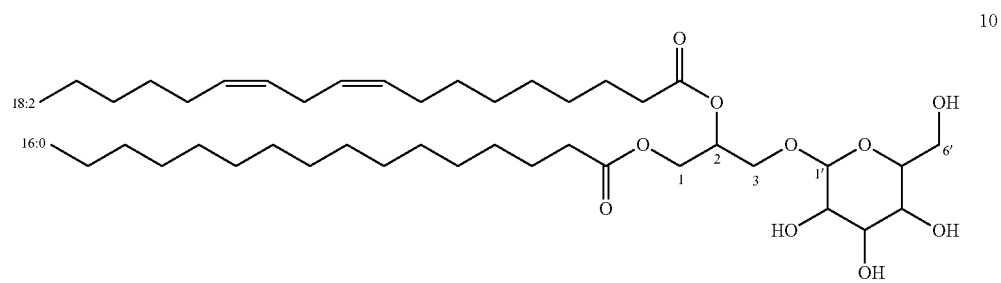 [SMILES: CCCCC/C=C\C/C=C\CCCCCCCC(=O)OC(COC(=O)CCCCCCCCCCCCCCC)COC1OC(CO)C(O)C(O)C1O]

10

Figure 71:
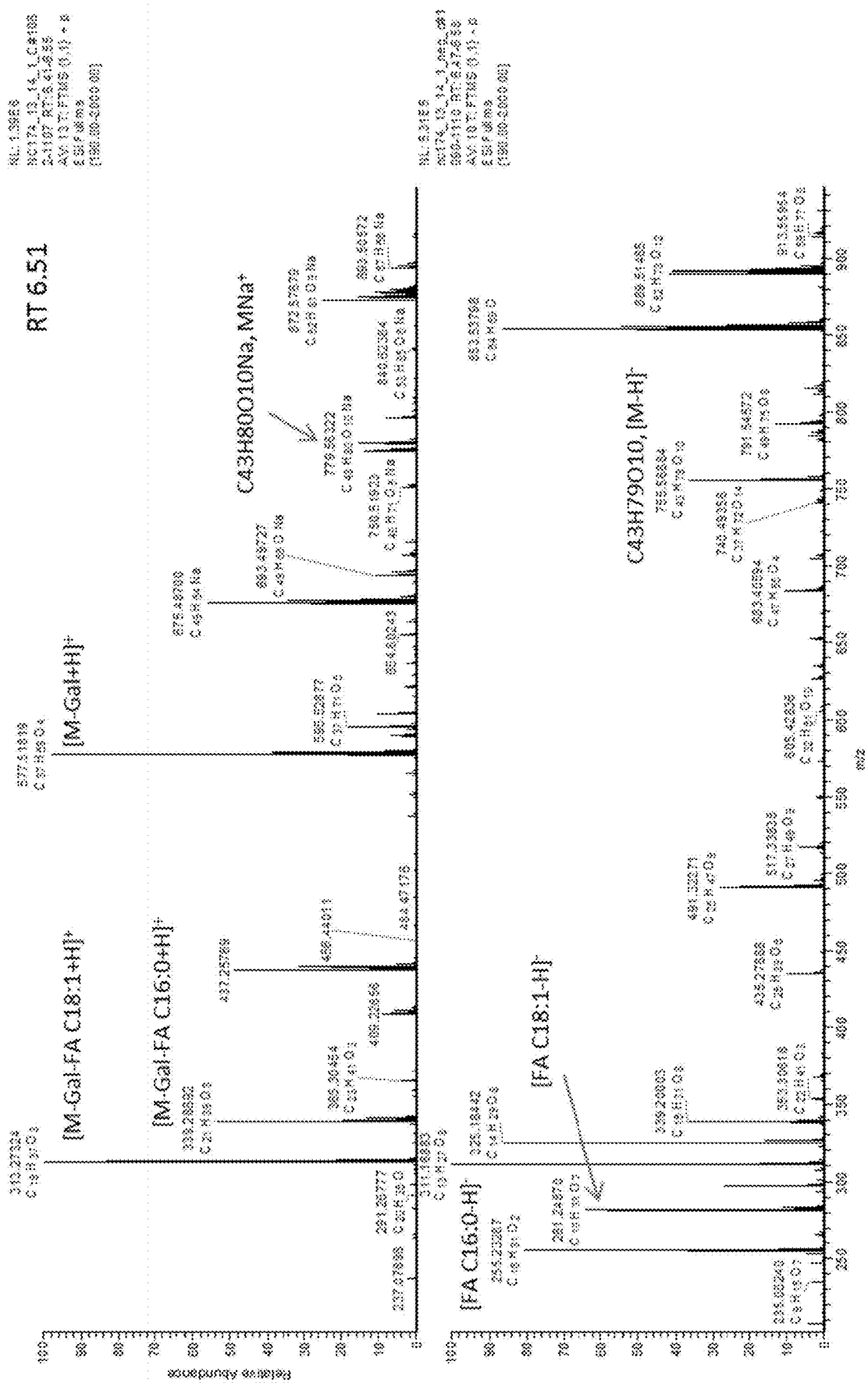
FIG. 71. HRMS spectra of peak RT 6.51 of NC174-13-14-1.

Peak RT 6.51 has a molecular formula of $C_{43}H_{80}O_{10}$ based on HRMS molecular ions of m/z 779.56322 ($C_{43}H_{80}O_{10}Na_+$, calculated 779.56437) and 755.56884 ($C_{43}H_{79}O_{10-}$, calculated 755.56787) in positive and negative mode HRMS (FIG. 71). Two fatty acids, C16:0 and C18:1, are shown in HRMS negative mode spectrum. The structure of peak RT 6.51 was thus determined to be glycolipid MGDG C16:0/18:1 (11).

NC174-13-14-2

Figure 73:
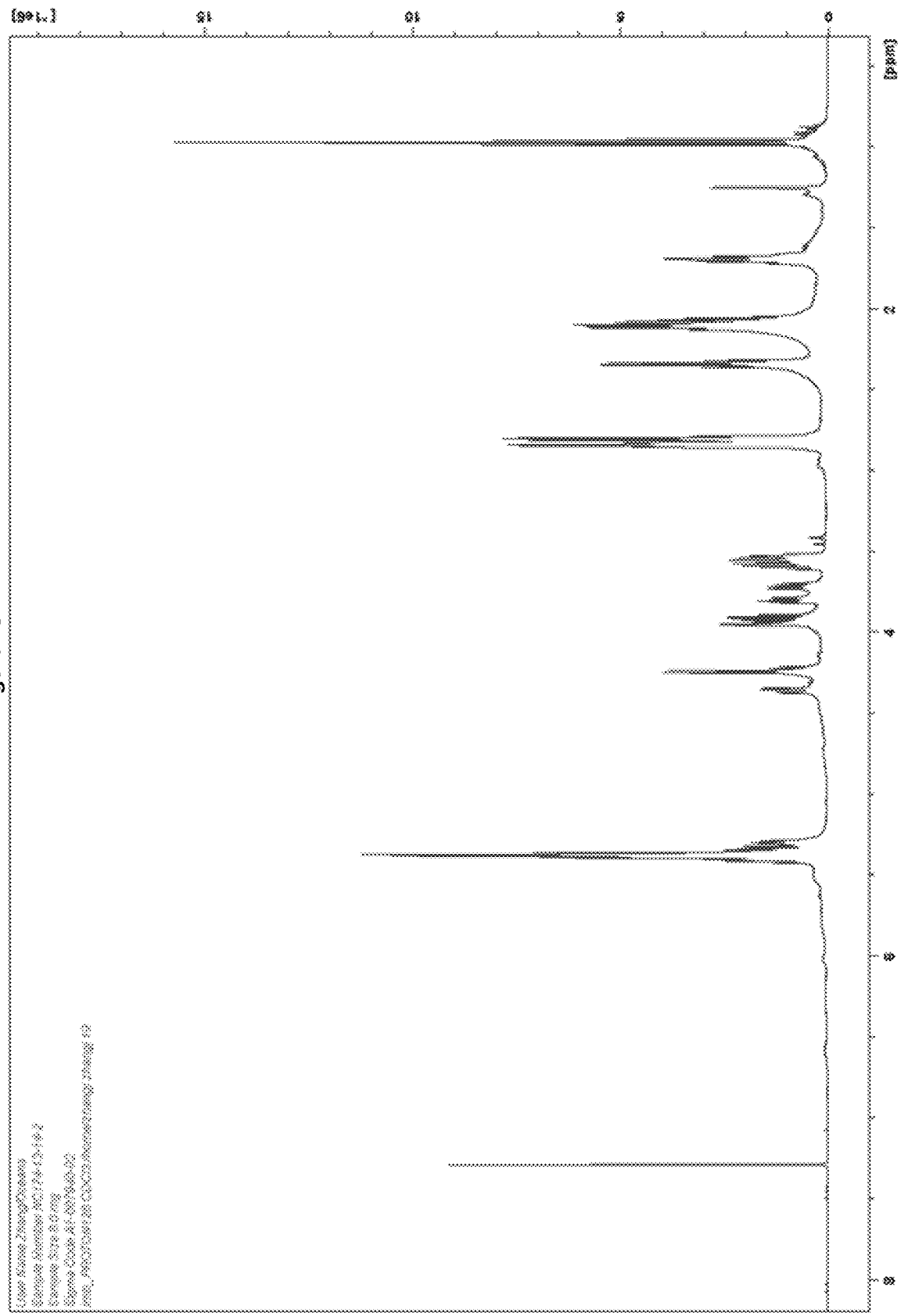
FIG. 73. 1H-RMS spectrum of NC174-13-14-2.
Figure 74:
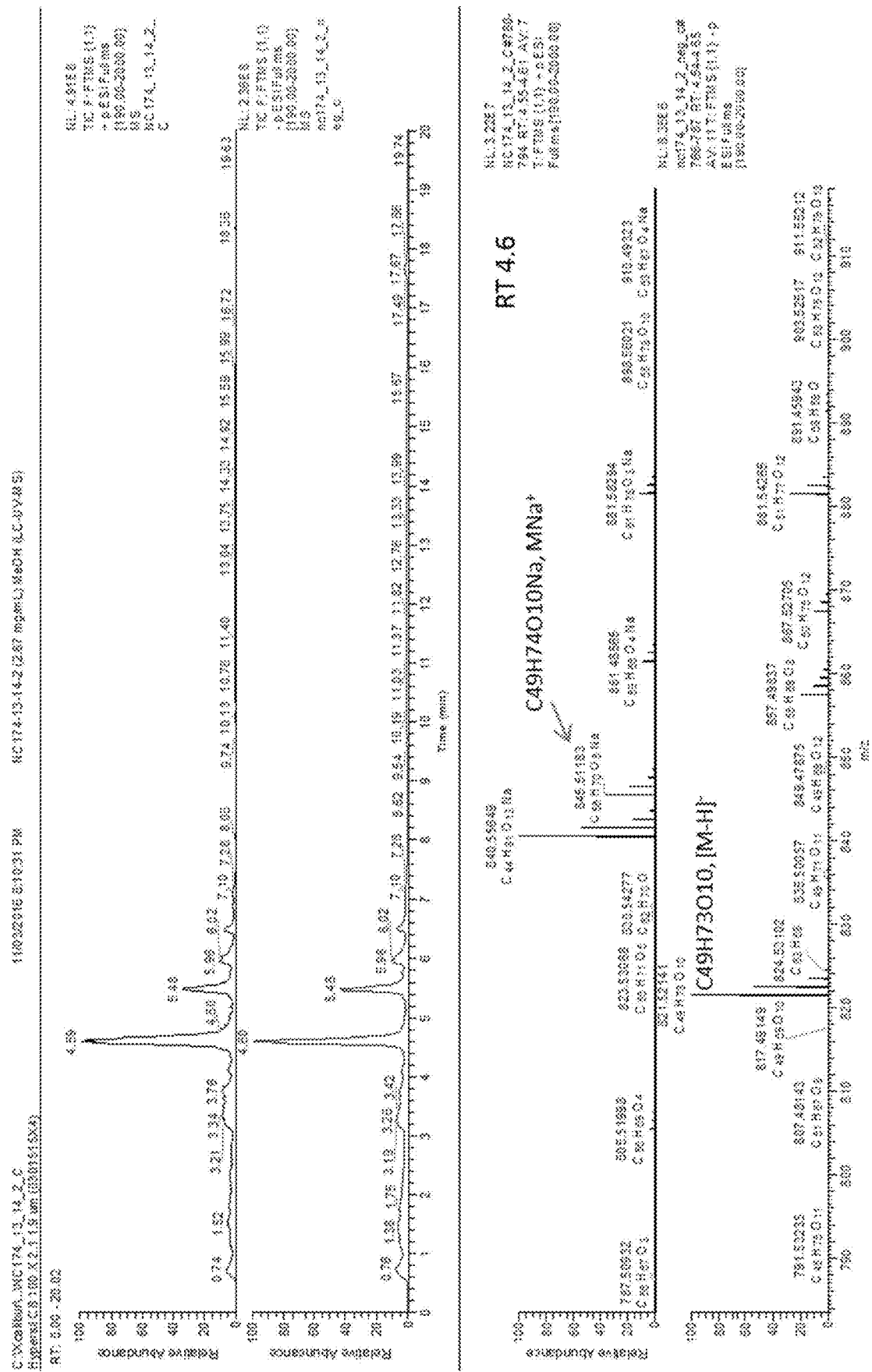
FIG. 74. UPLC-HRMS chromatograms of NC174-13-14-2 and HRMS of peak 4.6 of NC174-13-14-2.
Figure 75:
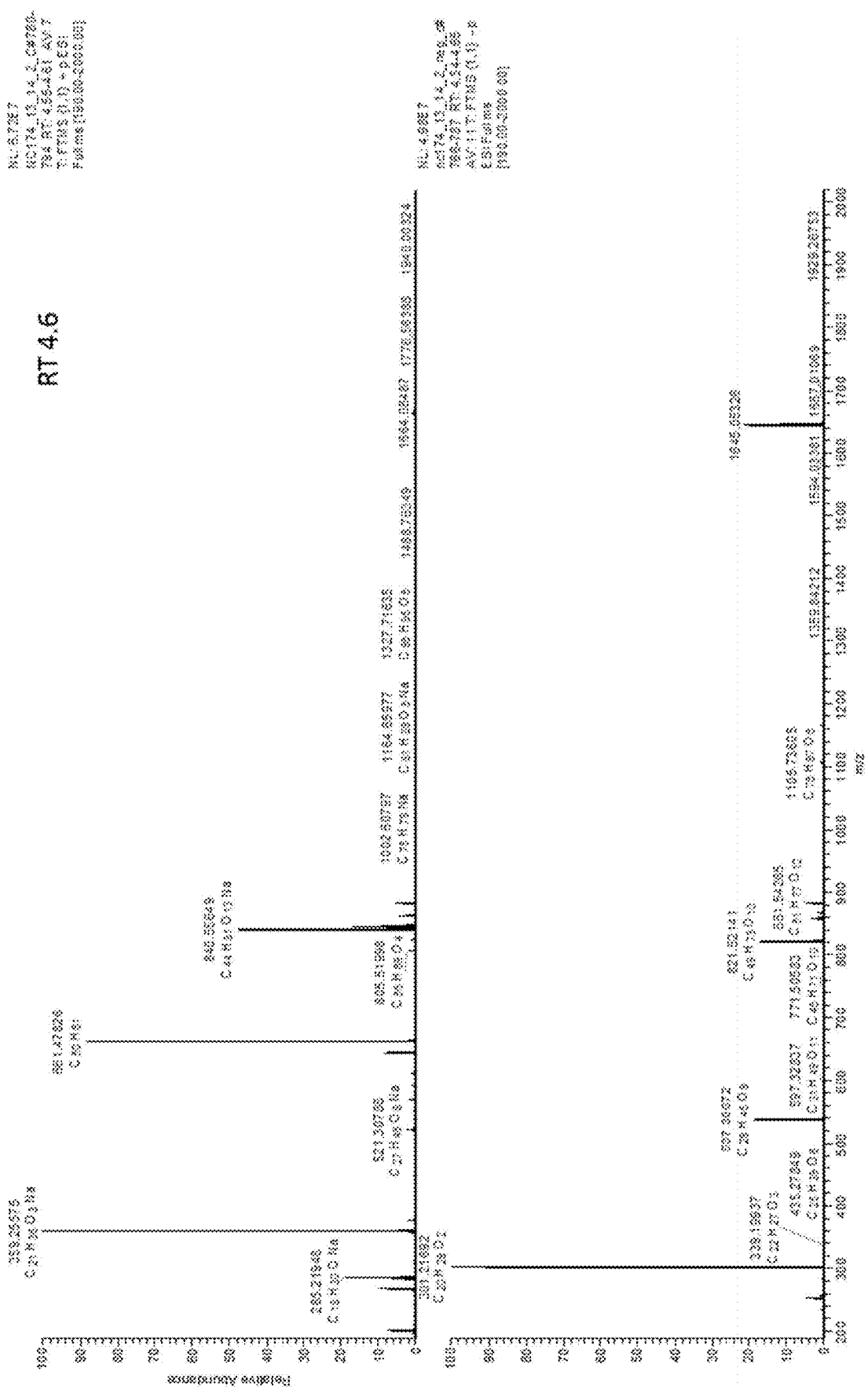
FIG. 75. HRMS of peak 4.6 of NC174-13-14-2 showing fatty acid fragments.

The $_1$H-NMR spectrum (FIG. 73) revealed the typical glycolipid structure features and higher unsaturation in fatty acid chains. Peak RT 4.6, the major component, was determined to be glycolipid MGDG C20:5/C20:5, same as compound 7 described above, based on retention time (not shown) and HRMS data (FIGS. 74 and 75). The 1H-NMR spectrum revealed the typical glycolipid structure features

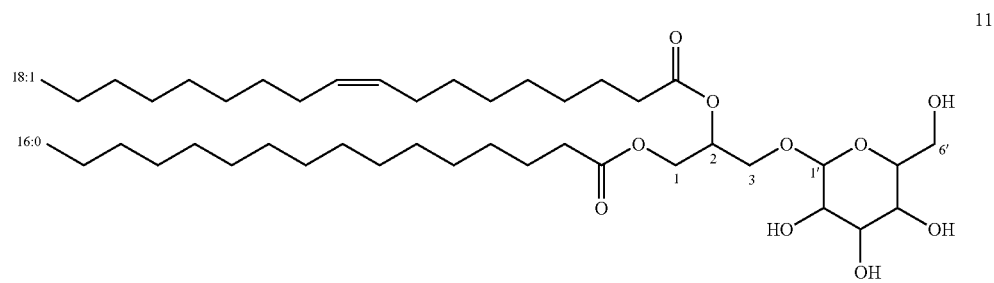 [SMILES: CCCCCCCC/C=C\CCCCCCCC(=O)OC(COC(=O)CCCCCCCCCCCCCCC)COC1OC(CO)C(O)C(O)C1O]

11

Figure 72:
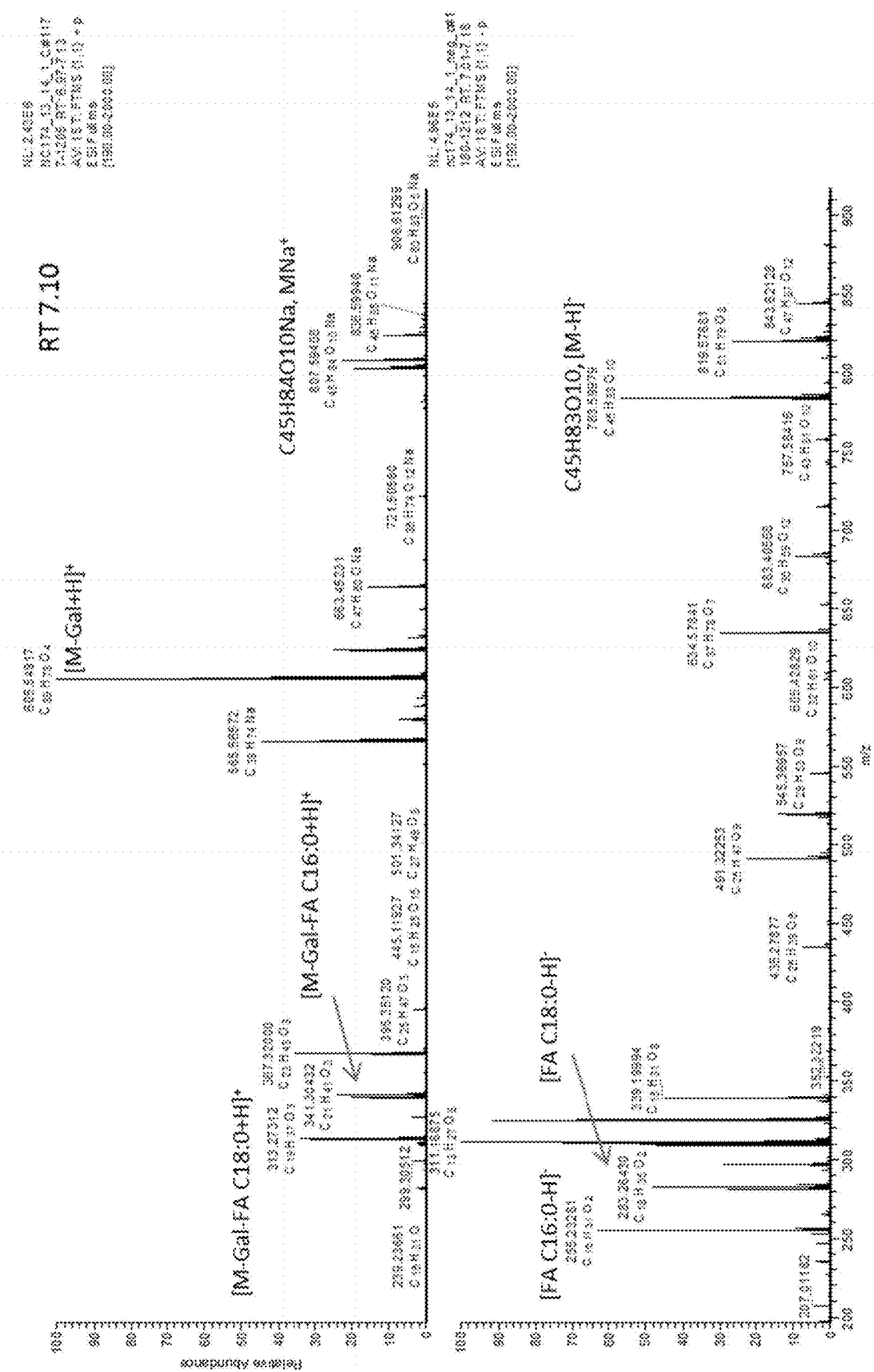
FIG. 72. HRMS spectra of peak RT 7.10 of NC174-13-14-1.

The exact position of unsaturation on the C18:1 fatty acid chain could not be determined but likely to be as shown below based on the presence of GC-MS analysis. Peak RT 7.10 was shown to have a molecular formula of $C_{45}H_{84}O_{10}$ based on HRMS molecular ions of m/z 807.59408 ($C_{45}H_{84}O_{10}Na_+$, calculated 807.59622 807.59567) and 783.59979 ($C_{45}H_{83}O_{10-}$, calculated 783.59862 783.59917) in positive and negative mode HRMS (FIG. 72). Two fatty acids, C16:0 and C18:0, are shown in HRMS negative mode spectrum. The structure of peak RT 7.10 was thus determined to be glycolipid MGDG C16:0/18:0 (12).

Figure 76:
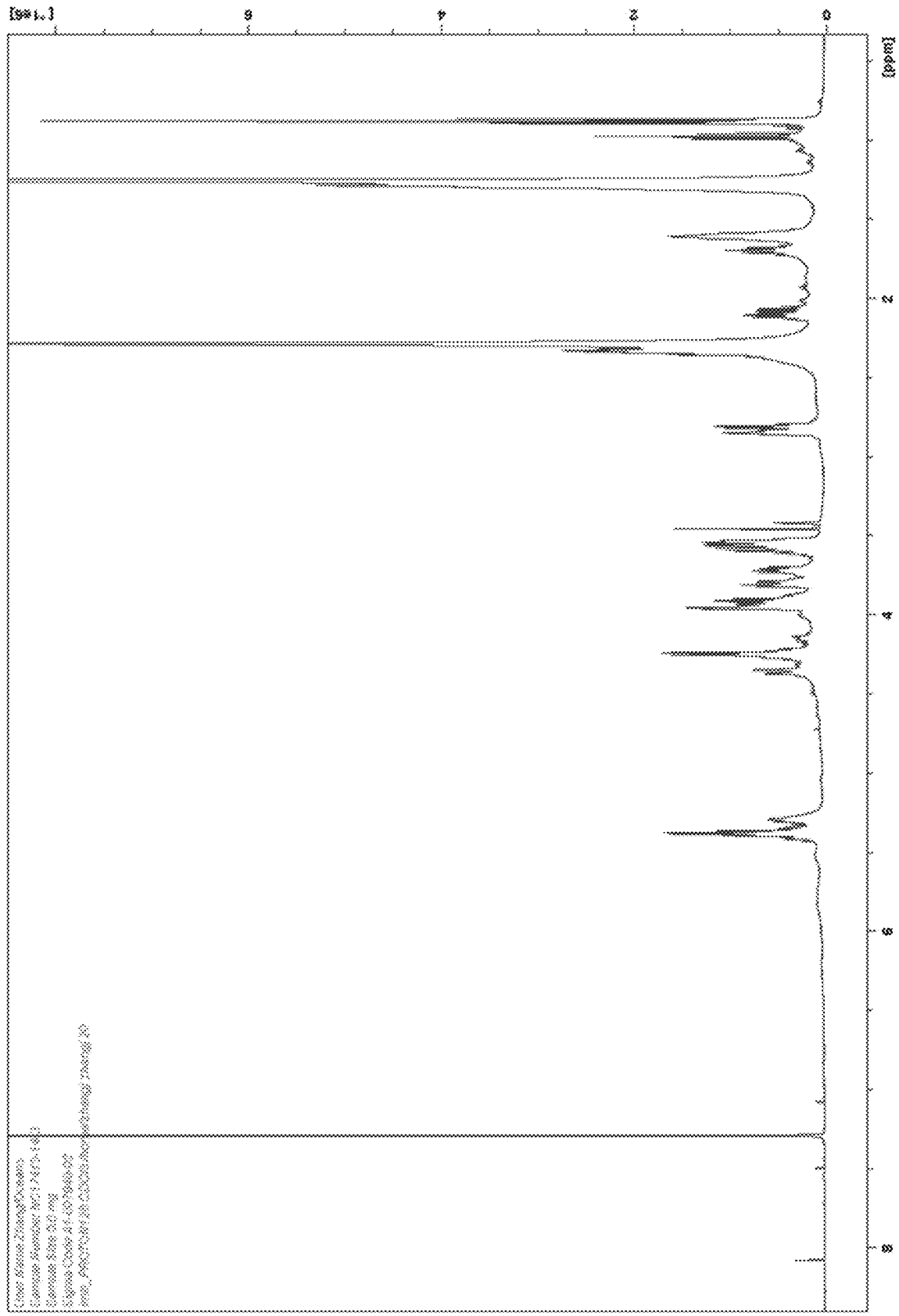
FIG. 76. 1H-NMR spectrum of NC174-13-14-3.
Figure 77:
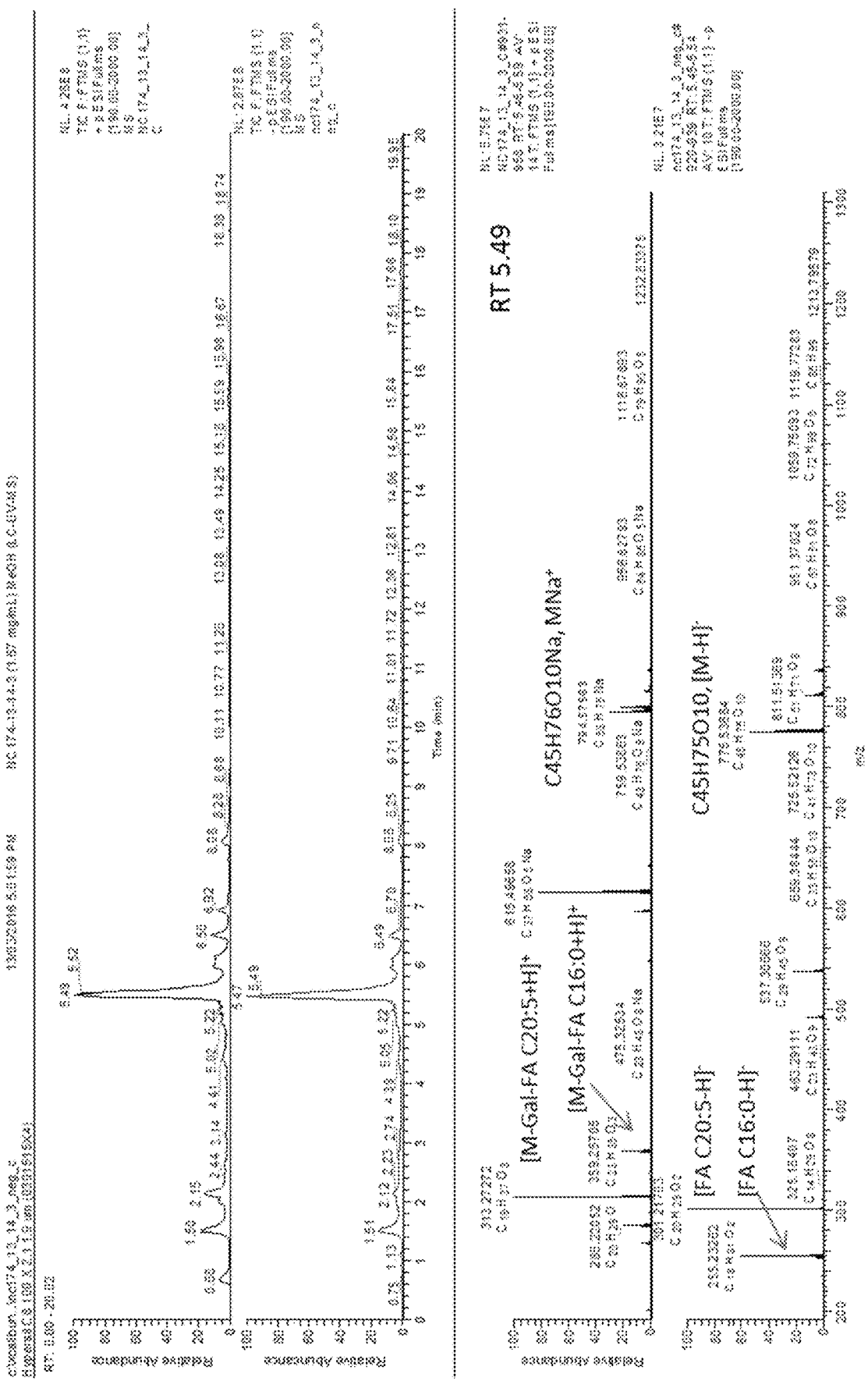
FIG. 77. UPLC-HRMS chromatograms of NC174-13-14-3 of HRMS of peak RT 5.49.

(FIG. 76). Peak RT 5.49, the major component, is identified as glycolipid 2 described above, based on retention time and HRMS data (FIG. 77).

NC174-18-19-3

Figure 78:
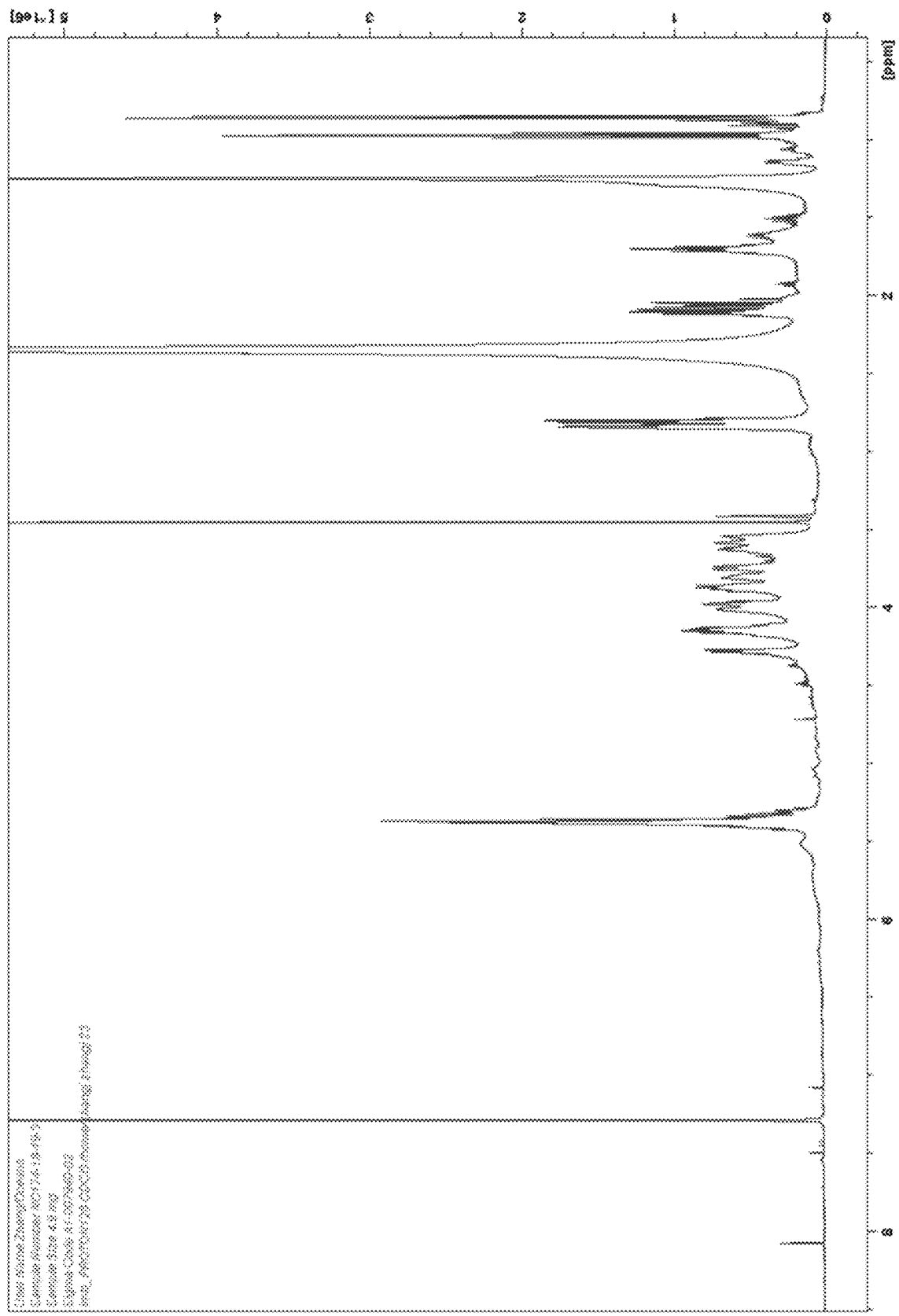
FIG. 78. 1H-NMR spectrum of NC174-18-19-3.
Figure 79:
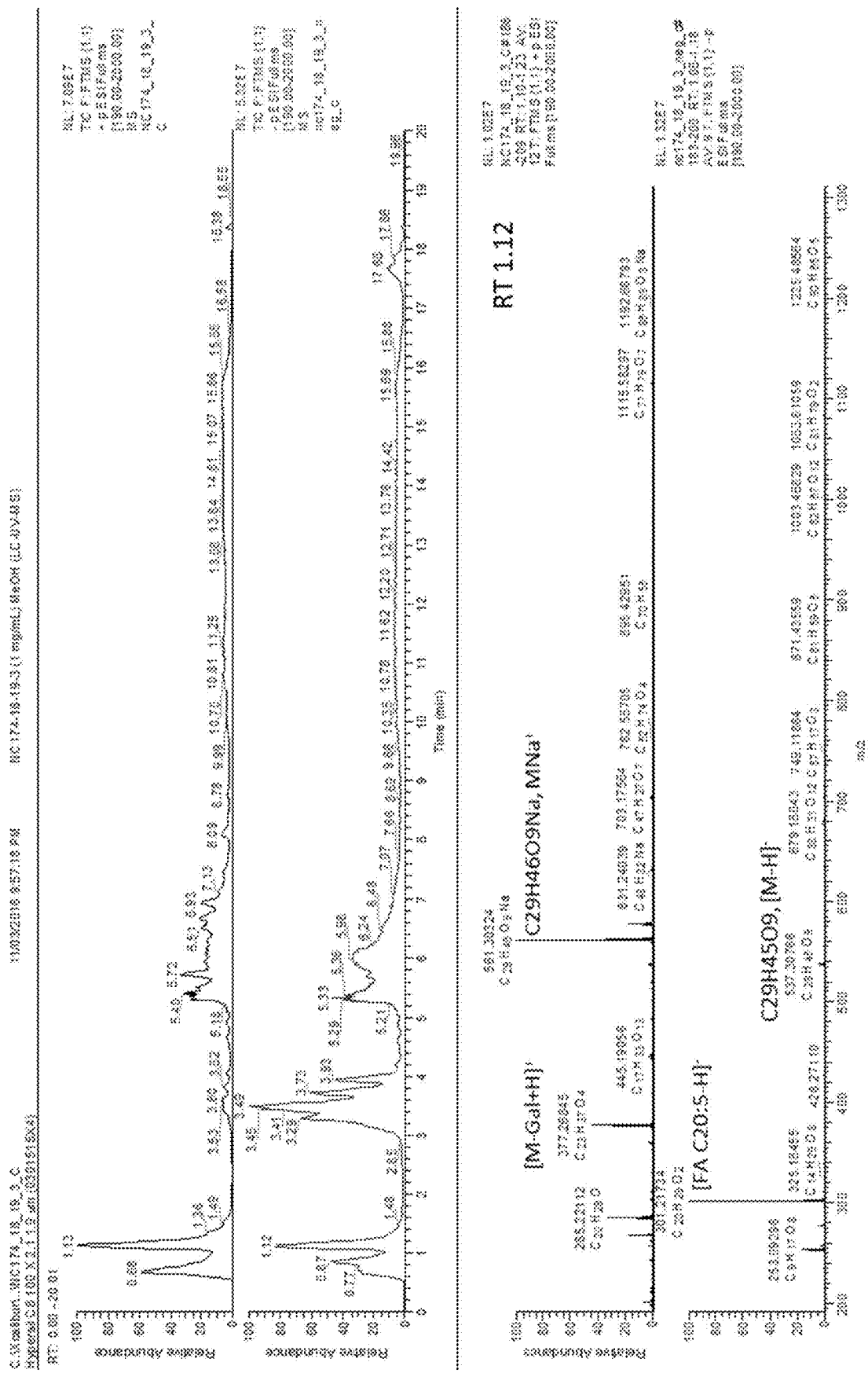
FIG. 79. UPLC-HRMS chromatograms of NC174-18-19-3 and HRMS of peak RT 1.12.

This sample was revealed to have the typical glycolipid structure features also in $_1$H-NMR spectrum (FIG. 78). Peak RT 1.12 was shown to have a molecular formula of $C_{29}H_{46}O_9$ based on HRMS molecular ions of m/z 561.30324 ($C_{29}H_{46}O_9Na_+$, calculated 561.30340) and 537.30766 ($C_{29}H_{45}O_{9-}$, calculated 537.30691) in positive and negative mode HRMS (FIG. 79). Only one fatty acid fragment (C20:5) present in HRMS indicating a lyso-MGDG glycolipid structure of lyso-MGDG C20:5 (13).

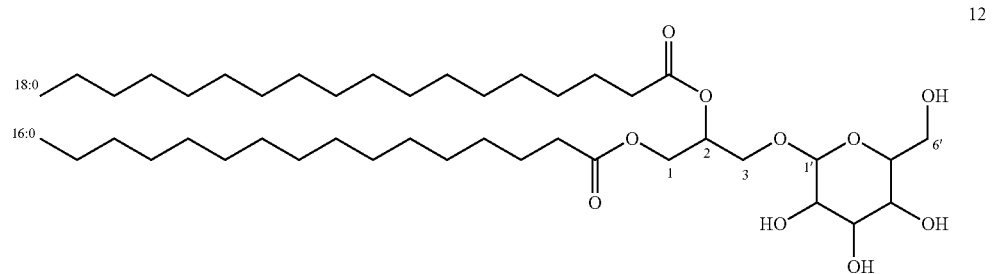 [SMILES: CCCCCCCCCCCCCCCCCC(=O)OC(COC(=O)CCCCCCCCCCCCCCC)COC1OC(CO)C(O)C(O)C1O]

12

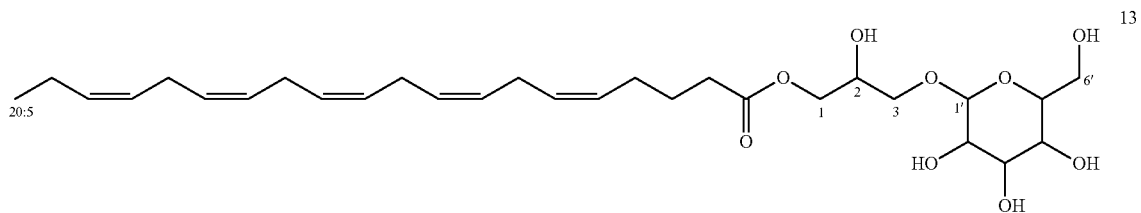 [SMILES: CC/C=C\C/C=C\C/C=C\C/C=C\C/C=C\CCCC(=O)OCC(O)COC1OC(CO)C(O)C(O)C1O]

SUMMARY

Figure 80:
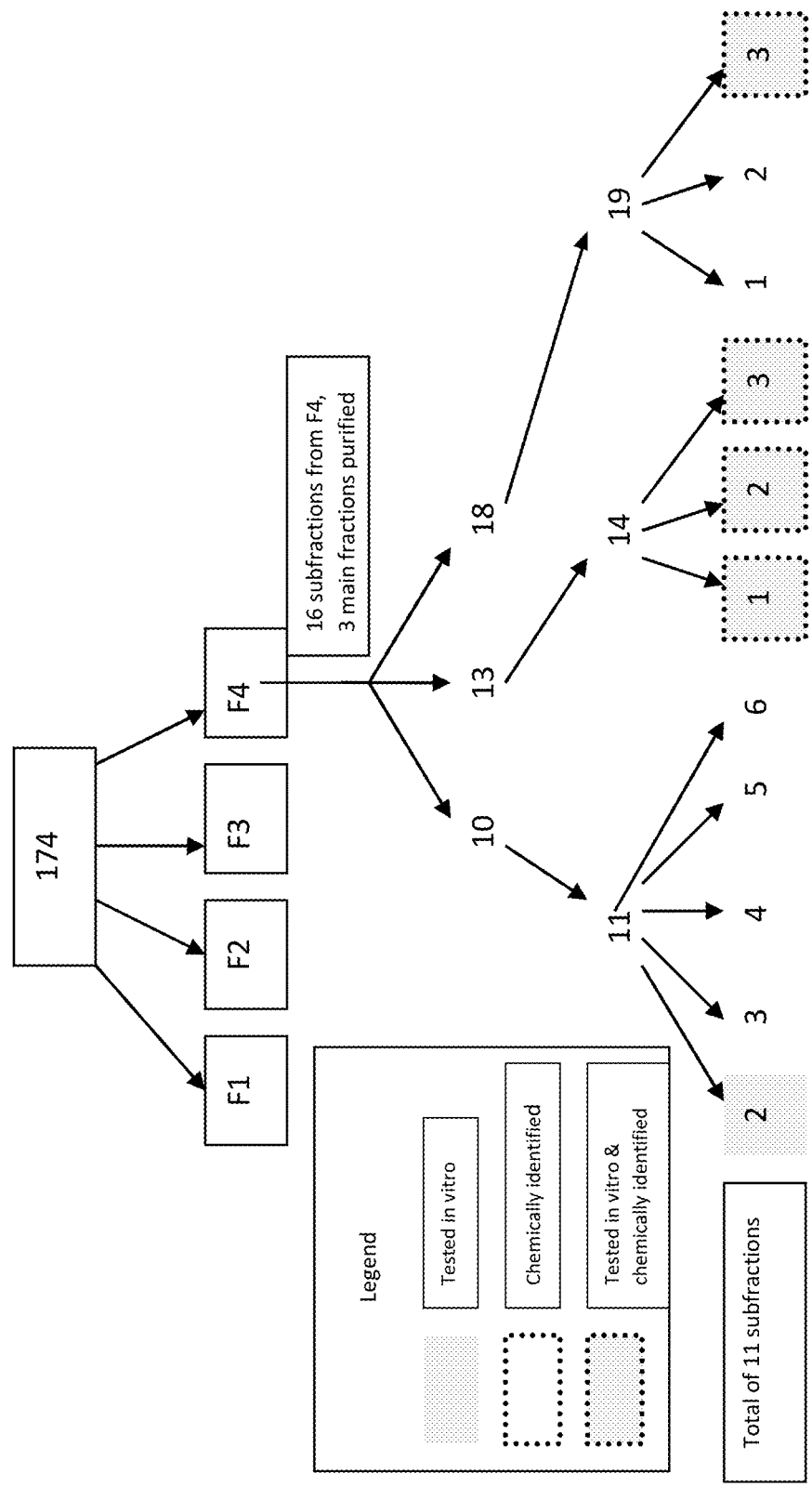
FIG. 80. Summary flowchart of fractionation, purification and in vitro testing of compounds from NC174.

In summary and as shown in FIG. 80, 11 subfractions were identified, 5 of which were tested in vitro. Of these, four (4) subfractions were chemically identified of which 3 were pure compounds (174-13-14-2; cpd #7; 174-13-14-3: cpd #2; and 174-18-19-3: cpd #13). It remains that subfraction 174-13-14-1 requires further purification to isolate compounds 1, 9, 10, 11, and 12. The structure of these compounds and their in vitro anti-cancer activity are shown in Table 11.

TABLE 11

| Sub-fraction | Compound # | | | | | | Mixed/Pure | | | | | | | Notes | |
|---|---|---|---|---|---|---|---|---|---|---|---|---|---|---|---|
| 174-13-14-1 | 1, 2, 7, 9, 10, 11, 12 | | | | | | Mixed Average cell viability: | | | | | | | | |
| | Vehicle cont-DMSO | 1% | | 96 | | 86 | 98 | | 93 | | 92 | | 91 | | 88 |
| | Positive cont-SDS | 250 ug/ml | | 8 | | 11 | 4 | | 9 | | 14 | | 5 | | 16 |
| | | ug/mL | | PC3 | | A549 | U373 | | SKOV | | MDA-MB | | CCD | | THP-1 |
| | | | AVG | ERROR | AVG | ERROR | AVG | ERROR | AVG | ERROR | AVG | ERROR | AVG | ERROR | AVG | ERROR |
| | | 100 | 0.11 | 0.01 | 10 | 0.01 | 45 | 0.00 | 63 | 0.07 | 25 | 0.02 | 18 | 0.00 | 53 | 0.01 |
| | | 50 | 0.19 | 0.03 | 19 | 0.04 | 57 | 0.01 | 98 | 0.07 | 31 | 0.02 | 23 | 0.01 | 49 | 0.06 |
| | | 10 | 1.09 | 0.03 | 105 | 0.05 | 57 | 0.12 | 103 | 0.16 | 100 | 0.02 | 95 | 0.02 | 96 | 0.02 |
| | | 1 | 1.09 | 0.05 | 105 | 0.05 | 58 | 0.09 | 100 | 0.15 | 100 | 0.05 | 98 | 0.07 | 98 | 0.03 |
| | | | | | | | Fold change in viability: | | | | | | | | | |
| Positive cont-SDS | 250 ug/mL | | 0.08 | 0.00 | 0.13 | 0.01 | 0.05 | 0.00 | 0.10 | 0.00 | 0.16 | 0.00 | 0.06 | 0.00 | 0.18 | 0.01 |
| | | PC3 | | | A549 | | U373 | | SKOV | | MDA-MB | | CCD | | THP-1 | |
| | | ug/mL | AVG | ERROR | AVG | ERROR | AVG | ERROR | AVG | ERROR | AVG | ERROR | AVG | ERROR | AVG | ERROR |
| | | 100 | 0.57 | 0.01 | 0.06 | 0.00 | 0.68 | 0.07 | 0.28 | 0.02 | 0.19 | 0.00 | 0.60 | 0.01 | | |
| | | 50 | 0.67 | 0.03 | 0.11 | 0.01 | 1.05 | 0.07 | 0.34 | 0.02 | 0.25 | 0.01 | 0.55 | 0.06 | | |
| | | 10 | 0.66 | 0.03 | 1.04 | 0.12 | 1.11 | 0.16 | 1.09 | 0.02 | 1.05 | 0.02 | 1.09 | 0.02 | | |
| | | 1 | 0.68 | 0.05 | 1.01 | 0.09 | 1.08 | 0.15 | 1.08 | 0.05 | 1.07 | 0.07 | 1.11 | 0.03 | | |
| | | | | | | | Pure Average cell viability: | | | | | | | | | |
| 174-13-14-2 | | | | | | | | | | | | | | | | |
| | Vehicle cont-DMSO | 1% | | 96 | | 86 | 98 | | 93 | | 92 | | 91 | | 88 |
| | Positive cont-SDS | 250 ug/ml | | 8 | | 11 | 4 | | 9 | | 14 | | 5 | | 16 |
| | | ug/mL | | PC3 | | A549 | U373 | | SKOV | | MDA-MB | | CCD | | THP-1 |
| | | 100 | 12 | | 34 | | 5 | | 46 | | 24 | | 17 | | 50 | |
| | | 50 | 14 | | 55 | | 6 | | 95 | | 27 | | 23 | | 52 | |
| | | 10 | 103 | | 56 | | 108 | | 113 | | 104 | | 97 | | 102 | |
| | | 1 | 107 | | 61 | | 120 | | 126 | | 106 | | 103 | | 108 | |

TABLE 11-continued

| Sub-fraction | Compound # | | | | | | | | | | | | | | | |
|---|---|---|---|---|---|---|---|---|---|---|---|---|---|---|---|---|
| | | | | | | Mixed/Pure | | | | | | | | Notes | | |
| | | | | | | Fold change in viability: | | | | | | | | | | |
| | Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| | | | PC3 | | A549 | | U373 | | SKOV | | MDA-MB | | CCD | | THP-1 | |
| | | ug/mL | AVG | ERROR | AVG | ERROR | AVG | ERROR | AVG | ERROR | AVG | ERROR | AVG | ERROR | AVG | ERROR |
| | | 100 | 0.13 | 0.01 | 0.40 | 0.06 | 0.05 | 0.00 | 0.49 | 0.02 | 0.27 | 0.01 | 0.19 | 0.00 | 0.57 | 0.04 |
| | | 50 | 0.14 | 0.02 | 0.64 | 0.08 | 0.06 | 0.01 | 1.02 | 0.11 | 0.30 | 0.01 | 0.25 | 0.01 | 0.59 | 0.01 |
| | | 10 | 1.07 | 0.03 | 0.65 | 0.05 | 1.10 | 0.04 | 1.21 | 0.10 | 1.13 | 0.03 | 1.06 | 0.05 | 1.16 | 0.03 |
| 174-13-14-3 | 2 | 1 | 1.11 | 0.04 | 0.72 | 0.03 | 1.22 | 0.08 | 1.36 | 0.06 | 1.16 | 0.01 | 1.13 | 0.07 | 1.17 | 0.01 |
| | Vehicle cont-DMSO | 1% | | | 96 | 8 | 86 | 11 | 98 | 4 | 93 | 9 | 92 | 14 | 91 | 5 | 88 | 16 |
| | Positive cont-SDS | 250 ug/ml | | | PC3 | | A549 | | U373 | | SKOV | | MDA-MB | | CCD | | THP-1 |
| | | ug/mL | | | | | Average cell viability: Pure | | | | | | | | | | |
| | | 100 | | | 5 | | 35 | | 8 | | 18 | | 20 | | 14 | | 21 |
| | | 50 | | | 5 | | 51 | | 13 | | 62 | | 21 | | 20 | | 21 |
| | | 10 | | | 69 | | 52 | | 73 | | 67 | | 83 | | 89 | | 88 |
| | | 1 | | | 97 | | 96 | | 85 | | 82 | | 102 | | 101 | | 91 |
| | | | | | | | Fold change in viability: | | | | | | | | | | |
| | Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| | | | PC3 | | A549 | | U373 | | SKOV | | MDA-MB | | CCD | | THP-1 | |
| | | ug/mL | AVG | ERROR | AVG | ERROR | AVG | ERROR | AVG | ERROR | AVG | ERROR | AVG | ERROR | AVG | ERROR |
| | | 100 | 0.05 | 0.01 | 0.41 | 0.06 | 0.08 | 0.00 | 0.19 | 0.01 | 0.22 | 0.02 | 0.15 | 0.01 | 0.23 | 0.01 |
| | | 50 | 0.05 | 0.01 | 0.60 | 0.03 | 0.13 | 0.02 | 0.67 | 0.03 | 0.23 | 0.02 | 0.22 | 0.02 | 0.24 | 0.03 |
| | | 10 | 0.71 | 0.01 | 0.60 | 0.05 | 0.74 | 0.01 | 0.72 | 0.02 | 0.90 | 0.02 | 0.98 | 0.01 | 1.00 | 0.01 |
| | | 1 | 1.00 | 0.03 | 1.12 | 0.01 | 0.86 | 0.02 | 0.89 | 0.01 | 1.11 | 0.02 | 1.11 | 0.06 | 1.03 | 0.02 |

TABLE 11-continued

| Sub-fraction | Compound # | | | | Mixed/Pure | | | Notes | |
|---|---|---|---|---|---|---|---|---|---|
| 174-18-19-3 | 13 | | | | Pure | | | | |

Structure of compound 13: a glycerol 20:5 fatty acid ester linked to a hexopyranose sugar (positions labeled 1, 2, 3 on glycerol; 1', 6' on sugar; multiple OH groups).

| | | PC3 | | A549 | | U373 | | SKOV | | MDA-MB | | CCD | | THP-1 | |
|---|---|---|---|---|---|---|---|---|---|---|---|---|---|---|---|
| Vehicle cont-DMSO | 1% | 96 | 8 | 86 | 11 | 98 | 4 | 93 | 9 | 92 | 14 | 91 | 5 | 88 | 16 |
| Positive cont-SDS | 250 ug/ml | PC3 | | A549 | | U373 | | SKOV | | MDA-MB | | CCD | | THP-1 | |

Average cell viability:

| ug/mL | | | | | | | | | | | | | | | |
|---|---|---|---|---|---|---|---|---|---|---|---|---|---|---|---|
| 100 | | 12 | | 32 | | 6 | | 34 | | 25 | | 14 | | 27 | |
| 50 | | 16 | | 57 | | 7 | | 78 | | 30 | | 22 | | 40 | |
| 10 | | 97 | | 55 | | 100 | | 105 | | 105 | | 99 | | 101 | |
| 1 | | 104 | | 57 | | 111 | | 125 | | 102 | | 103 | | 104 | |

Fold change in viability:

| | 250 ug/mL | PC3 | | A549 | | U373 | | SKOV | | MDA-MB | | CCD | | THP-1 | |
|---|---|---|---|---|---|---|---|---|---|---|---|---|---|---|---|
| Positive cont-SDS | | 0.08 | | 0.13 | | 0.05 | | 0.10 | | 0.16 | | 0.06 | | 0.18 | |
| | | AVG | ERROR | AVG | ERROR | AVG | ERROR | AVG | ERROR | AVG | ERROR | AVG | ERROR | AVG | ERROR |
| | | 0.00 | | 0.01 | | 0.00 | | 0.00 | | 0.00 | | 0.00 | | 0.01 | |
| ug/mL | | | | | | | | | | | | | | | |
| 100 | | 0.12 | 0.01 | 0.38 | 0.03 | 0.06 | 0.00 | 0.37 | 0.01 | 0.28 | 0.01 | 0.15 | 0.01 | 0.31 | 0.04 |
| 50 | | 0.16 | 0.00 | 0.67 | 0.09 | 0.07 | 0.01 | 0.84 | 0.05 | 0.33 | 0.01 | 0.24 | 0.00 | 0.46 | 0.01 |
| 10 | | 1.01 | 0.04 | 0.64 | 0.04 | 1.02 | 0.01 | 1.13 | 0.10 | 1.14 | 0.02 | 1.09 | 0.05 | 1.14 | 0.01 |
| 1 | | 1.08 | 0.04 | 0.67 | 0.00 | 1.13 | 0.05 | 1.34 | 0.02 | 1.11 | 0.01 | 1.13 | 0.06 | 1.19 | 0.02 |

Example 10. Isolation and Structure Elucidation of Compounds from NC175 (*Cladophora sericea*)

10.1. Fractionation and Purification of Main Components from NC175

Figure 81:
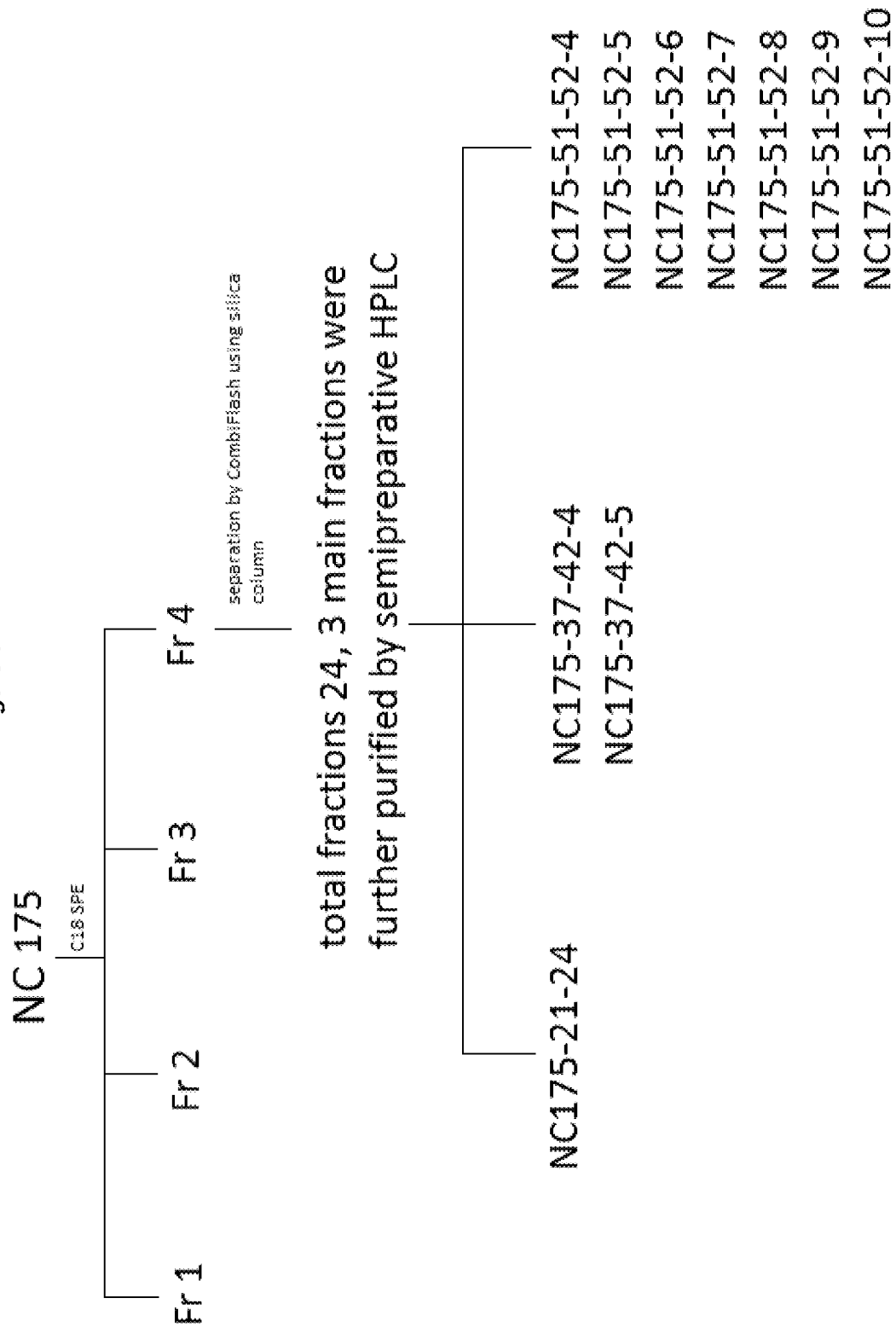
FIG. 81. Flowchart of fractionation and purification of main components from NC175.

The fractionation steps from NC175 are shown in FIG. 81. In short, 2.69 g of NC175 were dissolved in methanol and by following the same procedures described above, 5 fractions were prepared. Fr. 4 (1.3 g) was subjected to further fractionation based on previous bioassay result.

Similarly, Fr. 4 was dissolved in dichloromethane/methanol and mixed with celite and dried. The sample was loaded on 80 g Teledyne ISCO High Performance GOLD silica gel column and eluted with dichloromethane/methanol on CombiFlash® Rf, Teledyne ISCO. The eluting solvent gradient (A and B) was as the following: 0% B for 2 CV (column volume) then to 40% B for 15 CV and kept at 40% B for 2 CV, to 100% B for 2 CV and kept at 100% B for 2 CV. Total elution volume was 23 CV. A is dichloromethane and B is methanol/dichloromethane (1:1). Fractions were monitored by TLC and some combined and dried using rotavap and Genevac.

Based on HPLC chromatograms, three sub-fractions were further purified using semi preparative HPLC (Agilent). The column used was ZORBAX SB-C18 (9.4×50 mm, 5 μm) or ZORBAX XDB-C18 (9.4×250 mm, 5 μm), and the mobile phase was water/acetonitrile. Eluting gradient varied for different samples so to optimize separation. The column temperature was at 55° C. and flow rate 5 mL/min.

10.2 Structure Characterization of Main Components from Bioactive Fraction (Fr. 4)

Samples' preparation and analysis were carried as in section 8.2 above.

10.3. Characterization of Main Components from NC175-F4

GC/FID chromatograms of NC175 and NC175-Fr. 4 (not shown) show similar fatty acid profile. The retention time and tentative identification based on NIST GC-MS database matching are shown in Table 12. The major fatty acid is shown to be palmitic acid (C16:0), and less of eicosapentaenoic acid (EPA, C20:5) as compared to NC169 and NC174.

TABLE 12

Tentative identification of fatty acids using GC-MS analysis of NC175 and NC175-F4

| RT (min) | Compounds |
|---|---|
| 11.31 | Methyl tetradecanoate (Myristic acid, C14:0) |
| 13.52 | Hexadecanoic acid, methyl ester (Palmitic acid, C16:0) |
| 13.88 | 9-Hexadecenoic acid, methyl ester, (Z)- (Palmitoleic acid, C16:1) |
| 16.73 | 9 (or 11)-Octadecenoic acid, methyl ester (C18:1) |
| 16.86 | 11 (or 9)-Octadecenoic acid, methyl ester (C18:1) |
| 17.55 | 9,12-Octadecadienoic acid (Z,Z)-, methyl ester (Linoleic acid, C18:2) |
| 18.65 | 9,12,15-Octadecatrienoic acid, methyl ester, (Z,Z,Z)- (α-Linolenic acid, 18:3) |
| 23.50 | Methyl eicosa-5,8,11,14,17-pentaenoate (EPA, C20:5) |

Figure 82:
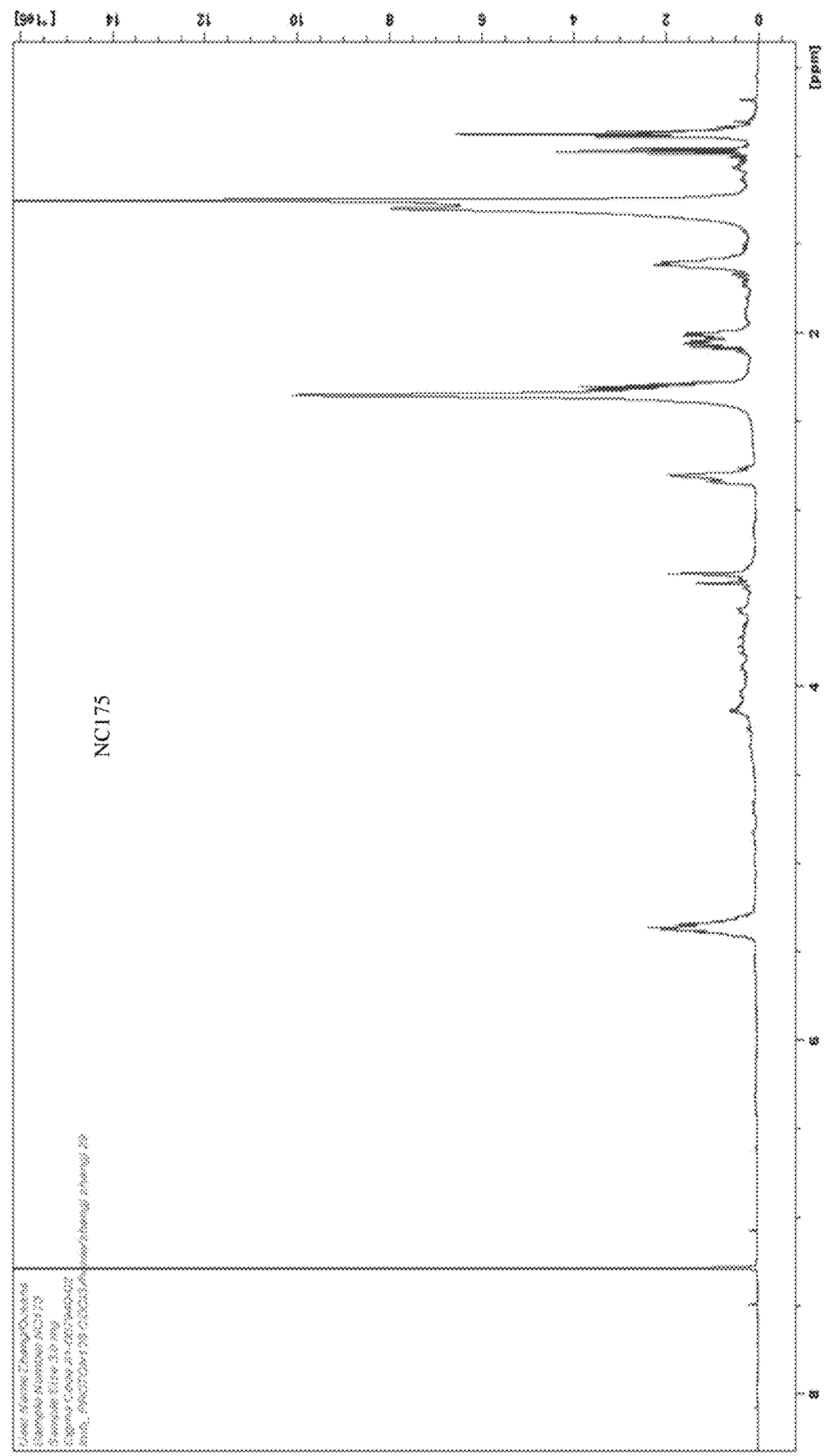
FIG. 82. 1H-NMR spectrum of NC-175.
Figure 83:
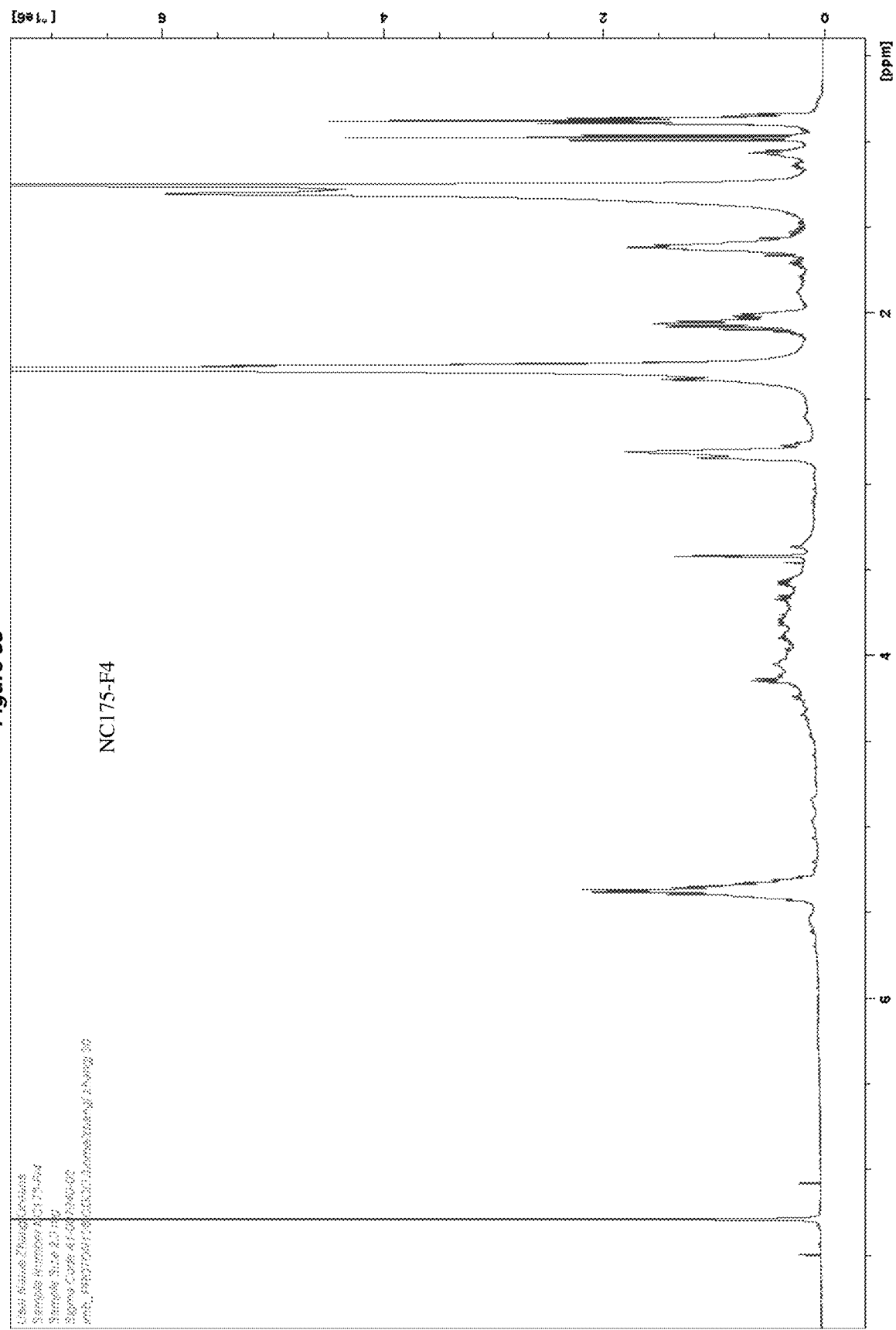
FIG. 83. 1H-NMR spectrum of NC-175-F4.

$_1$H-NMR spectra of NC175 and NC175-F4 (FIGS. 82 & 83) are similar, and glycolipids appear to be the major components. Compared to NC169 F4 and NC174 F4, it is evident that NC175 F4 has higher level of saturated fatty acids.

NC175-51-52-4

Figure 84:
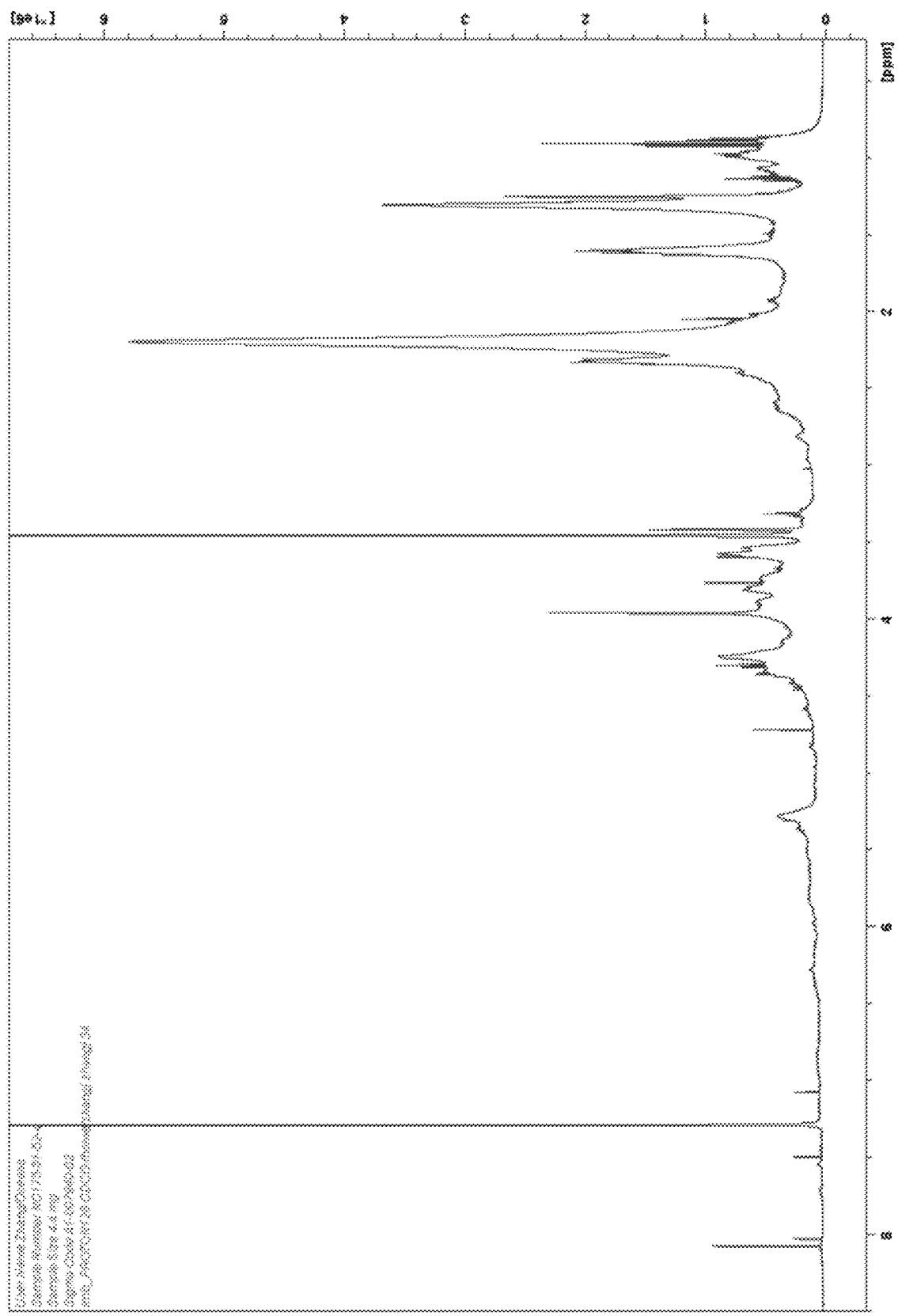
FIG. 84. 1H_NMR spectrum of NC175-51-52-4.
Figure 85:
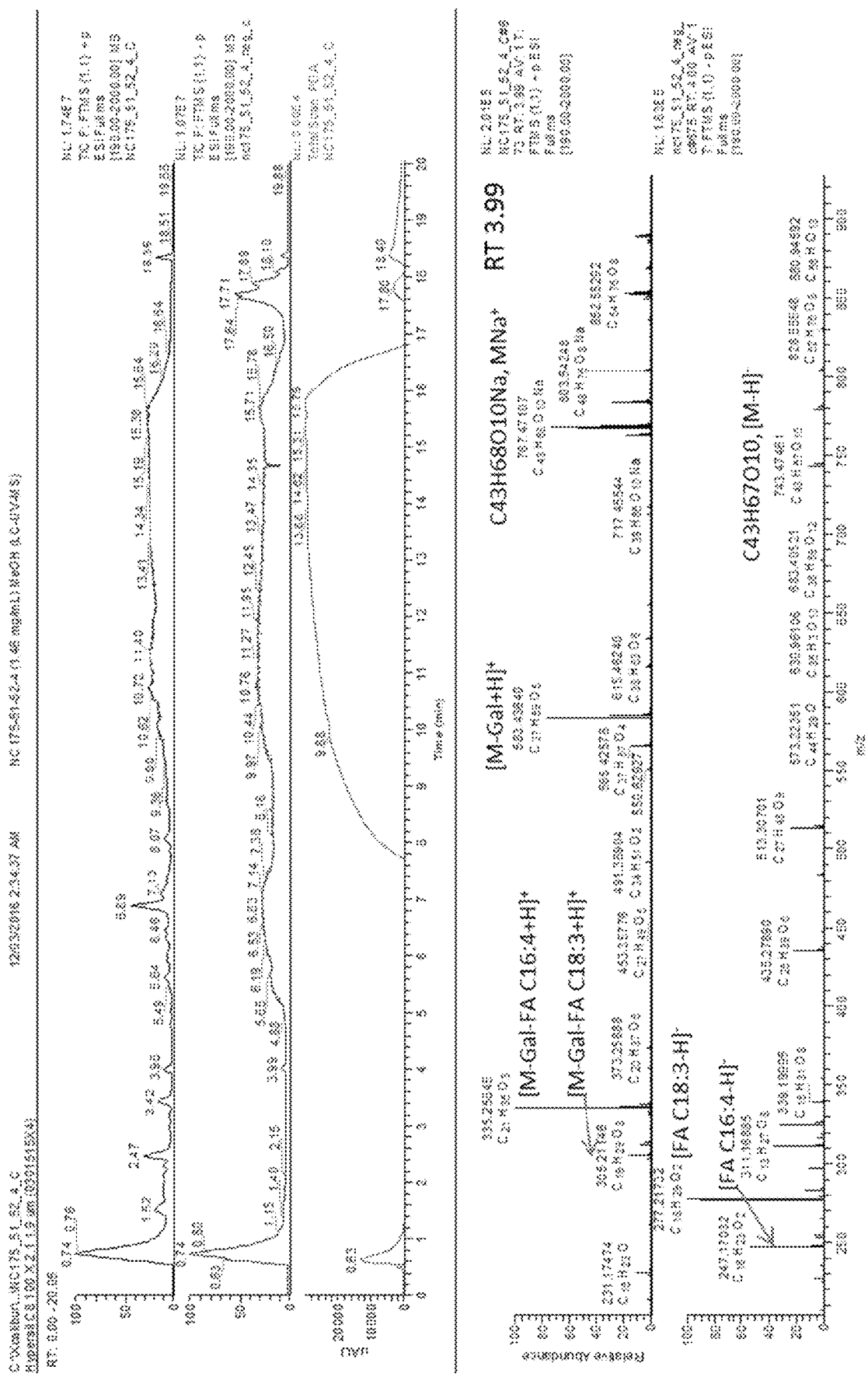
FIG. 85. UPLC-DAD/HRMS chromatograms of NC175-51-52-4 and HRMS of peak RT 3.99.

The sample was shown some glycolipid features from $_1$H-NMR spectrum (FIG. 84). Peak RT 3.99 is found to be a glycolipid with molecular formula of $C_{43}H_{68}O_{10}$ based on HRMS molecular ions of m/z 767.47407 ($C_{43}H_{68}O_{10}Na_+$, calculated 767.47047) and 743.47461 ($C_{43}H_{67}O_{10-}$, calculated 743.47397) in positive and negative mode HRMS (FIG. 85). With fatty acid fragments information from HRMS, peak RT 3.99 was characterized as glycolipid MGDG C18:3/C16:4 (14).

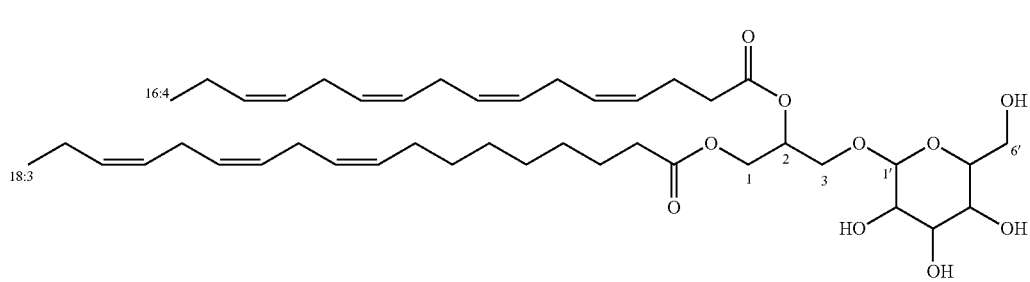

14

NC175-51-52-5

Figure 86:
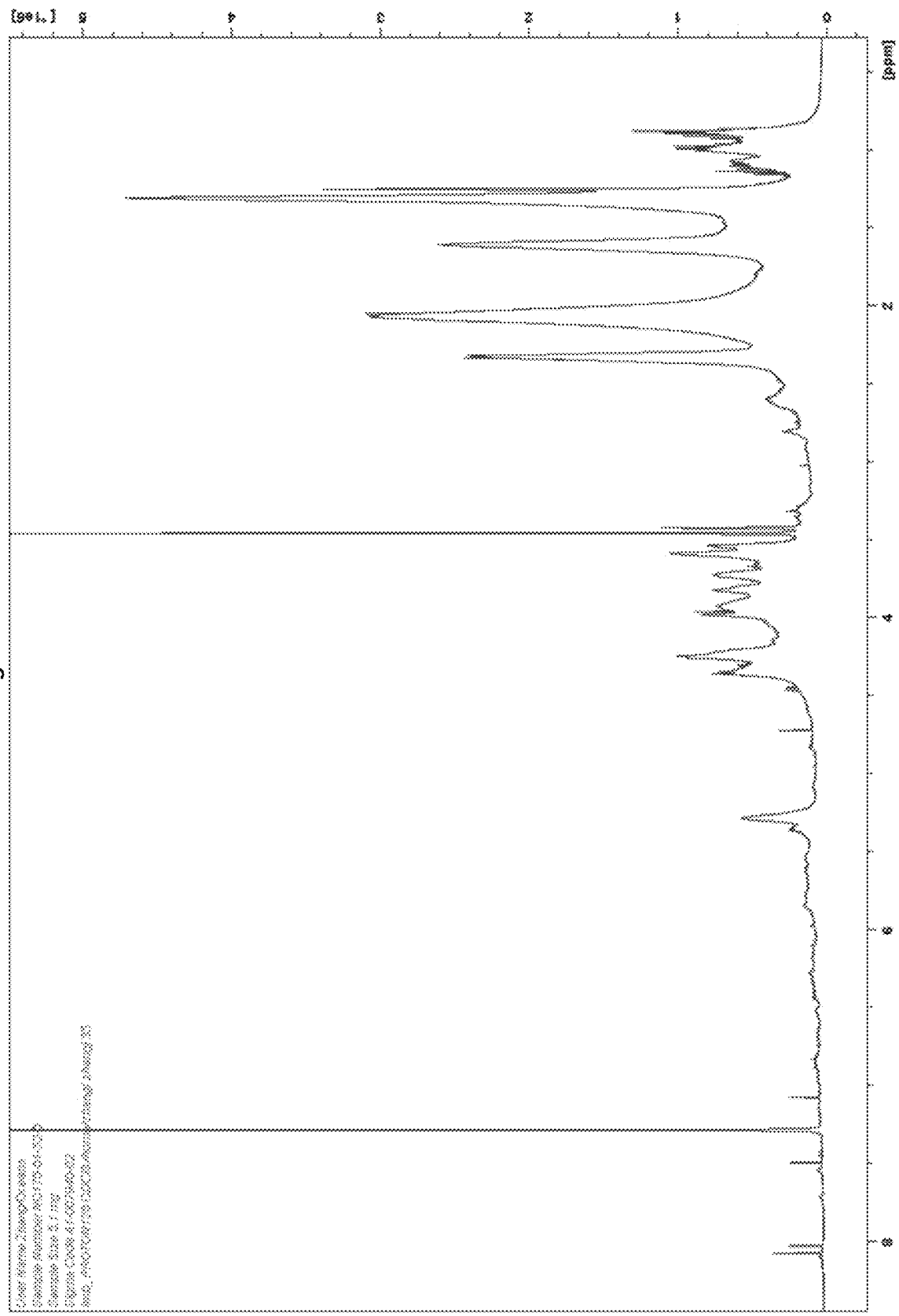
FIG. 86. 1H-NMR spectrum of NC175-51-52-5.
Figure 87:
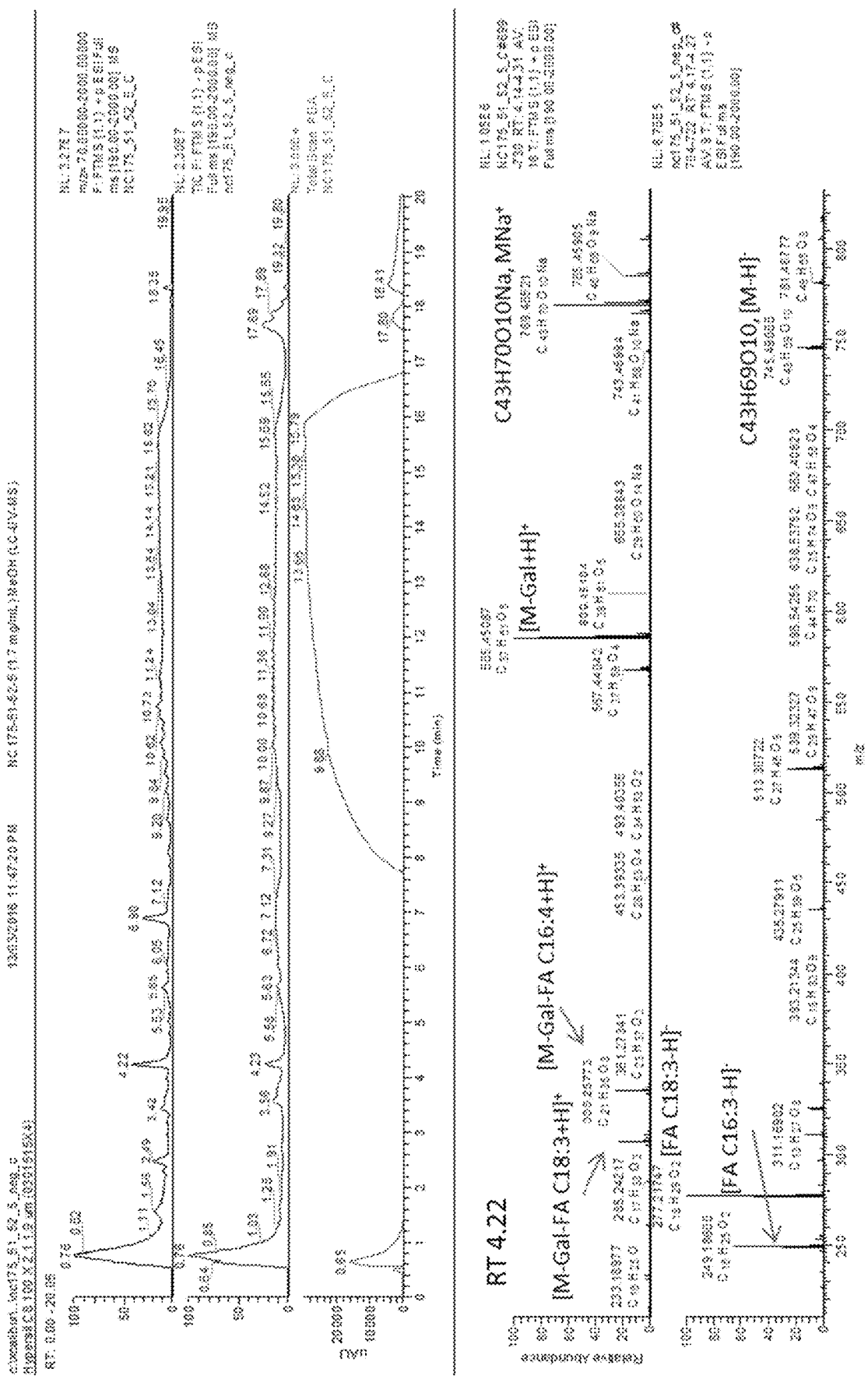
FIG. 87. UPLC-DAD/HRMS chromatograms of NC175-51-52-5 and HRMS of peak 4.22.

This sample also appeared to be a glycolipid from 1H-NMR data (FIG. 86). In UPLC-DAD/HRMS, the peak RT 4.22 was shown to have a molecular formula of $C_{43}H_{70}O_{10}$ based on HRMS molecular ions of m/z 769.48521 ($C_{43}H_{70}O_{10}Na_+$, calculated 769.48667 769.48612) and 745.49088 ($C_{43}H_{69}O_{10-}$, calculated 745.48907 745.48962) in positive and negative mode HRMS (FIG. 87). Considering the two fatty acid fragments present in HRMS, peak RT 4.22 was determined as glycolipid MGDG C18:3/C16:3 (15).

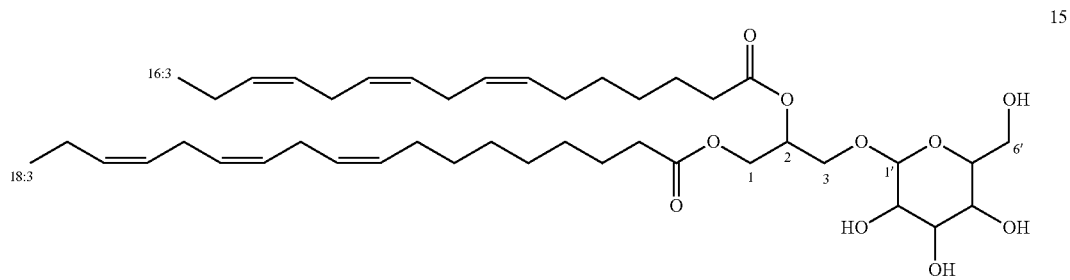 [SMILES: CC/C=C\C/C=C\C/C=C\CCCCCCCC(=O)OCC(COC1OC(CO)C(O)C(O)C1O)OC(=O)CCCCC/C=C\C/C=C\C/C=C\CC]

15

Figure 88:
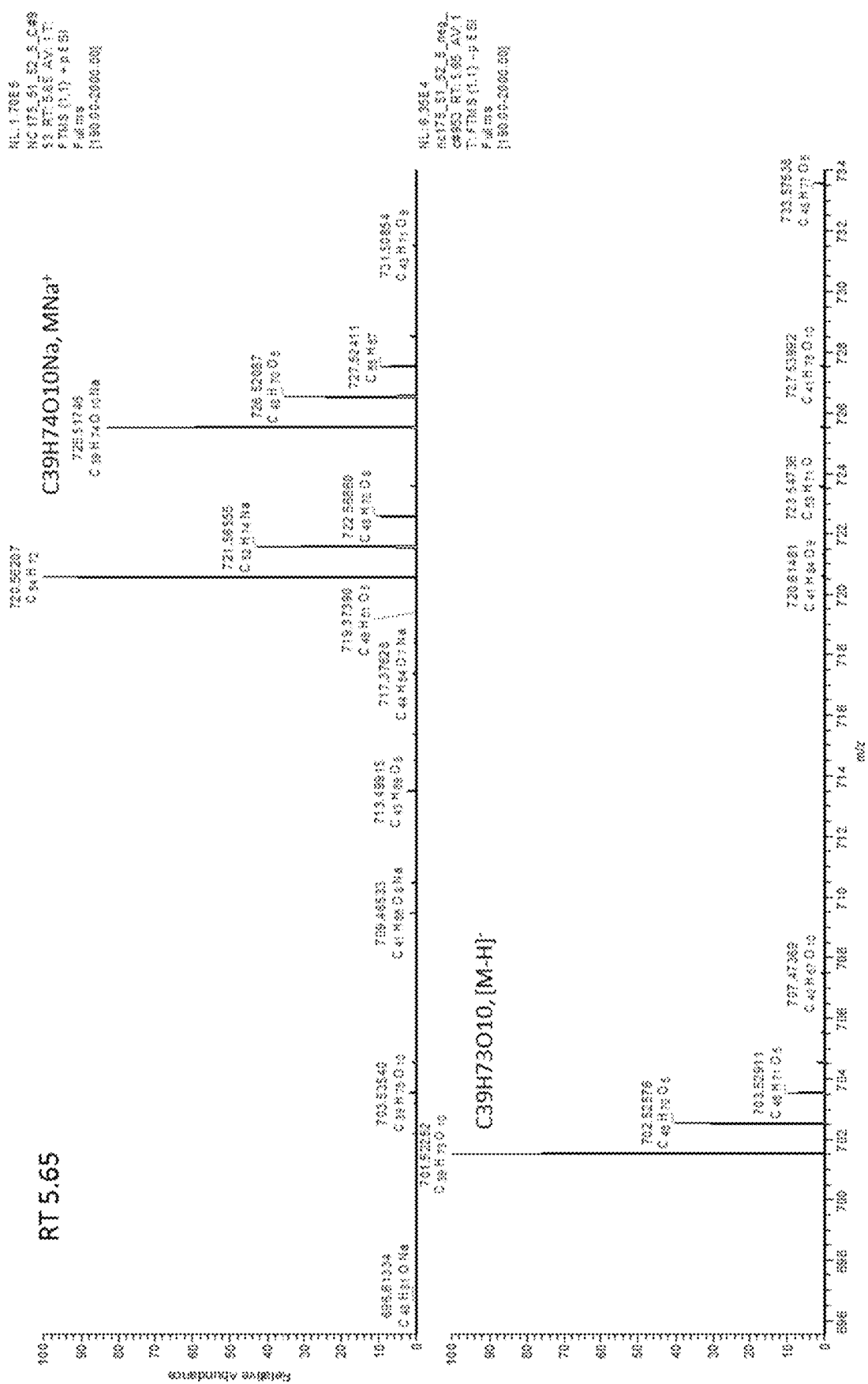
FIG. 88. HRMS spectra of peak RT 5.65 of NC175-51-52-5.
Figure 89:
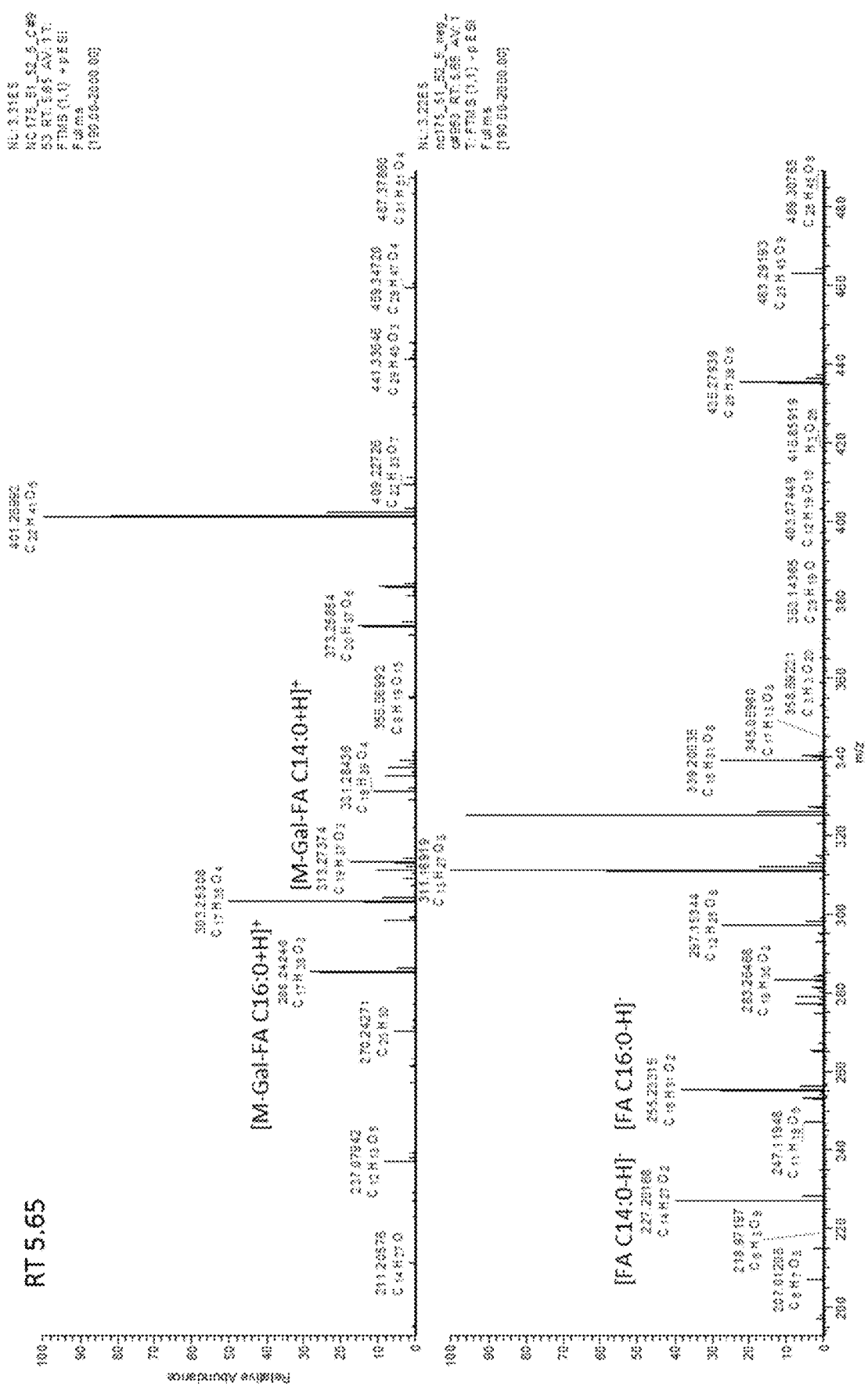
FIG. 89. HRMS spectra of peak RT 5.65 of NC175-51-52-5 showing fatty acid fragments.

For fatty acid C16:3, the unsaturation pattern could not be determined without further investigation, but likely to be n-3 as shown. Peak RT 5.65 showed a molecular formula of C39H74O10 based on HRMS molecular ions of m/z 725.51746 (C39H74O10Na+, calculated 725.51742) and 701.52252 (C39H73O10−, calculated 701.52092) in positive and negative mode HRMS (FIG. 88). Also in HRMS, two saturated fatty acid fragments are present (FIG. 89). As such, peak RT 5.65 was identified to be glycolipid MGDG C16:0/C14:0 (16).

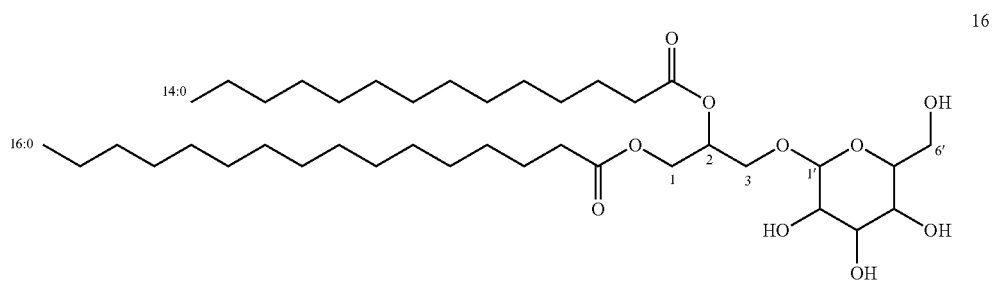 [SMILES: CCCCCCCCCCCCCCCC(=O)OCC(COC1OC(CO)C(O)C(O)C1O)OC(=O)CCCCCCCCCCCCC]

16

NC175-51-52-6

Figure 90:
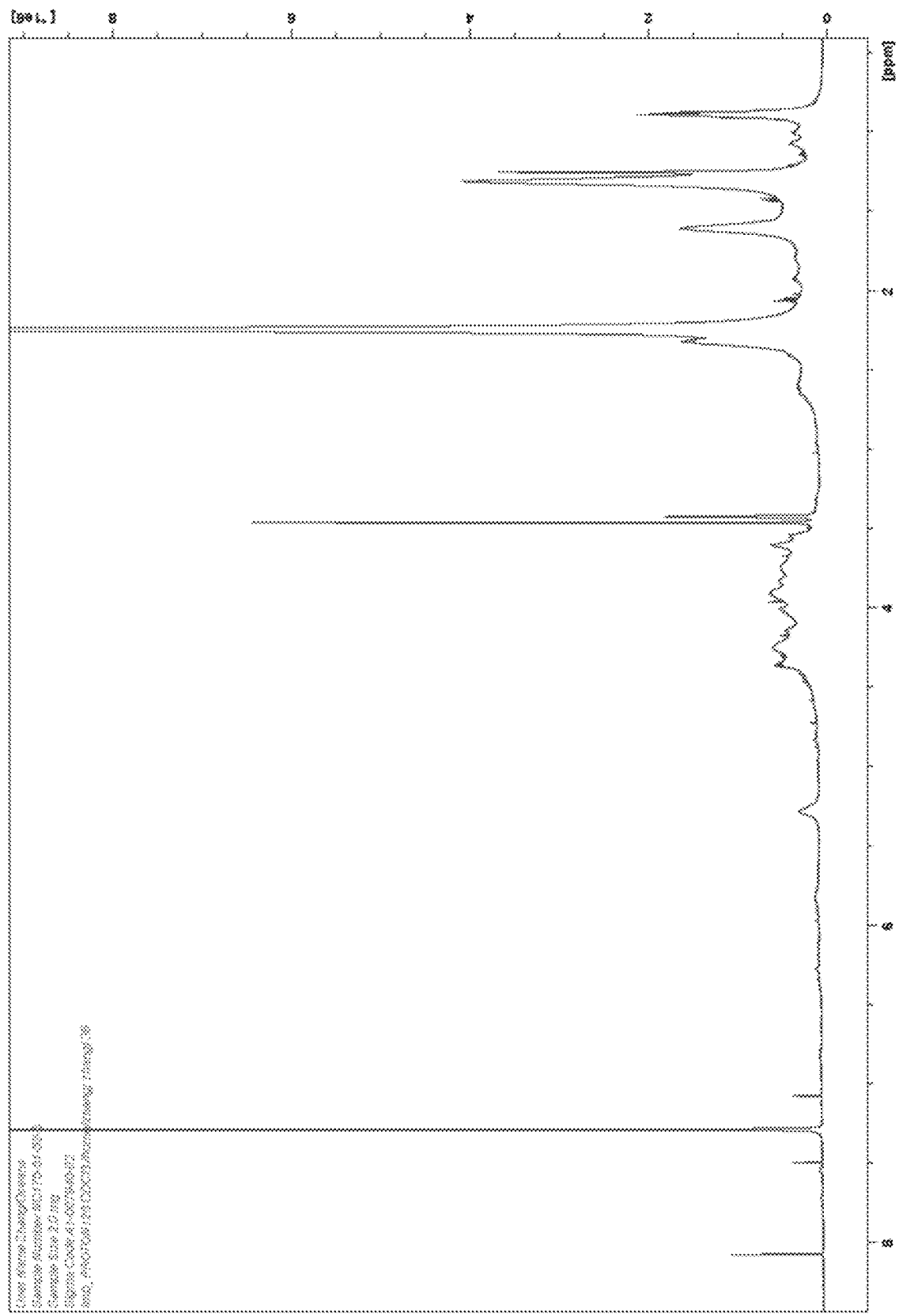
FIG. 90. 1H-NMR spectra of NC175-51-52-6.
Figure 91:
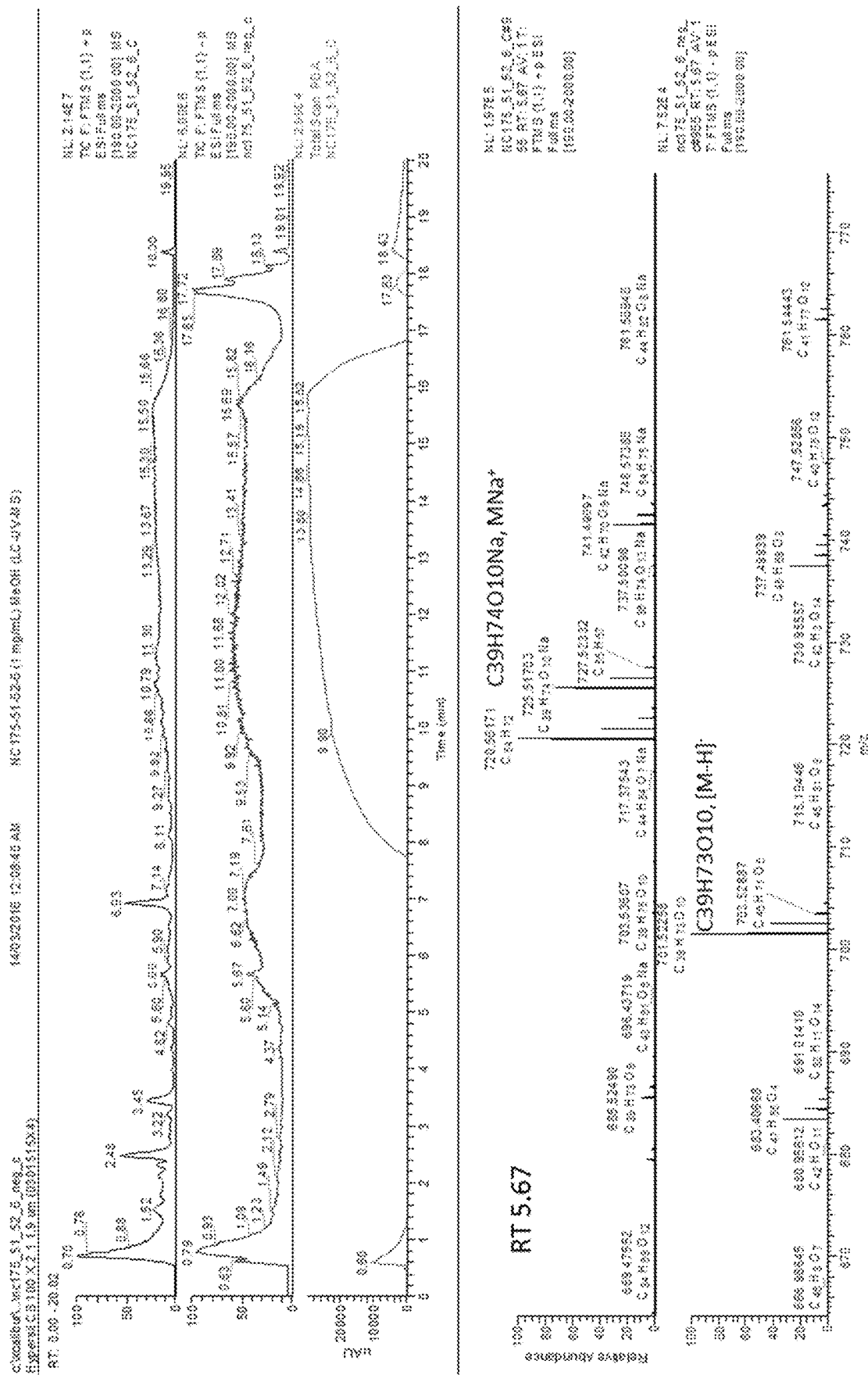
FIG. 91. HNMR spectra of peak RT 5.67 of NC175-51-52-6.
Figure 92:
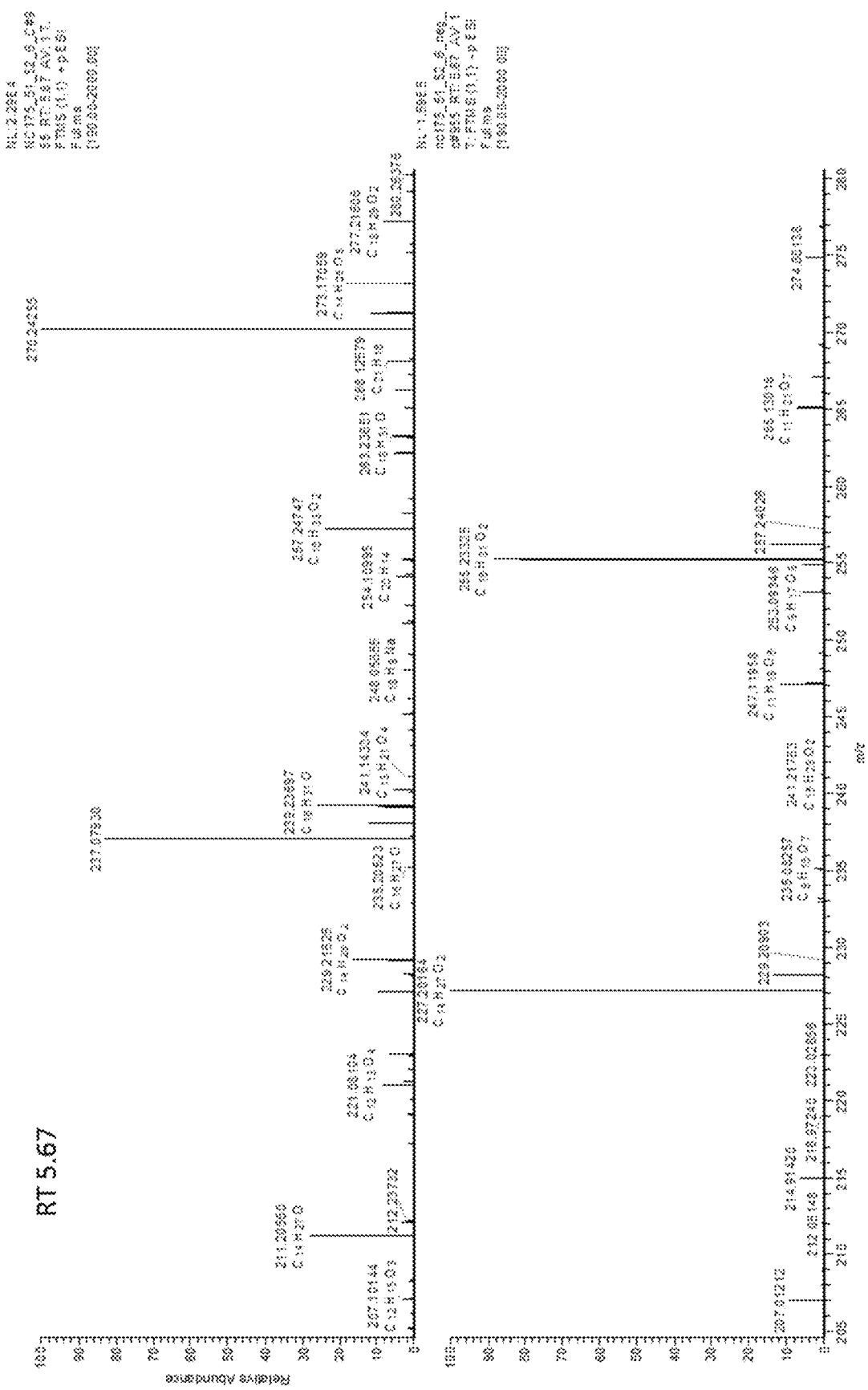
FIG. 92. HNMR spectra of peak RT 5.67 of NC175-51-52-6 showing fatty acid fragments.

This sample also presents characteristic signals of glycolipids from NMR spectrum (FIG. 90). In UPLC-DAD/HRMS (FIGS. 91 and 92), peak RT 5.67 was confirmed to be glycolipid 16 as described above.

NC175-51-52-7

Figure 93:
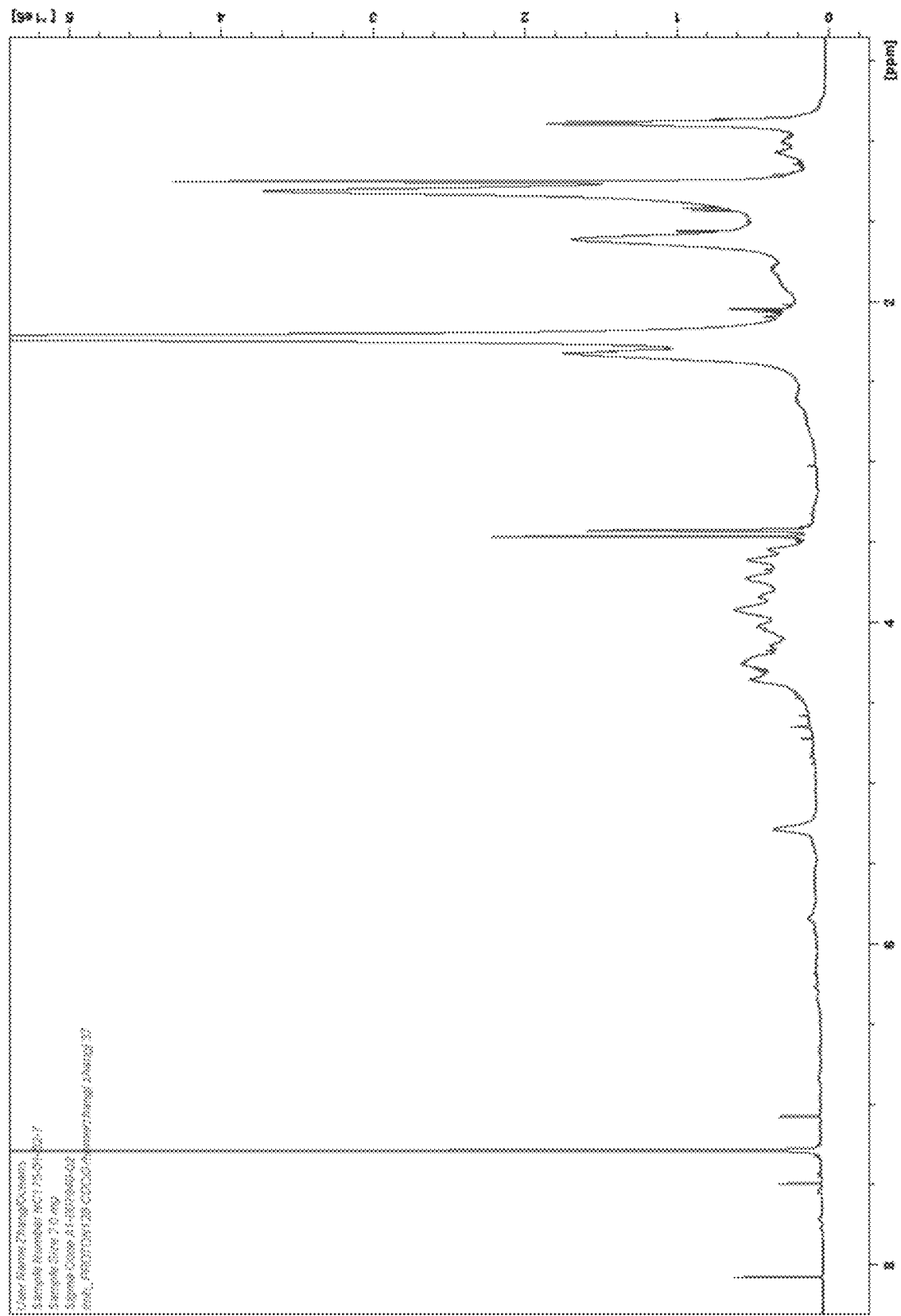
FIG. 93. 1H-NMR spectra of NC-175-51-52-7.
Figure 94:
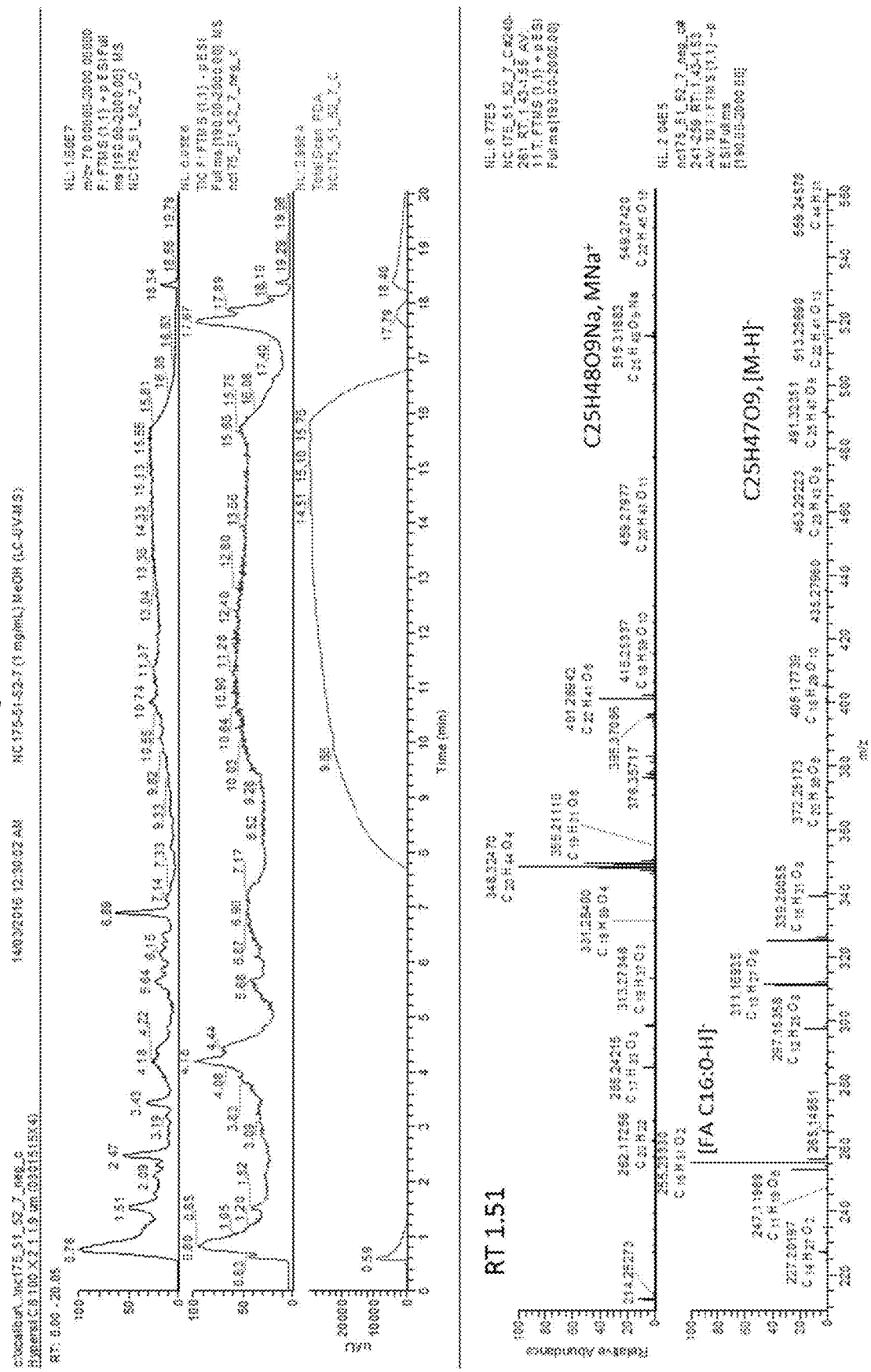
FIG. 94. UPLC-DAD/HRMS of peak RT 1.51 of NC175-51-52-7.
Figure 95:
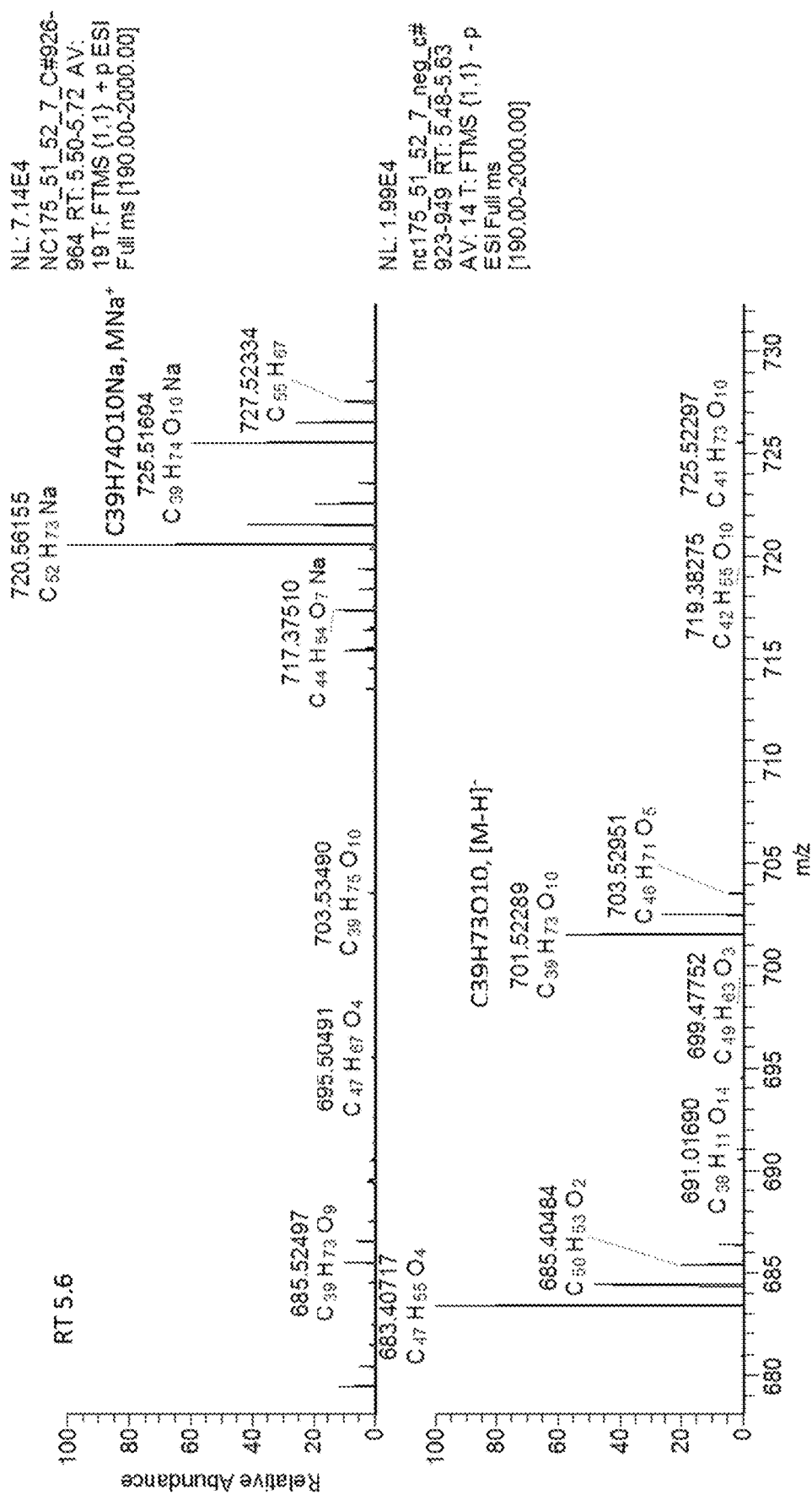
FIG. 95. HRMS spectra of peak RT 5.6 from NC175-51-52-7.

Again, glycolipid features were shown in 1H-NMR spectrum (FIG. 93). In FIG. 94, the HRMS of peak RT 1.51 was found to be lyso-MGDG C16:0 (5) characterized earlier from NC169 F4. Peak RT 5.6 has a molecular formula of $C_{39}H_{74}O_{10}$ as shown in its HRMS spectra (FIG. 95), the same as MGDG C16:0/C14:0 (16) discussed above.

NC175-51-52-9

Figure 96:
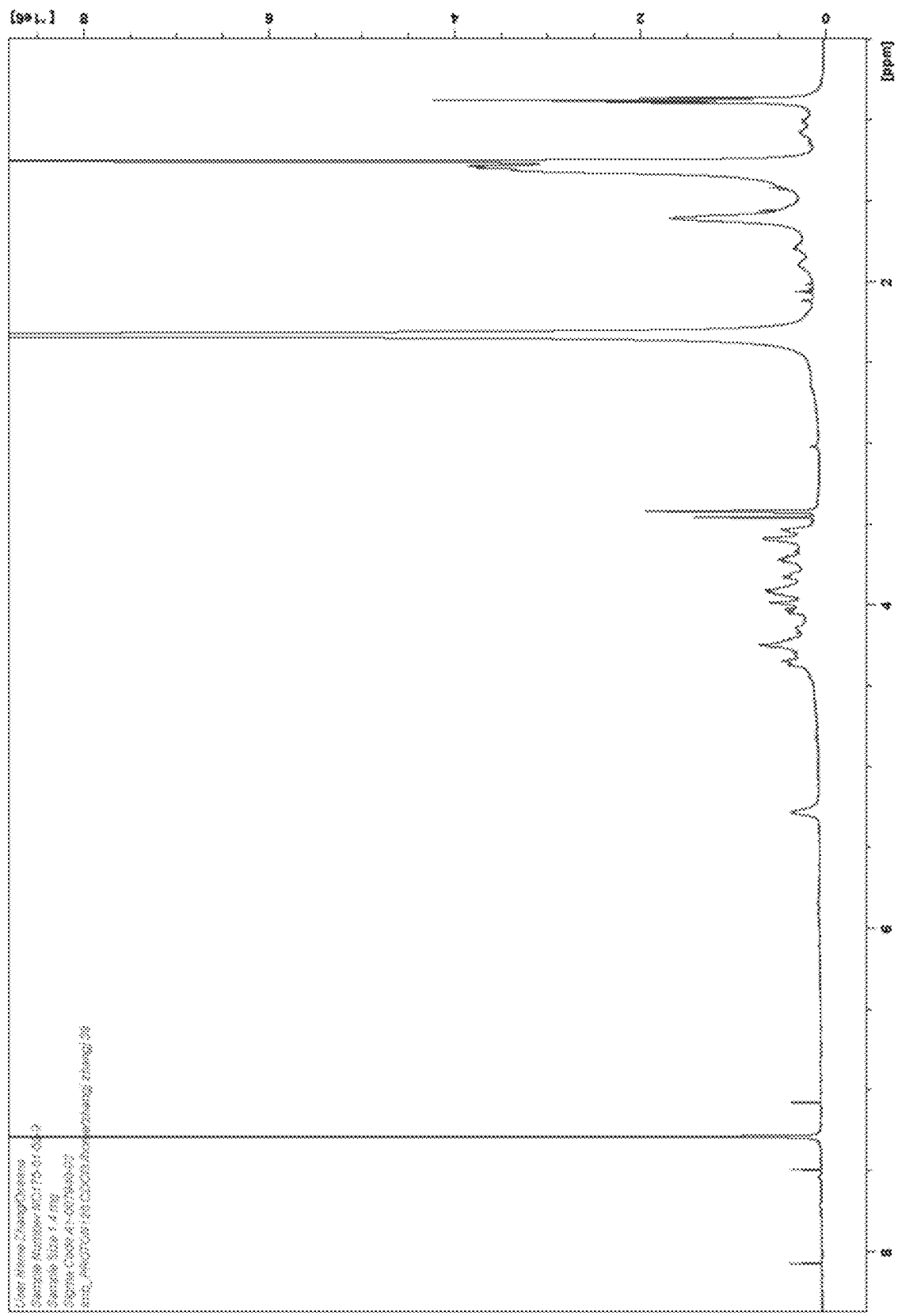
FIG. 96. 1H-NMR spectrum of NC175-51-52-9.
Figure 97:
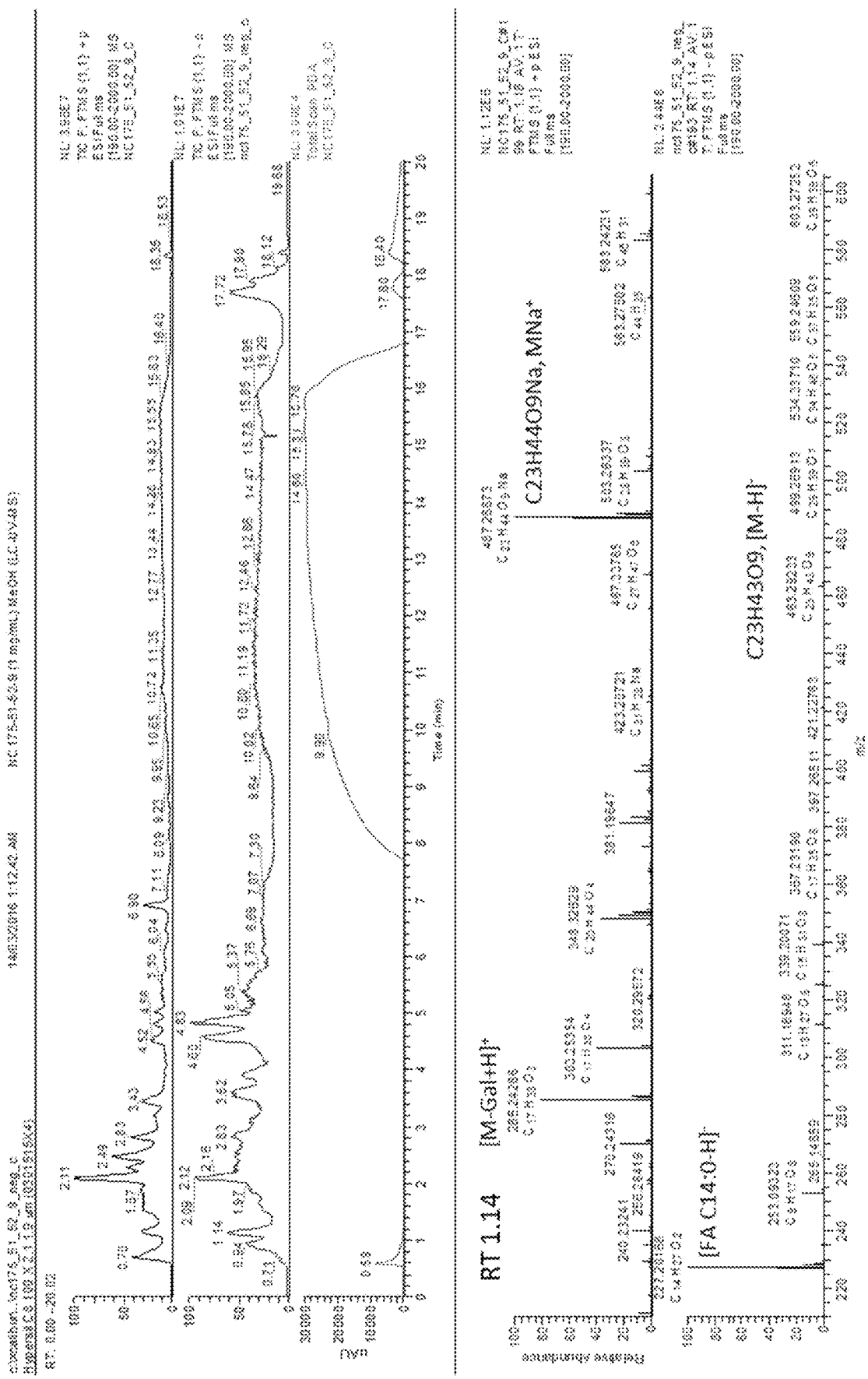
FIG. 97. UPLC-DAD/HRMS of peak RT 1.14 of NC175-51-52-9.

1H-NMR spectrum (FIG. 96) of this sample showed glycolipid features and the main fatty acid appeared to be saturated. Peak RT 1.14 shows a molecular formula of $C_{23}H_{44}O_9$ based on HRMS molecular ions of m/z 487.28873 ($C_{23}H_{44}O_9Na_+$, calculated 487.28775) and 463.29233 ($C_{23}H_{43}O_9-$, calculated 463.29126) in positive and negative mode HRMS (FIG. 97). A saturated fatty acid fragment is present (C14:0), thus peak RT 1.14 was identified to be a lyso glycolipid lyso-MGDG C14:0 (17).

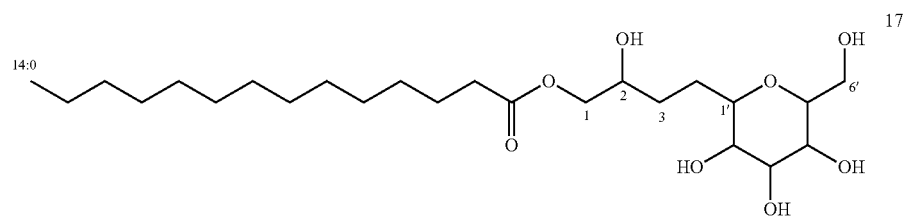 [SMILES: CCCCCCCCCCCCCC(=O)OCC(O)CCC1OC(CO)C(O)C(O)C1O]

17

Figure 98:
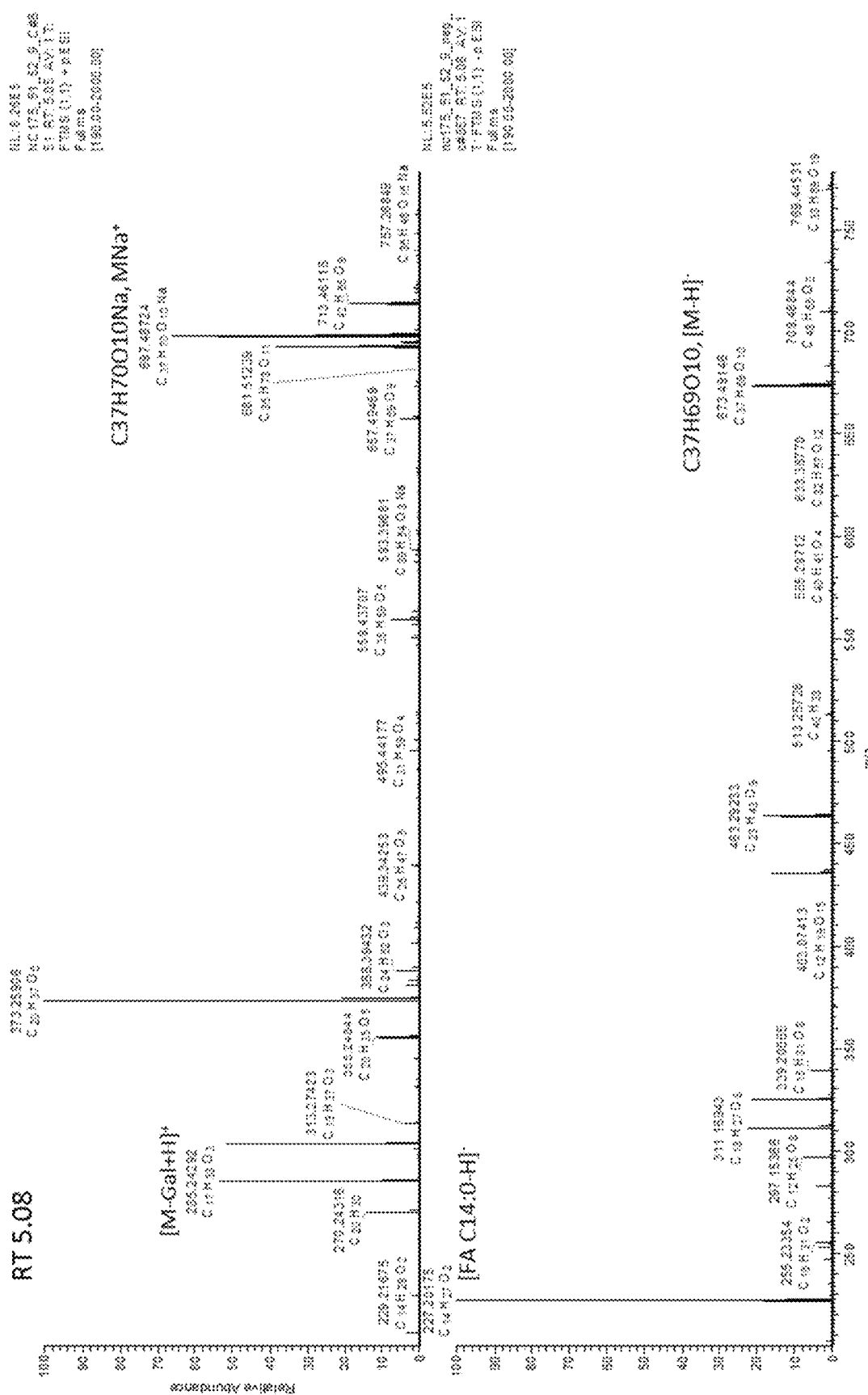
FIG. 98. HRMS of peak RT 5.08 from NC175-51-52-9.

Peak RT 5.08 gives a molecular formula of $C_{37}H_{70}O_{10}$ from HRMS molecular ions of m/z 697.48724 ($C_{37}H_{70}O_{10}Na_+$, calculated 697.48612) and 673.49146 ($C_{37}H_{69}O_{9-}$, calculated 673.48962) in positive and negative mode HRMS (FIG. 98). Only one saturated fatty acid fragment is present (C14:0), thus peak RT 1.14 was identified to be glycolipid MGDG C14:0/14:0 (18).

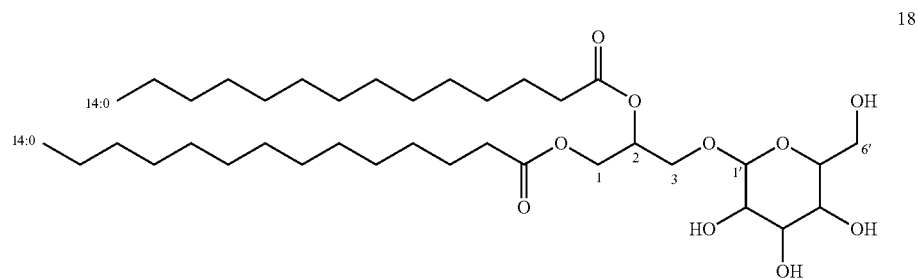 [SMILES: CCCCCCCCCCCCCC(=O)OCC(COC1OC(CO)C(O)C(O)C1O)OC(=O)CCCCCCCCCCCCC]

18

NC175-51-52-10

Figure 99:
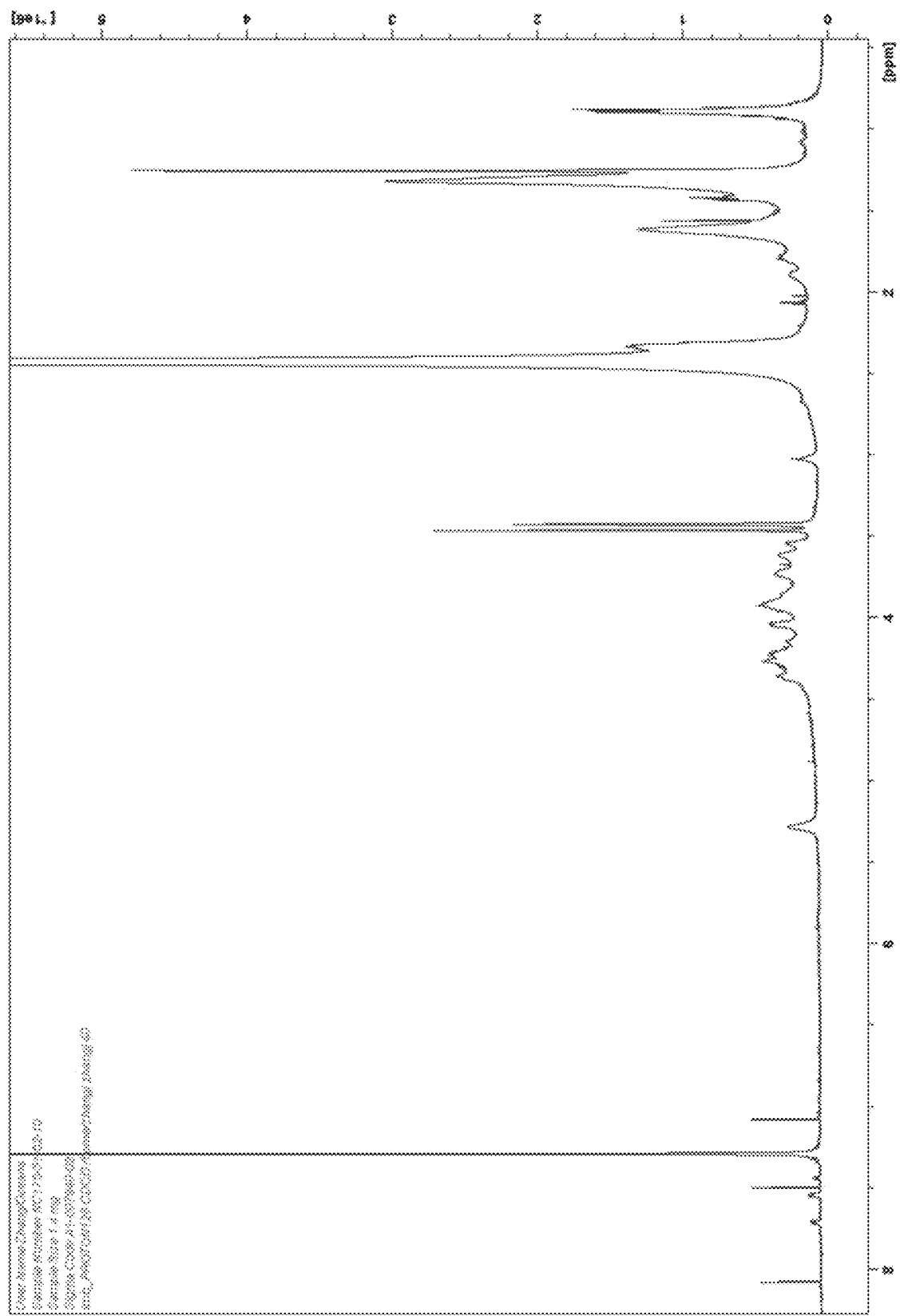
FIG. 99. 1H-NMR spectrum of NC175-51-52-10.
Figure 100:
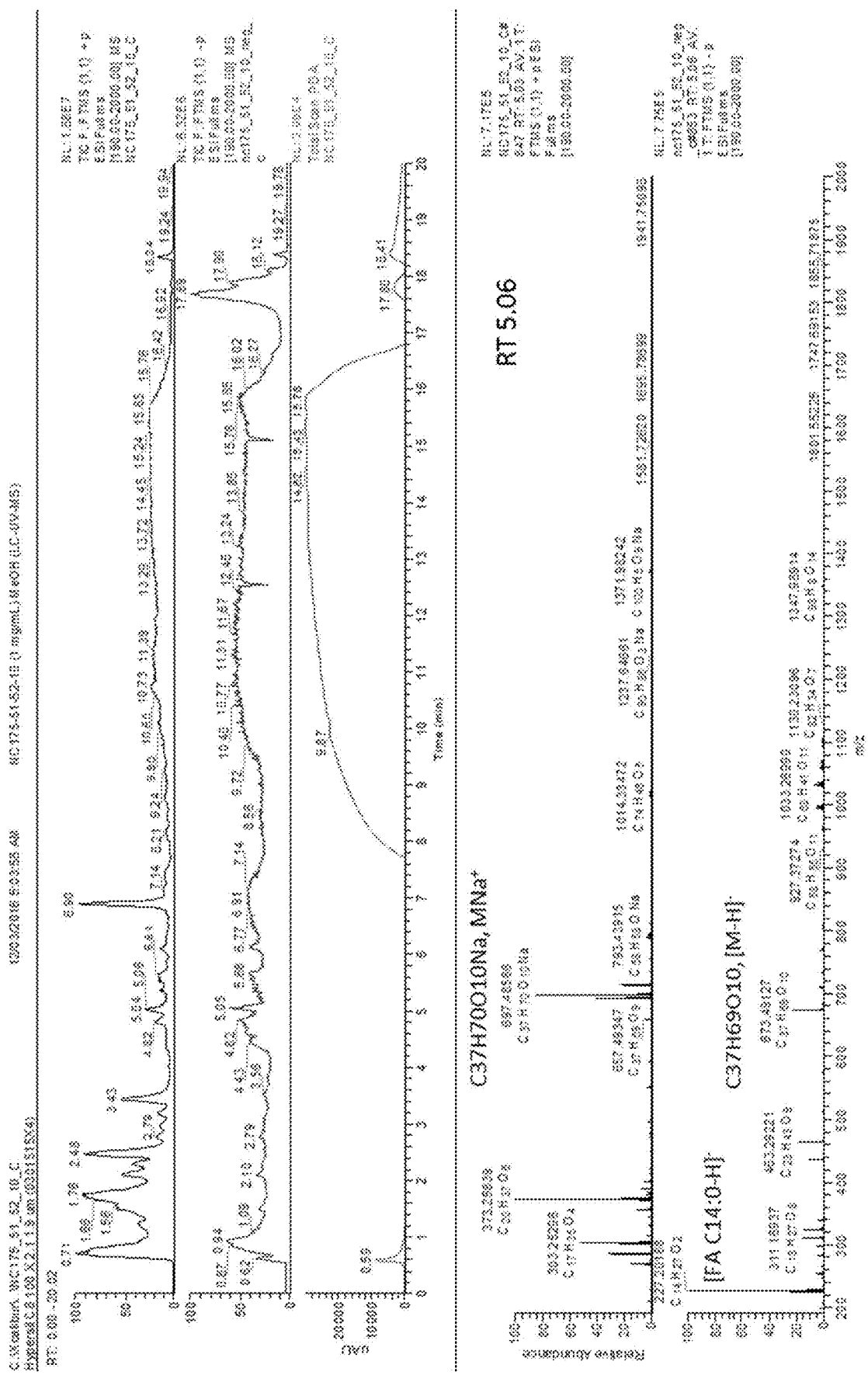
FIG. 100. UPLC-DAD/HRMS of NC175-51-52-10 and peak RT 5.06.

This sample has glycolipid features in 1H-NMR (FIG. 99), and was identified to be the same as MGDG C14:0/14:0 (18) described above based on HRMS data (FIG. 100).

SUMMARY

Figure 101:
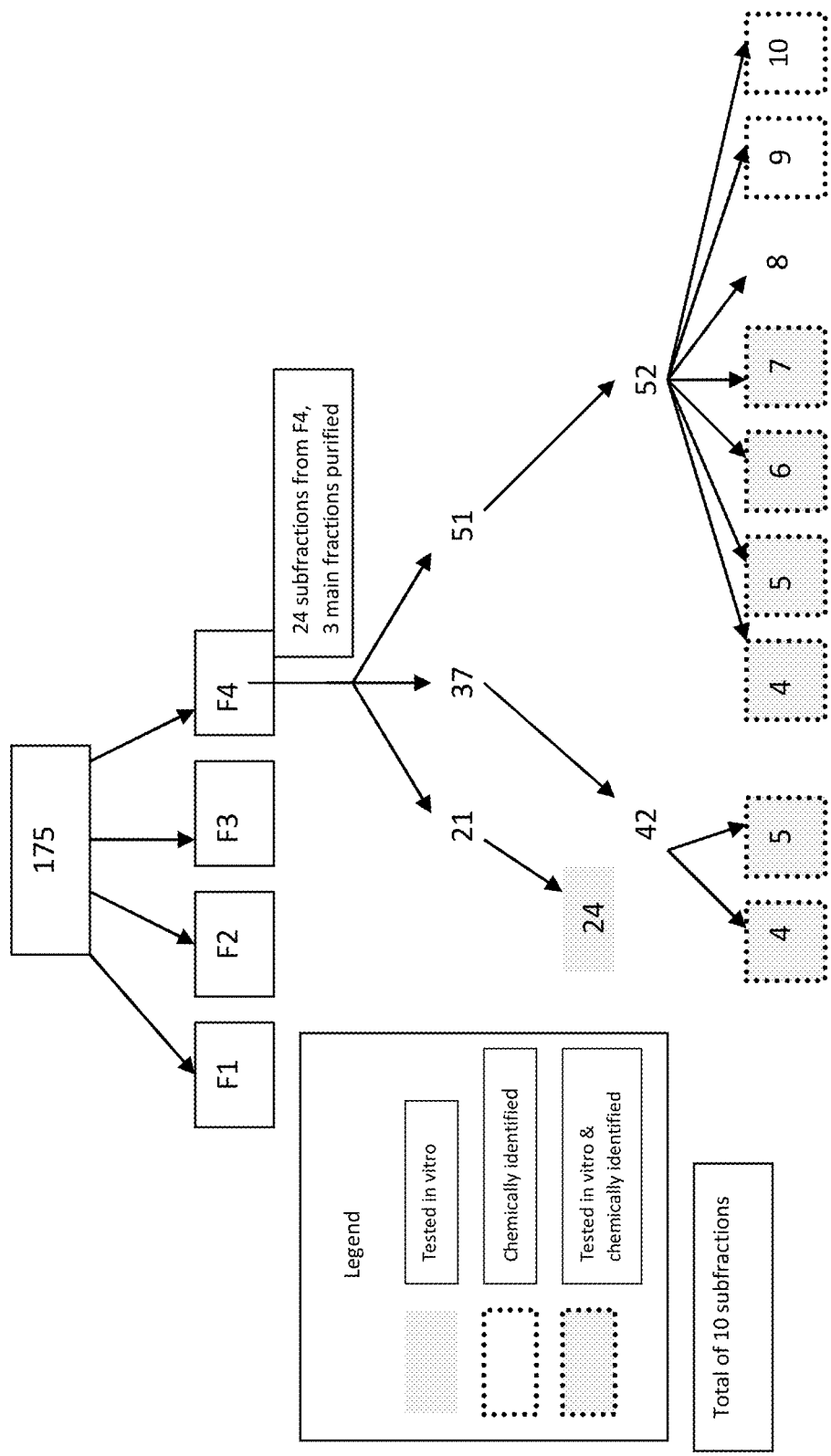
FIG. 101. Summary flowchart of fractionation, purification and in vitro testing of compounds from NC175.

In summary and as shown in FIG. 101, 10 subfractions were identified, 7 of which were tested in vitro, whereas 8 subfractions were chemically identified of which 3 were pure compounds (175-51-52-7; cpd #5; 175-51-52-5: cpd #15; and 175-: cpd #117). The structure of these compounds and their in vitro anti-cancer activity are shown in Table 13.

TABLE 13
| Sub-fraction | Compound # | Mixed/Pure | Notes |
|---|---|---|---|
| 175-51-52-4 | 14 | Pure | |
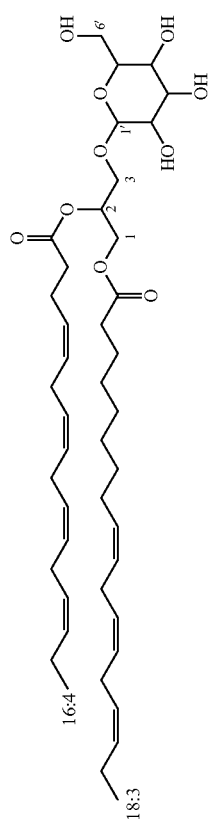
14
Average cell viability:
| | 1% | | | | | | | |
|---|---|---|---|---|---|---|---|---|
| Vehicle cont-DMSO | 250 ug/mL | 96 | 86 | 98 | 93 | 92 | 91 | 88 |
| Positive cont-SDS | ug/mL | 8 | 11 | 4 | 9 | 14 | 5 | 16 |
| | | PC3 | A549 | U373 | SKOV | MDA-MB | CCD | THP-1 |
| | 100 | 12 | 74 | 9 | 67 | 18 | 19 | 51 |
| | 50 | 66 | 88 | 41 | 92 | 68 | 49 | 62 |
| | 10 | 98 | 101 | 100 | 97 | 102 | 96 | 100 |
| | 1 | 103 | 99 | 109 | 109 | 104 | 102 | 99 |
Fold change in viability:
| | | PC3 | | A549 | | U373 | | SKOV | | MDA-MB | | CCD | | THP-1 | |
|---|---|---|---|---|---|---|---|---|---|---|---|---|---|---|---|
| Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| | ug/mL | AVG | ERROR | AVG | ERROR | AVG | ERROR | AVG | ERROR | AVG | ERROR | AVG | ERROR | AVG | ERROR |
| | 100 | 0.13 | 0.01 | 0.86 | 0.02 | 0.09 | 0.00 | 0.72 | 0.04 | 0.20 | 0.00 | 0.21 | 0.01 | 0.58 | 0.07 |
| | 50 | 0.68 | 0.00 | 1.03 | 0.02 | 0.42 | 0.03 | 0.89 | 0.03 | 0.74 | 0.00 | 0.54 | 0.07 | 0.70 | 0.04 |
| | 10 | 1.01 | 0.04 | 1.18 | 0.02 | 1.02 | 0.01 | 1.05 | 0.02 | 1.11 | 0.03 | 1.05 | 0.05 | 1.14 | 0.05 |
| | 1 | 1.07 | 0.01 | 1.15 | 0.02 | 1.10 | 0.02 | 1.17 | 0.03 | 1.13 | 0.06 | 1.12 | 0.01 | 1.12 | 0.03 |

TABLE 13-continued

| Sub-fraction | Compound # | Mixed/Pure | | | | | | | | | | | | | Notes |
|---|---|---|---|---|---|---|---|---|---|---|---|---|---|---|---|
| 175-51-52-5 | 15, 16 | Mixed | | | | | | | | | | | | | Required further purification to isolate compound 16 in mixture |

Average cell viability:

| | | | 1% | 96 | 86 | 98 | 93 | 92 | 91 | 88 | |
| --- | --- | --- | --- | --- | --- | --- | --- | --- | --- | --- | --- |
| Vehicle cont-DMSO | | | | 8 | 11 | 4 | 9 | 14 | 5 | 16 | |
| Positive cont-SDS | | 250 ug/ml | | PC3 | A549 | U373 | SKOV | MDA-MB | CCD | THP-1 | |
| | ug/mL | AVG | ERROR | AVG | ERROR | AVG | ERROR | AVG | ERROR | AVG | ERROR | AVG | ERROR | AVG | ERROR |
| | 100 | 0.13 | 0.01 | 12 | 0.04 | 57 | 0.01 | 78 | 0.02 | 20 | 0.00 | 21 | 0.01 | 47 | 0.03 |
| | 50 | 0.90 | 0.05 | 87 | 0.03 | 90 | 0.02 | 90 | 0.04 | 76 | 0.02 | 74 | 0.03 | 70 | 0.07 |
| | 10 | 1.00 | 0.04 | 97 | 0.02 | 96 | 0.04 | 87 | 0.02 | 104 | 0.01 | 90 | 0.01 | 89 | 0.02 |
| | 1 | 0.97 | 0.04 | 94 | 0.02 | 95 | 0.01 | 87 | 0.02 | 102 | 0.02 | 91 | 0.01 | 95 | 0.00 |

Fold change in viability:

| Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| --- | --- | --- | --- | --- | --- | --- | --- | --- | --- | --- | --- | --- | --- | --- | --- |
| | ug/mL | AVG | ERROR | AVG | ERROR | AVG | ERROR | AVG | ERROR | AVG | ERROR | AVG | ERROR | AVG | ERROR |
| | | PC3 | | A549 | | U373 | | SKOV | | MDA-MB | | CCD | | THP-1 | |
| | 100 | 0.13 | 0.01 | 0.66 | 0.04 | 0.12 | 0.01 | 0.84 | 0.01 | 0.22 | 0.00 | 0.23 | 0.01 | 0.54 | 0.03 |
| | 50 | 0.90 | 0.05 | 1.05 | 0.03 | 0.73 | 0.02 | 0.96 | 0.02 | 0.83 | 0.02 | 0.82 | 0.03 | 0.79 | 0.07 |
| | 10 | 1.00 | 0.04 | 1.12 | 0.02 | 0.89 | 0.04 | 0.93 | 0.04 | 1.13 | 0.01 | 0.99 | 0.01 | 1.01 | 0.02 |
| | 1 | 0.97 | 0.04 | 1.11 | 0.02 | 0.87 | 0.01 | 0.94 | 0.01 | 1.11 | 0.02 | 1.00 | 0.01 | 1.08 | 0.00 |

Pure

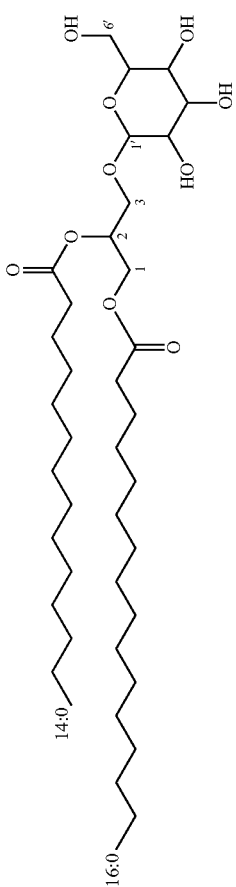

16

| Sub-fraction | | | | | | | | | | | | | | | |
|---|---|---|---|---|---|---|---|---|---|---|---|---|---|---|---|
| 175-51-52-6 | 16 | | | | | | | | | | | | | | |

Average cell viability:

| | | | 1% | 96 | 86 | 98 | 93 | 92 | 91 | 88 | |
| --- | --- | --- | --- | --- | --- | --- | --- | --- | --- | --- | --- |
| Vehicle cont-DMSO | | | | 8 | 11 | 4 | 9 | 14 | 5 | 16 | |
| Positive cont-SDS | | 250 ug/ml | | PC3 | A549 | U373 | SKOV | MDA-MB | CCD | THP-1 | |
| | 100 | | | 9 | | 52 | | 68 | | 20 | | 19 | | 46 | |
| | 50 | | | 72 | | 85 | | 48 | | 83 | | 70 | | 44 | | 86 |
| | 10 | | | 96 | | 99 | | 95 | | 95 | | 101 | | 98 | | 101 |
| | 1 | | | 100 | | 97 | | 108 | | 102 | | 99 | | 106 | | 101 |

TABLE 13-continued

| Sub-fraction | Compound # | | | | | | Mixed/Pure | | | | | | | | Notes |
|---|---|---|---|---|---|---|---|---|---|---|---|---|---|---|---|
| | | | | | | | Fold change in viability: | | | | | | | | |
| | Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| | | | PC3 | | A549 | | U373 | | SKOV | | MDA-MB | | CCD | | THP-1 | |
| | | ug/mL | AVG | ERROR | AVG | ERROR | AVG | ERROR | AVG | ERROR | AVG | ERROR | AVG | ERROR | AVG | ERROR |
| | | 100 | 0.10 | 0.00 | 0.60 | 0.04 | 0.09 | 0.00 | 0.74 | 0.03 | 0.21 | 0.02 | 0.21 | 0.01 | 0.52 | 0.03 |
| | | 50 | 0.75 | 0.06 | 0.99 | 0.01 | 0.49 | 0.05 | 0.90 | 0.01 | 0.76 | 0.06 | 0.48 | 0.05 | 0.75 | 0.11 |
| | | 10 | 0.99 | 0.04 | 1.16 | 0.02 | 0.97 | 0.03 | 1.02 | 0.00 | 1.09 | 0.02 | 1.08 | 0.04 | 1.15 | 0.09 |
| | | 1 | 1.04 | 0.02 | 1.13 | 0.02 | 1.09 | 0.07 | 1.09 | 0.05 | 1.08 | 0.01 | 1.16 | 0.10 | 1.14 | 0.01 |
| 175-51-52-7 | 5, 16 | | | | | | Mixed | | | | | | | | Required further purification to isolate 1 compound in mixture |

Average cell viability:

| | Vehicle cont-DMSO | 1% | | | 96 | 8 | 86 | 11 | 95 | 9 | 92 | 14 | 91 | 5 | 88 | 16 |
|---|---|---|---|---|---|---|---|---|---|---|---|---|---|---|---|---|
| | Positive cont-SDS | 250 ug/ml | | | | | | | | | | | | | | |
| | | ug/mL | | | PC3 | | A549 | | U373 | | SKOV | | MDA-MB | | CCD | THP-1 |
| | | 100 | | | 28 | | 73 | | 41 | | 95 | | 43 | | 24 | 51 |
| | | 50 | | | 91 | | 101 | | 82 | | 96 | | 85 | | 82 | 85 |
| | | 10 | | | 101 | | 101 | | 96 | | 98 | | 100 | | 102 | 99 |
| | | 1 | | | 100 | | 99 | | 95 | | 99 | | 100 | | 102 | 96 |

Fold change in viability:

| | Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
|---|---|---|---|---|---|---|---|---|---|---|---|---|---|---|---|---|
| | | | PC3 | | A549 | | U373 | | SKOV | | MDA-MB | | CCD | | THP-1 | |
| | | ug/mL | AVG | ERROR | AVG | ERROR | AVG | ERROR | AVG | ERROR | AVG | ERROR | AVG | ERROR | AVG | ERROR |
| | | 100 | 0.29 | 0.03 | 0.85 | 0.02 | 0.41 | 0.05 | 1.02 | 0.01 | 0.46 | 0.03 | 0.26 | 0.01 | 0.58 | 0.07 |
| | | 50 | 0.94 | 0.05 | 1.17 | 0.06 | 0.84 | 0.11 | 1.04 | 0.03 | 0.92 | 0.04 | 0.90 | 0.07 | 0.96 | 0.01 |
| | | 10 | 1.05 | 0.01 | 1.18 | 0.01 | 0.97 | 0.04 | 1.05 | 0.07 | 1.09 | 0.00 | 1.12 | 0.06 | 1.12 | 0.01 |
| | | 1 | 1.03 | 0.03 | 1.16 | 0.02 | 0.96 | 0.05 | 1.07 | 0.13 | 1.09 | 0.04 | 1.12 | 0.03 | 1.09 | 0.04 |

TABLE 13-continued

| Sub-fraction | Compound # | Mixed/Pure | Notes |
|---|---|---|---|
| 175-51-51-9 | 17, 18 | Mixed | Required further purification to isolate 1 compound in mixture |
| 175-51-52-10 | 18 | Pure | |
| 175-37-42-4 | 19 | Pure | |

18:3

19

Average cell viability:

| | 1% | | 96 | 86 | 98 | 93 | 92 | 91 | 88 |
|---|---|---|---|---|---|---|---|---|---|
| Vehicle cont-DMSO | 250 ug/ml | | 8 | 11 | 4 | 9 | 14 | 5 | 16 |
| Positive cont-SDS | ug/mL | PC3 | A549 | U373 | SKOV | MDA-MB | CCD | THP-1 |
| | 100 | | 11 | 57 | 10 | 83 | 24 | 21 | 31 |
| | 50 | | 88 | 88 | 57 | 101 | 81 | 77 | 72 |
| | 10 | | 103 | 100 | 108 | 111 | 108 | 105 | 99 |
| | 1 | | 105 | 99 | 116 | 117 | 108 | 109 | 102 |

Fold change in viability:

| | | PC3 | | A549 | | U373 | | SKOV | | MDA-MB | | CCD | | THP-1 | |
|---|---|---|---|---|---|---|---|---|---|---|---|---|---|---|---|
| Positive cont-SDS | 250 ug/mL | 0.08 | 0.00 | 0.13 | 0.01 | 0.05 | 0.00 | 0.10 | 0.08 | 0.00 | 0.00 | 0.06 | 0.00 | 0.18 | 0.01 |
| | ug/mL | AVG | ERROR | AVG | ERROR | AVG | ERROR | AVG | ERROR | AVG | ERROR | AVG | ERROR | AVG | ERROR |
| | 100 | 0.12 | 0.01 | 0.67 | 0.05 | 0.10 | 0.00 | 0.90 | 0.06 | 0.26 | 0.01 | 0.23 | 0.00 | 0.35 | 0.02 |
| | 50 | 0.91 | 0.06 | 1.02 | 0.03 | 0.58 | 0.07 | 1.09 | 0.11 | 0.88 | 0.05 | 0.85 | 0.10 | 0.82 | 0.03 |
| | 10 | 1.07 | 0.03 | 1.16 | 0.04 | 1.10 | 0.07 | 1.20 | 0.08 | 1.18 | 0.02 | 1.16 | 0.06 | 1.12 | 0.08 |
| | 1 | 1.09 | 0.05 | 1.16 | 0.07 | 1.18 | 0.06 | 1.26 | 0.06 | 1.17 | 0.00 | 1.20 | 0.08 | 1.16 | 0.08 |

TABLE 13-continued
| Sub-fraction | Compound # | | Mixed/Pure | | | | Notes | |
|---|---|---|---|---|---|---|---|---|
| 175-37-42-5 | 20 | | Pure | | | | | |
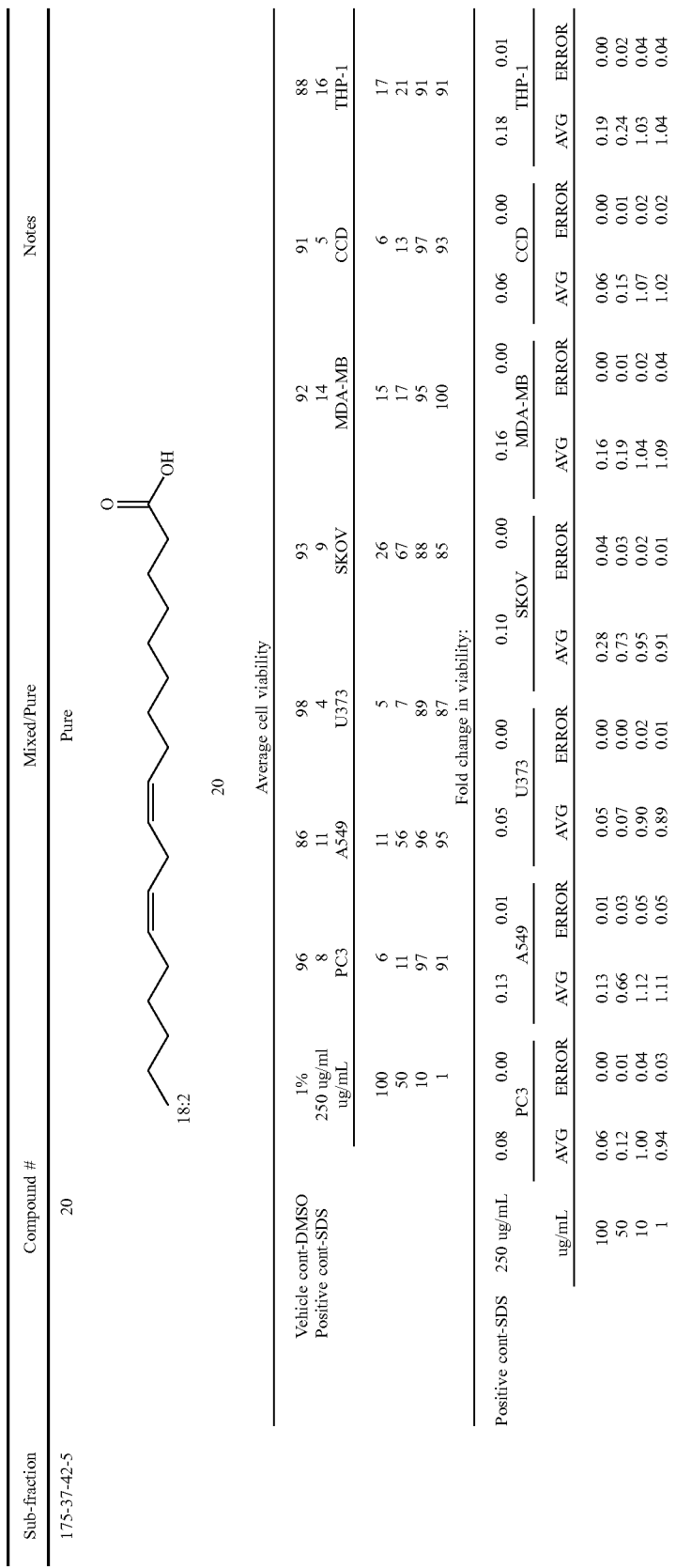
18:2          20
Average cell viability
| | | PC3 | | A549 | | U373 | | SKOV | | MDA-MB | | CCD | | THP-1 | |
|---|---|---|---|---|---|---|---|---|---|---|---|---|---|---|---|---|
| Vehicle cont-DMSO | 1% | 96 | 8 | 86 | 11 | 98 | 4 | 93 | 9 | 92 | 14 | 91 | 5 | 88 | 16 |
| Positive cont-SDS | 250 ug/ml | PC3 | | A549 | | U373 | | SKOV | | MDA-MB | | CCD | | THP-1 | |
| | ug/mL | | | | | | | | | | | | | | |
| | 100 | 6 | | 11 | | 5 | | 26 | | 15 | | 6 | | 17 | |
| | 50 | 11 | | 56 | | 7 | | 67 | | 17 | | 13 | | 21 | |
| | 10 | 97 | | 96 | | 89 | | 88 | | 95 | | 97 | | 91 | |
| | 1 | 91 | | 95 | | 87 | | 85 | | 100 | | 93 | | 91 | |
Fold change in viability:
| | | PC3 | | A549 | | U373 | | SKOV | | MDA-MB | | CCD | | THP-1 | |
|---|---|---|---|---|---|---|---|---|---|---|---|---|---|---|---|---|
| Positive cont-SDS | 250 ug/mL | 0.08 | 0.00 | 0.13 | 0.01 | 0.05 | 0.00 | 0.10 | 0.00 | 0.16 | 0.00 | 0.06 | 0.00 | 0.18 | 0.01 |
| | | AVG | ERROR | AVG | ERROR | AVG | ERROR | AVG | ERROR | AVG | ERROR | AVG | ERROR | AVG | ERROR |
| | ug/mL | | | | | | | | | | | | | | |
| | 100 | 0.06 | 0.00 | 0.13 | 0.01 | 0.05 | 0.00 | 0.28 | 0.04 | 0.16 | 0.00 | 0.06 | 0.00 | 0.19 | 0.00 |
| | 50 | 0.12 | 0.01 | 0.66 | 0.03 | 0.07 | 0.00 | 0.73 | 0.03 | 0.19 | 0.01 | 0.15 | 0.01 | 0.24 | 0.02 |
| | 10 | 1.00 | 0.04 | 1.12 | 0.05 | 0.90 | 0.02 | 0.95 | 0.02 | 1.04 | 0.02 | 1.07 | 0.02 | 1.03 | 0.04 |
| | 1 | 0.94 | 0.03 | 1.11 | 0.05 | 0.89 | 0.01 | 0.91 | 0.01 | 1.09 | 0.04 | 1.02 | 0.02 | 1.04 | 0.04 |

Example 11. Characterization of Other Components

NC175-37-42-4

Figure 102:
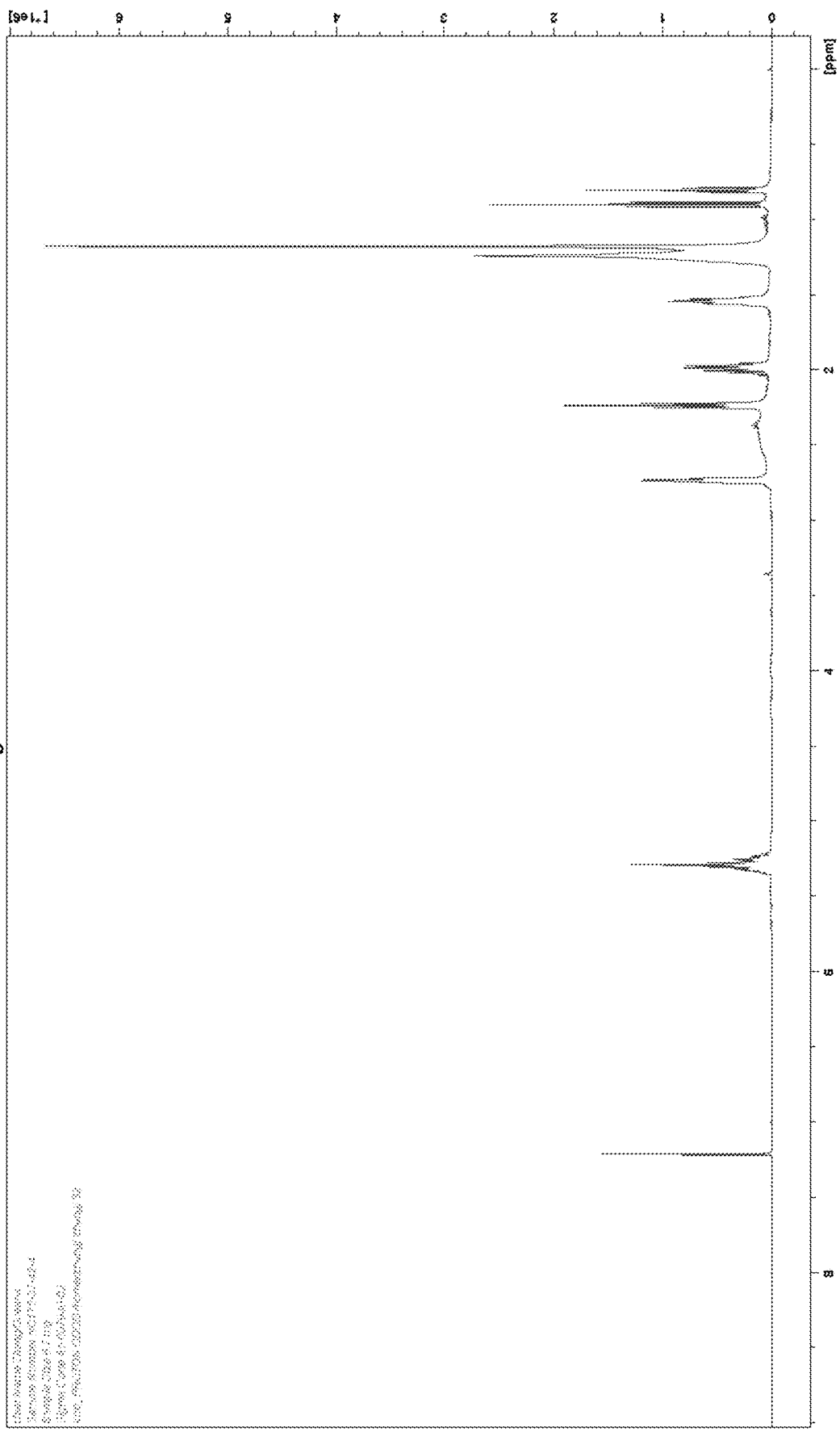
FIG. 102. 1H-NMR spectrum of NC175-37-42-4.
Figure 103:
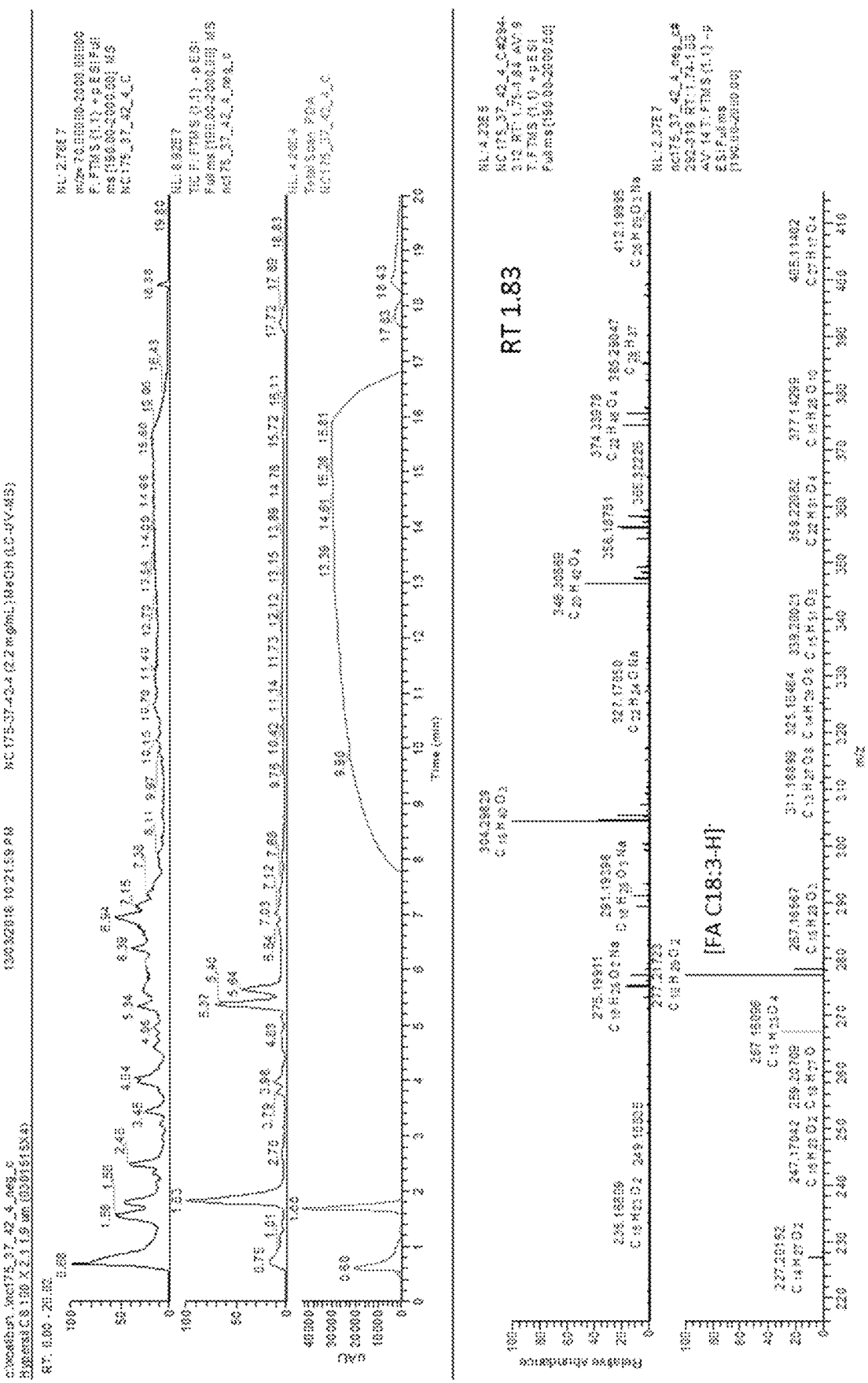
FIG. 103. UPLC-DAD/HRMS of NC175-37-42-4 and peak RT 1.83.

1H-NMR (FIG. 102) indicates that this sample to be a typical unsaturated fatty acid, likely a n-3 one. The absence of glycerol signal implied the possibility of free fatty acid. In UPLC-DAD/HRMS (FIG. 103), major peak RT 1.68 only shows a fatty acid anion m/z 277.21723 ($C_{18}H_{29}O_2-$, calculated 277.21730), confirming NC175-37-42-4 as a free fatty acid α-linolenic acid (19, C18:3 n-3).

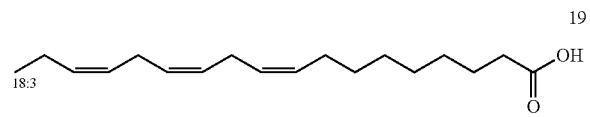 [SMILES: CC/C=C\C/C=C\C/C=C\CCCCCCCC(=O)O]

NC175-37-42-5

Figure 104:
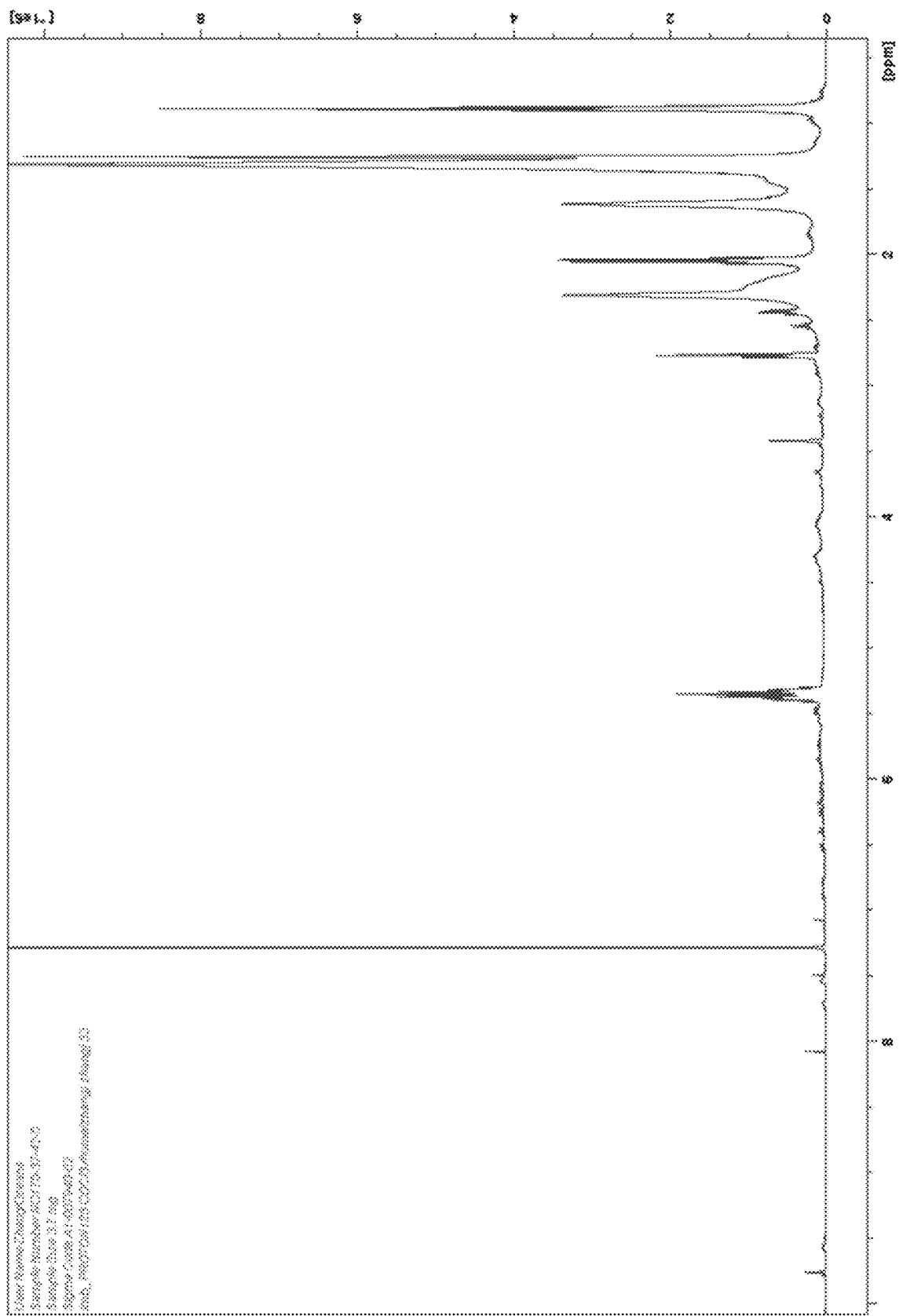
FIG. 104. 1H-NMR spectrum of NC175-37-42-5.
Figure 105:
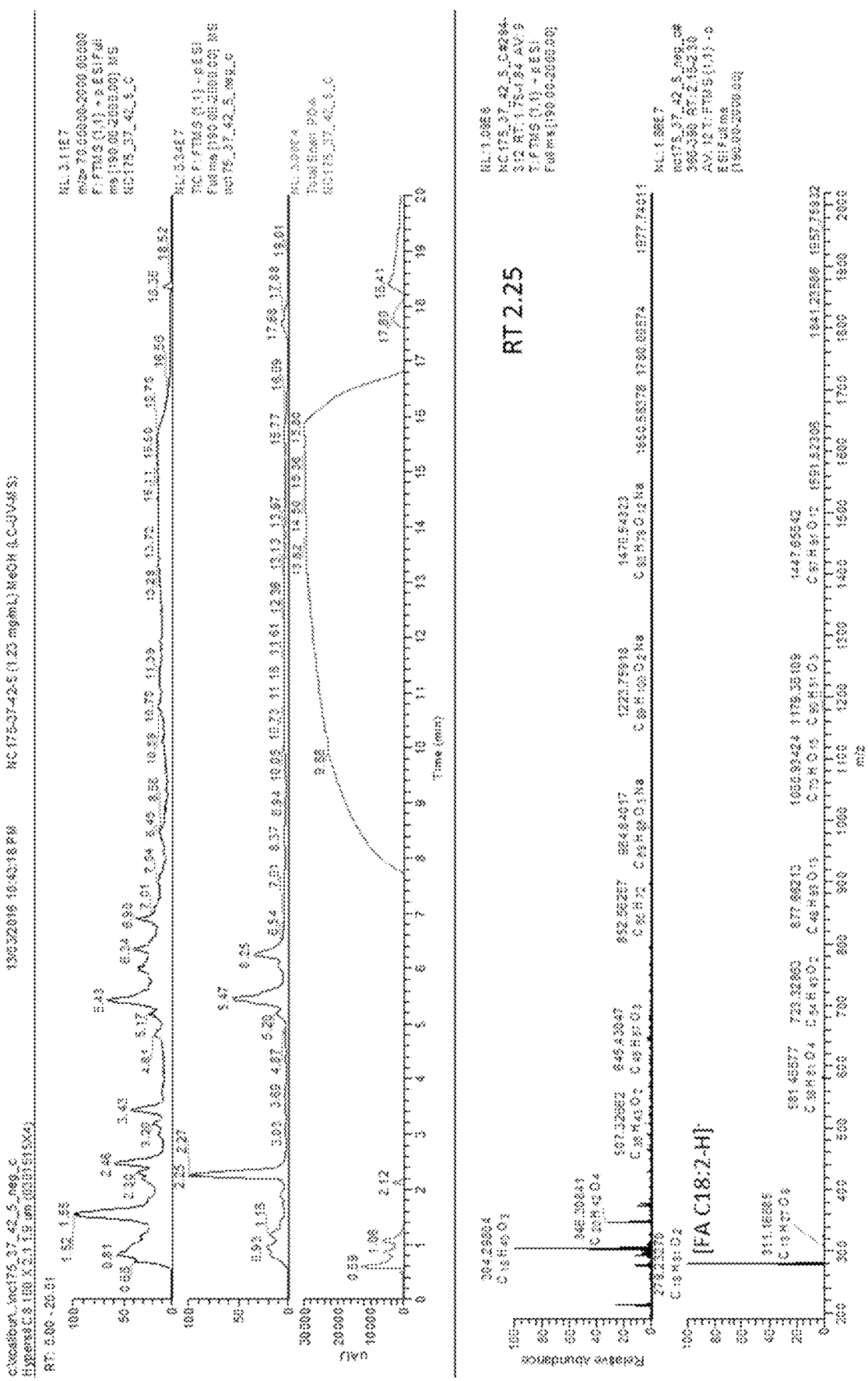
FIG. 105. UPLC-DAD/HRMS of NC175-37-42-5 and peak RT 2.25.

Similar to NC175-37-42-4, this is also a free unsaturated fatty acid characterized as linoleic acid (20, C18:2 n-6), based on H-NMR and HRMS (FIGS. 104 and 105).

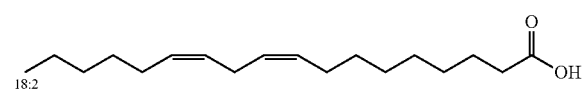

Example 12. Summary

Ten (10) subfractions were identified, of which 7 of 10 subfractions were tested in vitro (FIG. 101) and 8 of 10 subfractions were chemically identified of which four (4) were pure (175-51-52-4: cpd 14; 175-51-52-6: cpd 16; 175-51-52-10: cpd 18; 175-37-42-4: cpd 19 and 175-37-42-5: cpd 20). Moreover, subfraction 175-51-52-7 required further purification to isolate compound 5; subfraction 175-51-52-5 required further purification to isolate compound 15; and subfraction 175-51-52-9 required further purification to isolate compound 17.

In summary, the bioactive fractions (Fr. 4) of seaweed extracts NC169, NC174, and NC175 contain glycolipids as the main components. Table 14 is a list of glycolipids (1-18) characterized based on NMR and HRMS, primarily as MGDG type with a few as lyso MGDG form.

Additionally, two free fatty acids α-linolenic acid and linoleic acid (19-20) were also identified from fraction 4 of NC175. This is in agreement with the GC-FID/MS data, as the fatty acid profile of NC175 appeared to be different from that of NC169 and NC174. In NC169 and NC174, the major fatty acids were found to be palmitic acid (C16:0) and eicosapentaenoic acid (EPA, C20:5), whereas in NC175, the major fatty acid was shown to be palmitic acid (C16:0), with much less EPA.

Example 13. In Vitro Activity of Pure Compounds Identified

A total of 20 compounds were identified;
9 compounds were pure (found in isolated fractions);
whereas 12 compounds were in mixture and needed to be further purified;
7 subfractions required further purification due to a mixture of compounds within the fraction.

TABLE 14

List of glycolipids identified in fraction 4 of NC169, NC174, and NC175

| Compound No. | Molecular formula | Fatty acid composition sn1/sn-2 | Fraction/sample code |
|---|---|---|---|
| 1 | $C_{45}H_{68}O_{10}$ | MGDG C20:5/C16:4 | NC169-14-15-1 |
|   |   |   | NC174-13-14-1 |
| 2 | $C_{45}H_{76}O_{10}$ | MGDG C20:5/C16:0 | NC169-14-15-1 |
|   |   |   | NC169-14-15-2 |
|   |   |   | NC169-14-15-4 |
|   |   |   | NC174-13-14-1 |
|   |   |   | NC174-13-14-3 |
| 3 | $C_{43}H_{76}O_{10}$ | MGDG C20:5/C14:0 | NC169-14-15-1 |
| 4 | $C_{43}H_{76}O_{10}$ | MGDG C16:1/C18:2 | NC169-14-15-1 |
| 5 | $C_{25}H_{48}O_{9}$ | Lyso-MGDG C16:0 | NC169-14-15-2 |
|   |   |   | NC169-20-22-3 |
|   |   |   | NC169-20-22-4 |
|   |   |   | NC169-20-22-5 |
|   |   |   | NC175-51-52-7 |
| 6 | $C_{45}H_{70}O_{10}$ | MGDG C20:5/C16:3 | NC169-14-15-2 |
| 7 | $C_{49}H_{74}O_{10}$ | MGDG C20:5/C20:5 | NC169-14-15-2 |
|   |   |   | NC174-13-14-2 |
| 8 | $C_{41}H_{78}O_{10}$ | MGDG C16:0/C16:0 | NC169-20-22-5 |
| 9 | $C_{41}H_{76}O_{10}$ | MGDG C16:0/C16:1 | NC174-13-14-1 |
| 10 | $C_{43}H_{78}O_{10}$ | MGDG C16:0/C18:2 | NC174-13-14-1 |
| 11 | $C_{43}H_{80}O_{10}$ | MGDG C16:0/C18:1 | NC174-13-14-1 |
| 12 | $C_{45}H_{84}O_{10}$ | MGDG C16:0/C18:0 | NC174-13-14-1 |
| 13 | $C_{29}H_{46}O_{9}$ | Lyso-MGDG C20:5 | NC174-18-19-3 |
| 14 | $C_{43}H_{68}O_{10}$ | MGDG C18:3/C16:4 | NC175-51-52-4 |
| 15 | $C_{43}H_{70}O_{10}$ | MGDG C18:3/C16:3 | NC175-51-52-5 |
| 16 | $C_{39}H_{74}O_{10}$ | MGDG C16:0/C14:0 | NC175-51-52-5 |
|   |   |   | NC175-51-52-6 |
| 17 | $C_{23}H_{44}O_{9}$ | Lyso-MGDG C14:0 | NC175-51-52-9 |
| 18 | $C_{37}H_{70}O_{10}$ | MGDG C14:0/C14:0 | NC175-51-52-9 |
|   |   |   | NC175-51-52-10 |

The in vitro anti-cancer activity of all compounds is summarized in Table 15.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications and patent applications cited in this specification are herein incorporated by reference as if each individual publication or patent application were specifically and individually indicated to be incorporated by reference.

TABLE 15

In vitro activity against cancer cell lines of pure compounds

| Sample ID | ug/mL | PC3 AVG | PC3 ERROR | A549 AVG | A549 ERROR | U373 AVG | U373 ERROR | SKOV AVG | SKOV ERROR | MDA-MB AVG | MDA-MB ERROR | CCD AVG | CCD ERROR | THP-1 AVG | THP-1 ERROR |
|---|---|---|---|---|---|---|---|---|---|---|---|---|---|---|---|
| NC77 | 100 | 1.14 | 0.12 | 1.17 | 0.19 | 0.79 | 0.01 | 1.07 | 0.04 | 0.58 | 0.05 | 0.84 | 0.07 | 1.55 | 0.02 |
| | 50 | 1.04 | 0.11 | 1.23 | 0.11 | 1.02 | 0.08 | 1.09 | 0.04 | 0.71 | 0.07 | 0.93 | 0.03 | 1.59 | 0.07 |
| | 10 | 1.07 | 0.12 | 1.30 | 0.06 | 1.00 | 0.02 | 1.11 | 0.09 | 1.01 | 0.01 | 1.03 | 0.04 | 1.19 | 0.06 |
| | 1 | 1.08 | 0.14 | 1.21 | 0.12 | 0.98 | 0.03 | 1.16 | 0.05 | 1.05 | 0.05 | 1.05 | 0.05 | 1.15 | 0.06 |
| NC77 F4 | 100 | 1.06 | 0.06 | 1.20 | 0.15 | 0.48 | 0.02 | 0.89 | 0.08 | 0.46 | 0.04 | 0.86 | 0.02 | 0.18 | 0.01 |
| | 50 | 1.08 | 0.13 | 1.19 | 0.09 | 1.03 | 0.03 | 1.07 | 0.03 | 0.98 | 0.04 | 0.92 | 0.04 | 1.25 | 0.07 |
| | 10 | 1.17 | 0.02 | 1.26 | 0.10 | 1.07 | 0.07 | 1.18 | 0.05 | 1.12 | 0.03 | 1.08 | 0.03 | 1.19 | 0.06 |
| | 1 | 1.17 | 0.10 | 1.30 | 0.09 | 1.07 | 0.07 | 1.25 | 0.07 | 1.12 | 0.02 | 1.06 | 0.03 | 1.24 | 0.08 |
| 38-41-3 | 100 | 0.16 | 0.01 | 1.05 | 0.01 | 0.04 | 0.00 | 0.39 | 0.05 | 0.20 | 0.00 | 0.14 | 0.02 | 0.21 | 0.00 |
| | 50 | 0.19 | 0.03 | 1.08 | 0.04 | 0.07 | 0.01 | 0.86 | 0.02 | 0.49 | 0.05 | 0.23 | 0.01 | 0.41 | 0.05 |
| | 10 | 1.08 | 0.07 | 1.08 | 0.03 | 0.99 | 0.05 | 1.08 | 0.02 | 1.23 | 0.03 | 1.01 | 0.06 | 1.12 | 0.01 |
| | 1 | 1.14 | 0.03 | 1.18 | 0.05 | 1.00 | 0.04 | 1.22 | 0.05 | 1.14 | 0.02 | 1.04 | 0.01 | 1.22 | 0.04 |
| NC169 | 100 | 0.50 | 0.02 | 0.61 | 0.02 | 0.32 | 0.02 | 0.78 | 0.01 | 0.57 | 0.02 | 0.59 | 0.01 | 0.87 | 0.01 |
| | 50 | 1.06 | 0.11 | 0.95 | 0.07 | 0.49 | 0.01 | 0.76 | 0.02 | 0.74 | 0.01 | 0.67 | 0.02 | 0.98 | 0.04 |
| | 10 | 1.05 | 0.02 | 1.08 | 0.06 | 0.91 | 0.06 | 1.05 | 0.03 | 1.06 | 0.01 | 0.90 | 0.05 | 1.12 | 0.03 |
| | 1 | 1.02 | 0.07 | 1.11 | 0.08 | 0.97 | 0.03 | 1.03 | 0.02 | 1.15 | 0.08 | 1.05 | 0.04 | 1.09 | 0.04 |
| NC169 F4 | 100 | 0.64 | 0.04 | 0.95 | 0.07 | 0.55 | 0.04 | 0.75 | 0.01 | 0.62 | 0.06 | 0.67 | 0.01 | 0.80 | 0.01 |
| | 50 | 1.06 | 0.01 | 0.83 | 0.03 | 0.70 | 0.04 | 0.86 | 0.03 | 0.88 | 0.08 | 0.77 | 0.04 | 1.15 | 0.04 |
| | 10 | 1.05 | 0.00 | 1.07 | 0.02 | 1.01 | 0.03 | 1.06 | 0.05 | 1.09 | 0.05 | 0.99 | 0.01 | 1.13 | 0.06 |
| | 1 | 1.12 | 0.01 | 1.18 | 0.08 | 1.08 | 0.04 | 1.17 | 0.03 | 1.09 | 0.03 | 1.07 | 0.02 | 1.20 | 0.07 |
| 169-8-12-1 | 100 | 0.17 | 0.00 | 0.29 | 0.02 | 0.04 | 0.00 | 0.27 | 0.01 | 0.22 | 0.01 | 0.14 | 0.01 | 0.39 | 0.03 |
| | 50 | 0.18 | 0.00 | 0.99 | 0.10 | 0.05 | 0.00 | 0.58 | 0.04 | 0.24 | 0.01 | 0.19 | 0.02 | 0.52 | 0.03 |
| | 10 | 1.05 | 0.10 | 1.17 | 0.07 | 1.01 | 0.05 | 1.11 | 0.12 | 1.03 | 0.05 | 1.04 | 0.00 | 1.10 | 0.05 |
| | 1 | 0.98 | 0.06 | 1.11 | 0.07 | 1.07 | 0.13 | 1.10 | 0.10 | 1.15 | 0.01 | 1.06 | 0.05 | 1.15 | 0.07 |
| 169-8-12-2 | 100 | 0.15 | 0.02 | 0.34 | 0.02 | 0.05 | 0.00 | 0.40 | 0.01 | 0.24 | 0.00 | 0.18 | 0.01 | 0.39 | 0.02 |
| | 50 | 0.19 | 0.01 | 1.12 | 0.04 | 0.07 | 0.00 | 0.99 | 0.01 | 0.25 | 0.00 | 0.25 | 0.01 | 0.42 | 0.02 |
| | 10 | 1.08 | 0.11 | 1.18 | 0.10 | 1.00 | 0.13 | 1.18 | 0.03 | 1.08 | 0.02 | 1.09 | 0.04 | 1.10 | 0.05 |
| | 1 | 1.06 | 0.16 | 1.20 | 0.10 | 1.02 | 0.08 | 1.11 | 0.13 | 1.08 | 0.03 | 1.08 | 0.05 | 1.15 | 0.05 |
| 169-14-15-1 | 100 | 0.14 | 0.01 | 0.91 | 0.01 | 0.06 | 0.01 | 0.64 | 0.09 | 0.26 | 0.00 | 0.21 | 0.05 | 0.60 | 0.03 |
| | 50 | 0.26 | 0.03 | 1.20 | 0.11 | 0.23 | 0.06 | 0.96 | 0.02 | 0.49 | 0.01 | 0.25 | 0.00 | 0.62 | 0.03 |
| | 10 | 1.04 | 0.10 | 1.19 | 0.11 | 1.06 | 0.11 | 1.19 | 0.05 | 1.16 | 0.01 | 1.13 | 0.01 | 1.18 | 0.03 |
| | 1 | 1.18 | 0.10 | 1.29 | 0.06 | 1.10 | 0.01 | 1.29 | 0.06 | 1.15 | 0.01 | 1.15 | 0.06 | 1.19 | 0.02 |
| 169-14-15-2 | 100 | 0.17 | 0.01 | 0.80 | 0.02 | 0.16 | 0.01 | 0.62 | 0.02 | 0.24 | 0.06 | 0.21 | 0.02 | 0.60 | 0.06 |
| | 50 | 0.38 | 0.02 | 1.12 | 0.03 | 0.19 | 0.02 | 1.01 | 0.04 | 0.49 | 0.05 | 0.27 | 0.04 | 0.60 | 0.05 |
| | 10 | 0.97 | 0.04 | 1.13 | 0.04 | 0.90 | 0.01 | 0.98 | 0.01 | 1.08 | 0.02 | 1.06 | 0.03 | 1.08 | 0.01 |
| | 1 | 0.95 | 0.05 | 1.11 | 0.04 | 0.85 | 0.02 | 0.96 | 0.02 | 1.11 | 0.01 | 1.01 | 0.01 | 1.06 | 0.00 |
| 169-14-15-4 | 100 | 0.15 | 0.01 | 0.74 | 0.04 | 0.08 | 0.01 | 0.48 | 0.04 | 0.24 | 0.01 | 0.14 | 0.01 | 0.19 | 0.01 |
| | 50 | 0.51 | 0.02 | 0.98 | 0.04 | 0.30 | 0.05 | 0.72 | 0.02 | 0.49 | 0.03 | 0.36 | 0.03 | 0.31 | 0.01 |
| | 10 | 0.93 | 0.01 | 1.14 | 0.04 | 0.95 | 0.04 | 1.02 | 0.03 | 1.09 | 0.02 | 1.08 | 0.02 | 1.14 | 0.02 |
| | 1 | 1.11 | 0.02 | 1.19 | 0.04 | 1.08 | 0.06 | 1.16 | 0.08 | 1.08 | 0.03 | 1.18 | 0.03 | 1.16 | 0.02 |
| 169-20-22-5 | 100 | 0.15 | 0.08 | 0.40 | 0.04 | 0.70 | 0.10 | 0.11 | 0.01 | 0.18 | 0.00 | 0.11 | 0.01 | 0.18 | 0.01 |
| | 50 | 0.15 | 0.02 | 1.05 | 0.13 | 0.79 | 0.05 | 0.27 | 0.05 | 0.25 | 0.02 | 1.01 | 0.02 | 0.32 | 0.04 |
| | 10 | 0.96 | 0.01 | 1.10 | 0.00 | 0.87 | 0.04 | 0.95 | 0.02 | 1.02 | 0.06 | 1.00 | 0.05 | 1.03 | 0.04 |
| | 1 | 0.91 | 0.02 | 1.11 | 0.01 | 0.89 | 0.03 | 0.95 | 0.03 | 1.17 | 0.05 | 1.05 | 0.02 | 1.05 | 0.05 |

TABLE 15-continued

In vitro activity against cancer cell lines of pure compounds

| Sample ID | ug/mL | PC3 AVG | PC3 ERROR | A549 AVG | A549 ERROR | U373 AVG | U373 ERROR | SKOV AVG | SKOV ERROR | MDA-MB AVG | MDA-MB ERROR | CCD AVG | CCD ERROR | THP-1 AVG | THP-1 ERROR |
|---|---|---|---|---|---|---|---|---|---|---|---|---|---|---|---|
| NC174 | 100 | 0.92 | 0.01 | 1.07 | 0.05 | 0.84 | 0.05 | 0.86 | 0.02 | 0.87 | 0.02 | 0.86 | 0.04 | 0.97 | 0.05 |
|  | 50 | 0.97 | 0.04 | 1.11 | 0.05 | 0.98 | 0.05 | 0.93 | 0.01 | 1.00 | 0.02 | 0.90 | 0.03 | 1.18 | 0.04 |
|  | 10 | 0.93 | 0.05 | 1.13 | 0.02 | 0.97 | 0.03 | 1.00 | 0.03 | 1.13 | 0.05 | 1.11 | 0.08 | 1.13 | 0.05 |
|  | 1 | 1.10 | 0.02 | 1.23 | 0.03 | 1.10 | 0.04 | 1.14 | 0.01 | 1.08 | 0.02 | 1.13 | 0.00 | 1.19 | 0.04 |
| NC174 F4 | 100 | 1.14 | 0.06 | 1.28 | 0.09 | 1.02 | 0.08 | 1.16 | 0.10 | 0.87 | 0.04 | 0.92 | 0.05 | 1.06 | 0.03 |
|  | 50 | 0.98 | 0.15 | 1.17 | 0.02 | 1.00 | 0.08 | 1.06 | 0.08 | 0.98 | 0.03 | 0.99 | 0.05 | 1.18 | 0.03 |
|  | 10 | 1.00 | 0.06 | 1.18 | 0.05 | 1.01 | 0.08 | 1.08 | 0.11 | 1.11 | 0.00 | 1.12 | 0.08 | 1.13 | 0.01 |
|  | 1 | 0.99 | 0.11 | 1.19 | 0.06 | 0.97 | 0.14 | 1.08 | 0.07 | 1.11 | 0.03 | 1.15 | 0.08 | 1.11 | 0.07 |
| 174-13-14-1 | 100 | 0.11 | 0.01 | 0.57 | 0.01 | 0.06 | 0.00 | 0.68 | 0.07 | 0.28 | 0.02 | 0.19 | 0.00 | 0.60 | 0.03 |
|  | 50 | 0.19 | 0.01 | 0.67 | 0.04 | 0.11 | 0.00 | 1.05 | 0.07 | 0.34 | 0.02 | 0.19 | 0.01 | 0.55 | 0.01 |
|  | 10 | 1.09 | 0.03 | 0.66 | 0.05 | 1.04 | 0.12 | 1.11 | 0.16 | 1.09 | 0.02 | 1.05 | 0.02 | 1.09 | 0.06 |
|  | 1 | 1.09 | 0.05 | 0.68 | 0.05 | 1.01 | 0.09 | 1.08 | 0.15 | 1.08 | 0.05 | 1.07 | 0.07 | 1.11 | 0.02 |
| 174-13-14-2 | 100 | 0.13 | 0.01 | 0.40 | 0.06 | 0.05 | 0.00 | 0.49 | 0.02 | 0.27 | 0.02 | 0.19 | 0.00 | 0.57 | 0.04 |
|  | 50 | 0.14 | 0.02 | 0.64 | 0.08 | 0.06 | 0.00 | 1.02 | 0.11 | 0.30 | 0.01 | 0.25 | 0.01 | 0.59 | 0.01 |
|  | 10 | 1.07 | 0.03 | 0.65 | 0.05 | 1.10 | 0.01 | 1.21 | 0.10 | 1.13 | 0.03 | 1.06 | 0.05 | 1.16 | 0.03 |
|  | 1 | 1.11 | 0.04 | 0.72 | 0.03 | 1.22 | 0.08 | 1.36 | 0.06 | 1.16 | 0.01 | 1.13 | 0.07 | 1.17 | 0.01 |
| 174-13-14-3 | 100 | 0.05 | 0.01 | 0.41 | 0.06 | 0.08 | 0.00 | 0.19 | 0.01 | 0.22 | 0.02 | 0.15 | 0.01 | 0.23 | 0.01 |
|  | 50 | 0.05 | 0.01 | 0.60 | 0.02 | 0.09 | 0.00 | 0.92 | 0.03 | 0.23 | 0.02 | 0.22 | 0.02 | 0.24 | 0.03 |
|  | 10 | 0.71 | 0.01 | 0.60 | 0.04 | 0.94 | 0.03 | 0.91 | 0.02 | 0.90 | 0.02 | 0.98 | 0.01 | 1.00 | 0.01 |
|  | 1 | 1.00 | 0.03 | 1.12 | 0.01 | 0.86 | 0.02 | 0.89 | 0.01 | 1.11 | 0.02 | 1.11 | 0.06 | 1.03 | 0.02 |
| 174-18-19-3 | 100 | 0.16 | 0.01 | 0.38 | 0.03 | 0.06 | 0.01 | 0.37 | 0.03 | 0.28 | 0.01 | 0.15 | 0.01 | 0.31 | 0.04 |
|  | 50 | 0.16 | 0.00 | 0.67 | 0.09 | 0.07 | 0.07 | 0.84 | 0.05 | 0.33 | 0.01 | 0.24 | 0.00 | 0.46 | 0.02 |
|  | 10 | 1.01 | 0.04 | 0.64 | 0.04 | 1.02 | 0.05 | 1.13 | 0.10 | 1.14 | 0.01 | 1.09 | 0.05 | 1.14 | 0.01 |
|  | 1 | 1.08 | 0.04 | 0.67 | 0.00 | 1.13 | 0.05 | 1.34 | 0.02 | 1.11 | 0.01 | 1.13 | 0.06 | 1.19 | 0.02 |
| 174-10-11-2 | 100 | 0.11 | 0.00 | 0.36 | 0.02 | 0.05 | 0.00 | 0.46 | 0.01 | 0.28 | 0.00 | 0.18 | 0.01 | 0.56 | 0.03 |
|  | 50 | 0.15 | 0.02 | 0.91 | 0.04 | 0.09 | 0.00 | 0.92 | 0.03 | 0.29 | 0.01 | 0.27 | 0.01 | 0.56 | 0.03 |
|  | 10 | 0.97 | 0.02 | 1.16 | 0.05 | 0.94 | 0.03 | 0.91 | 0.03 | 1.12 | 0.04 | 1.03 | 0.05 | 0.98 | 0.02 |
|  | 1 | 0.95 | 0.04 | 1.16 | 0.04 | 0.87 | 0.05 | 0.88 | 0.03 | 1.08 | 0.03 | 1.03 | 0.03 | 1.07 | 0.03 |
| NC175 | 100 | 0.48 | 0.07 | 0.79 | 0.06 | 0.24 | 0.01 | 1.00 | 0.03 | 0.52 | 0.06 | 0.62 | 0.04 | 0.69 | 0.09 |
|  | 50 | 0.98 | 0.01 | 1.03 | 0.03 | 1.01 | 0.07 | 1.09 | 0.03 | 0.78 | 0.06 | 0.90 | 0.02 | 1.15 | 0.02 |
|  | 10 | 1.10 | 0.06 | 1.16 | 0.01 | 1.06 | 0.05 | 1.05 | 0.03 | 1.03 | 0.04 | 0.94 | 0.04 | 1.15 | 0.01 |
|  | 1 | 1.08 | 0.02 | 1.17 | 0.01 | 1.12 | 0.02 | 1.25 | 0.01 | 1.10 | 0.05 | 1.08 | 0.01 | 1.29 | 0.15 |
| NC175 F4 | 100 | 0.07 | 0.00 | 0.19 | 0.02 | 0.05 | 0.01 | 0.68 | 0.07 | 0.23 | 0.01 | 0.11 | 0.02 | 0.38 | 0.03 |
|  | 50 | 0.11 | 0.02 | 0.64 | 0.05 | 0.07 | 0.01 | 0.99 | 0.05 | 0.27 | 0.00 | 0.20 | 0.03 | 0.67 | 0.02 |
|  | 10 | 1.00 | 0.01 | 1.18 | 0.04 | 0.96 | 0.08 | 1.03 | 0.03 | 0.99 | 0.08 | 1.00 | 0.04 | 1.03 | 0.06 |
|  | 1 | 1.02 | 0.04 | 1.15 | 0.03 | 0.98 | 0.07 | 1.00 | 0.13 | 1.08 | 0.02 | 1.05 | 0.05 | 1.13 | 0.04 |
| 175-21-24 | 100 | 1.05 | 0.03 | 0.99 | 0.04 | 1.08 | 0.04 | 1.13 | 0.12 | 0.89 | 0.02 | 0.94 | 0.03 | 0.97 | 0.02 |
|  | 50 | 1.10 | 0.07 | 1.13 | 0.07 | 1.13 | 0.02 | 1.16 | 0.05 | 1.07 | 0.02 | 0.98 | 0.03 | 1.10 | 0.03 |
|  | 10 | 1.03 | 0.03 | 1.16 | 0.06 | 1.12 | 0.08 | 1.12 | 0.07 | 1.10 | 0.04 | 1.08 | 0.04 | 1.14 | 0.04 |
|  | 1 | 1.05 | 0.06 | 1.16 | 0.03 | 1.03 | 0.11 | 1.09 | 0.12 | 1.12 | 0.03 | 1.09 | 0.05 | 1.12 | 0.04 |
| 175-37-42-4 | 100 | 0.12 | 0.01 | 0.67 | 0.05 | 0.10 | 0.00 | 0.90 | 0.06 | 0.26 | 0.01 | 0.23 | 0.00 | 0.35 | 0.02 |
|  | 50 | 0.91 | 0.06 | 1.02 | 0.03 | 0.58 | 0.07 | 1.09 | 0.11 | 0.88 | 0.05 | 0.85 | 0.10 | 0.82 | 0.03 |
|  | 10 | 1.07 | 0.03 | 1.16 | 0.04 | 1.10 | 0.07 | 1.20 | 0.08 | 1.18 | 0.02 | 1.16 | 0.06 | 1.12 | 0.08 |
|  | 1 | 1.09 | 0.05 | 1.16 | 0.07 | 1.18 | 0.06 | 1.26 | 0.06 | 1.17 | 0.00 | 1.20 | 0.08 | 1.16 | 0.08 |

TABLE 15-continued

In vitro activity against cancer cell lines of pure compounds

| Sample ID | ug/mL | PC3 AVG | PC3 ERROR | A549 AVG | A549 ERROR | U373 AVG | U373 ERROR | SKOV AVG | SKOV ERROR | MDA-MB AVG | MDA-MB ERROR | CCD AVG | CCD ERROR | THP-1 AVG | THP-1 ERROR |
|---|---|---|---|---|---|---|---|---|---|---|---|---|---|---|---|
| 175-37-42-5 | 100 | 0.06 | 0.00 | 0.13 | 0.01 | 0.05 | 0.00 | 0.28 | 0.04 | 0.16 | 0.00 | 0.06 | 0.00 | 0.19 | 0.00 |
|  | 50 | 0.12 | 0.01 | 0.66 | 0.03 | 0.07 | 0.00 | 0.73 | 0.03 | 0.19 | 0.01 | 0.15 | 0.01 | 0.24 | 0.02 |
|  | 10 | 1.00 | 0.04 | 1.12 | 0.05 | 0.90 | 0.02 | 0.95 | 0.02 | 1.04 | 0.02 | 1.07 | 0.02 | 1.03 | 0.04 |
|  | 1 | 0.94 | 0.03 | 1.11 | 0.05 | 0.89 | 0.01 | 0.91 | 0.01 | 1.09 | 0.04 | 1.02 | 0.01 | 1.04 | 0.04 |
| 175-51-52-4 | 100 | 0.13 | 0.01 | 0.86 | 0.02 | 0.09 | 0.00 | 0.72 | 0.04 | 0.20 | 0.00 | 0.21 | 0.07 | 0.58 | 0.07 |
|  | 50 | 0.68 | 0.00 | 1.03 | 0.02 | 0.42 | 0.03 | 0.89 | 0.03 | 0.74 | 0.00 | 0.54 | 0.05 | 0.70 | 0.04 |
|  | 10 | 1.01 | 0.04 | 1.18 | 0.02 | 1.02 | 0.01 | 1.05 | 0.02 | 1.11 | 0.03 | 1.05 | 0.01 | 1.14 | 0.05 |
|  | 1 | 1.07 | 0.01 | 1.15 | 0.02 | 1.10 | 0.02 | 1.17 | 0.03 | 1.13 | 0.06 | 1.12 | 0.01 | 1.13 | 0.03 |
| 175-51-52-5 | 100 | 0.13 | 0.01 | 0.66 | 0.04 | 0.12 | 0.01 | 0.84 | 0.02 | 0.22 | 0.00 | 0.23 | 0.01 | 0.54 | 0.03 |
|  | 50 | 0.90 | 0.05 | 1.05 | 0.03 | 0.73 | 0.02 | 0.96 | 0.04 | 0.83 | 0.02 | 0.82 | 0.03 | 0.79 | 0.07 |
|  | 10 | 1.00 | 0.04 | 1.12 | 0.02 | 0.89 | 0.04 | 0.93 | 0.02 | 1.13 | 0.01 | 0.99 | 0.01 | 1.01 | 0.02 |
|  | 1 | 0.97 | 0.04 | 1.11 | 0.02 | 0.87 | 0.01 | 0.94 | 0.03 | 1.11 | 0.02 | 1.00 | 0.01 | 1.08 | 0.00 |
| 175-51-52-6 | 100 | 0.10 | 0.00 | 0.60 | 0.04 | 0.09 | 0.00 | 0.74 | 0.03 | 0.21 | 0.02 | 0.21 | 0.01 | 0.52 | 0.03 |
|  | 50 | 0.75 | 0.06 | 0.99 | 0.01 | 0.49 | 0.05 | 0.90 | 0.01 | 0.76 | 0.06 | 0.48 | 0.05 | 0.75 | 0.11 |
|  | 10 | 0.99 | 0.04 | 1.16 | 0.02 | 0.97 | 0.03 | 1.02 | 0.00 | 1.09 | 0.02 | 1.08 | 0.04 | 1.15 | 0.09 |
|  | 1 | 1.04 | 0.02 | 1.13 | 0.02 | 1.09 | 0.07 | 1.09 | 0.05 | 1.08 | 0.01 | 1.16 | 0.10 | 1.14 | 0.01 |
| 175-51-52-7 | 100 | 0.29 | 0.03 | 0.85 | 0.02 | 0.41 | 0.05 | 1.02 | 0.01 | 0.46 | 0.03 | 0.26 | 0.01 | 0.58 | 0.07 |
|  | 50 | 0.94 | 0.05 | 1.17 | 0.06 | 0.84 | 0.11 | 1.04 | 0.03 | 0.92 | 0.04 | 0.90 | 0.07 | 0.96 | 0.01 |
|  | 10 | 1.05 | 0.01 | 1.18 | 0.01 | 0.97 | 0.04 | 1.05 | 0.07 | 1.09 | 0.00 | 1.12 | 0.06 | 1.12 | 0.01 |
|  | 1 | 1.03 | 0.03 | 1.16 | 0.02 | 0.96 | 0.05 | 1.07 | 0.13 | 1.09 | 0.04 | 1.12 | 0.03 | 1.09 | 0.04 |
| 38-41-1 | 100 | 0.16 | 0.02 | 0.30 | 0.02 | 0.07 | 0.00 | 0.24 | 0.01 | 0.30 | 0.03 | 0.79 | 0.02 | 1.19 | 0.05 |
|  | 50 | 0.54 | 0.08 | 0.81 | 0.03 | 0.13 | 0.01 | 0.56 | 0.07 | 0.70 | 0.02 | 0.85 | 0.03 | 1.10 | 0.04 |
| 31-34-6 | 100 | 0.05 | 0.00 | 0.08 | 0.00 | 0.04 | 0.00 | 0.57 | 0.03 | 0.13 | 0.01 | 0.14 | 0.00 | 0.07 | 0.01 |
| 42-44-1 | 100 | 0.17 | 0.02 | 0.76 | 0.03 | 0.07 | 0.01 | 0.71 | 0.05 | 0.29 | 0.02 | 0.27 | 0.01 | 0.50 | 0.01 |
| 42-44-3 | 100 | 0.16 | 0.00 | 0.70 | 0.04 | 0.06 | 0.00 | 0.69 | 0.03 | 0.25 | 0.01 | 0.27 | 0.00 | 0.43 | 0.05 |
| cont-SDS | 250 | 0.08 | 0.00 | 0.13 | 0.01 | 0.05 | 0.00 | 0.10 | 0.00 | 0.16 | 0.00 | 0.06 | 0.00 | 0.18 | 0.01 |
|  | ug/ml |  |  |  |  |  |  |  |  |  |  |  |  |  |  |

The invention claimed is:
1. A compound having the formula (1):

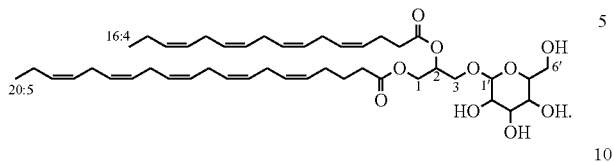

2. The compound of claim 1, incorporated into a formulation for oral use.
3. The compound of claim 2, wherein said oral formulation is a nutraceutical or nutritional formulation.
4. A composition comprising the compound of claim 1, in admixture with a physiologically acceptable excipient.
5. The composition of claim 4, wherein said excipient is suitable for oral administration, and said composition is for oral administration.
6. The oral composition of claim 5, in combination with one or more other therapeutic agent.
7. The composition of claim 6, wherein said other therapeutic agent is a anti-cancer agent.

* * * * *

UNITED STATES PATENT AND TRADEMARK OFFICE
CERTIFICATE OF CORRECTION

PATENT NO. : 11,292,807 B2  
APPLICATION NO. : 16/836658  
DATED : April 5, 2022  
INVENTOR(S) : Bobbitt et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 14 days.

Signed and Sealed this  
Seventh Day of February, 2023

Katherine Kelly Vidal  
*Director of the United States Patent and Trademark Office*